US009771562B2

(12) United States Patent
Shen et al.

(10) Patent No.: US 9,771,562 B2
(45) Date of Patent: Sep. 26, 2017

(54) METHOD FOR CULTURE OF HUMAN AND MOUSE PROSTATE ORGANOIDS AND USES THEREOF

(71) Applicant: THE TRUSTEES OF COLUMBIA UNIVERSITY IN THE CITY OF NEW YORK, New York, NY (US)

(72) Inventors: Michael M. Shen, New York, NY (US); Chee Wai Chua, New York, NY (US); Ming Lei, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 14/722,065

(22) Filed: May 26, 2015

(65) Prior Publication Data
US 2015/0329829 A1 Nov. 19, 2015

Related U.S. Application Data

(63) Continuation-in-part of application No. PCT/US2013/072098, filed on Nov. 26, 2013.

(60) Provisional application No. 61/730,030, filed on Nov. 26, 2012.

(51) Int. Cl.
C12N 5/071 (2010.01)
C12N 5/09 (2010.01)
G01N 33/50 (2006.01)
G01N 33/574 (2006.01)

(52) U.S. Cl.
CPC ......... C12N 5/0683 (2013.01); C12N 5/0693 (2013.01); G01N 33/5011 (2013.01); G01N 33/57434 (2013.01); C12N 2501/11 (2013.01); C12N 2501/392 (2013.01)

(58) Field of Classification Search
None
See application file for complete search history.

(56) References Cited

U.S. PATENT DOCUMENTS

| 4,347,935 | A | 9/1982 | Merrill |
| 4,777,145 | A | 10/1988 | Luotola et al. |
| 5,096,815 | A | 3/1992 | Ladner et al. |
| 5,198,346 | A | 3/1993 | Ladner et al. |
| 5,223,409 | A | 6/1993 | Ladner et al. |
| 5,367,474 | A | 11/1994 | Auer et al. |
| 5,712,171 | A | 1/1998 | Zambias et al. |
| 8,004,661 | B2 | 8/2011 | Luscher |

FOREIGN PATENT DOCUMENTS

| WO | WO-93/20242 | 10/1993 |
| WO | WO-94/18318 | 8/1994 |
| WO | WO-95/18972 | 7/1995 |
| WO | WO-96/22529 | 7/1996 |
| WO | WO-03/014334 | 2/2003 |
| WO | WO-2005/097974 | 10/2005 |
| WO | WO-2012/065067 | 5/2012 |

OTHER PUBLICATIONS

Janson, et al. (Jul. 20, 2002) "Clinical Protocol. Gene therapy of Canavan disease: AAV-2 vector for neurosurgical delivery of aspartoacylase gene (ASPA) to the human brain", Human Gene Therapy, 13(11): 1391-1412.*
Maarouf, et al. (2013) "Molecular Differences and Similarities Between Alzheimer's Disease and the 5XFAD Transgenic Mouse Model of Amyloidosis", Biochemistry Insights, 6:1-7.*
Aytes et al., "Cross-species regulatory network analysis identifies a synergistic interaction between FOXM1 and CENPF that drives prostate cancer malignancy," Cancer Cell. 25, pp. 638-651 (2014).
Aytes et al., "ETV4 promotes metastasis in response to activation of PI3-kinase and Ras signaling in a mouse model of advanced prostate cancer," Proc. Natl. Acad. Sci. USA 110, pp. E3506-3515 (2013).
Barker et al., "Lgr5$^{+ve}$ stem cells drive self-renewal in the stomach and build long-lived gastric units in vitro," Cell Stem Cell. 6, pp. 25-36 (2010).
Bhatia-Gaur et al., "Roles for Nkx3.1 in prostate development and cancer," Genes Dev. 13, p. 966-977 (1999).
BioLegend, Inc., "APC Anti-human CD326 (EpCAM) Antibody Anti-CD326—9C4—BioLegend," <http://www.biolegend.com/apc-anti-human-cd326-epcam-antibody-3758.html> 2 pages (2014).
BioLegend, Inc., "APC anti-mouse CD326 (Ep-CAM) Antibody," <http://www.biolegend.com/apc-anti-mouse-cd326-ep-cam-antibody-4974.html> 2 pages (2014).
Yu et al., "Structural basis for the binding of proline-rich peptides to SH3 domains," Cell 76, pp. 933-945 (1994).
Blondelle et al., "Novel antimicrobial compounds identified using synthetic combinatorial library technology," Trends Biotechnol., 14(2), pp. 60-65 (1996).
Bock et al., "Selection of single-stranded DNA molecules that bind and inhibit human thrombin," Nature 355, pp. 564-566 (1992).
Brenner and Lerner, "Encoded combinatorial chemistry," Proc. Natl. Acad. Sci. USA 89, pp. 5381-5383 (1992).
Zhang et al., "Rock inhibitor Y-27632 suppresses dissociation-induced apoptosis of murine prostate stem/progenitor cells and increases their cloning efficiency," PLoS One 6(e18271), pp. 1-9 (2011).
Cano et al., "Stromal-Epithelial Cell Interactions and Androgen Receptor-Coregulator Recruitment Is Altered in the Tissue Microenvironment of Prostate Cancer" Cancer Res. 67, pp. 511-519 (2007).
Carver et al., "Reciprocal feedback regulation of PI3K and androgen receptor signaling in PTEN-deficient prostate cancer," Cancer Cell. 19, pp. 575-586 (2011).
Centenera et al., "Ex vivo culture of human prostate tissue and drug development," Nat. Rev. Urol. 10, 483-487 (2013).
Choi et al., "Adult murine prostate basal and luminal cells are self-sustained lineages that can both serve as targets for prostate cancer initiation," Cancer Cell. 21, 253-265 (2012).

(Continued)

Primary Examiner — Robert M Kelly
(74) Attorney, Agent, or Firm — Wilmer Cutler Pickering Hale and Dorr LLP

(57) ABSTRACT

The invention discloses a methodology for the culture of prostate tissue organoids from mouse and human prostate.

14 Claims, 67 Drawing Sheets
(67 of 67 Drawing Sheet(s) Filed in Color)

(56) References Cited

OTHER PUBLICATIONS

Chua et al., "Single luminal epithelial progenitors can generate prostate organoids in culture," Nature Cell Biology, 16(10), pp. 951-961 (2014) and Supplementary Information pp. 1-4.
Cunha, "Mesenchymal-epithelial interactions: past, present, and future," Differentiation 76, pp. 578-586 (2008).
Ellington and Szostak, "Selection in vitro of single-stranded DNA molecules that fold into specific ligand-binding structures," Nature 355, pp. 850-852 (1992).
Ellwood-Yen et al., "Myc-driven murine prostate cancer shares molecular features with human prostate tumors" Cancer Cell. 4, 223-238 (2003).
Erb et al., "Recursive deconvolution of combinatorial chemical libraries," Proc. Natl. Acad. Sci. USA 91, pp. 11422-11426, (1994).
Festuccia et al., "Epithelial and prostatic marker expression in short-term primary cultures of human prostate tissue samples," Int. J. Oncol. 26(5), pp. 1353-1362 (2005).
Floc'h et al., "Dual targeting of the Akt/mTOR signaling pathway inhibits castration-resistant prostate cancer in a genetically engineered mouse model," Cancer Res. 72, pp. 4483-4493 (2012).
Fodor et al., "Light-directed, spatially addressable parallel chemical synthesis," Science 251, pp. 767-773 (1991).
Fowlkes et al., "Multipurpose Vectors for Peptide Expression on the M13 Viral Surface," Biotechniques 13, pp. 422-427 (1992).
Gallop et al., "Applications of Combinatorial Technologies to Drug Discovery. 1. Background and Peptide Combinatorial Libraries," J. Medicinal Chemistry 37(9), pp. 1233-1251 (1994).
Gao et al., "Forkhead box A1 regulates prostate ductal morphogenesis and promotes epithelial cell maturation," Development 132, pp. 3431-3443 (2005).
Gao et al., "Organoid Cultures Derived from Patients with Advanced Prostate Cancer," Cell 159(1), pp. 176-187 (2014).
Garraway et al., "Human prostate sphere-forming cells represent a subset of basal epithelial cells capable of glandular regeneration in vivo," Prostate 70(5), pp. 491-501 (2010).
Giannico et al., "Aberrant expression of p63 in adenocarcinoma of the prostate: a radical prostatectomy study," Am. J. Surg. Pathol. 37, pp. 1401-1406 (2013).
Gil et al., "Immortalization of Primary Human Prostate Epithelial Cells by c-Myc," Cancer Research, 65(6), pp. 2179-2185 (2005).
Goldstein et al., "Trop2 identifies a subpopulation of murine and human prostate basal cells with stem cell characteristics," Proc. Natl. Acad. Sci. USA 105, pp. 20882-20887 (2008).
Greenberg et al., "Prostate cancer in a transgenic mouse," Proc. Natl. Acad. Sci. USA 92, pp. 3439-3443 (1995).
Greggio et al., "Artificial three-dimensional niches deconstruct pancreas development in vitro," Development 140, pp. 4452-4462 (2013).
Grisanzio and Signoretti "p63 in prostate biology and pathology," J. Cell Biochem. 103, pp. 1354-1368 (2008).
Guo et al., "Isolation and characterization of human prostate stem/progenitor cells," Methods Mol. Biol. 879, pp. 315-326 (2012).
Guo et al., "Slug and Sox9 Cooperatively Determine the Mammary Stem Cell State," Cell 148, pp. 1015-1028 (2012).
Hansen "Towards selective Kir6.2/SUR1 potassium channel openers, medicinal chemistry and therapeutic perspectives," Curr. Med. Chem. 13(4), pp. 361-376 (2006).
Houghten et al., "Generation and use of synthetic peptide combinatorial libraries for basic research and drug discovery," Nature 354, pp. 84-86 (1991).
Houghten et al., "The use of synthetic peptide combinatorial libraries for the identification of bioactive peptides," Biotechniques 13 pp. 412-421 (1992).
Yui et al., "Functional engraftment of colon epithelium expanded in vitro from a single adult Lgr5+ stem cell," Nat. Med. 18, pp. 618-623 (2012).
Huang and Gao, "A method for generation of arbitrary peptide libraries using genomic DNA," Mol. Biotechnol. 30(2), pp. 135-142 (2005).

Huch et al., "In vitro expansion of single Lgr5+ liver stem cells induced by Wnt-driven regeneration," Nature 494, pp. 247-250 (2013).
Huch et al., "Unlimited in vitro expansion of adult bi-potent pancreas progenitors through the Lgr5/R-spondin axis," EMBO J. 32, pp. 2708-2721 (2013).
Humphrey, "Diagnosis of adenocarcinoma in prostate needle biopsy tissue," J. Clin. Pathol. 60, pp. 35-42 (2007).
International Search Report and Written Opinion for International Application No. PCT/US2013/072098 mailed Feb. 12, 2014 (17 pages).
Irshad et al., "A molecular signature predictive of indolent prostate cancer," Sci. Transl. Med. 5, pp. 1-12 (2013).
Jackson et al. "Analysis of lung tumor initiation and progression using conditional expression of oncogenic K-ras," Genes Dev. 15, pp. 3243-3248 (2001).
Jayawickreme et al., "Creation and functional screening of a multiuse peptide library," Proc. Natl. Acad. Sci. USA 91, pp. 1614-1618 (1994).
Karthaus et al., "Identification of Multipotent Luminal Progenitor Cells in Human Prostate Organoid Cultures," Cell 159(1), pp. 163-175 (2014).
Kim et al., "Cooperativity of Nkx3.1 and Pten loss of function in a mouse model of prostate carcinogenesis," Proc. Natl. Acad. Sci. USA 99, pp. 2884-2889 (2002).
Kim et al., "Nkx3.1 mutant mice recapitulate early stages of prostate carcinogenesis," Cancer Res. 62, pp. 2999-3004 (2002).
Kondo et al., "Retaining cell-cell contact enables preparation and culture of spheroids composed of pure primary cancer cells from colorectal cancer," Proc. Natl. Acad. Sci. USA 108, pp. 6235-6240 (2011).
Koo et al., "Controlled gene expression in primary Lgr5 organoid cultures," Nature Methods 9, pp. 81-83 (2012).
Korenchuk et al., "VCaP, a cell-based model system of human prostate cancer," In Vivo. 15, pp. 163-168 (2001).
Lam et al., "A new type of synthetic peptide library for identifying ligand-binding activity," Nature 354 pp. 82-84 (1991).
Lamb et al., "E-cadherin-mediated survival of androgen-receptor-expressing secretory prostate epithelial cells derived from a stratified in vitro differentiation model," J. Cell Sci. 123, pp. 266-276 (2010).
Lancaster and Knoblich, "Organogenesis in a dish: modeling development and disease using organoid technologies," Science 345, 1247125 epub (2014).
Lang et al., "Differentiation of prostate epithelial cell cultures by matrigel/stromal cell glandular reconstruction. In vitro cellular & developmental biology," Animal 42, pp. 273-280 (2006).
Lang et al., "Experimental prostate epithelial morphogenesis in response to stroma and three-dimensional matrigel culture," Cell Growth Differ. 12, 631-640 (2001).
Lawson et al., "Basal epithelial stem cells are efficient targets for prostate cancer initiation," Proc. Natl. Acad. Sci. USA 107, pp. 2610-2615 (2010).
Lawson et al., "Isolation and functional characterization of murine prostate stem cells," Proc. Natl. Acad. Sci. USA 104, pp. 181-186 (2007).
Lesche et al., "Cre/loxP-mediated inactivation of the murine Pten tumor suppressor gene," Genesis 32(2), pp. 148-149 (2002).
Lin et al., "High fidelity patient-derived xenografts for accelerating prostate cancer discovery and drug development," Cancer Res. 74, pp. 1272-1283 (2014).
Liu et al., "Regenerated luminal epithelial cells are derived from preexisting luminal epithelial cells in adult mouse prostate," Mol. Endocrinol. 25, pp. 1849-1857 (2011).
Liu et al., "Rock Inhibitor and Feeder Cells Induce the Conditional Reprogramming of Epithelial Cells," Am. J. Pathol. 180, pp. 599-607 (2012).
Lu et al., "Conditionally ablated Pten in prostate basal cells promotes basal-to-luminal differentiation and causes invasive prostate cancer in mice," Am. J. Pathol. 182, pp. 975-991 (2013).
Lukacs et al., "Isolation, cultivation and characterization of adult murine prostate stem cells," Nat. Protoc. 5, pp. 702-713 (2010).

(56) References Cited

OTHER PUBLICATIONS

Madisen et al., "A robust and high-throughput Cre reporting and characterization system for the whole mouse brain," Nature neuroscience 13, pp. 133-140 (2010).
Mannhold, "Structure-activity relationships of $K_{ATP}$ channel openers," Curr. Top. Med. Chem. 6(10), pp. 1031-1047 (2006).
Marker et al., "Hormonal, cellular, and molecular control of prostatic development," Dev. Biol. 253, pp. 165-174 (2003).
Masumori et al., "A probasin-large T antigen transgenic mouse line develops prostate adenocarcinoma and neuroendocrine carcinoma with metastatic potential," Cancer Res. 61, pp. 2239-2249 (2001).
McKeehan et al., "Direct mitogenic effects of insulin, epidermal growth factor, glucocorticoid, cholera toxin, unknown pituitary factors and possibly prolactin, but not androgen, on normal rat prostate epithelial cells in serum-free, primary cell culture," Cancer Res. 44, pp. 1998-2010 (1984).
Medynski, "Synthetic peptide combinatorial libraries," Biotechnology 12, pp. 709-710 (1994).
Niranjan et al., "Primary culture and propagation of human prostate epithelial cells," Methods Mol. Biol. 945, pp. 365-382 (2012).
Nolan, "Three-Dimensional Morphogenesis of Mammary Epithelial Cell," Experimental Protocol, pp. 1-2 (2008).
Ohlmeyer et al., "Complex synthetic chemical libraries indexed with molecular tags," Proc. Natl. Acad. Sci. USA 90, pp. 10922-10926 (1993).
Oldenburg et al., "Peptide ligands for a sugar-binding protein isolated from a random peptide library," Proc. Natl. Acad. Sci. USA 89, pp. 5393-5397 (1992).
Ootani et al., "Sustained in vitro intestinal epithelial culture within a Wnt-dependent stem cell niche," Nat. Med. 15, pp. 701-706 (2009).
Ousset et al., "Multipotent and unipotent progenitors contribute to prostate postnatal development" Nat. Cell Biol. 14, pp. 1131-1138 (2012) and Supplementary Information pp. 1-4.
Parmley and Smith, "Filamentous fusion phage cloning vectors for the study of epitopes and design of vaccines," Adv. Exp. Med. Biol. 251, pp. 215-218 (1989).
Peehl, "Primary cell cultures as models of prostate cancer development," Endocr. Relat. Cancer 12(1), pp. 19-47 (2005).
Ranga et al., "Drug discovery through stem cell-based organoid models," Advanced drug delivery reviews 69-70, pp. 19-28 (2014).
Rebar et al., "Zinc finger phage: affinity selection of fingers with new DNA-binding specificities," Science 263, pp. 671-673 (1993).
Ripple et al., "Prooxidant-Antioxidant Shift Induced by Androgen Treatment of Human Prostate Carcinoma Cells," Journal of the National Cancer Institute 89(1), pp. 40-48 (1997).
Rock et al. "Basal cells as stem cells of the mouse trachea and human airway epithelium," Proc. Natl. Acad. Sci. USA 106, pp. 12771-12775 (2009).
Sachs and Clevers, "Organoid cultures for the analysis of cancer phenotypes," Curr. Opin. Genet. Dev. 24, pp. 68-73 (2014).
Salmon et al., "Discovery of biologically active peptides in random libraries: Solution-phase testing after staged orthogonal release from resin beads," Proc. Natl. Acad. Sci. USA 90, pp. 11708-11712 (1993).
Sasai, "Next-generation regenerative medicine: organogenesis from stem cells in 3D culture," Cell Stem Cell 12, pp. 520-530 (2013).
Sato and Clevers, "Primary mouse small intestinal epithelial cell cultures," Methods Mol Biol., vol. 945, pp. 319-328 (2013).
Sato et al., "Long-term expansion of epithelial organoids from human colon, adenoma, adenocarcinoma, and Barrett's epithelium," Gastroenterology 141, pp. 1762-1772 (2011).
Sato et al., "Paneth cells constitute the niche for Lgr5 stem cells in intestinal crypts," Nature 469, pp. 415-418 (2011).
Sato et al., "Single Lgr5 stem cells build crypt-villus structures in vitro without a mesenchymal niche," Nature 459(7244), pp. 262-265 (2009).
Schwank et al. "Functional repair of CFTR by CRISPR/Cas9 in intestinal stem cell organoids of cystic fibrosis patients," Cell Stem Cell. 13, pp. 653-658 (2013).
Scott and Smith, "Searching for peptide ligands with an epitope library," Science 249 pp. 386-390 (1990).
Shen and Abate-Shen "Molecular genetics of prostate cancer: new prospects for old challenges," Genes Dev. 24 pp. 1967-2000 (2010).
Shi et al., "Anchorage-independent culture maintains prostate stem cells," Dev. Biol. 312, pp. 396-406 (2007).
Sobel and Sadar, "Cell lines used in prostate cancer research: a compendium of old and new lines—part 1," J. Urol. 173(2), pp. 342-359 (2005).
Srinivas et al. "Cre reporter strains produced by targeted insertion of EYFP and ECFP into the ROSA26 locus," BMC Dev. Biol. 1:4, 8 pages (2001).
Stange et al., "Differentiated Troy+ Chief Cells Act as Reserve Stem Cells to Generate All Lineages of the Stomach Epithelium," Cell 155, pp. 357-368 (2013).
Staudt et al., "Cloning of a lymphoid-specific cDNA encoding a protein binding the regulatory octamer DNA motif," Science 241, pp. 577-580 (1988).
Toivanen et al., "A preclinical xenograft model identifies castration-tolerant cancer-repopulating cells in localized prostate tumors," Sci. Transl. Med. 5, 187ral 71 epub (2013).
Tuerk et al., "RNA pseudoknots that inhibit human immunodeficiency virus type 1 reverse transcriptase," Proc. Natl. Acad. Sci. USA 89, pp. 6988-6992 (1992).
U.S. Cancer Statistics Working Group. United States Cancer Statistics: 1999-2008 Incidence and Mortality Web-based Report. Atlanta: U.S. Department of Health and Human Services, Centers for Disease Control and Prevention and National Cancer Institute; 2012 (21 pages). Available at: https://wonder.cdc.gov/wonder/help/cancermort-v2008.html.
Van Keymeulen et al. "Epidermal progenitors give rise to Merkel cells during embryonic development and adult homeostasis," J. Cell Biol. 187, pp. 91-100 (2009).
Van Keymeulen et al., "Distinct stem cells contribute to mammary gland development and maintenance," Nature 479, pp. 189-193 (2011).
Wang et al., "A luminal epithelial stem cell that is a cell of origin for prostate cancer," Nature 461(7263), pp. 495-500 (2009).
Wang et al., "ATP-sensitive potassium channel openers and 2,3-dimethyl-2-butylamine derivatives," Curr. Med. Chem. 14(2), pp. 133-155 (2007).
Wang et al., "Lineage analysis of basal epithelial cells reveals their unexpected plasticity and supports a cell-of-origin model for prostate cancer heterogeneity," Nature Cell Biology 15, pp. 274-283 (2013) and Supplementary Information pp. 1-7.
Xin et al., "Self-renewal and multilineage differentiation in vitro from murine prostate stem cells," Stem Cells 25, pp. 2760-2769 (2007).
Xu et al., "Revealing a core signaling regulatory mechanism for pluripotent stem cell survival and self-renewal by small molecules," Proc. Natl. Acad. Sci. USA 107, pp. 8129-8134 (2010).

\* cited by examiner

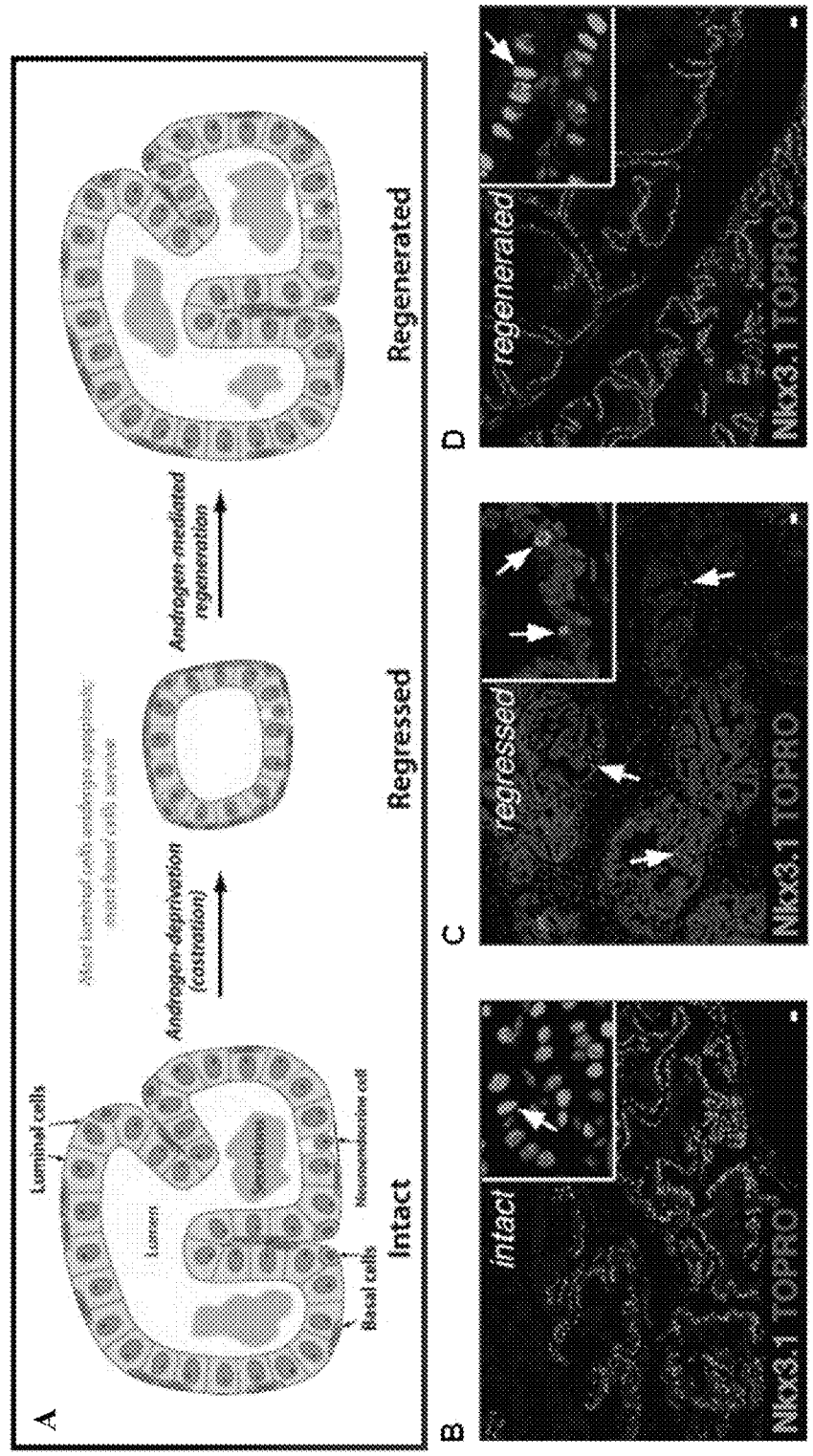
Figures 2A-D

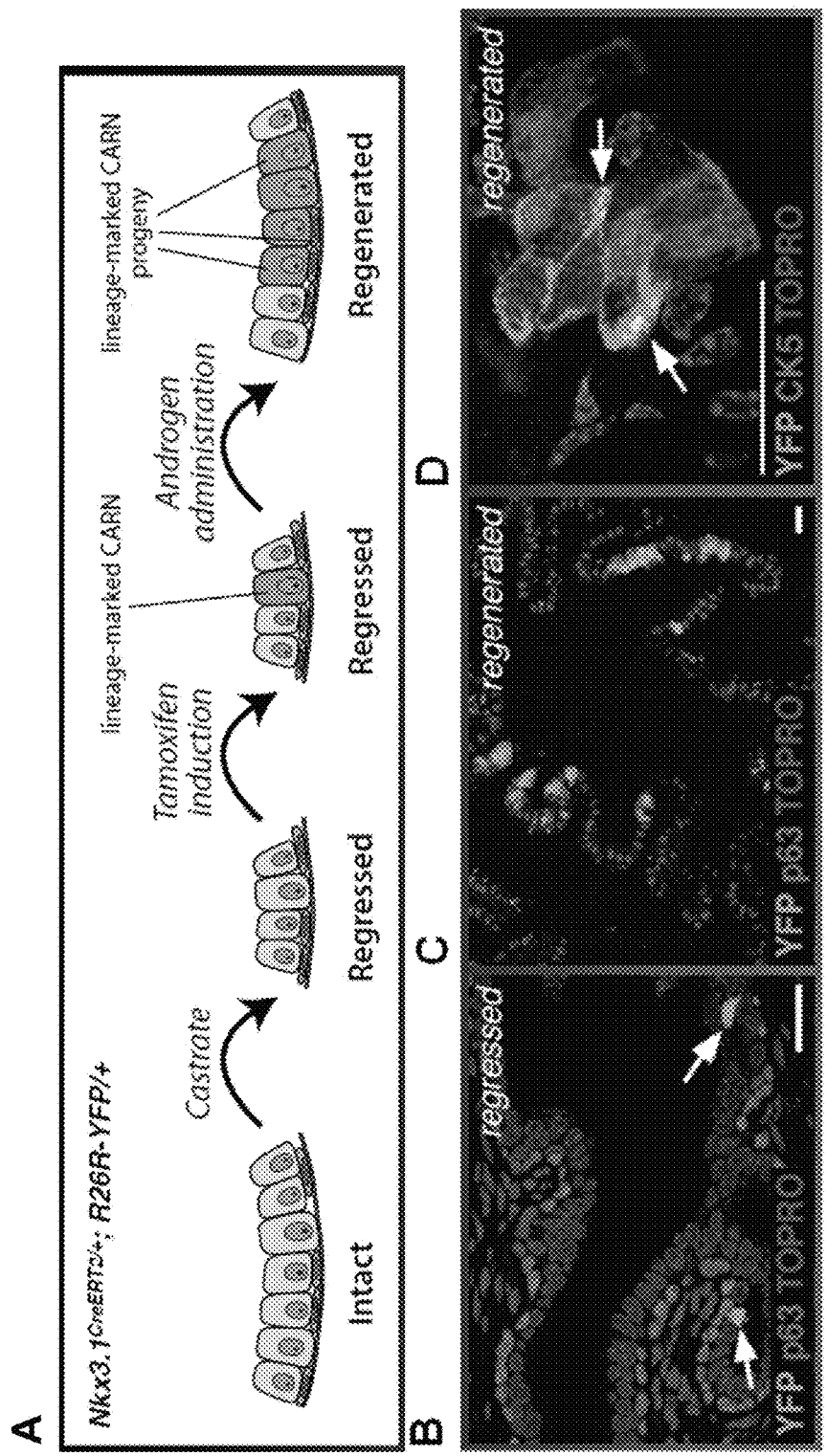
Figures 4A-D

Figures 14A-D

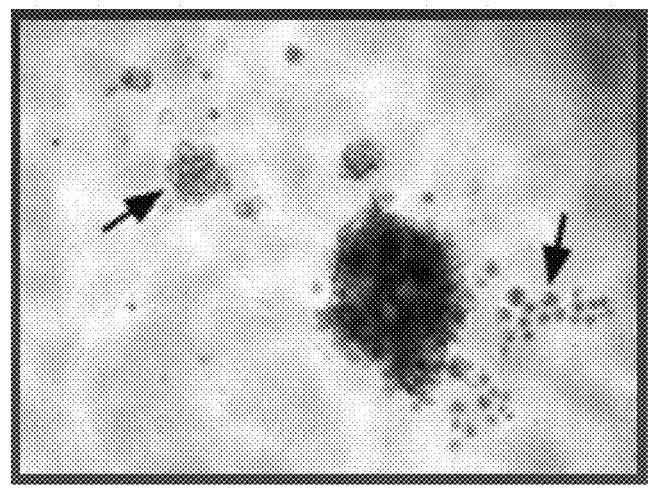
Figure 24G
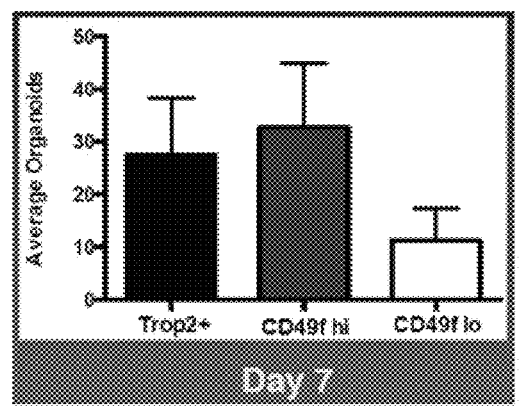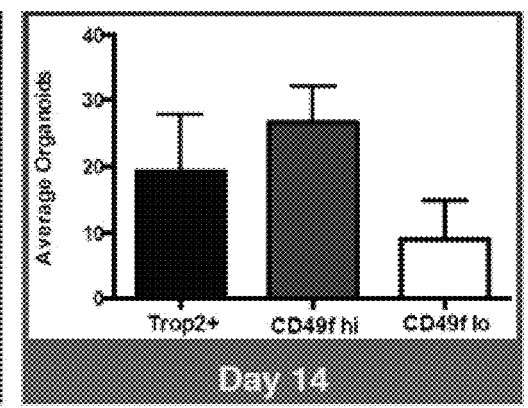
Figures 25A-25C

A

B

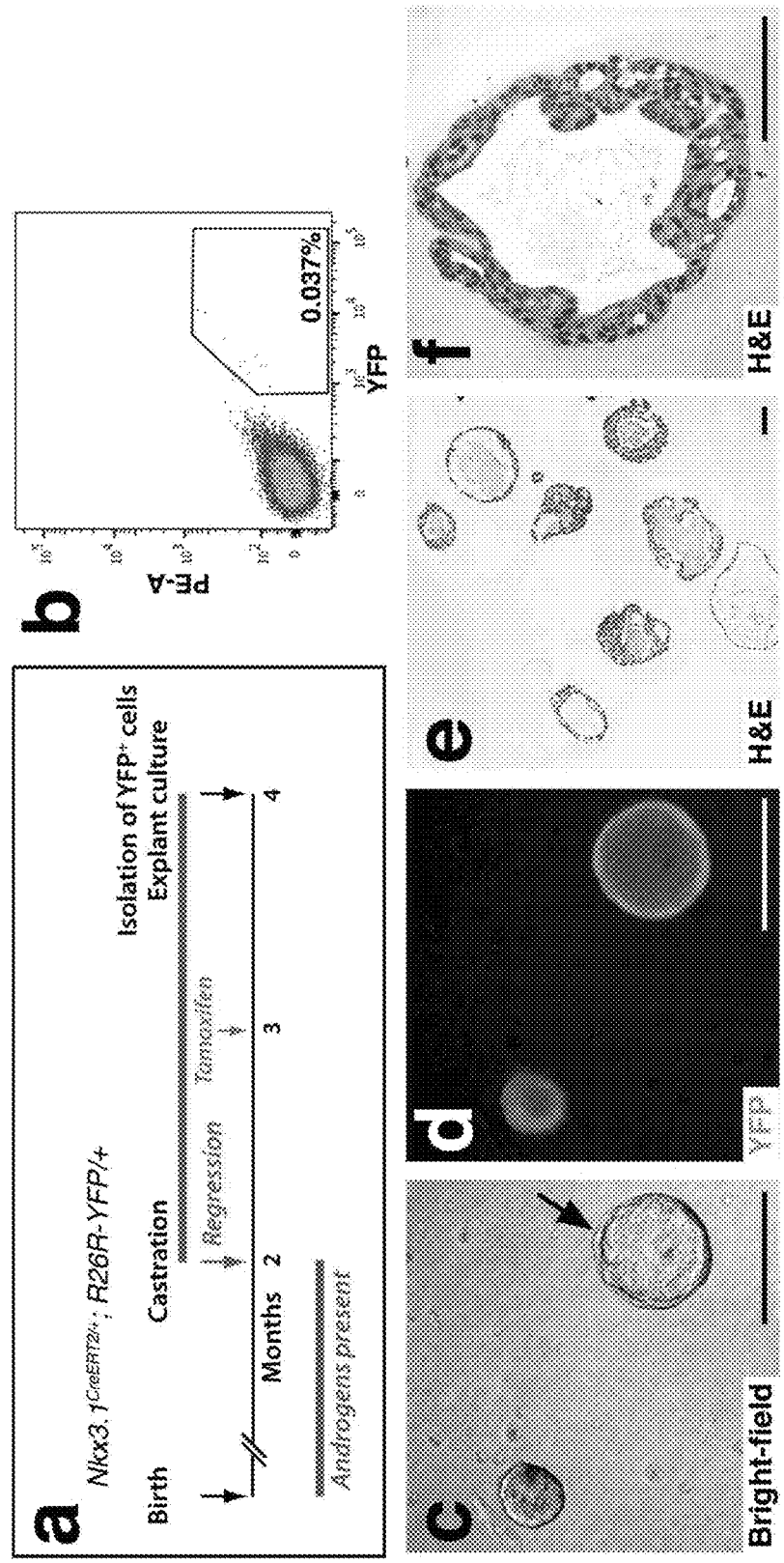
Figures 30A-F

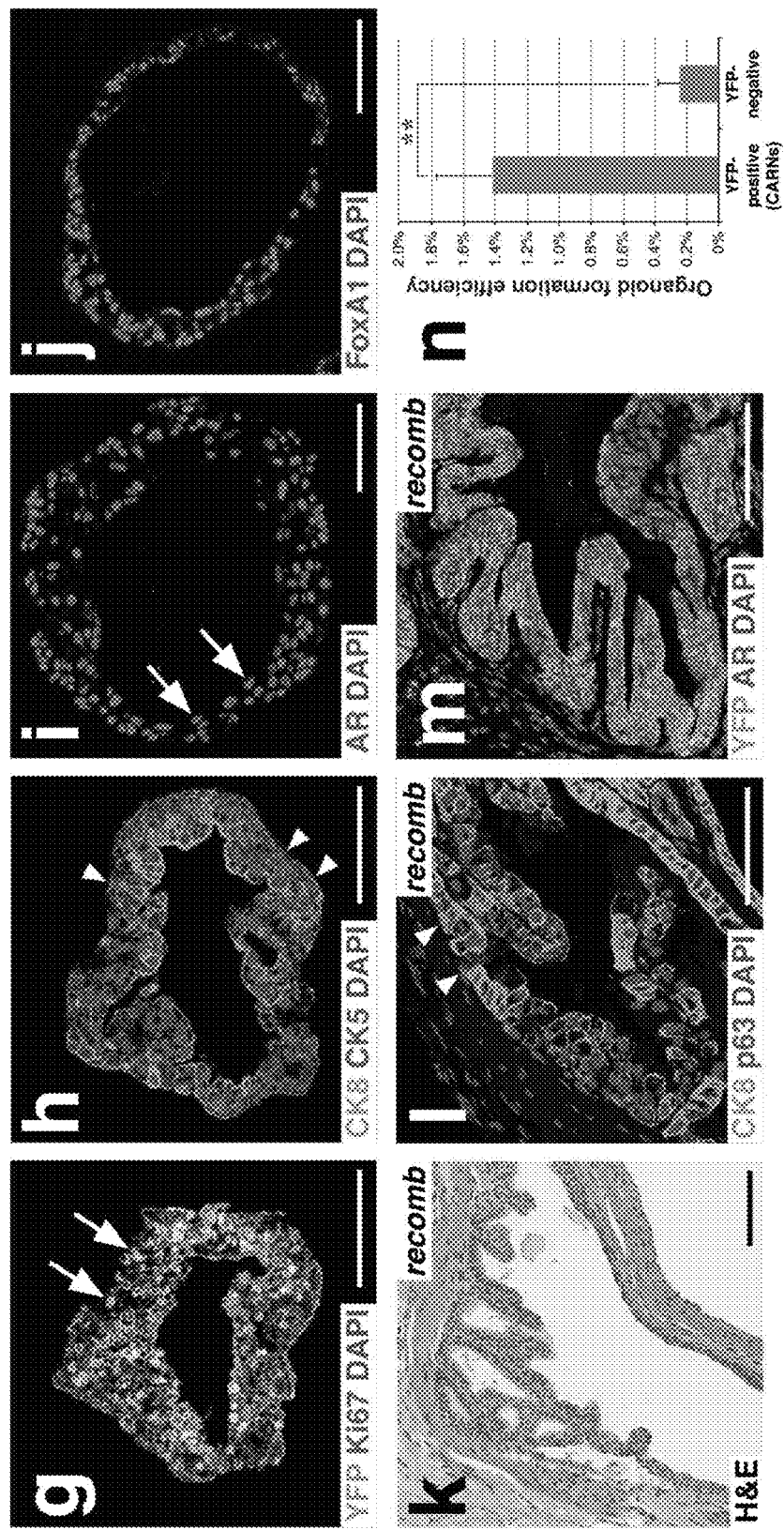
Figures 30G-N

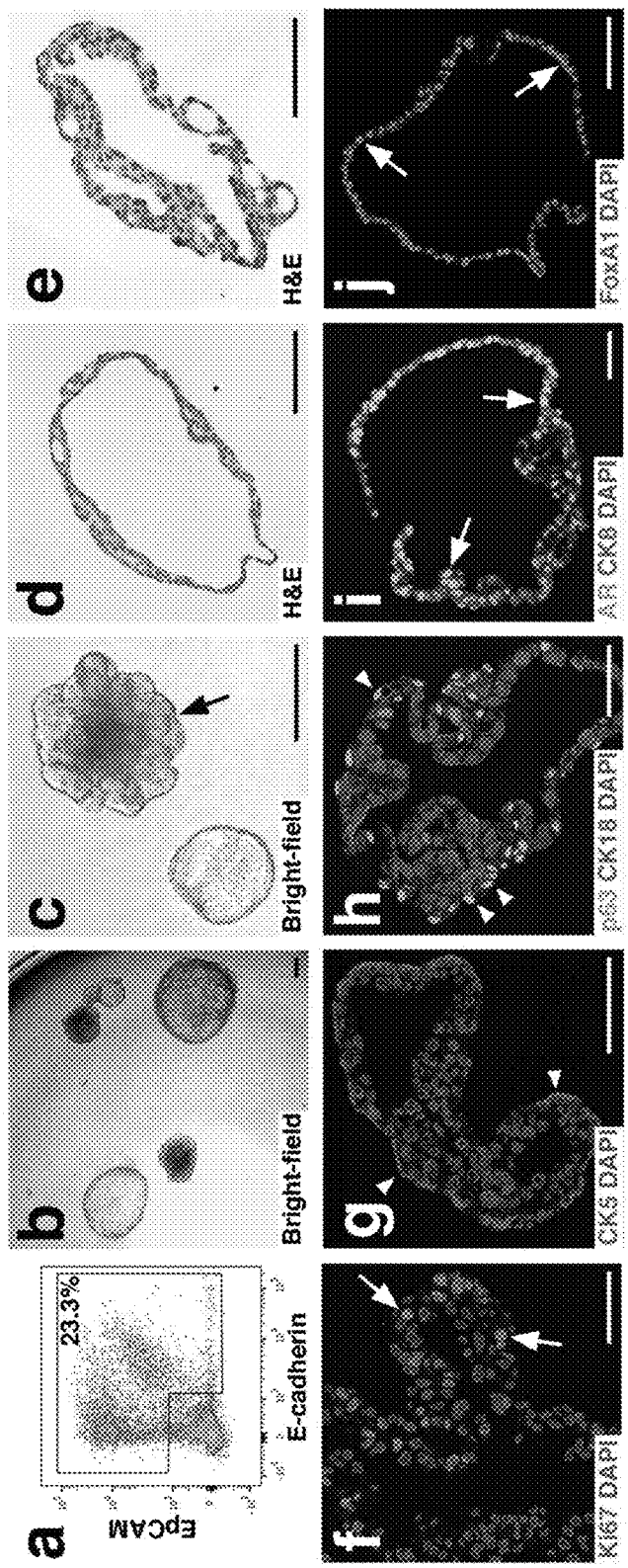
Figures 31A-J

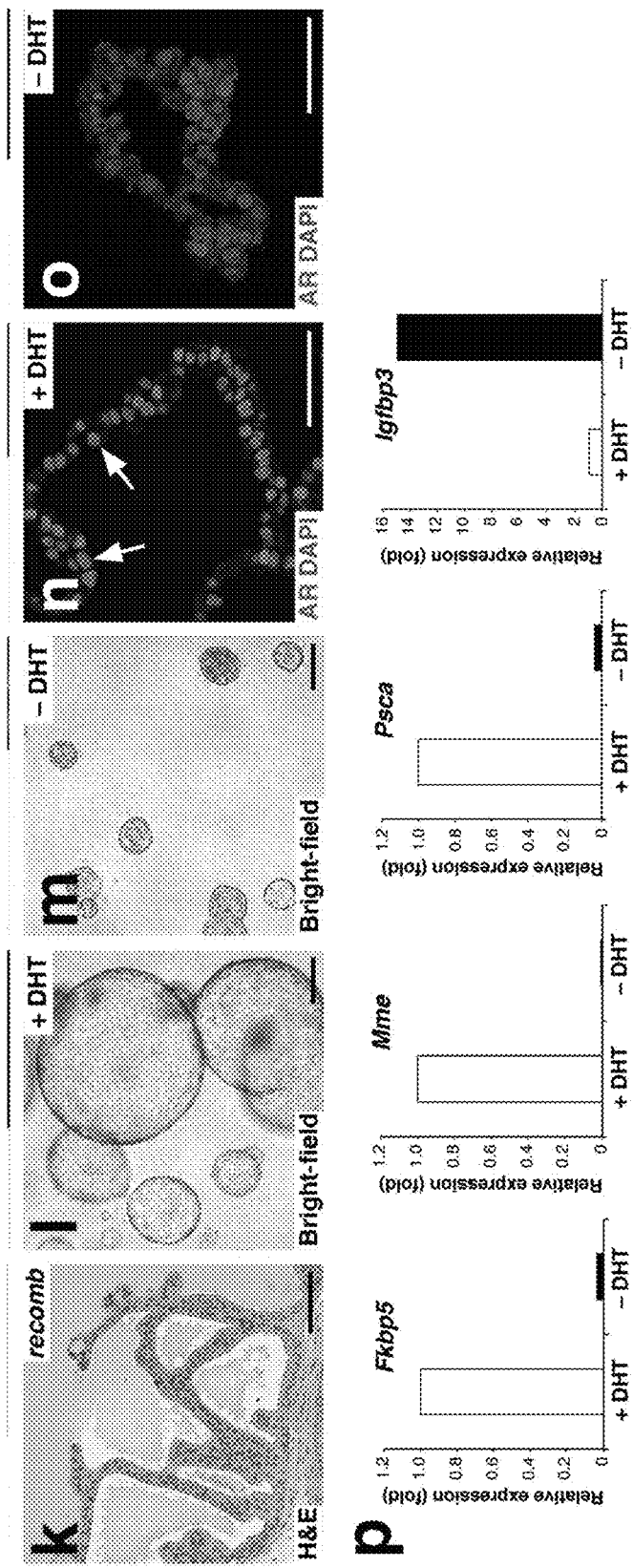
Figures 31K-P

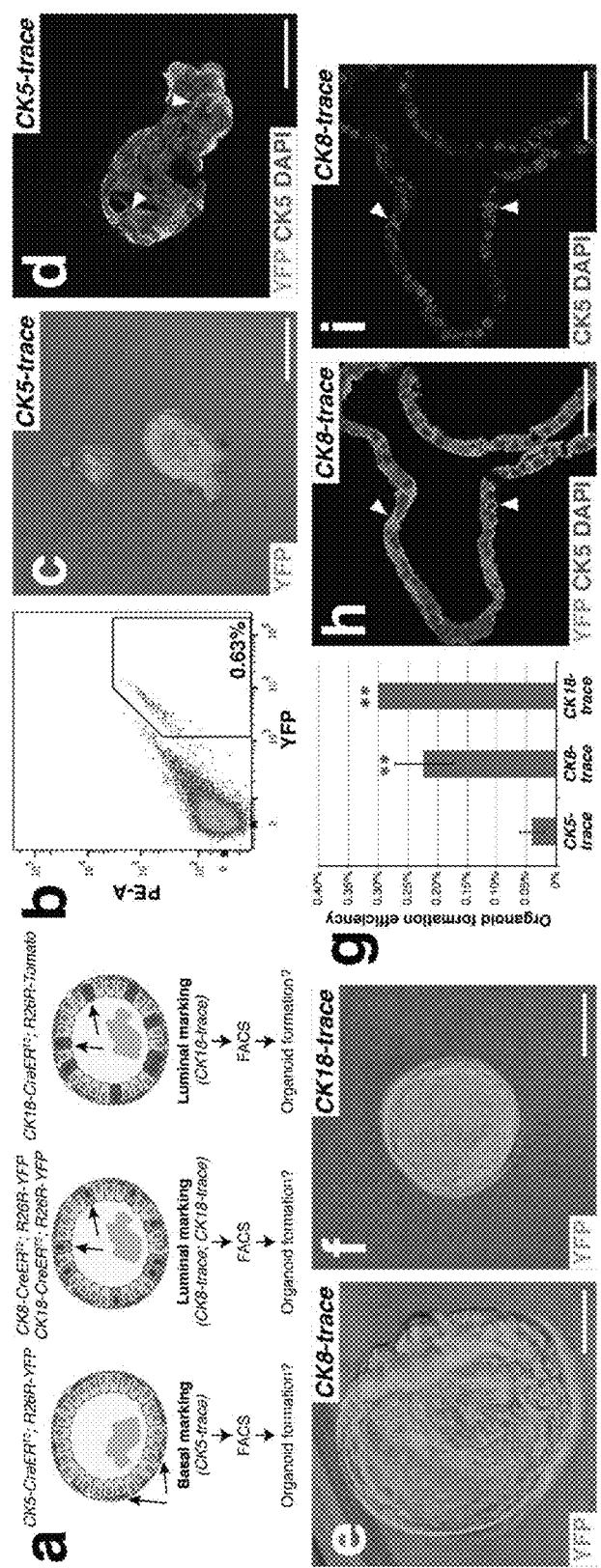
Figures 32A-I

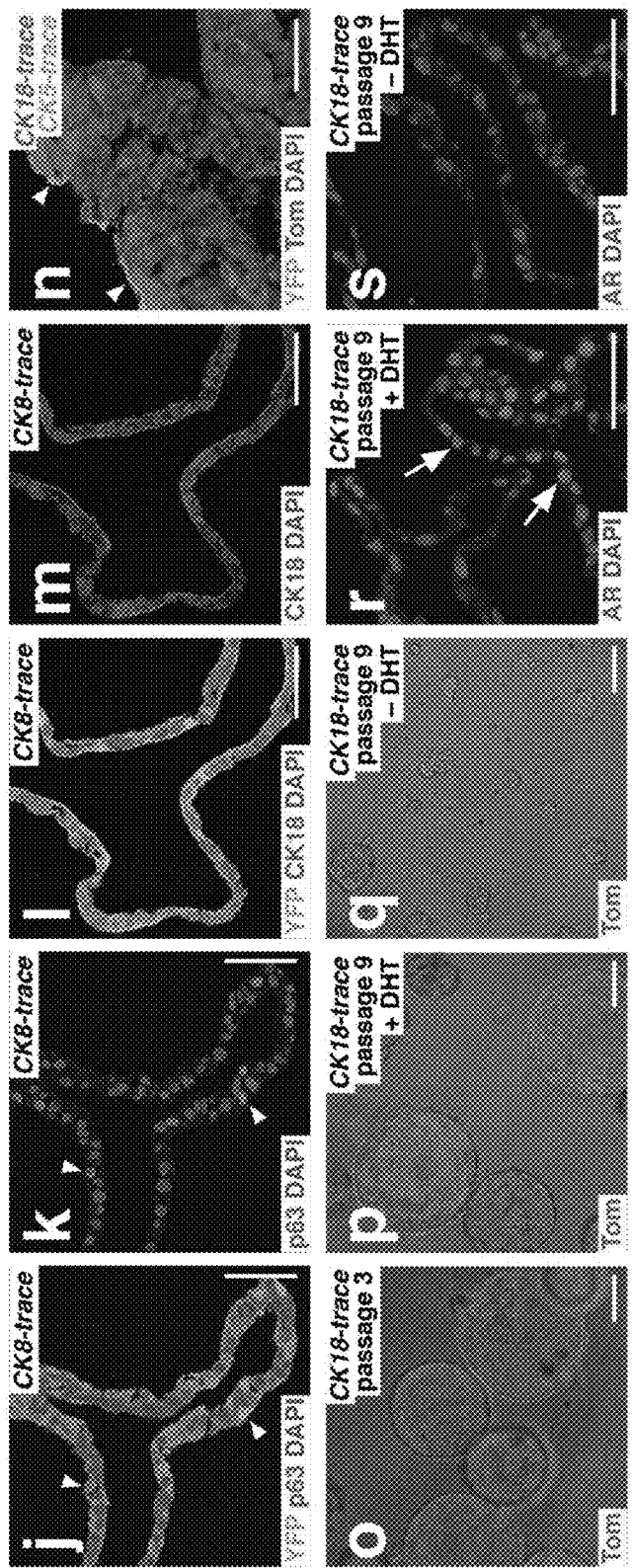
Figures 32J-S

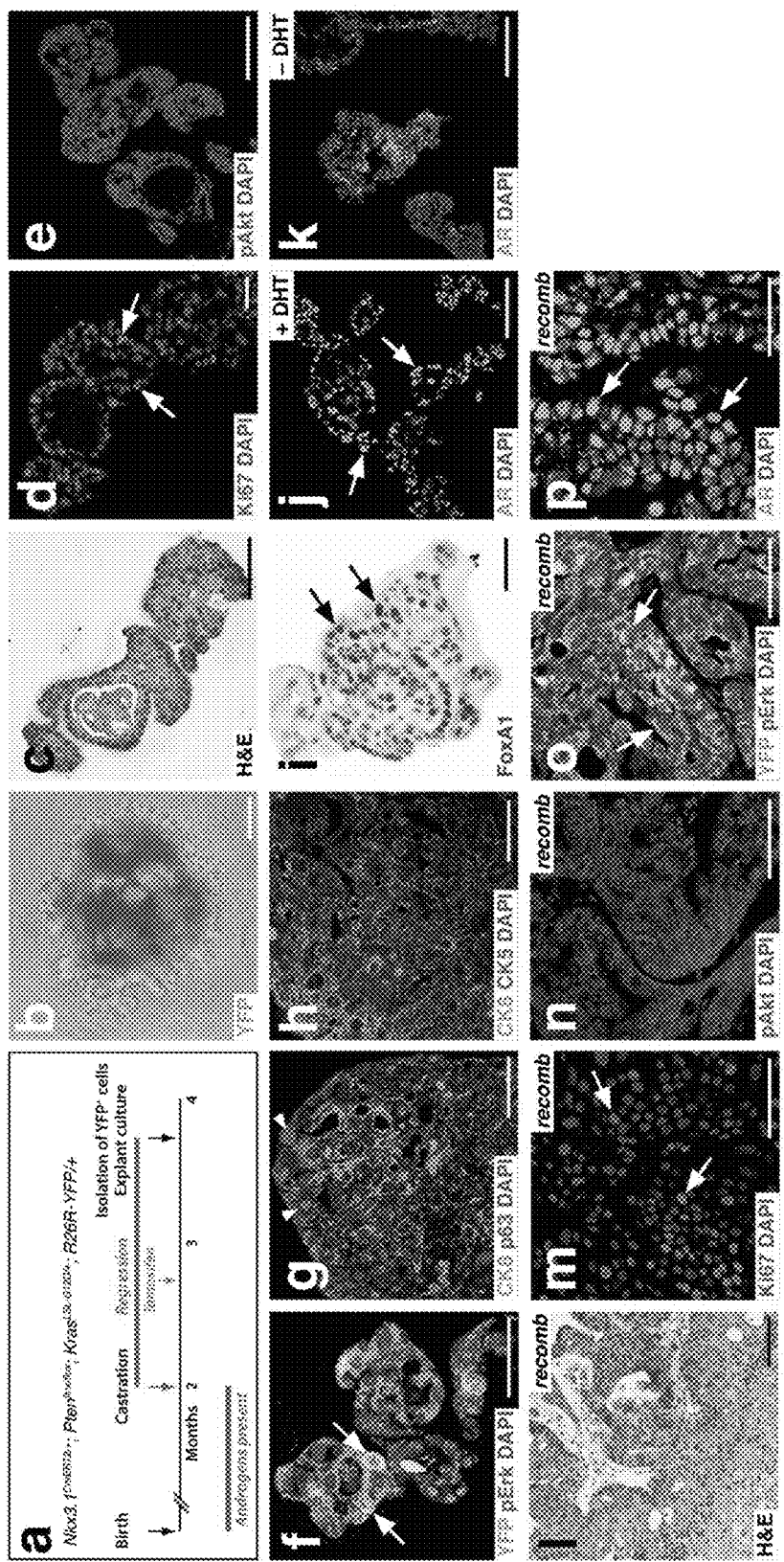
Figures 33A-P

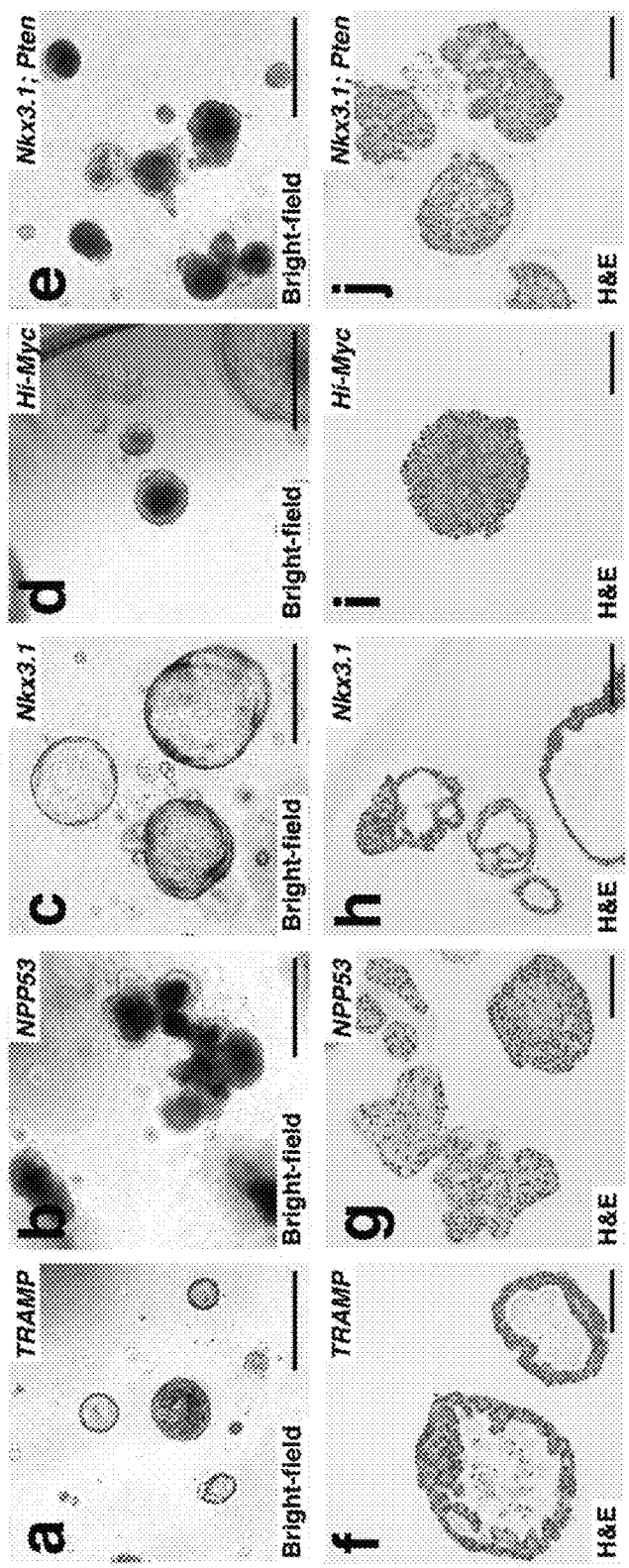
Figures 34A-J

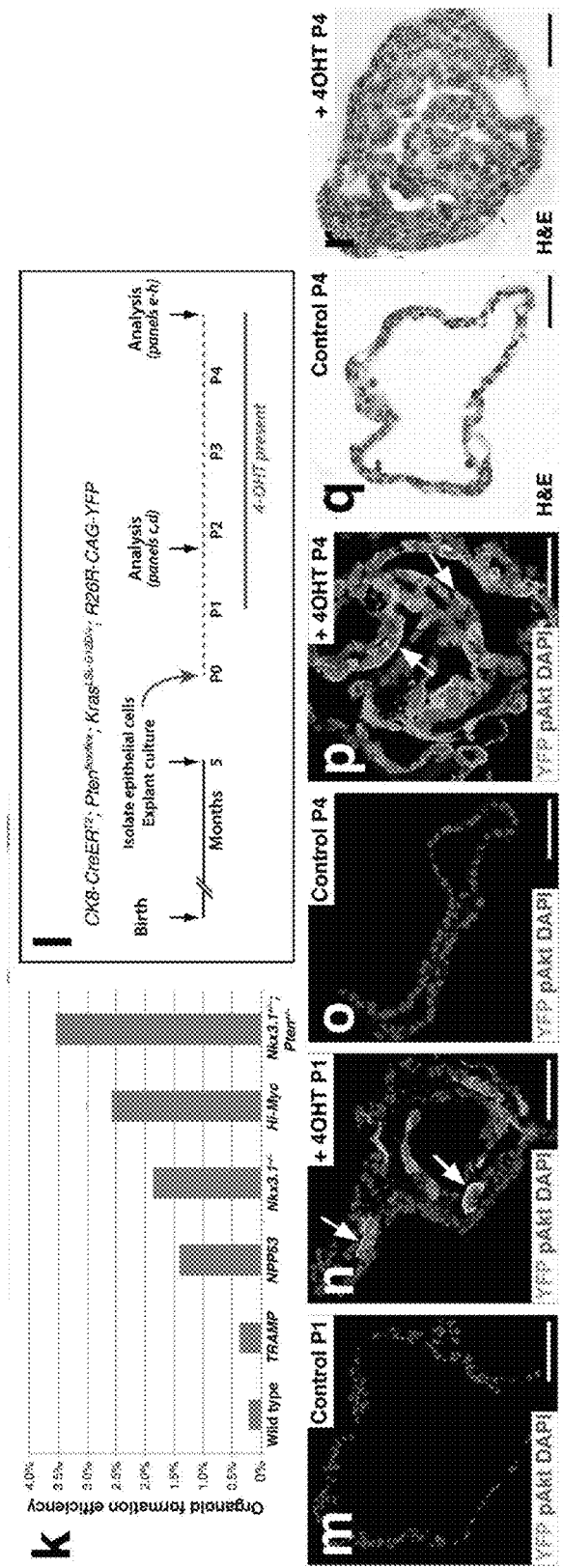
Figures 34K-R

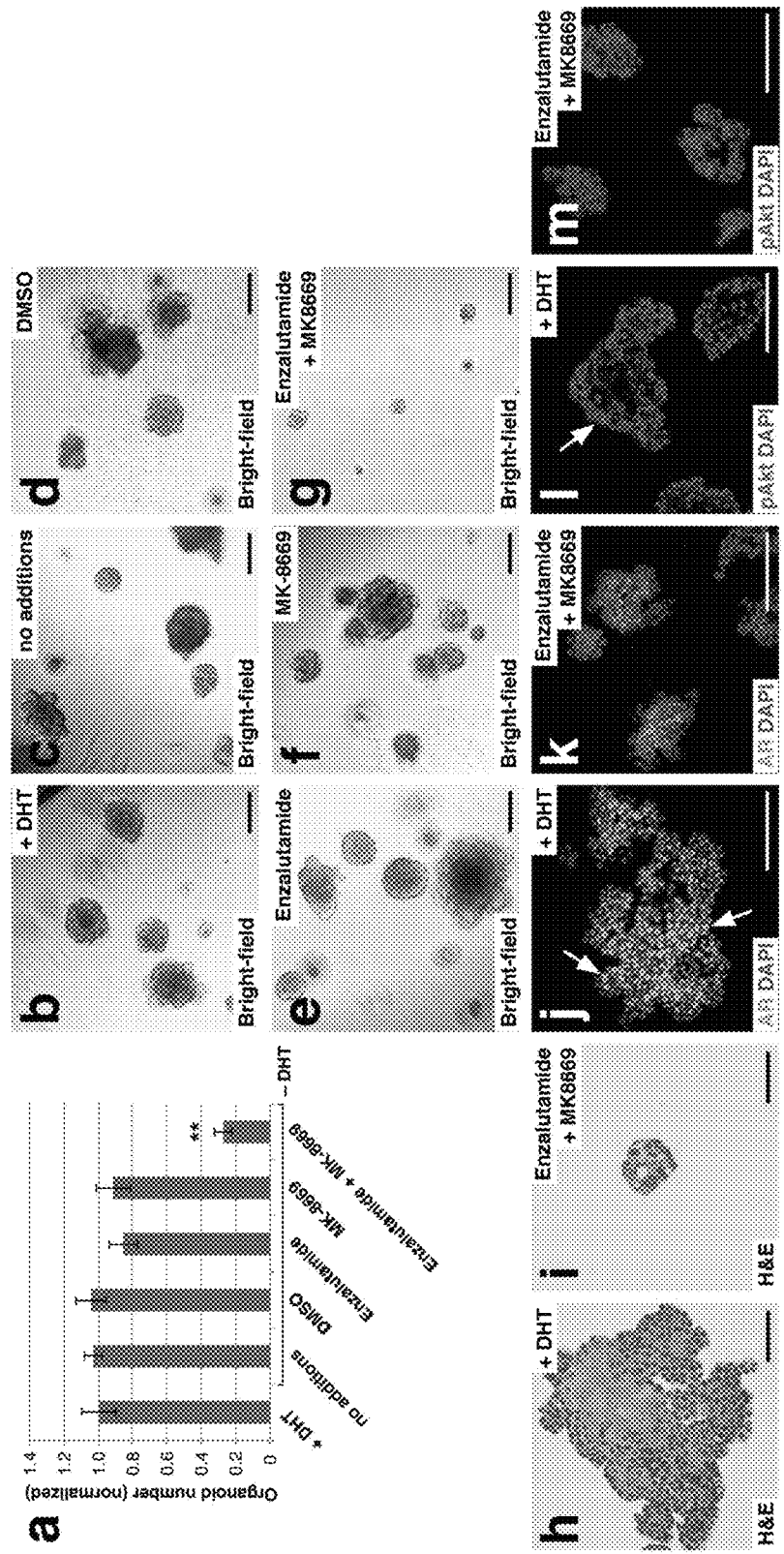
Figures 35A-M

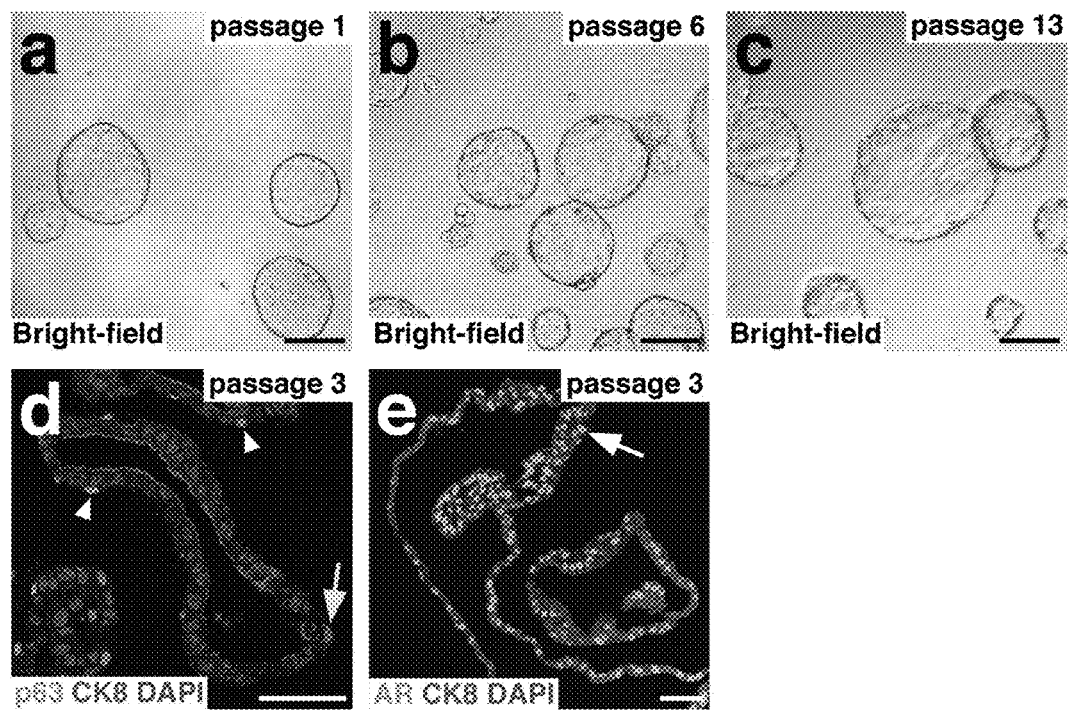
Figures 36A-E
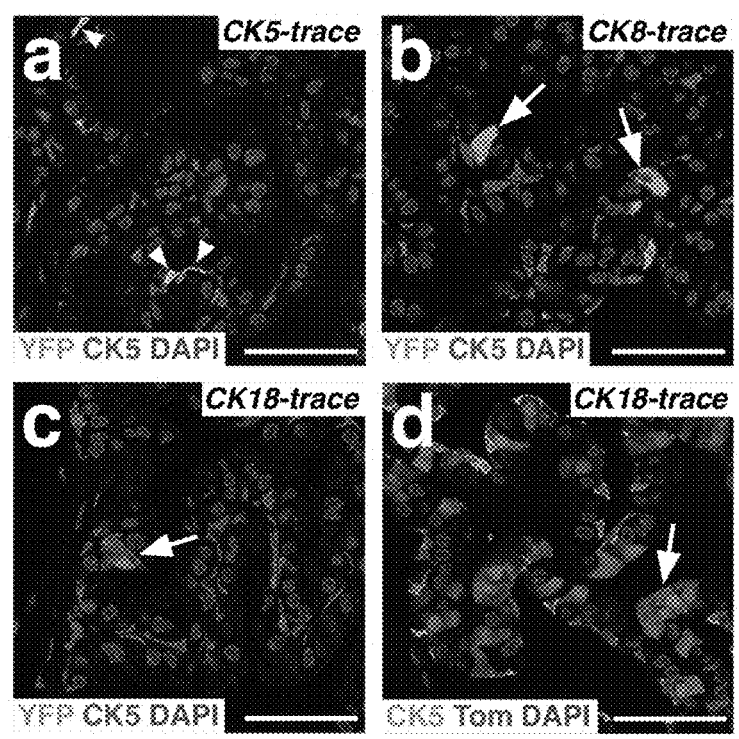
Figures 37A-D

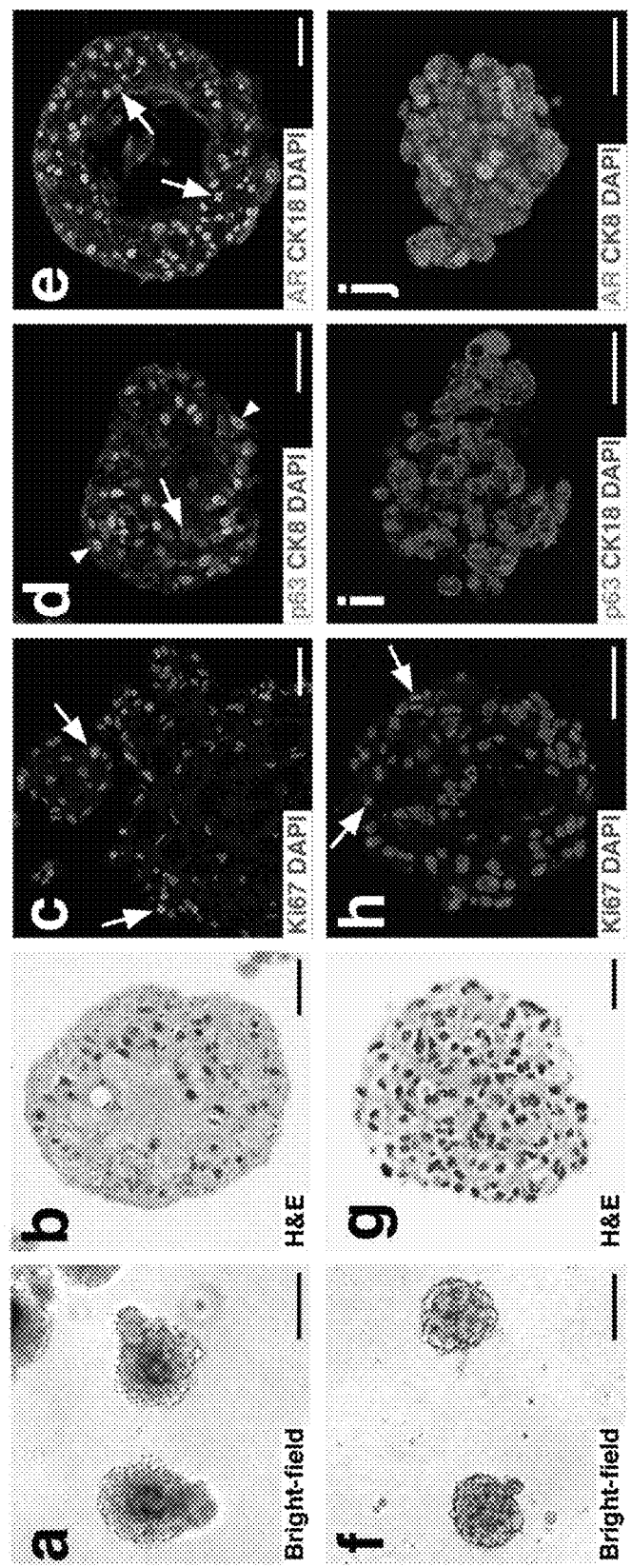
Figures 38A-J

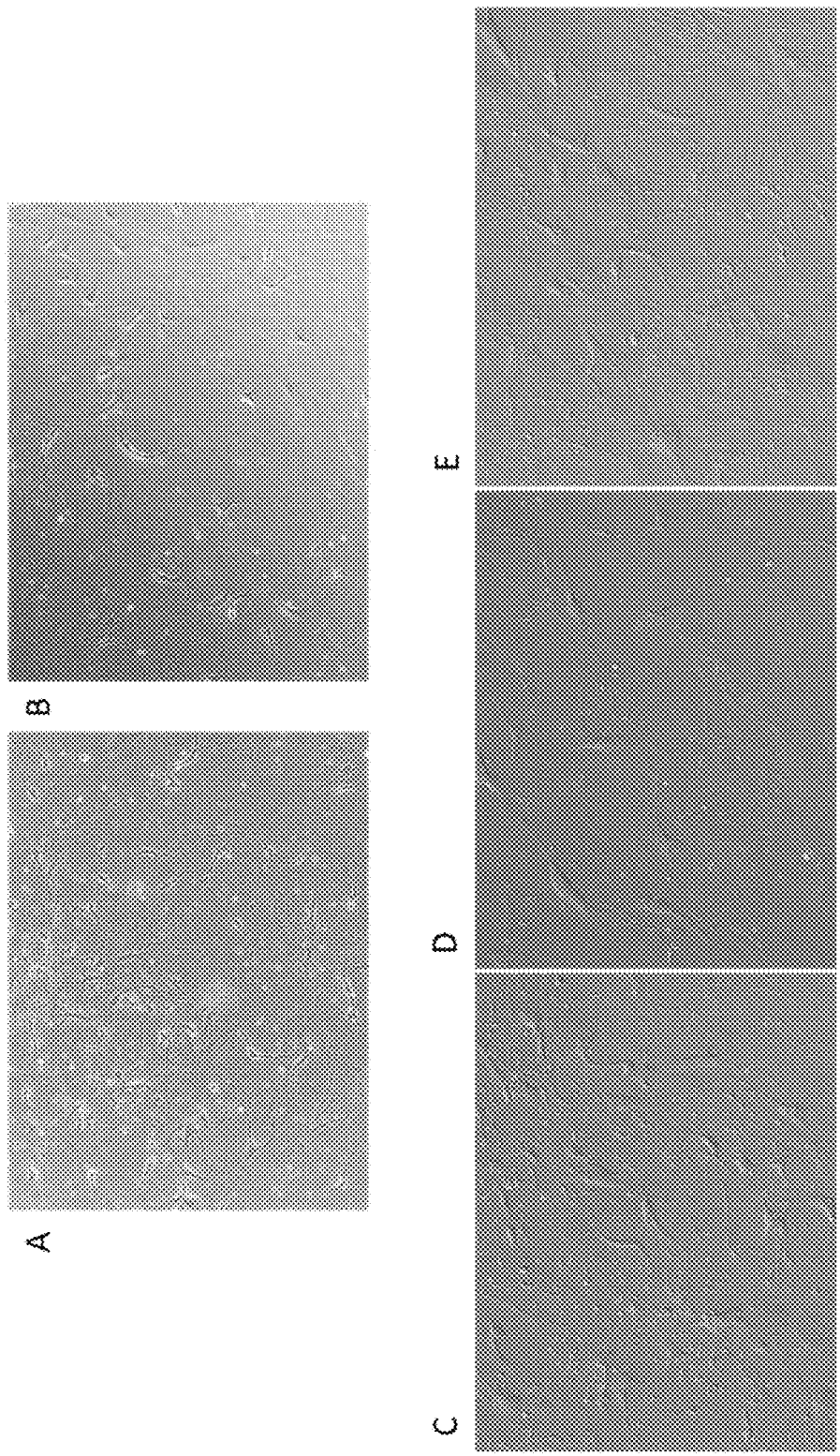
Figures 39A-E

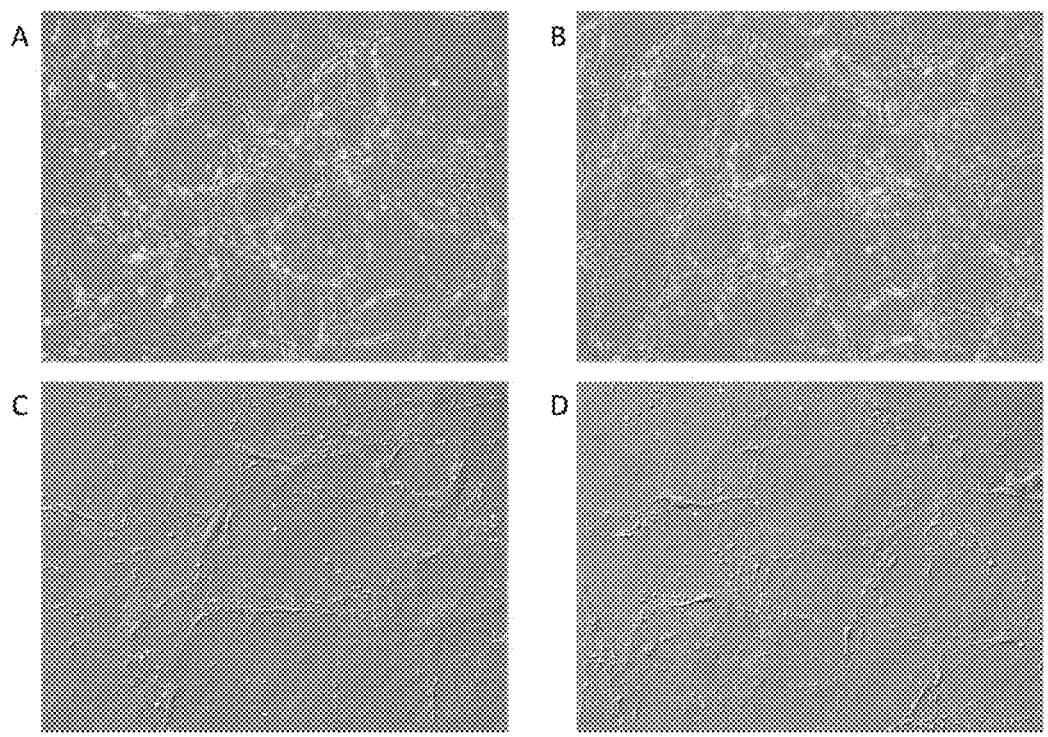
Figures 40A-D

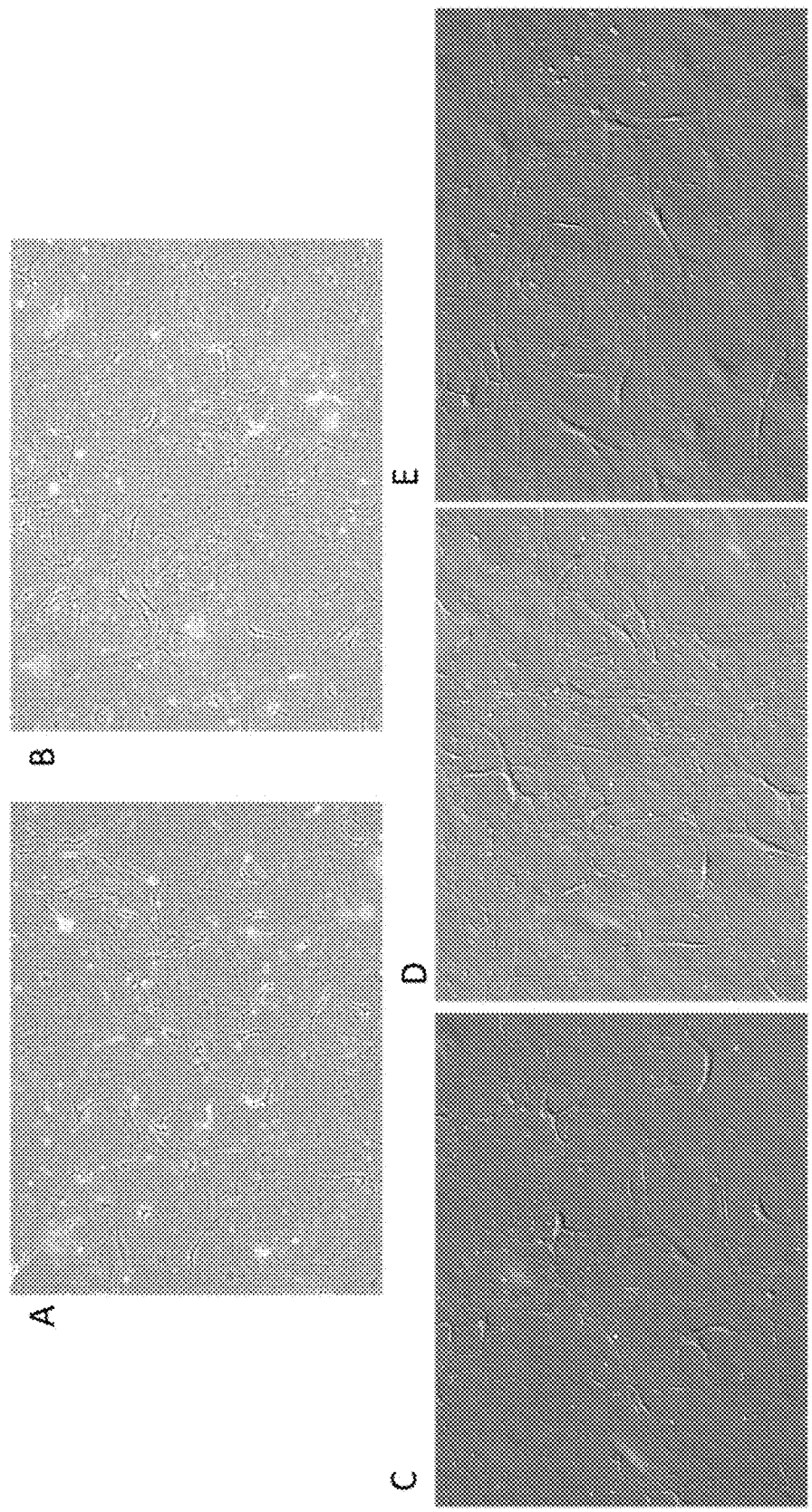
Figures 41A-E

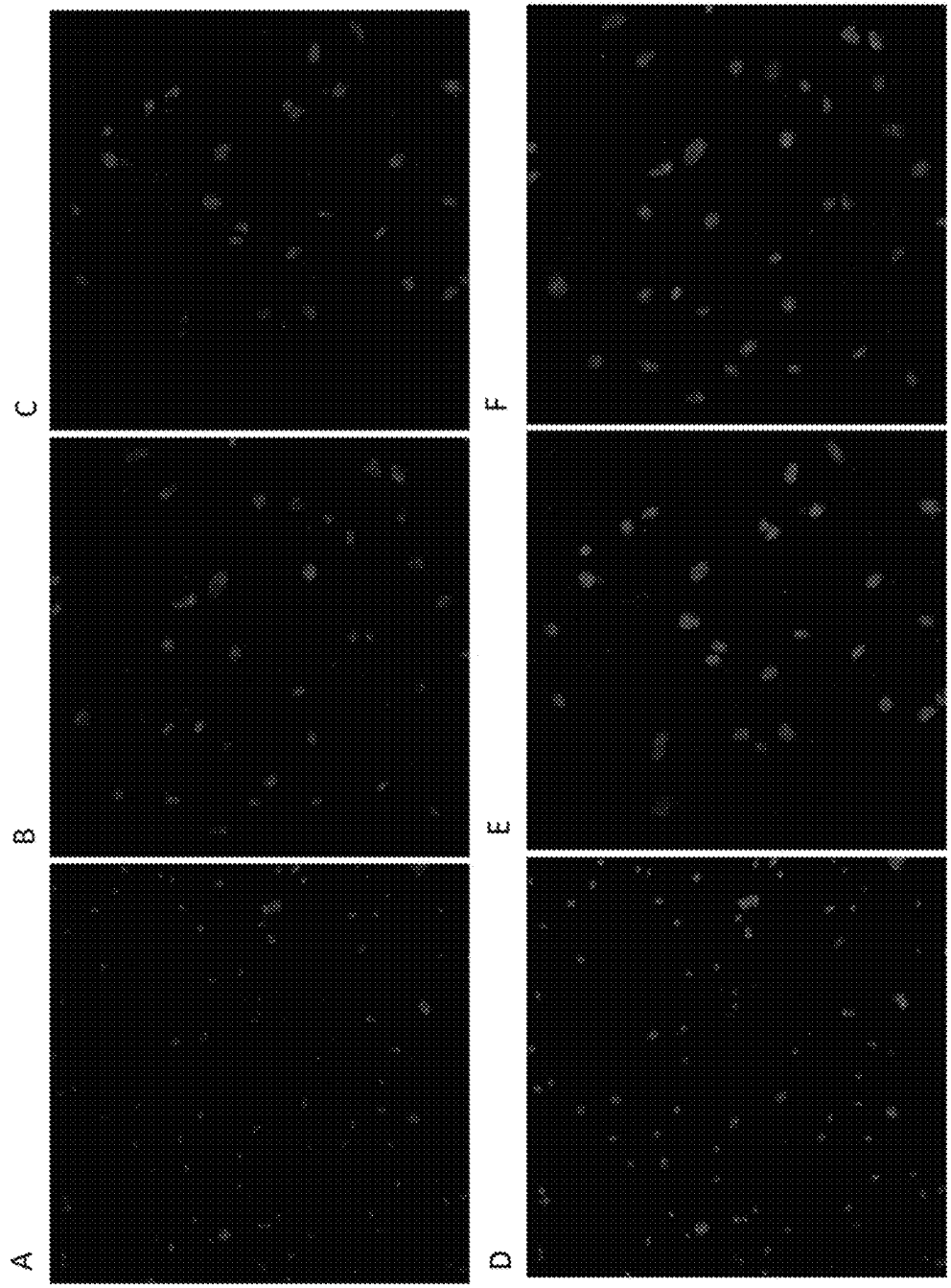
Figures 42A-F

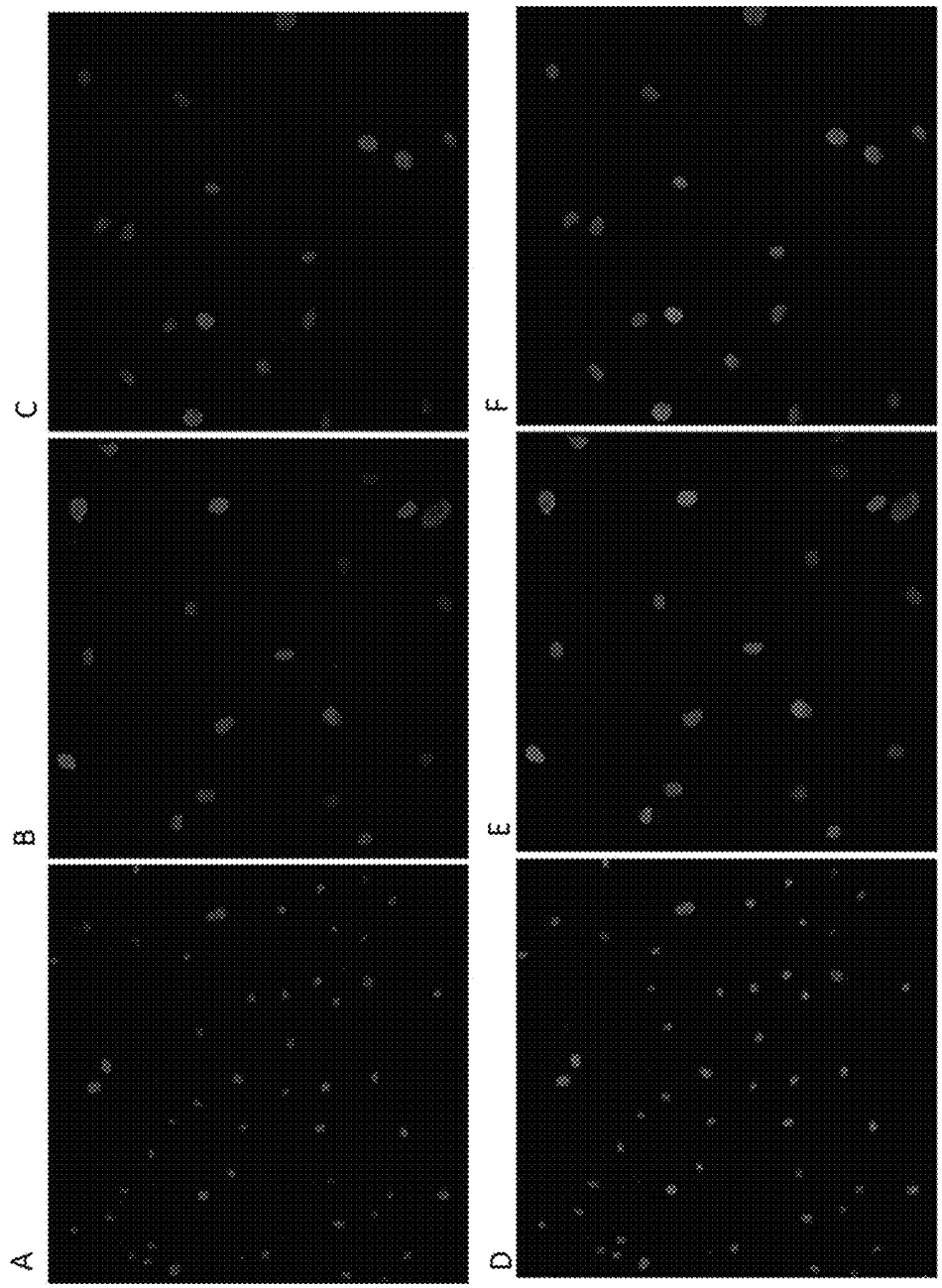
Figures 43A-F

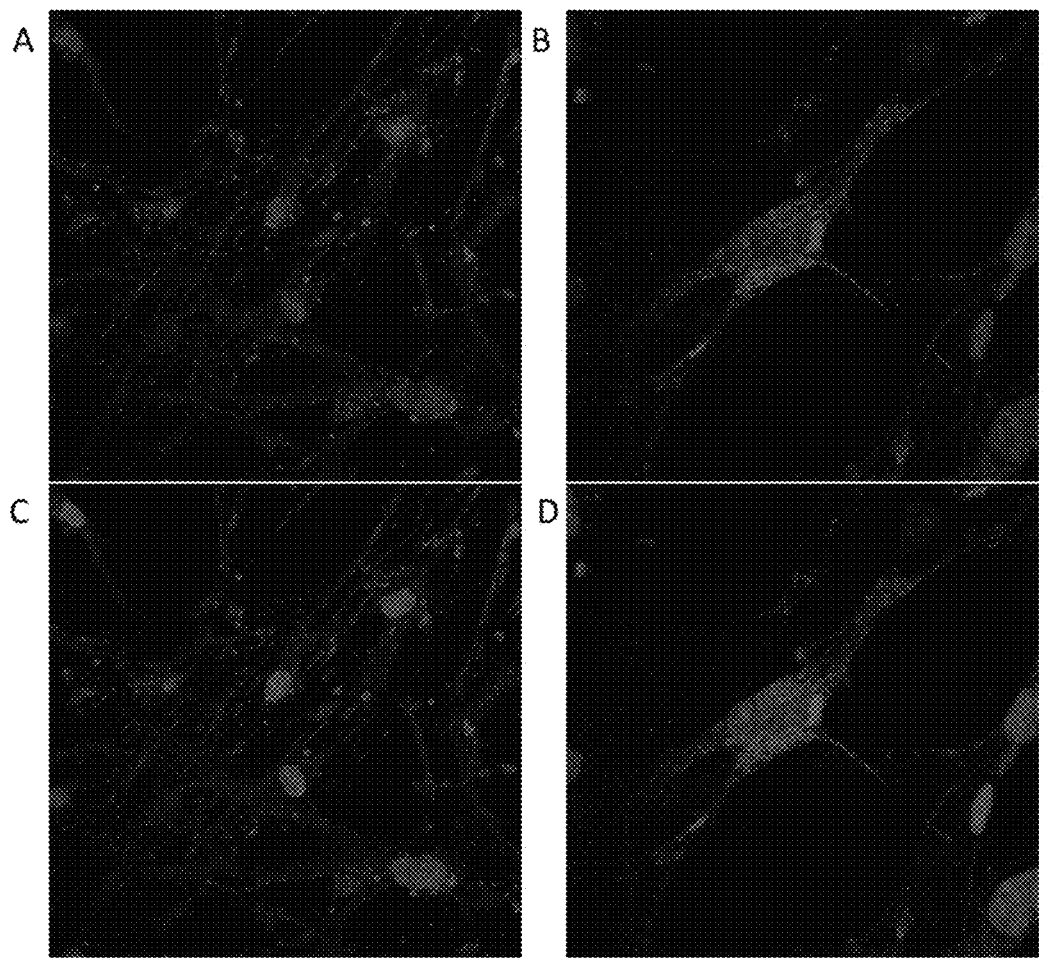
Figures 44A-D

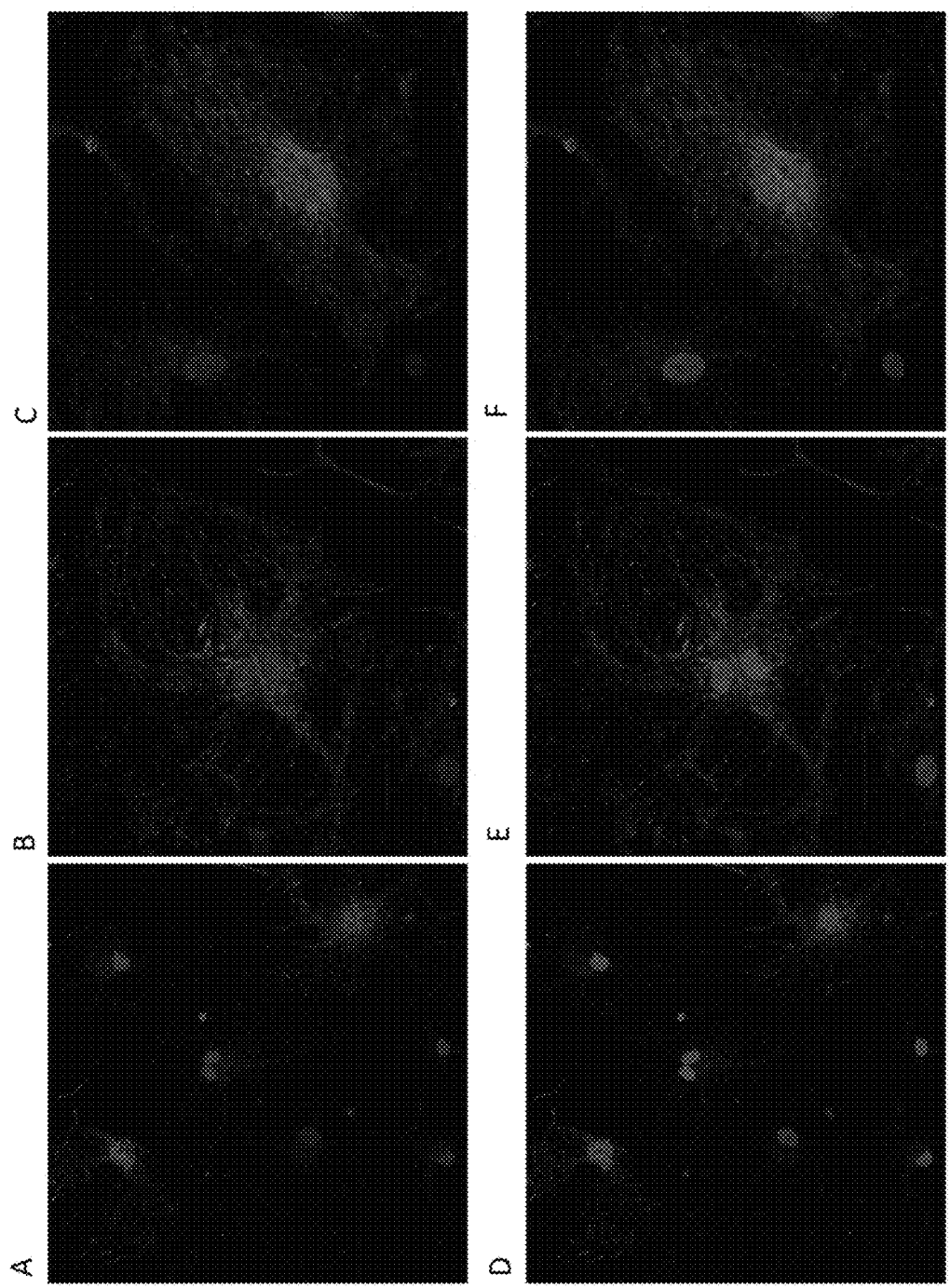
Figures 45A-F

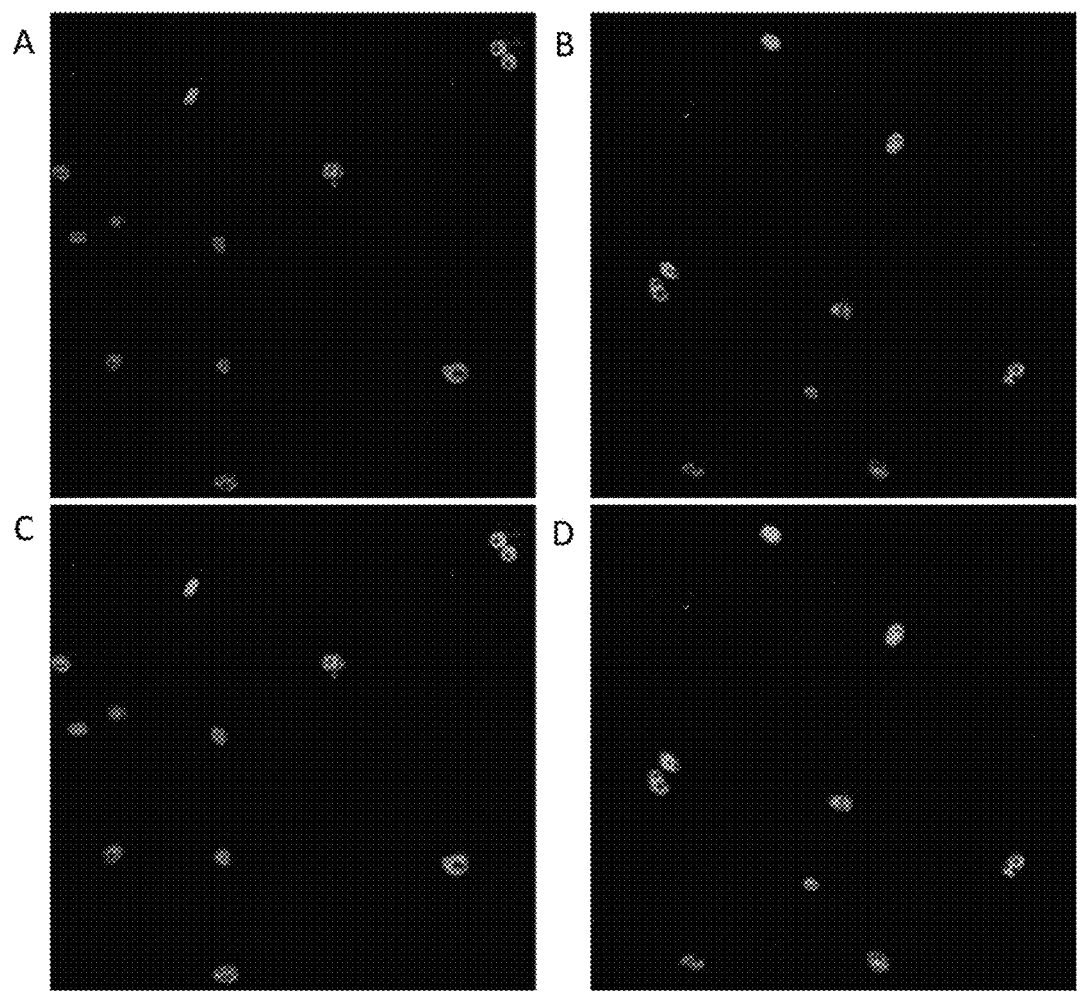
Figures 46A-D

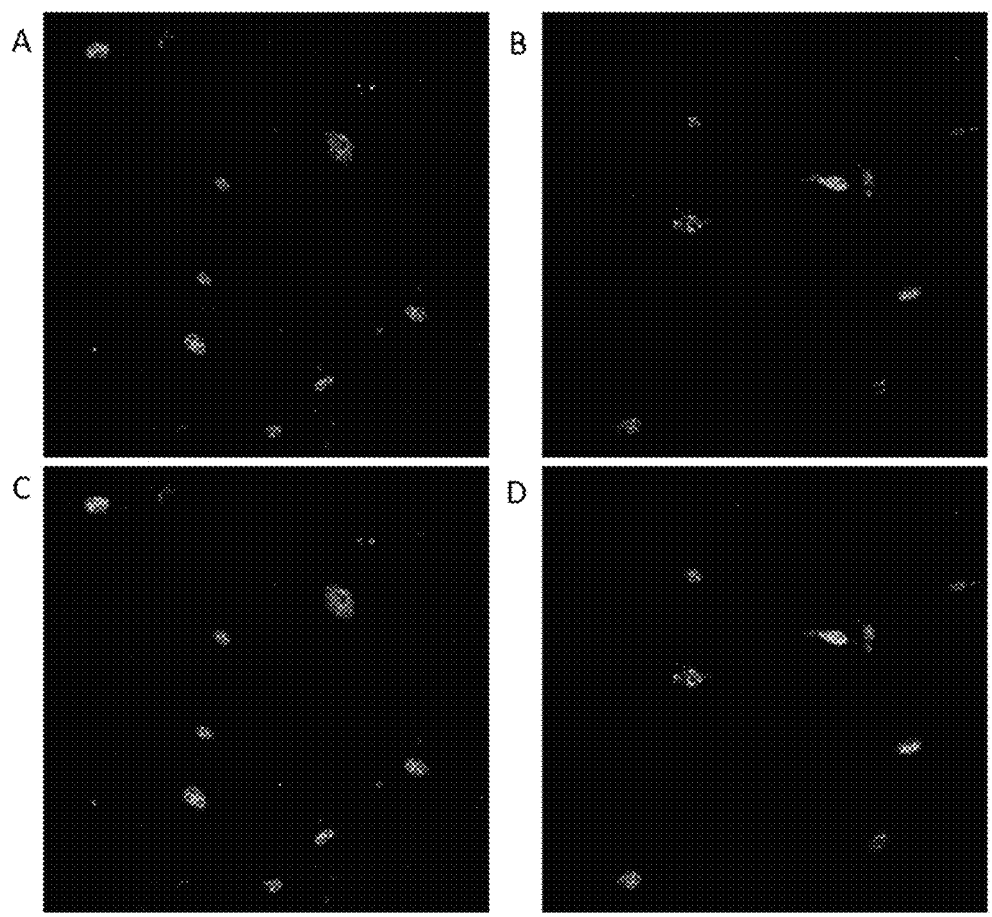
Figures 47A-D

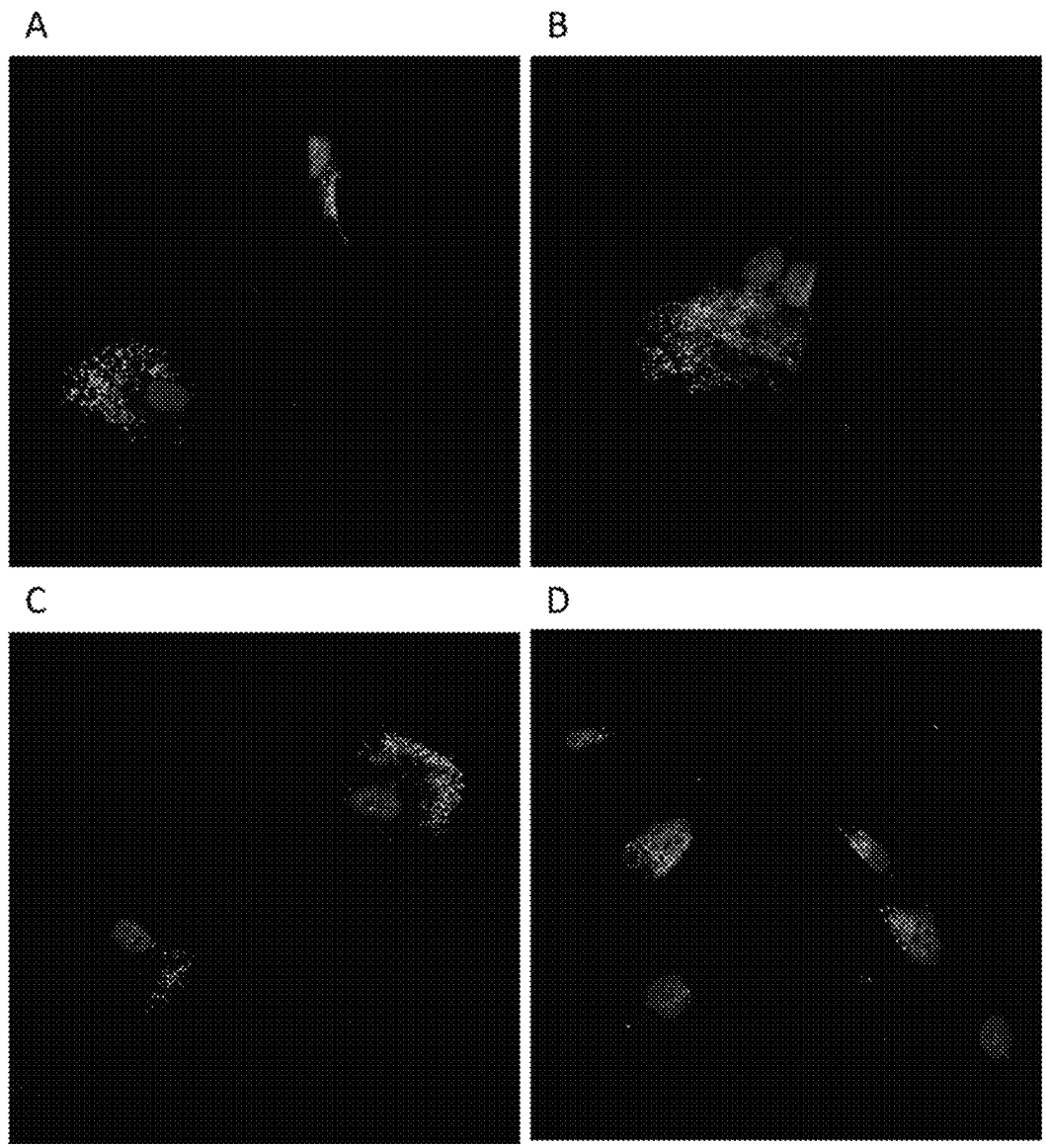
Figures 48A-D

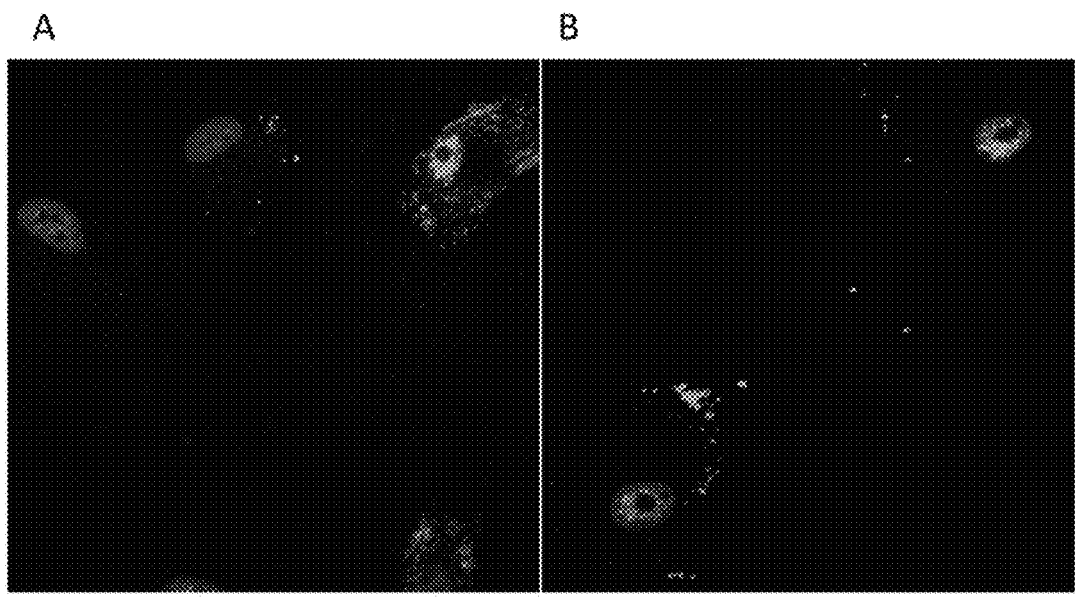
Figures 49A-B
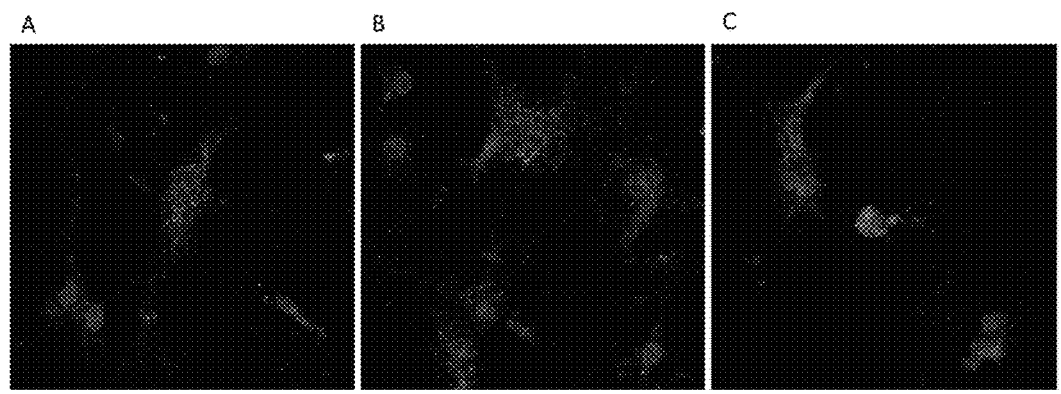
Figures 50A-C

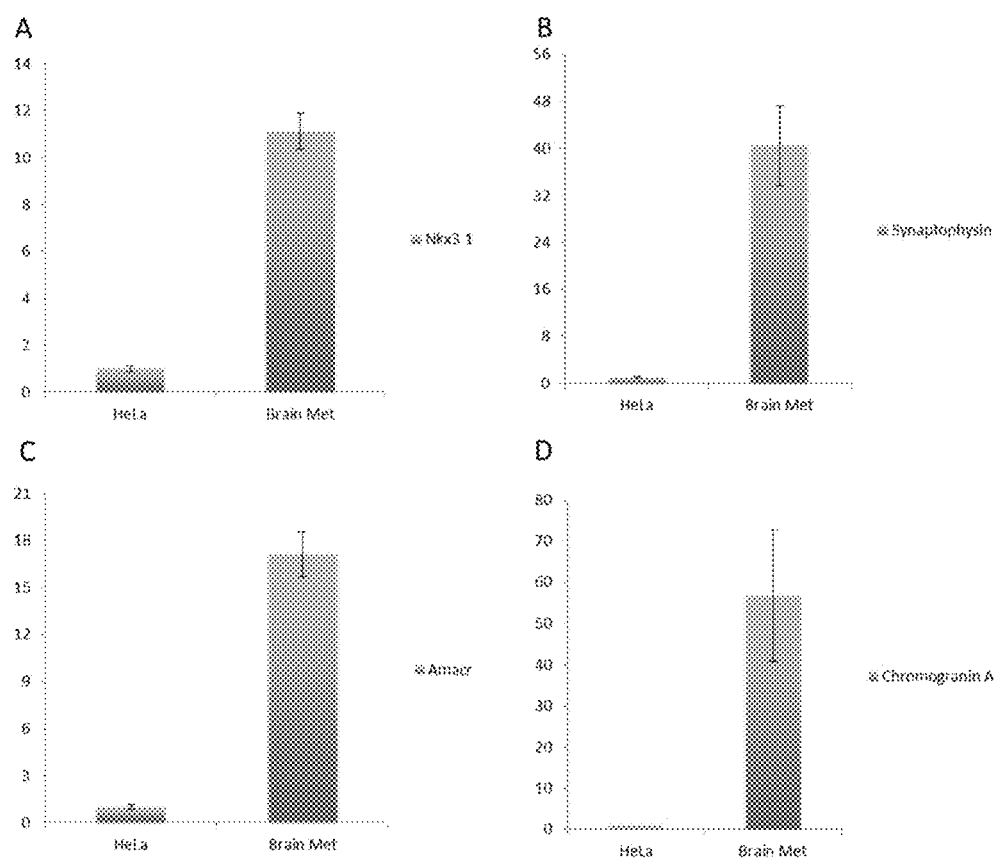
Figures 51A-D

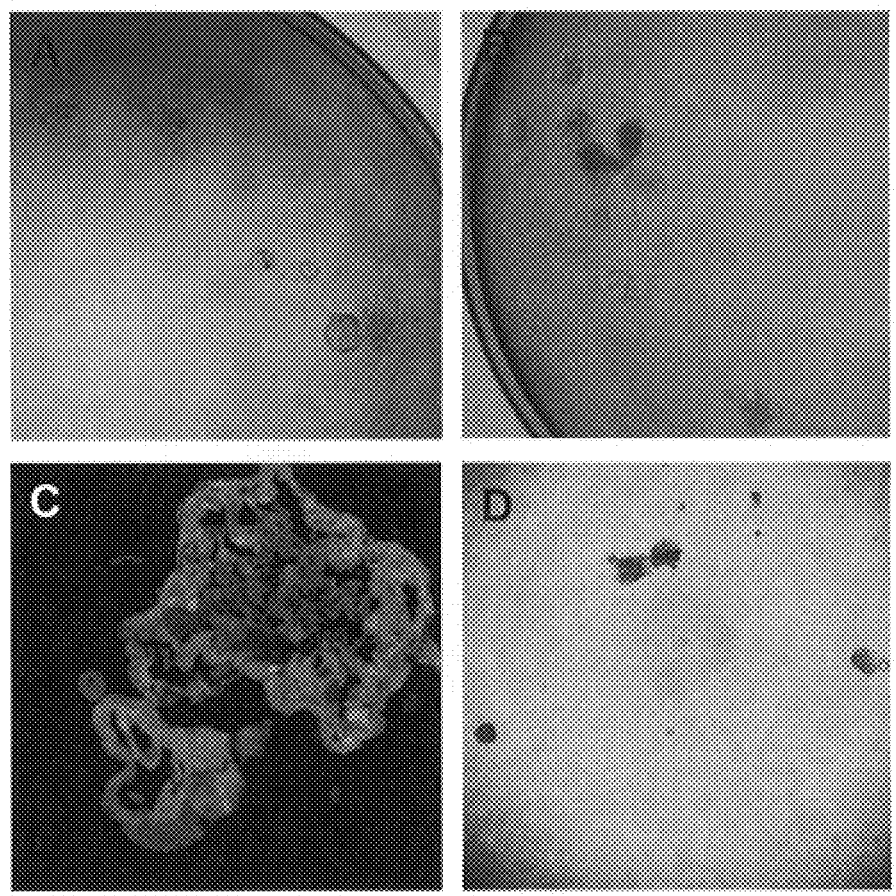
Figures 52A-D

SEQUENCE LISTING

<160> NUMBER OF SEQ ID NOS: 44

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tgagggcacc agtaacaatg g                                              21

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caacatccct ttgtagtgga cat                                            23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agggtcccgg agacgataag                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agggcggaga tgtcttttgc                                                20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctctctgtgc ttgtcttgct c                                              21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacgttgcgt ttcaaccagc                                                20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggaccagcac agttgcttta c          21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtagttctcc gagtcatcct ca         22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccaggaaaca tcagtgagtc c          21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggatggaact tggaatcggt ca         22

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagatggcgc ggcaacacc            19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgcggtctg gcagtaaaaa c         21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctccgctacc ctaagcatcc                                              20

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gacactgtca tattacttgg acc                                          23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttccacatac acttcattct cagt                                         24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccaacctgc ctcaatcact aagg                                         24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtcttggaga agaactcacc attg                                         24

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagatggcgc ggcaacacc                                               19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

-continued

```
gcgcggtctg gcagtaaaaa c                                              21
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
aaagtcgctc tgagttgtta t                                              21
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
aagaccgcga agagtttgtc                                                20
```

<210> SEQ ID NO 22

<400> SEQUENCE: 22

000

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
ggagcgggag aaatggatat g                                              21
```

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
ctgttcctgt acggcatgg                                                 19
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
ggcattaaag cagcgtatcc                                                20
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acatggtcct gctggagttc                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcattaaag cagcgtatcc                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aagggagctg cagtggagta                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccgaaaatct gtgggaagtc                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caagcactct gcgaactgag                                              20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31 aagttttga aggcaagatg c                                             21

<210> SEQ ID NO 32
<211> LENGTH: 21
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 32
ttgcacagta tccttttgaa g                                              21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acgagactag tgagacgtgc                                                20

<210> SEQ ID NO 34

<400> SEQUENCE: 34

000

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtctctggtc cttacttcc                                                 19

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agctagccac catggcttga gtaagtctgc a                                   31

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctttacaag cgcacgcaga ctgtaga                                        27

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtcgacaagc tcatgcgggt g                                              21
```

```
<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcgctgctga ctttctaaac ataag                                            25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gagctcacgt taagttttga tgtgt                                            25

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cacaaaaaca ggttaaaccc ag                                               22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agcacatagg aggcagagac                                                  20

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aaacatgatg actaccaagc ttggc                                            25

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atgatagcat cttgttctta gtcttttct taataggg                              38
```

METHOD FOR CULTURE OF HUMAN AND MOUSE PROSTATE ORGANOIDS AND USES THEREOF

This application is a continuation-in-part of International Application No. PCT/US2013/072098, filed on Nov. 26, 2013, which claims priority to U.S. Provisional Patent Application No. 61/730,030, filed Nov. 26, 2012, the contents of each of which are hereby incorporated by reference in their entireties.

GOVERNMENT SUPPORT

This invention was made with government support under Grant Nos. DK076602 and CA154293 awarded by the National Institute of Health and Grant W81WH-11-1-0463 awarded by the Army. The government has certain rights in the invention.

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Prostate cancer is among the most diagnosed and prevalent types of cancer in men over the age of 55. In 2005, around 232,100 American men were diagnosed with this cancer (U.S. Cancer Molecular Diagnostics Markets N39E-55 Frost & Sullivan). This invention relates to the culture of prostate tissue from mouse and human prostate tissue.

SUMMARY OF THE INVENTION

The present invention provides methods for culturing prostate tissue. In one aspect the present invention provides methods for culturing prostate tissue that maintains the differentiated state of the luminal epithelial cells of the prostate, or recapitulates the phenotype of prostate tumors.

In one aspect, the invention provides a method for culturing prostate organoids, the method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate organoids in culture. In one embodiment, the prostate tissue is non-cancerous. In another embodiment, the prostate tissue is cancerous. In a further embodiment, the subject is a human. In another embodiment, the subject is a mouse. In one embodiment, the mouse is a genetically-engineered mouse. In another embodiment, the mouse comprises a prostate cancer xenograft. In one embodiment, the prostate tissue is isolated from a cystectomy. In another embodiment, the prostate tissue is isolated from a radical prostatectomy. In a further embodiment, the organoids display the luminal differentiation of the non-cancerous prostate tissue. In one embodiment, the organoids display the basal differentiation of the non-cancerous prostate tissue. In another embodiment, the organoids display the luminal phenotype of the cancerous prostate tissue. In another embodiment, the organoids maintain the transformed phenotype of the cancerous prostate tissue. In another embodiment, the culture medium comprises DHT. In one embodiment, the culture medium comprises EGF. In another embodiment, culture of the organoids is not dependent on androgens. In one embodiment, prostate cell cultures are obtained from the organoids. In another embodiment, cells in the prostate cell cultures grow as attached cells in two-dimensional culture. In yet another embodiment, the cell cultures comprise prostate cell lines.

In another aspect, the invention provides a method for culturing prostate organoids, the method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate organoids in culture. In one embodiment, the CARNs are non-cancerous cells. In another embodiment, the CARNs are transformed cells. In a further embodiment, the subject is a human. In another embodiment, the subject is a mouse. In one embodiment, the mouse is a genetically-engineered mouse. In another embodiment, the mouse comprises a prostate cancer xenograft. In one embodiment, the prostate tissue is isolated from a cystectomy. In another embodiment, the prostate tissue is isolated from a radical prostatectomy. In one embodiment, the organoids maintain the luminal differentiation of the CARNs. In another embodiment, the organoids maintain the transformed phenotype of the transformed CARNs. In another embodiment, the culture medium comprises DHT. In one embodiment, the culture medium comprises EGF. In one embodiment, the CARNs express Nkx3.1 in the absence of androgens, and cytokeratin 8 (CK8), cytokeratin 18 (CK18), Androgen receptor (AR), or a combination thereof. In one embodiment, prostate cell cultures are obtained from the organoids. In another embodiment, cells in the prostate cell cultures grow as attached cells in two-dimensional culture. In yet another embodiment, the cell cultures comprise prostate cell lines.

In another aspect, the invention provides a prostate organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate organoids in culture. In one embodiment, the organoid displays the luminal differentiation of non-cancerous prostate. In another embodiment, the organoid displays the basal differentiation of non-cancerous prostate. In one embodiment, the organoid expresses CK8 and/or CK18. In another embodiment, the organoid expresses CK5 and/or p63. In another embodiment, the organoid expresses androgen receptor. In one embodiment, the organoid is preserved in a tissue bank.

In another aspect, the invention provides a prostate organoid, wherein the organoid is obtained by a method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate organoids in culture. In one embodiment, the organoid displays the luminal differentiation of non-cancerous prostate. In another embodiment, the organoid displays the basal differentiation of non-cancerous prostate. In one embodiment, the organoid expresses CK8 and/or CK18. In another embodiment, the organoid expresses CK5 and/or p63. In another embodiment, the organoid expresses androgen receptor. In one embodiment, the organoid is preserved in a tissue bank.

In another aspect, the invention provides a prostate tumor organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate tumor organoids in culture. In one embodiment, the organoid displays the luminal phenotype of prostate tumors. In another embodiment, the organoid expresses androgen receptor. In one embodiment, the subject is a mouse. In another embodiment, the organoid displays the luminal phenotype of prostate tumors. In one embodiment, the subject is a human. In another embodiment, the organoid maintains the luminal phenotype of prostate tumors. In one embodiment, the organoid is preserved in a tissue bank.

In another aspect, the invention provides a prostate tumor organoid, wherein the organoid is obtained by a method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate tumor organoids in culture. In one embodiment, the organoid displays the luminal phenotype of prostate tumors. In another embodiment, the organoid expresses androgen receptor. In one embodiment, the subject is a mouse. In another embodiment, the organoid displays the luminal phenotype of prostate tumors. In one embodiment, the subject is a human. In another embodiment, the organoid maintains the luminal phenotype of prostate tumors. In one embodiment, the organoid is preserved in a tissue bank.

In another aspect, the invention provides a method for identifying a compound that inhibits prostate cancer, the method comprising: (a) contacting one or more prostate organoids with a test compound; (b) determining whether growth of the organoids is inhibited in the presence of the test compound, as compared to growth of the organoids in the absence of the test compound; wherein inhibition of growth of the organoids indicates the identification of a compound that inhibits prostate cancer. In one embodiment, the organoid is a prostate organoid obtained by the method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate organoids in culture. In another embodiment, the organoid is a prostate organoid obtained by the method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate organoids in culture. In a further embodiment, the organoid is a prostate tumor organoid obtained by the method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate tumor organoids in culture. In another embodiment, the organoid is a prostate tumor organoid obtained by the method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate tumor organoids in culture. In one embodiment, the test compound is a small molecule.

In another aspect, the invention provides a cell culture medium comprising a basal hepatocyte medium, Matrigel, FBS, ROCK inhibitor, or any combination thereof. In one embodiment, the medium further comprises EGF. In one embodiment, the medium comprises 10 ng/ml of EGF. In another embodiment, the medium comprises 5% Matrigel. In one embodiment, the medium comprises 5% heat-inactivated charcoal-stripped FBS. In another embodiment, the ROCK inhibitor is Y-27632. In a further embodiment, the medium is used to culture prostate organoids. In another embodiment, the organoids are non-cancerous. In a further embodiment, the organoids are cancerous.

In one aspect, the invention provides a method for culturing prostate organoids, the method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e); wherein the prostate epithelial cells form prostate organoids in culture. In one embodiment, the medium further comprises EGF. In another embodiment, the medium comprises 10 ng/ml of EGF. In one embodiment, the medium further comprises DHT. In another embodiment, the medium comprises 5% heat-inactivated charcoal-stripped FBS. In another embodiment, the ROCK inhibitor is Y-27632. In another embodiment, the prostate tissue sample is non-cancerous. In another embodiment, the prostate tissue sample is cancerous. In another embodiment, the organoid comprises luminal cells. In another embodiment, the organoid comprises basal cells. In another embodiment, the organoid maintains the transformed phenotype of the cancerous prostate tissue. In another embodiment, prostate cell cultures are obtained from the organoids.

In one aspect, the invention provides a method for culturing prostate organoids, the method comprising: (a) obtaining a sample of prostate tissue from a subject; (b) isolating CARNs from the sample of prostate tissue; (c) contacting the CARNs with a Matrigel solution and plating in a cell culture support, wherein the Matrigel solution forms a matrix; (d) providing an overlay layer of liquid culture medium comprising basal hepatocyte medium, FBS and ROCK inhibitor; and (e) incubating the culture of (d); wherein the CARNs form prostate organoids in culture. In one embodiment, the medium further comprises EGF. In another embodiment, the medium comprises 10 ng/ml of EGF. In one embodiment, the medium further comprises DHT. In another embodiment, the medium comprises 5% heat-inactivated charcoal-stripped FBS. In another embodiment, the ROCK inhibitor is Y-27632. In another embodiment, the prostate tissue sample is non-cancerous. In another embodiment, the prostate tissue sample is cancerous. In another embodiment, the organoid comprises luminal cells. In another embodiment, the organoid comprises basal cells. In another embodiment, the organoid maintains the transformed phenotype of the cancerous prostate tissue. In another embodiment, the CARNs express Nkx3.1 in the absence of androgens, and cytokeratin 8 (CK8), cytokeratin 18 (CK18), Androgen receptor (AR), or a combination thereof. In another embodiment, prostate cell cultures are obtained from the organoids.

In one aspect, the invention provides a prostate organoid obtained by the method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e); wherein the prostate epithelial cells form prostate organoids in culture. In one embodiment, the organoid comprises luminal cells. In another embodiment, the organoid comprises basal cells. In another embodiment, the organoid expresses CK8, CK18, CK5, p63, androgen receptor, or a combination thereof.

In one aspect, the invention provides a prostate organoid obtained by the method comprising: (a) obtaining a sample of prostate tissue from a subject; (b) isolating CARNs from the sample of prostate tissue; (c) contacting the CARNs with a Matrigel solution and plating in a cell culture support, wherein the Matrigel solution forms a matrix; (d) providing an overlay layer of liquid culture medium comprising basal hepatocyte medium, FBS and ROCK inhibitor; and (e) incubating the culture of (d); wherein the CARNs form prostate organoids in culture. In one embodiment, the organoid comprises luminal cells. In another embodiment, the organoid comprises basal cells. In another embodiment, the organoid expresses CK8, CK18, CK5, p63, androgen receptor, or a combination thereof.

In one aspect, the invention provides a prostate tumor organoid obtained by the method comprising: (a) obtaining a sample of cancerous prostate tissue from a subject; (b) dissociating the sample of prostate tissue; (c) isolating dissociated prostate epithelial cells from the sample of prostate tissue; (d) contacting the dissociated prostate epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e); wherein the prostate epithelial cells form prostate organoids in culture. In one embodiment, the organoid displays the transformed phenotype of the cancerous prostate tissue.

In one aspect, the invention provides a prostate tumor organoid obtained by the method comprising: (a) obtaining a sample of cancerous prostate tissue from a subject; (b) isolating CARNs from the sample of prostate tissue; (c) contacting the CARNs with a Matrigel solution and plating in a cell culture support, wherein the Matrigel solution forms a matrix; (d) providing an overlay layer of liquid culture medium comprising basal hepatocyte medium, FBS and ROCK inhibitor; and (e) incubating the culture of (d); wherein the CARNs form prostate organoids in culture. In one embodiment, the organoid displays the transformed phenotype of the cancerous prostate tissue.

In one aspect, the invention provides a method for culturing prostate organoids, the method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the prostate tissue is non-cancerous. In another embodiment, the prostate tissue is cancerous.

In one aspect, the invention provides a method for culturing prostate organoids, the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; and (d) culturing the dissociated metastatic prostate cancer cells in a culture medium comprising basal hepatocyte medium, Matrigel, FBS and ROCK inhibitor; wherein the dissociated metastatic prostate cancer cells form prostate organoids in culture. In one embodiment, the organoids display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland.

In one aspect, the invention provides a method for culturing prostate organoids, the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form prostate organoids in culture. In one embodiment, the organoids display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland.

In one aspect, the invention provides a method for culturing prostate organoids, the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form prostate organoids in culture. In one embodiment, the organoids display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland.

In another aspect, the invention provides a method for culturing prostate organoids, the method comprising: (a) obtaining a sample of prostate tissue from a subject; (b) isolating CARNs from the sample of prostate tissue; (c) contacting the CARNs with a collagen solution and plating in a cell culture support, wherein the collagen solution forms a matrix; (d) providing an overlay layer of liquid culture medium comprising basal hepatocyte medium, FBS and ROCK inhibitor; and (e) incubating the culture of (d) wherein the CARNs form prostate organoids in culture. In one embodiment, the CARNs are non-cancerous cells. In another embodiment, the CARNs are transformed cells. In yet another embodiment, the CARNs are cancerous cells.

In one aspect, the invention provides a method for culturing prostate organoids, the method comprising culturing prostate cancer cell line cells in a culture medium comprising basal hepatocyte medium, Matrigel, FBS and ROCK inhibitor; wherein the prostate cancer cell line cells form prostate organoids in culture. In one embodiment, the prostate organoids maintain the transformed phenotype of the prostate cancer cell line. In one embodiment, the prostate cancer cell line is VCaP.

In one aspect, the invention provides a method for culturing prostate organoids, the method comprising: (a) contacting prostate cancer cell line cells with a Matrigel solution and plating in a cell culture support, wherein the Matrigel solution forms a matrix; (b) providing an overlay layer of liquid culture medium comprising basal hepatocyte medium, FBS and ROCK inhibitor; and (c) incubating the culture of (b) wherein the prostate cancer cell line cells form prostate organoids in culture. In one embodiment, the prostate organoids maintain the transformed phenotype of the prostate cancer cell line. In one embodiment, the prostate cancer cell line is VCaP.

In one aspect, the invention provides a method for culturing prostate organoids, the method comprising: (a) contacting prostate cancer cell line cells with a collagen solution and plating in a cell culture support, wherein the collagen solution forms a matrix; (b) providing an overlay layer of liquid culture medium comprising basal hepatocyte medium, FBS and ROCK inhibitor; and (c) incubating the culture of (b) wherein the prostate cancer cell line cells form prostate organoids in culture. In one embodiment, the prostate organoids maintain the transformed phenotype of the prostate cancer cell line. In one embodiment, the prostate cancer cell line is VCaP.

In one aspect, the invention provides a method for culturing a metastatic prostate cell line, the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) plating the isolated dissociated metastatic prostate cancer cells of (c) on an adherent cell culture support; and (e) culturing the dissociated metastatic prostate cancer cells in a culture medium comprising basal hepatocyte medium, Matrigel, FBS and ROCK inhibitor; wherein the dissociated metastatic prostate cancer cells form metastatic prostate cell lines in culture. In one embodiment, the metastatic prostate cell line displays the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland. In another embodiment, the metastatic prostate cancer tissue is a prostate cancer that has metastasized to an organ other than the prostate.

In one aspect, the invention provides a prostate organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the organoid displays the luminal differentiation of non-cancerous prostate. In another embodiment, the organoid displays the basal differentiation of non-cancerous prostate. In one embodiment, the organoid expresses CK8, CK18, or a combination thereof. In another embodiment, the organoid expresses CK5, p63, or a combination thereof. In one embodiment, the organoid expresses Nkx3.1. In another embodiment, the organoid expresses androgen receptor, Foxa1, or a combination thereof.

In one aspect, the invention provides a prostate organoid, wherein the organoid is obtained by a method comprising: (a) obtaining a sample of prostate tissue from a subject; (b) isolating CARNs from the sample of prostate tissue; (c) contacting the CARNs with a collagen solution and plating in a cell culture support, wherein the collagen solution forms a matrix; (d) providing an overlay layer of liquid culture medium comprising basal hepatocyte medium, FBS and ROCK inhibitor; and (e) incubating the culture of (d) wherein the CARNs form prostate organoids in culture. In one embodiment, the CARNs are non-cancerous cells. In another embodiment, the CARNs are transformed cells. In yet another embodiment, the CARNs are cancerous cells. In one embodiment, the organoid displays the luminal differentiation of non-cancerous prostate. In another embodiment, the organoid displays the basal differentiation of non-cancerous prostate. In one embodiment, the organoid expresses CK8, CK18, or a combination thereof. In another embodiment, the organoid expresses CK5, p63, or a combination thereof. In one embodiment, the organoid expresses Nkx3.1.

In another embodiment, the organoid expresses androgen receptor, Foxa1, or a combination thereof.

In one aspect, the invention provides a prostate tumor organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the organoid displays the luminal phenotype of prostate tumors. In another embodiment, the organoid expresses pAkt. In one embodiment, the organoid expresses Nkx3.1. In another embodiment, the organoid expresses androgen receptor, Foxa1, or a combination thereof.

In one aspect, the invention provides a prostate tumor organoid, wherein the organoid is obtained by a method comprising: (a) obtaining a sample of prostate tissue from a subject; (b) isolating CARNs from the sample of prostate tissue; (c) contacting the CARNs with a collagen solution and plating in a cell culture support, wherein the collagen solution forms a matrix; (d) providing an overlay layer of liquid culture medium comprising basal hepatocyte medium, FBS and ROCK inhibitor; and (e) incubating the culture of (d) wherein the CARNs form prostate tumor organoids in culture. In one embodiment, the organoid displays the luminal phenotype of prostate tumors. In another embodiment, the organoid expresses pAkt. In one embodiment, the organoid expresses Nkx3.1. In another embodiment, the organoid expresses androgen receptor, Foxa1, or a combination thereof.

In one aspect, the invention provides a metastatic prostate cell line, wherein the cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) plating the isolated dissociated metastatic prostate cancer cells of (c) on an adherent cell culture support; and (e) culturing the dissociated metastatic prostate cancer cells in a culture medium comprising basal hepatocyte medium, Matrigel, FBS and ROCK inhibitor; wherein the dissociated metastatic prostate cancer cells form metastatic prostate cell lines in culture. In one embodiment, the metastatic prostate cell line displays the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland. In another embodiment, the cell line is preserved in a tissue bank. In some embodiments the metastatic prostate cell line has a neuroendocrine phenotype.

In one aspect, the invention provides a metastatic prostate cell line, wherein the cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form metastatic prostate cell lines in culture. In one embodiment, the metastatic prostate cell lines display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland. In another embodiment, the cell line is preserved in a tissue bank. In some embodiments the metastatic prostate cell line has a neuroendocrine phenotype.

In one aspect, the invention provides a metastatic prostate cell line, wherein the cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form metastatic prostate cell lines in culture. In one embodiment, the organoids display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland. In another embodiment, the cell line is preserved in a tissue bank. In some embodiments the metastatic prostate cell line has a neuroendocrine phenotype.

In one aspect, the invention provides a method for culturing a prostate organoid with rat urogenital mesenchyme, the method comprising: (a) culturing a prostate organoid; (b) contacting the prostate organoid with rat urogenital mesenchyme; (c) contacting the prostate organoid and rat urogenital mesenchyme with a Matrigel solution and plating in a cell culture support, wherein the Matrigel solution forms a matrix; (d) providing an overlay layer of liquid culture medium comprising hepatocyte medium and FBS; and (e) incubating the culture of (d), wherein prostate organoids are formed. In one embodiment, the prostate organoids formed comprise epithelial and stromal cells.

In one aspect, the invention provides a method for culturing a prostate organoid with rat urogenital mesenchyme, the method comprising: (a) culturing a prostate organoid; (b) contacting the prostate organoid with rat urogenital mesenchyme; (c) contacting the prostate organoid and rat urogenital mesenchyme with a collagen solution and plating in a cell culture support, wherein the collagen solution forms a matrix; (d) providing an overlay layer of liquid culture medium comprising hepatocyte medium and FBS; and (e) incubating the culture of (d), wherein prostate organoids are formed. In one embodiment, the prostate organoids formed comprise epithelial and stromal cells.

In one aspect, the invention provides a method for identifying a compound that inhibits cancer, the method comprising: (a) contacting metastatic prostate cell line with a test compound; (b) determining whether growth of the metastatic prostate cell line is inhibited in the presence of the test compound, as compared to growth of the metastatic prostate cell line in the absence of the test compound; wherein inhibition of growth of the metastatic prostate cell line indicates the identification of a compound that inhibits cancer.

BRIEF DESCRIPTION OF THE FIGURES

This patent or application file contains at least one drawing executed in color. Copies of this patent application publication with color drawings will be provided by the Office upon request and payment of the necessary fee.

FIGS. 2A-D. Detection of CAstration-Resistant NKx3.1-expressing cells (CARNs) and expression of Nkx3.1 in epithelial cells of the intact, regressed and regenerated anterior prostate. FIG. 2A. Diagram shows the prostate duct in the intact, regressed, and regenerated states. Most luminal cells undergo apoptosis during regression, whereas most basal cells survive; hence, the process of regeneration primarily produces luminal cells. FIG. 2B. Immunostaining for Nkx3.1 showing expression of Nkx3.1 in all luminal cells of a wild-type intact prostate. FIG. 2C. Immunostaining showing that Nkx3.1 expression is mostly absent in regressed prostate, except for rare castration-resistant Nkx3.1-expressing cells (CARNs, arrows). FIG. 2D. Immunostaining showing that expression of Nkx3.1 in regenerated prostate. Scale bars correspond to 25 microns. See Wang et al. (2009) Nature 461: 495-500, the contents of which is hereby incorporated by reference in its entirety.

FIGS. 4A-D. The CARNs population contains bipotential progenitors and can self-renew in vivo. FIG. 4A. Diagram showing the strategy for lineage-marking experiments. FIG. 4B. YFP does not co-localize with p63 in lineage-marked cells of a castrated and tamoxifen-induced Nkx3.1$^{CreERT2/+}$; R26R-YFP/+ anterior prostate. FIG. 4C. Clusters of YFP+ cells in a lineage-marked and regenerated prostate. FIG. 4D. Co-localization of YFP and cytokeratin 5 (CK5) in lineage-marked basal cells (arrows) of a regenerated prostate. Scale bars correspond to 25 microns. See Wang et al. (2009) Nature 461: 495-500, the contents of which is hereby incorporated by reference in its entirety.

FIG. 5A. Diagram showing single-cell transplantation assay and the strategy for tissue recombinant/renal graft analyses using a single YFP$^+$ cell (or single YFP$^-$ cell as a control). FIG. 5B. An isolated single cell. FIG. 5C. Hematoxylin-eosin (H&E) staining of prostatic ducts in a graft derived from a single YFP+ cell. FIG. 5D. All epithelial cells in single-YFP+ derived duct express YFP, including p63+ basal cells (arrows).

FIG. 14B. H&E staining FIG. 14C. Immunostaining of luminal marker expression (CK18 (green) and p63 (red)). FIG. 14D. Immunostaining showing epithelial-mesenchymal transition (YFP (green) and N-cadherin (red)).

FIG. 19H shows YFP expression (CARN) and FIG. 19E shows the merge.

FIGS. 24A-G. Growth of tumor organoids from transformed mouse CARNs. Organoids grown from transformed mouse CARNs (derived from Nkx3.1$^{CreERT2/}$+; K-ras$^{LSL/+}$; Pten$^{flox/flox}$; R26R-YFP/+ mice) stained with H&E and grown with (FIG. 24A) and without (FIG. 24B) DHT. Immunostaining of organoids from transformed mouse CARNs grown with DHT for CK8 (green) and p63 (red) (FIG. 24C), pAkt (green) (FIG. 24D), or AR (green) (FIG. 24E). Growth of tumor organoids from single transformed CARNs with 7.5% efficiency (n=6/80) (FIGS. 24F-G).

FIGS. 25A-C. Cell types or origin for human prostate organoid formation. Table showing flow cytometry populations (FIG. 25A) and graphs showing the average number of organoids formed for different cell of origin at Day 7 (FIG. 25B) and Day 14 (FIG. 25C).

FIGS. 30A-O. Generation of prostate epithelial organoids from lineage-marked CARNs. (FIG. 30A) Time course of lineage-marking of CARNs in Nkx3.1$^{CreERT2/+}$; R26R-YFP/+ mice. (FIG. 30B) Isolation of YFP-positive lineage-marked CARNs by flow cytometry. (FIGS. 30C-D) Brightfield (FIG. 30C) and epifluorescent (FIG. 30D) views of CARN-derived organoids that are filled or hollow (arrow). (FIGS. 30E-F) Hematoxylin-eosin (H&E) staining of CARN organoids at low-power (FIG. 30E) showing range of phenotypes, and high-power (FIG. 30F). (FIG. 30G) Uniform YFP expression with Ki67 immunostaining (arrows). (FIG. 30H) The basal marker CK5 is expressed on the exterior (arrowheads), while the luminal marker CK8 is expressed internally. (FIGS. 30I-J) Strong nuclear expression of AR (arrows, FIG. 30I) and Foxa1 (FIG. 30J). (FIGS. 30K-M) Renal grafts generated by tissue recombination of CARN-derived organoids with rat embryonic urogenital mesenchyme (FIG. 30K) display normal stratification of basal (arrowheads, FIG. 30L) and luminal cells (FIG. 30L), and uniform YFP and nuclear AR immunostaining (FIG. 30M); note that the slightly atypical histology in (FIG. 30K) likely reflects the heterozygous phenotype of Nkx3.1 mutants [40, 41]. (FIG. 30N) Efficiency of organoid formation by lineage-marked CARNs (YFP-positive cells from tamoxifen-induced and castrated Nkx3.1$^{CreERT2/+}$; R26R-YFP/+ mice; n=4 experiments) and non-CARNs (YFP-negative cells from the same mice; n=3 experiments). Source data are provided in Table 1. Error bars represent one standard deviation; the difference between CARNs and non-CARNs is statistically significant (p=0.002, two-tailed Student's t-test). (FIG. 30O) Generation of organoids from single CARNs. Time course of paired images shown under brightfield (top) and epifluorescent (bottom) illumination shows organoid growth from isolated single CARN. Scale bars in FIG. 30O correspond to 25 microns, in FIGS. 30E-J, L, M to 50 microns, and in FIGS. 30C-E, K to 100 microns.

FIGS. 31A-P. Growth and androgen-responsiveness of prostate organoids from normal prostate epithelium. (FIG. 31A) Flow-sorting strategy to eliminate EpCAM⁻ E-cadherin⁻ cells from dissociated prostate tissue for organoid culture. (FIG. 31B) Low-power view of organoids at 20 days after plating, showing heterogeneity of phenotype. (FIG. 31C) Higher-power view showing hollow and filled budding organoid (arrow). (FIGS. 31D-E) H&E staining of sections from a hollow organoid (FIG. 31D) and a multi-layered organoid (FIG. 31E). (FIG. 31F) Many proliferating cells are detectable by Ki67 immunostaining (arrows). (FIG. 31G) Organoids have an outer layer that expresses the basal marker CK5 (arrowheads). (FIG. 31H) Outer cells express the basal marker p63 (arrowheads), while interior cells are positive for the luminal marker CK18. (FIG. 31I) Nuclear immunostaining of AR (arrows) in organoids cultured in standard conditions with DHT. (FIG. 31J) Nuclear immunostaining for Foxa1 (arrows). (FIG. 31K) Tissue recombination of normal organoids with rat embryonic urogenital mesenchyme followed by renal grafting results in reconstitution of prostate tissue. (FIGS. 31L-M) Organoids at passage 4 were passaged as single-cell suspensions and plated in the presence of DHT (FIG. 31L) or absence of DHT (FIG. 31M). (FIGS. 31N-O) Strong nuclear AR immunostaining in the presence of DHT (FIG. 31N) and weak cytoplasmic AR immunostaining in the absence of DHT (FIG. 31O). (FIG. 31P) qPCR analysis of expression of AR downstream genes in organoids cultured in the presence or absence of DHT. Results are from a single experiment representative of 2 independent experiments. All assays were performed using three technical replicates and normalized to GAPDH expression; Scale bars in FIGS. 31E-J, N, O correspond to 50 microns, and in FIGS. 31B-D, K, L, M to 100 microns.

FIGS. 32A-S. Lineage-tracing shows that luminal cells are favored for generation of prostate organoids. (FIG. 32A) Strategy for lineage-marking of basal and luminal epithelial cells for organoid culture. (FIG. 32B) Isolation of YFP-positive luminal cells from CK8-CreER$^{T2}$; R26R-YFP (CK8-trace) mice by flow cytometry. (FIG. 32C) CK5-trace organoid. (FIG. 32D) Many cells within a CK5-trace organoid are CK5-positive, including internal cells (arrowheads). (FIG. 32E) CK8-trace organoid. (FIG. 32F) CK18-trace organoid. (FIG. 32G) Efficiency of organoid formation from YFP-positive CK5-trace (n=4 experiments), CK8-trace (n=3 experiments), and CK18-trace (n=2 experiments) epithelial cells. The differences in efficiency between CK5-trace and CK8-trace (p=0.001) and between CK5-trace and CK18-trace (p=0.0009) are statistically significant (**) using a two-tailed Student's t-test; error bars correspond to one standard deviation. Source data are provided in Table 1. (FIGS. 32H-I) Expression of the basal marker CK5 (arrowheads) in a CK8-trace organoid, shown with (FIG. 32H) and without (FIG. 32I) YFP overlay. (FIGS. 32J-K) Expression of the basal marker p63 (arrowheads) in a CK8-trace organoid, shown with (FIG. 32J) and without (FIG. 32K) YFP overlay. (FIGS. 32L-M) Expression of the luminal marker CK18 in a CK8-trace organoid, shown with (FIG. 32L) and without (FIG. 32M) YFP overlay. (FIG. 32N) Organoid generated from mixing of red CK18-trace cells and green CK5-trace cells shows green cells on the exterior, consistent with the localization of basal cells. (FIG. 32O) Serial passaging of CK18-trace organoids at passage 3. (FIGS. 32P-Q) CK18-trace organoids at passage 9 cultured in the presence (FIG. 32P) and absence (FIG. 32Q) of DHT. (FIGS. 32R-S) AR immunostaining is nuclear in CK18-trace organoids in the presence of DHT (FIG. 32R), but is weakly cytoplasmic in the absence of DHT (FIG. 32S). Scale bars in FIGS. 32C-F, H-N correspond to 50 microns, and in FIGS. 32O-S to 100 microns.

FIGS. 33A-Q. Tumor organoids can be generated from single transformed CARNs. (FIG. 33A) Time course for generation of transformed CARNs in Nkx3.1$^{CreERT2/+}$; Pten$^{flox/flox}$; Kras$^{LSL/+}$; R26R-YFP/+ (NPK) mice. (FIG. 33B) NPK-CARN organoid shows extensive budding. (FIG. 33C) H&E staining of NPK-CARN organoids. (FIGS. 33D-F) NPK-CARN organoids display Ki67 immunostaining (arrows, FIG. 33D), membrane localization of phospho-Akt (FIG. 33E), and patchy expression of phospho-Erk (arrows, FIG. 33F). (FIG. 33G-H) Luminal phenotype of NPK-CARN organoids, with limited expression of p63 (arrowheads, FIG. 33G) or CK5 (FIG. 33H). (FIG. 33I) Nuclear expression of Foxa1 (arrows). (FIG. 33J-K) AR expression is nuclear in the presence of DHT (arrows, FIG. 33J), but is cytoplasmic in the absence of DHT (FIG. 33K). (FIGS. 33L-P) Renal grafts generated by recombination of NPK-CARN organoids with rat embryonic urogenital mesenchyme display high-grade PIN/carcinoma histological phenotypes (FIG. 33L), abundant Ki67 immunostaining (arrows, FIG. 33M), membrane-localized pAkt (FIG. 33N), patchy pErk (arrows, FIG. 33O), and nuclear AR (arrows, FIG. 33P). (FIG. 33Q) Generation of organoids from single NPK CARNs. Time course of paired images shown under bright-field (top) and epifluorescent (bottom) illumination shows organoid growth from isolated single NPK CARN. Scale bars in FIG. 33Q correspond to 25 microns, in FIGS. 33D-H, M-P to 50 microns, and in FIGS. 33B, C, I-L to 100 microns.

FIGS. 34A-R. Modeling tumor phenotypes in organoid culture. (FIGS. 34A-J) Formation of organoids from mouse models of prostate cancer, shown in bright-field (FIGS. 34A-E) and H&E stained sections (FIGS. 34F-J). (FIGS. 34A, F) Organoids generated from TRAMP mice at 22 weeks of age. (FIGS. 34B, G) Organoids from Nkx3.1$^{CreERT2/+}$; Pten$^{flox/flox}$; p53$^{flox/flox}$ (NPP53) mice induced with tamoxifen at two months of age and assayed at 10 months. (FIGS. 34C, H) Organoids from Nkx3.1$^{--}$ null mutant mice at 14 months of age. (FIGS. 34D, I) Organoids from Hi-Myc transgenic mice at 9 months. (FIGS. 34E, J) Organoids from Nkx3.1$^{+/-}$; Pten$^{+/-}$ mice at 10 months. (FIG. 34K) Organoid formation efficiency from the indicated mouse models (data are from 10 technical replicates). (FIGS. 34L-R) Induction of tumor phenotypes in culture by tamoxifen treatment of organoids derived from CK8-Cre-ER$^{T2}$; Pten$^{flox/flox}$; Kras$^{LSL-G12D/+}$; R26R-CAG-YFP mice. (FIG. 34L) Time course of induction experiment. (FIGS. 34M-P) Immunostaining for YFP and pAkt in control untreated organoids (FIGS. 34M, O) or 4-hydroxy-tamoxifen (4OHT) treated organoids (FIGS. 34N, P) at passage 1 (FIGS. 34M, N) and at passage 4 (FIGS. 34O,P). (FIGS. 34Q,R) H&E staining of control (FIG. 34Q) and 4OHT-treated organoids (FIG. 34R) at passage 4. Scale bars in FIGS. 34A-J correspond to 100 microns, and in FIGS. 34M-R to 50 microns.

FIGS. 35A-M. Modeling drug treatment response in organoid culture. (FIG. 35A) Efficiency of organoid formation using organoids from Nkx3.1$^{CreERT2/+}$; Pten$^{flox/flox}$; R26R-YFP/+ (NP) mice. Passaged organoids were treated with the indicated compounds (n=3 samples analyzed per treatment condition); source data are provided in Table 1. (FIGS. 35B-G) Bright-field images of treated NP organoids. (FIG. 35H, I) H&E sections from control +DHT organoids (FIG. 35H) and enzalutamide+MK8669 treated organoids (FIG. 35I). (FIGS. 35J,K) AR expression in control +DHT organoids (arrows, FIG. 35J) and enzalutamide treated organoids (FIG. 35K). (FIG. 35L, M) pAkt expression in control +DHT organoids (arrow, FIG. 35L) and enzalutamide+MK8669 treated organoids (FIG. 35M). Scale bars in FIGS. 35H-M correspond to 50 microns, and in FIGS. 35B-G correspond to 100 microns. Error bars represent one standard deviation; **p<0.01.

FIGS. 36A-E. Analysis of normal organoids during serial passaging. (FIGS. 36A-C) Bright-field images of organoids from normal prostate epithelium at passage 1 (FIG. 36A), passage 6 (FIG. 36B), and passage 13 (FIG. 36C). (FIGS. 36D, E) Analysis of organoids at passage 3 shows normal expression of the basal marker p63 (arrowheads, FIG. 36D) and the luminal marker CK8 (FIGS. 36D, E), as well as nuclear expression of AR (arrows, FIG. 36E); yellow arrow in FIG. 36D indicates intermediate cell that co-expresses p63 and CK8. Scale bars in FIGS. 36D, E correspond to 50 microns and in FIGS. 36A-C to 100 microns.

FIGS. 37A-D. Specificity of luminal and basal lineage-marking in prostate epithelium in vivo. Sections from the anterior prostate of CK5-CreER$^{T2}$; R26R-YFP mice (FIG. 37A), CK8-CreER$^{T2}$; R26R-YFP mice (FIG. 37B), CK18-CreER$^{T2}$; R26R-YFP mice (FIG. 37C), and CK18-CreER$^{T2}$; R26R-Tomato mice (FIG. 37D) demonstrate specificity of basal marking (arrowheads, FIG. 37A) and luminal marking (arrows, FIGS. 37B-D). Scale bars correspond to 100 microns.

FIGS. 38A-J. Generation of human prostate organoids. (FIGS. 38A-E) Establishment of organoids from benign human prostate specimens. (FIGS. 38F-J) Generation of organoids from the VCaP prostate cancer cell line. (FIGS. 38A, F) Bright-field images. (FIGS. 38B, G) H&E staining (FIGS. 38C, H) Ki67 immunostaining; arrows indicate proliferating cells. (FIG. 38D) Most exterior cells in benign human organoids are CK8$^+$p63$^+$ cells (arrowheads), while many interior cells are CK8$^+$ only (arrow). (FIG. 38E) Most cells in benign human organoids are AR$^+$CK18$^+$ cells (arrows). (FIG. 38I) VCaP organoids display immunostaining for CK18, but not p63. (FIG. 38J) VCaP organoids are strongly positive for both AR and CK8. Scale bars in FIGS. 38B-E, G-J correspond to 50 microns, and in FIGS. 38A, F correspond to 100 microns.

FIGS. 39A-E show clone B2 cultured without DHT at Day 18. 10× and 20× magnifications are shown.

FIGS. 40A-D show clone C5 cultured without DHT at Passage 5, Day 14. 10× and 20× magnifications are shown.

FIGS. 41A-E show clone B4 cultured with DHT at Passage 6, Day 14. 10× and 20× magnifications are shown.

FIGS. 42A-F show immunostainning for androgen receptor in clone C5 (cultured without DHT).

FIGS. 43A-F show immunostainning for androgen receptor in clone B4 (cultured with DHT).

FIGS. 44A-D show immunostainning for CK5 in clone C5 (cultured without DHT).

FIGS. 45A-F show immunostainning for CK5 in clone B4 (cultured with DHT).

FIGS. 46A-D show immunostainning for Foxa1 in clone B4 (cultured with DHT).

FIGS. 47A-D show immunostainning for Foxa1 in clone C5 (cultured without DHT).

FIGS. 48A-D show immunostainning for Chromogranin A in clone B4 (cultured with DHT) (FIGS. 48A-C) and clone C5 (cultured without DHT) (FIG. 48D).

FIGS. 49A-B show immunostainning for Amacr in passage 5 of clone B1 (cultured without DHT).

FIGS. 50A-C show immunostainning for synaptophysin in passage 6 of clone B5 (cultured without DHT).

FIGS. 51A-D show expression levels of Nkx3.1 (FIG. 51A), synaptophysin (FIG. 51B), Amacr (FIG. 51C), and Chromogranin A (FIG. 51D) in HeLa cells and brain metastasis clones.

FIGS. 52A-D shows lentiviral infection of mouse prostate organoids with RFP construct.

DETAILED DESCRIPTION

Definitions and Abbreviations

Figures 1A, 1B, 1C, 1D, 1E, 1F:
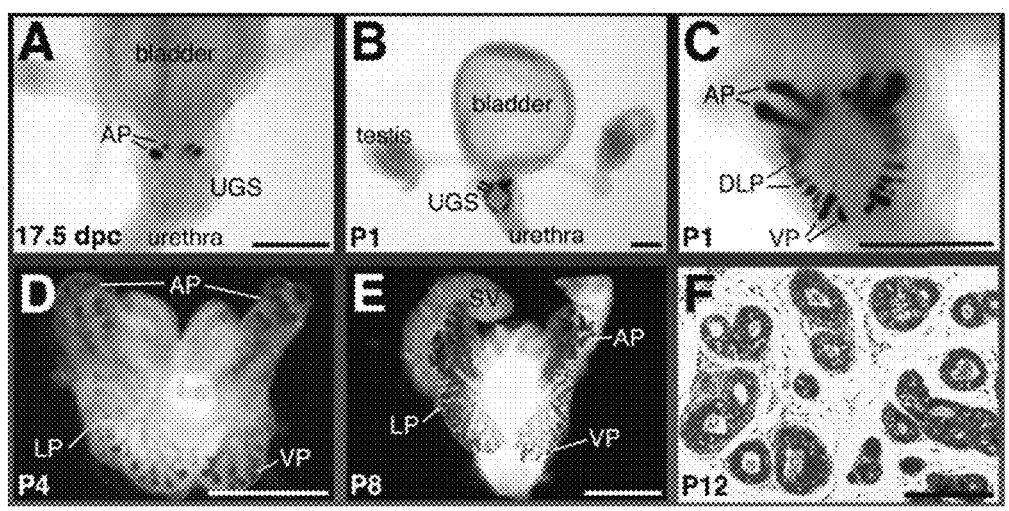
FIGS. 1A-F. Histology showing that Nkx3.1 is the earliest specific prostate epithelial marker.

The term "CARN" or "CARNs" designates castration-resistant Nkx3.1-expressing cells. CARNs are a population of luminal prostate cells that are distinct from other prostate cells and express NKx3.1 in the absence of androgens.

The term "FBS" designates fetal bovine serum.
The term "DHT" designates dihydrotestosterone.
The term "EGF" designates epidermal growth factor.
The term "DMEM" designates Dulbecco's Modified Eagle Medium.

The term "F-12" designates Nutrient Mixture F-12.
The term "HBSS" designates Hanks' Balanced Salt Solution.
The term "EDTA" designates ethylenediaminetetraacetic acid.
The term "HEPES" designates 4-(2-hydroxyethyl)-1-piperazineethanesulfonic acid.
The term "AR" designates androgen receptor.
The term "CK8" designates cytokeratin 8.
The term "CK5" designates cytokeratin 5.
The term "CK18" designates cytokeratin 18.
The term "pAkt" designates Protein Kinase B.
The term "ROCK" designates Rho-Associated Coil Kinase.

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Detailed Description

The present invention relates to a methodology for the culture of prostate tissue (organoids) from mouse and human prostate, both benign as well as cancer tissue. Previous work in the field has not been successful in culturing prostate tissue that maintains the differentiated state of luminal epithelial cells of the prostate, or that can recapitulate the phenotype of prostate tumors.

In some embodiments, the present invention relates to culture conditions that can support the growth of dissociated prostate epithelial cells to form large tissue masses (organoids) in culture. This can be achieved using cells from mouse prostate, including genetically-engineered mouse models, as well as from human patient specimens (using fresh prostate tissue), human cancer cell lines, and prostate xenografts.

In some embodiments, the present invention relates to the growth of organoids from normal human prostate tissue from cystectomies, as well as human prostate cancer tissue from radical prostatectomies and from biopsies.

In some embodiments, the organoids of the present invention display luminal differentiation and/or basal differentiation in organoids of normal prostate. In other embodiments, the organoids of the present invention display the luminal phenotype of prostate tumors, and can maintain the transformed phenotype of tumor organoids.

The present invention also relates to a methodology for the culture of prostate tissue organoids from metastatic cancer tissue. In some embodiments, a prostate organoid can be grown from metastatic prostate cancer cells. In some embodiments, the metastatic prostate cancer cells are isolated from the prostate, or from another tissue, including but not limited to the bone, brain, liver, or adrenal gland. In some embodiments, the present invention relates to culture conditions that can support the growth of dissociated or isolated metastatic prostate cancer cells to form large tissue masses (organoids) in culture. The can be achieved using metastatic cells from mouse, including genetically-engineered mouse models, as well as from human patient specimens. In some embodiments, the organoids maintain the transformed phenotype of the metastases from which they are derived. In one embodiment, cell cultures that grow as attached cells in two-dimensional culture are derived from the metastatic organoids. In one embodiment, the cells are cancerous. In another embodiment, the cells are tumor cells. In another embodiment, the cell cultures are used as cell lines. In one embodiment, the cell cultures are used as prostate cell lines. In one embodiment, the cell cultures are used as prostate metastatic cancer cell lines.

The present invention also relates to a methodology for the culture of metastatic prostate cell lines. In some embodiments, a metastatic prostate cell line can be grown from metastatic prostate cancer cells. In some embodiments, the metastatic prostate cancer cells are isolated from the prostate, or from another tissue, including but not limited to the bone, brain, liver, or adrenal gland. In some embodiments, the present invention relates to culture conditions that can support the growth of dissociated or isolated metastatic prostate cancer cells to form metastatic prostate cell lines in culture. The can be achieved using metastatic cells from mouse, including genetically-engineered mouse models, as well as from human patient specimens. In some embodiments, the organoids maintain the transformed phenotype of the metastases from which they are derived. In one embodiment, cell cultures that grow as attached cells in two-dimensional culture are derived from the metastatic prostate cancer cells. In one embodiment, the cells are cancerous. In another embodiment, the cells are tumor cells.

In some embodiments, the present invention relates to the growth of organoids from single isolated CARNs or oncogenically transformed CARNs. CARNs are castration-resistant Nkx3.1-expressing cells, which were previously shown to have stem cell properties in vivo.

In some embodiments, the present invention relates to screening methods for the identification of new candidate therapeutics for prostate cancer. This screening can be performed on a patient-specific basis using organoids or cell lines grown from surgically-isolated tumor or metastatic tissue.

In some embodiments, additional cell types can give rise to organoids. Without being bound by theory, organoid phenotype can be dependent upon androgen and androgen receptor function, and can be tested using drugs such as abiraterone and MDV3100.

In some embodiments, the present invention relates to small molecule screens for the identification of candidate therapeutics. In other embodiments, the present invention relates to an assay for the identification of human prostate cancer stem cells.

In some embodiments, the present invention relates to tumor tissue banks in which patient-specific organoids or patient-specific cell lines can be stored and used for the large-scale screening of candidate therapeutic compounds. Such organoid banks can also be useful for patient-specific diagnostics, assays for the efficacy of potential treatments, and identification of the appropriate targeted tumor population (cancer stem cells), as well as other applications in personalized medicine.

The organoid culture method described herein originated in attempts to culture single CARNs ("castration-resistant Nkx3.1 cells") from androgen-deprived mouse prostate. Previous studies showed that CARNs have stem cell properties, for example as shown by their ability to generate prostate ducts in single-cell transplantation assays.

Other organoid culture methodologies have been developed (see, e.g., Sato et al., 2009, Single Lgr5 stem cells build crypt-villus structures in vitro without a mesenchymal niche, 459(7244):262-5). The culture conditions of these methodologies comprise the use of defined culture media supplemented with EGF, Noggin (which inhibits BMP signaling), and R-spondin (which promotes canonical Wnt signaling). Without being bound by theory, previous studies have not identified the cell type(s) that give rise to the organoids, nor have the conditions in these studies been shown to support the growth of human prostate cancer cells in organoids grown from localized tumors.

The culture conditions of the instant invention can include EGF and 5% fetal calf serum, but can also lack Noggin and/or R-spondin.

In some embodiments, CARNs and transformed CARNs can give rise to organoids. In some embodiments, the organoid approach provides a methodology for the culture and long-term maintenance of viable human prostate cancer tissue. Similar approaches can be applicable for other cancer types. The availability of this methodology allows many applications for tumor screening and experimental therapeutics in an ex vivo culture-based setting, providing patient-specific reagents to investigate tumor response without the use of elaborate mouse models or extensive clinical trials.

The present invention provides methods for culturing prostate tissue. In one aspect the present invention provides methods for culturing prostate tissue that maintains the differentiated state of the luminal epithelial cells of the prostate, or recapitulates the phenotype of prostate tumors.

Methods of Culturing Organoids

In one aspect, the present invention provides a method for culturing organoids, the method comprising: (a) obtaining a sample of organ tissue from a subject; (b) dissociating the sample of organ tissue; (c) isolating dissociated cells from the sample of organ tissue; and (d) culturing the dissociated cells in a culture medium comprising basal hepatocyte medium, Matrigel, FBS and ROCK inhibitor; wherein the dissociated cells form organoids in culture.

In one aspect, the present invention provides a method for culturing organoids, the method comprising: (a) obtaining a sample of organ tissue from a subject; (b) dissociating the sample of organ tissue; (c) isolating dissociated cells from the sample of organ tissue; (d) contacting the dissociated organ tissue with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated cells form organoids in culture.

In one aspect, the present invention provides a method for culturing organoids, the method comprising: (a) obtaining a sample of organ tissue from a subject; (b) dissociating the sample of organ tissue; (c) isolating dissociated cells from the sample of organ tissue; (d) contacting the dissociated organ tissue with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated cells form organoids in culture.

In one embodiment, the organoid is a prostate organoid. In another embodiment, the organoid is a bladder organoid. In another embodiment, the organoid is a liver organoid. In yet another embodiment, the organoid is a kidney organoid. In a further embodiment, the organoid is a breast organoid. In another embodiment, the organoid is a lung organoid. In one embodiment, the organoid is a heart organoid. In another embodiment, the organoid is a skin organoid. In one embodiment, the organoid is a stomach organoid. In another embodiment, the organoid is a brain organoid. In one embodiment, the organoid is a pancreas organoid. In another embodiment, the organoid is a colon organoid. In yet another embodiment, the organoid is an intestine organoid. In yet other embodiments, any organoid can be used in the methods of the invention.

The present invention provides methods for dissociating cells from a tissue or mixed population of cells. In one embodiment, cells are dissociated from prostate tissue. In another embodiment, cells are dissociated from bladder tissue. In another embodiment, cells are dissociated from liver tissue. In yet another embodiment, cells are dissociated from kidney tissue. In a further embodiment, cells are dissociated from breast tissue. In another embodiment, cells are dissociated from lung tissue. In one embodiment, cells are dissociated from heart tissue. In another embodiment, cells are dissociated from skin tissue. In one embodiment, cells are dissociated from stomach tissue. In another embodiment, cells are dissociated from brain tissue. In one embodiment, cells are dissociated from pancreatic tissue. In another embodiment, cells are dissociated from colon tissue. In another embodiment, cells are dissociated from intestinal tissue.

In one embodiment, cells are dissociated from normal tissue. In one embodiment, cells are dissociated from non-cancerous tissue. In another embodiment, cells are dissociated from cancerous tissue. In another embodiment, cells are dissociated from human tissue. In a further embodiment, cells are dissociated from mouse tissue. In other embodiments, cells are dissociated from tissue from any mammal. In one embodiment, cells are dissociated from localized tumors. In another embodiment, cells are dissociated from malignant tumors. In another embodiment, cells are dissociated from metastasized tumors.

In a further embodiment, the organoids are cultured from one or more localized tumors. In one embodiment, the organoids are cultured from malignant tumors. In another embodiment, the organoids are cultured from metastasized tumors. In one embodiment, the tumor is a prostate tumor. In another embodiment, the tumor is a breast, heart, lung, liver, bladder, kidney, skin, stomach, brain, pancreas, colon, or intestinal tumor.

In one embodiment, a sample of tissue can be obtained by biopsy. Methods of obtaining tissue samples are known to one of skill in the art. In one embodiment, the sample of tissue is obtained from a bladder biopsy. In another embodiment, the sample of tissue is obtained from a liver biopsy. In yet another embodiment, the sample of tissue is obtained from a kidney biopsy. In a further embodiment, the sample of tissue is obtained from a breast biopsy. In another embodiment, the sample of tissue is obtained from a lung biopsy. In one embodiment, the sample of tissue is obtained from a heart biopsy. In another embodiment, the sample of tissue is obtained from a skin biopsy. In one embodiment, the sample of tissue is obtained from a stomach biopsy. In another embodiment, the sample of tissue is obtained from a brain biopsy. In one embodiment, the sample of tissue is obtained from a pancreas biopsy. In one embodiment, the sample of tissue is obtained from a colon biopsy. In another embodiment, the sample of tissue is obtained from an intestine biopsy.

In some embodiments, a sample of tissue is obtained by fine needle aspiration biopsy. In another embodiment, a sample of tissue is obtained by core needle biopsy. In a further embodiment, a sample of tissue is obtained by surgical biopsy.

In one embodiment, a sample of prostate tissue can be obtained from a cystectomy. In another embodiment, a sample of prostate tissue can be obtained from a radical prostatectomy. In a further embodiment, a sample of prostate tissue can be obtained from a transurethral radical prostatectomy. In yet another embodiment, a sample of prostate tissue is obtained from a prostate biopsy.

In one embodiment, the subject is an animal. In other embodiments, the subject is a human. In other embodiments, the subject is a mammal. In some embodiments, the subject is a rodent, such as a mouse or a rat. In some embodiments, the subject is a cow, pig, sheep, goat, cat, horse, dog, and/or any other species of animal used as livestock or kept as pets.

In one aspect, the invention provides a method for culturing prostate organoids, the method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate organoids in culture. In one embodiment, the prostate tissue is non-cancerous. In another embodiment, the prostate tissue is cancerous.

In one aspect, the invention provides a method for culturing prostate organoids, the method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the prostate tissue is non-cancerous. In another embodiment, the prostate tissue is cancerous.

In one aspect, the invention provides a method for culturing prostate organoids, the method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the prostate tissue is non-cancerous. In another embodiment, the prostate tissue is cancerous.

In one aspect, the invention provides a method for culturing prostate organoids, the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; and (d) culturing the dissociated metastatic prostate cancer cells in a culture medium comprising basal hepatocyte medium, Matrigel, FBS and ROCK inhibitor; wherein the dissociated metastatic prostate cancer cells form prostate organoids in culture. In one embodiment, the organoids display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland.

In one aspect, the invention provides a method for culturing prostate organoids, the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form prostate organoids in culture. In one embodiment, the organoids display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland.

In one aspect, the invention provides a method for culturing prostate organoids, the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form prostate organoids in culture. In one embodiment, the organoids display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland.

In a further embodiment, the subject is a human. In another embodiment, the subject is a mouse. In one embodiment, the mouse is a genetically-engineered mouse. In another embodiment, the mouse comprises a prostate cancer xenograft. In one embodiment, the mouse is a LuCAP xenograft mouse. In one embodiment, the prostate tissue is isolated from a cystectomy. In another embodiment, the prostate tissue is isolated from a radical prostatectomy. In another embodiment, the prostate tissue is isolated from a biopsy. In a further embodiment, the organoids display the luminal differentiation of the non-cancerous prostate tissue. In one embodiment, the organoids display the basal differentiation of the non-cancerous prostate tissue. In another embodiment, the organoids display the luminal phenotype of the cancerous prostate tissue. In another embodiment, the organoids maintain the transformed phenotype of the cancerous prostate tissue.

In one embodiment, the culture medium does not comprise Noggin. In another embodiment, the culture medium comprises Noggin. In one embodiment, the culture medium does not comprise R-spondin. In another embodiment, the culture medium comprises R-spondin. In one embodiment, the culture medium comprises DHT. In another embodiment, the culture medium does not comprise DHT. In one embodiment, the culture medium comprises EGF. In another embodiment, the culture medium does not comprise EGF.

In one embodiment, culture of the organoids is not dependent on androgens. In another embodiment, culture of the organoids is dependent on androgens. In one embodiment, culture of the organoids is not dependent on androgen receptor function. In another embodiment, culture of the organoids is dependent on androgen receptor function. In one embodiment, the culture medium comprises serum, including, but not limited to, FBS. In another embodiment, the culture medium does not comprise serum, including, but not limited to, FBS. In one embodiment, the culture medium comprises a ROCK inhibitor. In another embodiment, the culture medium does not comprise a ROCK inhibitor. In one embodiment, the culture medium comprises Matrigel. In another embodiment, the culture medium does not comprise Matrigel.

In another aspect, the invention provides a method for culturing prostate organoids, the method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate organoids in culture. In one embodiment, the CARNs are non-cancerous cells. In another embodiment, the CARNs are transformed cells. In yet another embodiment, the CARNs are cancerous cells.

In another aspect, the invention provides a method for culturing prostate organoids, the method comprising: (a) obtaining a sample of prostate tissue from a subject; (b) isolating CARNs from the sample of prostate tissue; (c) contacting the CARNs with a Matrigel solution and plating in a cell culture support, wherein the Matrigel solution forms a matrix; (d) providing an overlay layer of liquid culture medium comprising basal hepatocyte medium, FBS and ROCK inhibitor; and (e) incubating the culture of (d) wherein the CARNs form prostate organoids in culture. In one embodiment, the CARNs are non-cancerous cells. In another embodiment, the CARNs are transformed cells. In yet another embodiment, the CARNs are cancerous cells.

In another aspect, the invention provides a method for culturing prostate organoids, the method comprising: (a) obtaining a sample of prostate tissue from a subject; (b) isolating CARNs from the sample of prostate tissue; (c) contacting the CARNs with a collagen solution and plating in a cell culture support, wherein the collagen solution forms a matrix; (d) providing an overlay layer of liquid culture medium comprising basal hepatocyte medium, FBS and ROCK inhibitor; and (e) incubating the culture of (d) wherein the CARNs form prostate organoids in culture. In one embodiment, the CARNs are non-cancerous cells. In another embodiment, the CARNs are transformed cells. In yet another embodiment, the CARNs are cancerous cells.

In a further embodiment, the subject is a human. In another embodiment, the subject is a mouse. In one embodiment, the mouse is a genetically-engineered mouse. In another embodiment, the mouse comprises a prostate cancer xenograft. In another embodiment, the mouse is a LuCAP xenograft mouse. In one embodiment, the prostate tissue is isolated from a cystectomy. In another embodiment, the prostate tissue is isolated from a radical prostatectomy. In a further embodiment, the organoids display the luminal differentiation of the non-cancerous prostate tissue. In one embodiment, the organoids display the basal differentiation of the non-cancerous prostate tissue. In another embodiment, the organoids display the luminal phenotype of the cancerous prostate tissue. In another embodiment, the organoids maintain the transformed phenotype of the cancerous prostate tissue. In one embodiment, the organoids maintain the luminal differentiation of the CARNs. In another embodiment, the organoids maintain the transformed phenotype of the transformed CARNs.

In one embodiment, the culture medium does not comprise Noggin. In another embodiment, the culture medium comprises Noggin. In one embodiment, the culture medium does not comprise R-spondin. In another embodiment, the culture medium comprises R-spondin. In one embodiment, the culture medium comprises DHT. In another embodiment, the culture medium does not comprise DHT. In one embodiment, the culture medium comprises EGF. In another embodiment, the culture medium does not comprise EGF.

In one embodiment, culture of the organoids is not dependent on androgens. In another embodiment, culture of the organoids is dependent on androgens. In one embodiment, culture of the organoids is not dependent on androgen receptor function. In another embodiment, culture of the organoids is dependent on androgen receptor function. In one embodiment, the culture medium comprises serum, including, but not limited to, FBS. In another embodiment, the culture medium does not comprise serum, including, but not limited to, FBS. In one embodiment, the culture medium comprises a ROCK inhibitor. In another embodiment, the culture medium does not comprise a ROCK inhibitor. In one embodiment, the culture medium comprises Matrigel. In another embodiment, the culture medium does not comprise Matrigel.

In one embodiment, cell cultures that grow as attached cells in two-dimensional culture are derived from the organoids. In one embodiment, the cells are cancerous. In another embodiment, the cells are tumor cells. In another embodiment, the cells are normal. In yet another embodiment, the cells are non-cancerous.

In another embodiment, the cell cultures are used as cell lines. In one embodiment, the cell cultures are used as prostate cell lines. In another embodiment, the cell cultures are used as breast, heart, lung, liver, bladder, kidney, skin, stomach, brain, pancreas, colon, or intestinal cell lines. In one embodiment, the cell cultures are used as cancer cell lines. In another embodiment, the cell cultures are used as prostate cancer cell lines. In yet another embodiment, the cell cultures are used as breast, heart, lung, liver, bladder, kidney, skin, stomach, brain, pancreas, colon, or intestinal cancer cell lines.

In one embodiment, cell cultures are obtained from the organoids. In another embodiment, cells in the cell cultures grow as attached cells in two-dimensional culture. In yet another embodiment, the cell cultures comprise cell lines. In one embodiment, the cells are cancerous. In another embodiment, the cells are tumor cells. In another embodiment, the cells are normal. In yet another embodiment, the cells are non-cancerous.

In one embodiment, the cell cultures comprise prostate cell lines. In another embodiment, the cell cultures comprise breast, heart, lung, liver, bladder, kidney, skin, stomach, brain, pancreas, colon, or intestinal cell lines. In one embodiment, the cell cultures comprise cancer cell lines. In another embodiment, the cell cultures comprise prostate cancer cell lines. In yet another embodiment, the cell cultures are used as breast, heart, lung, liver, bladder, kidney, skin, stomach, brain, pancreas, colon, or intestinal cancer cell lines.

In one embodiment, the CARNs express Nkx3.1 in the absence of androgens, and cytokeratin 8 (CK8), cytokeratin 18 (CK18), Androgen receptor (AR), or a combination thereof.

In one embodiment, the CARNs express CK8. In another embodiment, the CARNs express CK18. In one embodiment, the CARNs express AR. In another embodiment, the CARNs express p63. In one embodiment, the CARNs express CK5. In another embodiment, the CARNs express pAkt. In yet another embodiment, the CARNs express Ki67. In a further embodiment, the CARNs express Nkx3.1 in the absence of androgens.

CARNs are prostate stem cells and cells of origin for prostate cancer, distinct from all the other prostate stem cells that have been reported. Thus, they can be more physiologically relevant, especially given that human prostate cancer has a luminal phenotype.

A Nkx3.1 gene, also known as NK-3 transcription factor, encodes the NK3 homeobox 1 protein. The homeodomain-containing transcription factor NKX3.1 is a putative prostate tumor suppressor that is expressed in a largely prostate-specific and androgen-regulated manner. Loss of NKX3.1 protein expression is a common finding in human prostate carcinomas and prostatic intraepithelial neoplasia. In the context of the invention, the Nkx3.1 gene also encompasses its variants, analogs and fragments thereof, including alleles thereof (e.g., germline mutations) which are related to susceptibility to prostate cancer.

The Nkx3.1 gene locus can comprise all Nkx3.1 sequences or products in a cell or organism, including Nkx3.1 coding sequences, Nkx3.1 non-coding sequences (e.g., introns), Nkx3.1 regulatory sequences controlling transcription and/or translation (e.g., promoter, enhancer, terminator).

According to this invention, a Nkx3.1 molecule encompasses orthologs of human Nkx3.1. For example, a Nkx3.1 molecule encompasses the orthologs in mouse, rat, non-human primates, canines, goat, rabbit, porcine, feline, and horses. In other words, a Nkx3.1 molecule can comprise a nucleic acid sequence homologous to the human nucleic acid that encodes a human Nkx3.1, wherein the nucleic acid is found in a different species and wherein that homolog encodes a protein with a homeobox transcription factor function similar to Nkx3.1 molecule.

In one aspect, the invention provides a method for culturing prostate organoids, the method comprising culturing prostate cancer cell line cells in a culture medium comprising basal hepatocyte medium, Matrigel, FBS and ROCK inhibitor; wherein the prostate cancer cell line cells form prostate organoids in culture. In one embodiment, the prostate organoids maintain the transformed phenotype of the prostate cancer cell line. In one embodiment, the prostate cancer cell line is VCaP.

In one aspect, the invention provides a method for culturing prostate organoids, the method comprising: (a) contacting prostate cancer cell line cells with a Matrigel solution and plating in a cell culture support, wherein the Matrigel solution forms a matrix; (b) providing an overlay layer of liquid culture medium comprising basal hepatocyte medium, FBS and ROCK inhibitor; and (c) incubating the culture of (b) wherein the prostate cancer cell line cells form prostate organoids in culture. In one embodiment, the prostate organoids maintain the transformed phenotype of the prostate cancer cell line. In one embodiment, the prostate cancer cell line is VCaP.

In one aspect, the invention provides a method for culturing prostate organoids, the method comprising: (a) contacting prostate cancer cell line cells with a collagen solution and plating in a cell culture support, wherein the collagen solution forms a matrix; (b) providing an overlay layer of liquid culture medium comprising basal hepatocyte medium, FBS and ROCK inhibitor; and (c) incubating the culture of (b) wherein the prostate cancer cell line cells form prostate organoids in culture. In one embodiment, the prostate organoids maintain the transformed phenotype of the prostate cancer cell line. In one embodiment, the prostate cancer cell line is VCaP.

In one embodiment, the organoids are grown by a Matrigel floating culture method. In one embodiment, cells are cultured in a low attachment cell culture support. In one embodiment, the low attachment cell culture support is a tissue culture plate. Tissue culture plates and supports can be used in a variety of shapes, sizes and materials, including, but not limited to, plates, flasks, wells, and bags. Tissue culture supports can be coated with various substances, to decrease adhesion properties. In another embodiment, the low attachment cell culture support is a tissue culture plate that minimizes or prevents attachment of the cells to the surface of the support. In one embodiment, the low attachment cell culture support is a Corning Ultra-Low Attachment cell culture plate. In one embodiment, the low attachment cell culture support is a Corning Ultra-Low Attachment 96 well plate. The Corning Ultra-Low Attachment cell culture plate is an example of a type of tissue culture support that minimizes or prevents attachment of the cells to the surface of the support. A variety of alternative cell culture supports that minimize or prevent attachment of cells to the surface of the support are known in the art and can be found, for example, in Corning Cell Culture Selection Guide, the contents of which is hereby incorporated by reference in its entirety. In another embodiment, the low attachment cell culture support is a polystyrene plate. In a further embodiment, the low attachment cell culture support is a surface modified polystyrene plate. For example, the surface of the support can be modified to be hydrophilic and/or neutrally charged to minimize or prevent the attachment of the cells to the surface of the support. In another embodiment, the surface of the support can be modified so the plate has a covalently bonded hydrogel surface to minimize or prevent the attachment of the cells to the surface if the plate. In one embodiment, the low attachment cell culture support is a 6 well plate, a 12 well plate, a 24 well plate, a 48 well plate, or a 96 well plate.

In one embodiment, the organoids are grown by a Matrigel embedding method. In one embodiment, the cell culture support is a tissue culture plate. In one embodiment, the cell culture support is a 6-well tissue culture plate. Tissue culture plates and supports can be used in a variety of shapes, sizes and materials, including, but not limited to, plates, flasks, wells, and bags. A variety of cell culture supports are known in the art and can be found, for example, in Corning Cell Culture Selection Guide, the contents of which is hereby incorporated by reference in its entirety. In another embodiment, the cell culture support is a polystyrene plate. In a further embodiment, the cell culture support is a surface modified polystyrene plate. In one embodiment, the cell culture support is a 6 well plate, a 12 well plate, a 24 well plate, a 48 well plate, or a 96 well plate.

In one embodiment, the contacting of cells with a Matrigel solution is performed below about 10° C. in order to maintain the Matrigel solution in liquid form. After plating in the cell culture support the temperature can be raised above about 10° C. and the Matrigel solution can form a matrix or gel. In one embodiment, the Matrigel solution solidifies or forms a gel by incubation at 37° C. for 30 minutes. In one embodiment, the Matrigel solution solidifies or forms a gel at about 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C.

In another embodiment, before plating the cells and Matrigel solution in the cell culture support, the cell culture support is surface modified. In one embodiment, the support surface is pre-coated by rinsing Matrigel solution over the support surface and incubating the cell culture support at 37° C. for at least 30 minutes. In one embodiment, the Matrigel solution comprises hepatocyte medium and Matrigel. In one embodiment, the Matrigel solution comprises serum, including, but not limited to, FBS. In another embodiment, the Matrigel solution does not comprise serum, including, but not limited to, FBS. In one embodiment, the Matrigel solution comprises 3 parts Matrigel to 2 parts hepatocyte medium. In one embodiment, the Matrigel solution comprises 60% Matrigel and 40% hepatocyte medium. In one embodiment, the Matrigel solution comprises 100% Matrigel. In one embodiment, the Matrigel solution forms a matrix.

In one embodiment, the cells (for e.g. dissociated prostate epithelial cells, dissociated metastatic prostate cancer cells, CARNs, prostate cancer cell line cells) are contacted with a matrigel solution that forms a matrix and an overlay layer of liquid culture medium is provided. In one embodiment the matrigel solution and cells are plated in a cell culture support. In one embodiment, the Matrigel solution comprises Matrigel and basal hepatocyte medium. In one embodiment, the Matrigel solution comprises serum, including, but not limited to, FBS. In another embodiment, the Matrigel solution does not comprise serum, including, but not limited to, FBS. In one embodiment, the Matrigel solution comprises 3 parts Matrigel to 2 parts hepatocyte medium. In one embodiment, the Matrigel solution comprises 60% Matrigel and 40% hepatocyte medium. In one embodiment, the Matrigel solution comprises 100% Matrigel. In one embodiment, the Matrigel solution forms a matrix.

In one embodiment, the organoids are grown in a collagen matrix. In one embodiment, the organoids are grown in an extracellular matrix or scaffold, including, but not limited to collagen, laminin, fibronectin, gelatin, or Geltrex®. In one embodiment, the collagen matrix comprises collagen I. In one embodiment, the collagen matrix comprises rat tail collagen I.

In one embodiment, after plating in the cell culture support the temperature can be raised above about 10° C. and the collagen solution can form a matrix or gel. In one embodiment, the collagen solution solidifies or forms a gel by incubation at 37° C. for 30 minutes. In one embodiment, the collagen solution solidifies or forms a gel at about 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C.

In another embodiment, before plating the cell and collagen solution in the cell culture support, the cell culture support is surface modified. In one embodiment, the support surface is pre-coated by rinsing collagen solution over the support surface and incubating the cell culture support at 37° C. for at least 30 minutes. In one embodiment, the collagen solution comprises setting solution and collagen. In one embodiment, the collagen solution comprises 9 parts collagen to 1 parts setting solution. In one embodiment, setting solution comprises EBSS, sodium bicarbonate and sodium hydroxide.

In one embodiment, the cells (for example, dissociated prostate epithelial cells, dissociated metastatic prostate cancer cells, CARNs, prostate cancer cell line cells) are contacted with a collagen solution that forms a matrix and an overlay layer of liquid culture medium is provided. In one embodiment the collagen solution and cells are plated in a cell culture support. In one embodiment the collagen solution and cells are plated into wells of a tissue culture plate. In another embodiment, the plate is a polystyrene plate. In a further embodiment, the cell culture support is a surface modified polystyrene plate. In one embodiment, the support surface is pre-coated by rinsing collagen solution over the support surface and incubating the cell culture support at 37° C. for at least 30 minutes. In one embodiment, the collagen solution comprises setting solution and collagen. In one embodiment, the collagen solution comprises 9 parts collagen to 1 parts setting solution. In one embodiment, setting solution comprises EBSS, sodium bicarbonate and sodium hydroxide.

Methods of Culturing Metastatic Cell Lines

The present invention also relates to a methodology for the culture of metastatic prostate cell lines. In some embodiments, a metastatic prostate cell line can be grown from metastatic prostate cancer cells. In some embodiments, the metastatic prostate cancer cells are isolated from a tissue of a subject with a prior medical history of prostate cancer, including, but not limited to, the bone, brain, liver, or adrenal gland. In some embodiments, the present invention relates to culture conditions that can support the growth of dissociated or isolated metastatic prostate cancer cells to form metastatic prostate cell lines in culture. In some embodiments, the organoids maintain the transformed phenotype of the metastasis from which they are derived. In one embodiment, cell cultures that grow as attached cells in two-dimensional culture are derived from the metastatic prostate cancer cells. In one embodiment, the cells are cancerous. In another embodiment, the cells are tumor cells.

In one aspect, the invention provides a method for culturing a metastatic prostate cell line, the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) plating the isolated dissociated metastatic prostate cancer cells of (c) on an adherent cell culture support; and (e) culturing the dissociated metastatic prostate cancer cells in a culture medium comprising basal hepatocyte medium, Matrigel, FBS and ROCK inhibitor; wherein the dissociated metastatic prostate cancer cells form metastatic prostate cell lines in culture.

Cells can be grown in suspension or adherent cultures. Some cells can be cultured without being attaching to a surface (suspension cultures), while other cells require a surface (adherent cells). Cells can also grow in a three-dimensional environment such as a matrix or a scaffold (e.g. Matrigel or collagen).

In one embodiment, the metastatic prostate cell lines grow as attached cells in two-dimensional culture. In one embodiment, the metastatic prostate cell lines grow as adherent cells. In one embodiment, the adherent cell culture support is a tissue culture plate. Tissue culture plates and supports can be used in a variety of shapes, sizes and materials, including, but not limited to, plates, flasks, wells, and bags. Tissue culture supports can be coated with various substances, including, but not limited to, extracellular matrix components to increase adhesion properties for example. In one embodiment, the adherent cell culture support is a tissue culture plate that enhances or maximizes attachment of the cells to the surface of the support. In one embodiment, the adherent cell culture support is a Primaria™ surface modified cell culture plate. In one embodiment, the adherent cell culture support is a Primaria™ 24 well flat bottom surface modified multiwell cell culture plate. The Primaria™ surface modified cell culture plate is an example of a type of tissue culture support that enhances or maximizes attachment of the cells to the surface of the support. A variety of alternative cell culture supports that enhance or maximize attachment of cells to the surface of the support are known in the art and can be found, for example, in Corning Cell Culture Selection Guide, the contents of which is hereby incorporated by reference in its entirety. In another embodiment, the adherent cell culture support is a polystyrene plate. In a further embodiment, the adherent cell culture support is a surface modified polystyrene plate. For example, the surface of the plate can be modified to incorporate anionic and cationic functional groups to enhance the attachment of the cells to the surface of the support. In one embodiment, the adherent cell culture support is a 6 well plate, a 12 well plate, a 24 well plate, a 48 well plate, or a 96 well plate.

In one embodiment, the metastatic prostate cell line displays the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland. In another embodiment, the metastatic prostate cancer tissue is a prostate cancer that has metastasized to an organ other than the prostate (for example, to bone, brain, liver, adrenal gland).

In a further embodiment, the subject is a human. In another embodiment, the metastatic prostate cancer tissue is obtained from a biopsy. In one embodiment, the culture medium further comprises Glutamax. In another embodiment, the culture medium further comprises EGF. In a further embodiment, the culture medium further comprises antibiotic-antimycotic. In another embodiment, the culture medium comprises 10 ng/ml of EGF. In another embodiment, the culture medium comprises 5% Matrigel. In another embodiment, the culture medium comprises 5% heat-inactivated charcoal stripped FBS. In another embodiment, the ROCK inhibitor is Y-27632. In another embodiment, the culture medium comprises 10 µM of Y-27632. In another embodiment, the culture medium further comprises DHT. In another embodiment, the culture medium does not comprise DHT. In another embodiment, the culture medium comprises 100 nM DHT.

In one embodiment, the cells of the metastatic prostate cell line grow as attached cells in two-dimensional culture. In another embodiment, a single cell suspension is obtained by the dissociating of (b). In another embodiment, (b) comprises dissociating the sample of metastatic prostate cancer tissue with collagenase, hyaluronidase, dispase, or a combination thereof. In another embodiment, the isolating of (c) is by immunomagnetic cell separation. In another embodiment, the isolating of (c) is by centrifugation. In one embodiment, the method further comprises: (e) serially passaging the bladder cell line colonies.

The present invention provides methods for dissociating cells from a tissue or mixed population of cells. In one embodiment, cells are dissociated from metastatic prostate cancer tissue. In another embodiment, cells are dissociated from cancerous tissue. In another embodiment, cells are dissociated from human tissue. In one embodiment, cells are dissociated from localized tumors. In another embodiment, cells are dissociated from malignant tumors. In another embodiment, cells are dissociated from metastasized tumors.

In a further embodiment, the metastatic prostate cell lines are cultured from one or more localized tumors. In one embodiment, the metastatic prostate cell lines are cultured from malignant tumors. In another embodiment, the metastatic prostate cell lines are cultured from metastasized tumors. In one embodiment, the tumor is a prostate tumor.

In one embodiment, a sample of tissue can be obtained by biopsy. Methods of obtaining tissue samples are known to one of skill in the art. In one embodiment, the sample of tissue is obtained from a brain, liver, or adrenal gland biopsy or resection.

In one embodiment, the subject is an animal. In other embodiments, the subject is a human. In other embodiments, the subject is a mammal. In some embodiments, the subject is a rodent, such as a mouse or a rat. In some embodiments, the subject is a cow, pig, sheep, goat, cat, horse, dog, and/or any other species of animal used as livestock or kept as pets. In some embodiments, the subject has a prior medical history of prostate cancer.

In one aspect, the invention provides a method for culturing a metastatic prostate cell line, wherein the cell line maintains or displays the phenotype of the sample of metastatic prostate cancer tissue from which the cell line is derived. The phenotype of the cell line can be determined by evaluating markers. Expression of markers can be evaluated by a variety of methods known in the art. In one embodiment, the metastatic prostate cell lines display the transformed phenotype of the cancerous metastatic tissue.

In one embodiment, the culture medium comprises EGF. In another embodiment, the culture medium does not comprise EGF. In one embodiment, the culture medium comprises Glutamax. In another embodiment, the culture medium does not comprise Glutamax. In one embodiment, the culture medium comprises antibiotic-antimycotic. In another embodiment, the culture medium does not comprise antibiotic-antimycotic. In one embodiment, the culture medium comprises DHT. In another embodiment, the culture medium does not comprise DHT.

In one embodiment, the culture medium comprises serum, including, but not limited to, FBS. In another embodiment, the culture medium does not comprise serum, including, but not limited to, FBS. In one embodiment, the culture medium comprises a ROCK inhibitor. In another embodiment, the culture medium does not comprise a ROCK inhibitor. In one embodiment, the culture medium comprises Matrigel. In another embodiment, the culture medium does not comprise Matrigel.

In one embodiment, the metastatic prostate cell lines grow as attached cells in two-dimensional culture. In one embodiment, the cells are cancerous. In another embodiment, the cells are tumor cells.

In another embodiment, the cell cultures are used as cell lines. In one embodiment, the cell cultures are used as metastatic prostate cell lines. In one embodiment, the cell cultures are used as cancer cell lines. In another embodiment, the cell cultures are used as prostate cancer cell lines.

In one embodiment, the cells of the metastatic prostate cell lines express CK5, androgen receptor, Foxa1, Nkx3.1, Chromogranin A, Amacr, synaptophysin, or a combination thereof. In some embodiments, the cells of the metastatic prostate cell line express CK5. In some embodiments, the cells of the metastatic prostate cell line express androgen receptor. In some embodiments, the cells of the metastatic prostate cell line express Foxa1. In some embodiments, the cells of the metastatic prostate cell line express Nkx3.1. In some embodiments, the cells of the metastatic prostate cell line express Chromogranin A. In some embodiments, the cells of the metastatic prostate cell line express Amacr. In some embodiments, the cells of the metastatic prostate cell line express synaptophysin. In some embodiments, the cells of the metastatic prostate cell line are chemotherapy resistant.

Isolation of Cells from Tissue

The present invention provides methods for separating, enriching, isolating or purifying cells from a tissue or mixed population of cells. In one embodiment, the isolated cells are epithelial cells. In another embodiment, the isolated cells are prostate epithelial cells. In one embodiment, cells are dissociated from normal prostate specimens. In one embodiment, cells are dissociated from non-cancerous prostate specimens. In another embodiment, cells are dissociated from cancerous prostate specimens. In a further embodiment, the isolated cells are luminal cells. In another embodiment, the isolated cells are basal cells. In another embodiment, the isolated cells are luminal prostate cells. In another embodiment, the isolated cells are basal prostate cells. In another embodiment, the isolated cells are a mixed population. In a further embodiment, the isolated cells are not a mixed population. In another embodiment, the isolated cells are a mixed population of basal and luminal cells. In another embodiment, the isolated cells are metastatic cancer cells. In another embodiment, the isolated cells are metastatic prostate cancer cells. In another embodiment, the isolated cells are metastatic cancer cells that metastasized from the prostate to another organ such as the breast, heart, lung, liver, bladder, kidney, skin, stomach, brain, pancreas, colon, or intestine.

In another embodiment, the isolated cells are breast, heart, lung, liver, bladder, kidney, skin, stomach, brain, pancreatic, colon, or intestinal cells. In another embodiment, the isolated breast, heart, lung, liver, bladder, kidney, skin, stomach, brain, pancreatic, colon, or intestinal cells are epithelial cells. In one embodiment, the cells are dissociated from normal organ specimens. In another embodiment, the cells are dissociated from non-cancerous organ specimens. In another embodiment, the cells are dissociated from cancerous organ specimens.

In one embodiment, prostate tissue is collected during surgery including, but not limited to, during cystectomies, prostatectomies, radical prostatectomies, transurethral radical prostatectomy and prostate biopsies. In one embodiment, the prostate tissue is normal. In another embodiment, the prostate tissue is cancerous. In another embodiment, the prostate tissue is non-cancerous. In another embodiment, the prostate epithelial cells are cancerous. In another embodiment, the prostate epithelial cells is non-cancerous. In another embodiment, the CARNs are cancerous. In another embodiment, the CARNs are non-cancerous. In one embodiment, the prostate tissue is collected from a human subject. In another embodiment, prostate tissue is collected from a mouse. In a further embodiment, prostate tissue is collected from a mouse which has been genetically engineered. For example, prostate tissue may be collected from a mouse with a genetically engineered genome including, but not limited to, Nkx3.1-CreER$^{T2}$; R26R-YFP mice, or Nkx3.1-CreER$^{T2}$; KRas$^{LSL}$; Pten$^{flox/flox}$; R26R-YFP mice. In a further embodiment, prostate tissue is collected from a LuCAP xenograft mouse. In other embodiments, prostate tissue can be acquired from a mouse which has a wild-type genome.

In one embodiment, tissue from breast, heart, lung, liver, bladder, kidney, skin, stomach, brain, pancreas, colon, or intestine, is collected during surgery including, but not limited to, during cystectomies and biopsies. In one embodiment, the tissue is normal. In another embodiment, the tissue is cancerous. In another embodiment, the tissue is non-cancerous. In another embodiment, the organ epithelial cells are cancerous. In another embodiment, the organ epithelial cells are non-cancerous. In another embodiment, the tissue is a metastatic cancer. In another embodiment, the tissue is a metastatic prostate cancer. In another embodiment, the tissue is a metastatic cancer that metastasized from the prostate to another organ. In a further embodiment, the tissue is a metastatic cancer that that metastasized from the prostate to the bone, breast, heart, lung, liver, bladder, kidney, skin, stomach, brain, pancreas, colon, intestine, or adrenal gland.

In one embodiment, cells are dissociated from a tissue sample by cutting into small chunks. In one embodiment the tissue sample is a prostate tissue sample. In another embodiment, the tissue sample is a breast, heart, lung, liver, bladder, kidney, breast, skin, stomach, brain, pancreas, colon, or intestine tissue sample. In another embodiment 1 gram of tissue is used. In one embodiment, at least 0.1 gram, at least 0.2 grams, at least 0.3 grams, at least 0.4 grams, at least 0.5 grams, at least 0.6 grams, at least 0.7 grams, at least 0.8 grams, at least 0.9 grams, at least 1.0 grams, at least 2.0 grams, at least 3.0 grams, at least 4.0 grams, at least 5.0 grams, at least 6.0 grams, at least 7.0 grams, at least 8.0 grams, at least 9.0 grams, or at least 10.0 grams of tissue is used. In another embodiment, the whole organ is used. In another embodiment, the whole prostate is used.

In one embodiment, the tissue sample, for example, the prostate tissue sample, is incubated in a cell culture medium. In one embodiment, the cell culture medium is Dulbecco's Modified Eagle Medium (DMEM). In another embodiment, the cell culture medium is Dulbecco's Modified Eagle Medium/Nutrient Mixture F-12 (DMEM/F-12). In another embodiment, the cell culture medium is supplemented with serum. In one embodiment, the cell culture medium is supplemented with fetal bovine serum (FBS). In another embodiment, the cell culture medium is supplemented with 5% fetal bovine serum (FBS). In one embodiment, the cell culture medium is supplemented with about 0.1% FBS, about 0.2% FBS, about 0.3% FBS, about 0.4% FBS, about 0.5% FBS, about 0.6% FBS, about 0.7% FBS, about 0.8% FBS, about 0.9% FBS, about 1% FBS, about 2% FBS, about 3% FBS, about 4% FBS, about 5% FBS, about 6% FBS, about 7% FBS, about 8% FBS, about 9% FBS, about 10% FBS, about 15% FBS, or about 20% FBS, or more.

In one embodiment, the cell culture medium is supplemented with at least 0.1% FBS, with at least 0.2% FBS, with at least 0.3% FBS, with at least 0.4% FBS, with at least 0.5% FBS, with at least 0.6% FBS, with at least 0.7% FBS, with at least 0.8% FBS, with at least 0.9% FBS, with at least 1% FBS, with at least 2% FBS, with at least 3% FBS, with at least 4% FBS, with at least 5% FBS, with at least 6% FBS, with at least 7% FBS, with at least 8% FBS, with at least 9% FBS, with at least 10% FBS, or with at least 20% FBS.

In one embodiment, the tissue sample, for example, the prostate tissue sample, is dissociated enzymatically. In one embodiment, the tissue sample is dissociated enzymatically by incubation of tissue with cell culture medium supplemented with collagenase. Collagenase can break down the collagen found in tissues. In one embodiment, the final concentration of collagenase in the cell culture medium is 300 units/ml. In another embodiment, the final concentration of collagenase in the cell culture medium is at least 50 units/ml, at least 100 units/ml, at least 200 units/ml, at least 300 units/ml, at least 400 units/ml, at least 500 units/ml, at least 600 units/ml, at least 700 units/ml, at least 800 units/ml, at least 900 units/ml, or at least 1000 units/ml.

In one embodiment, the tissue sample, for example, the prostate tissue sample, is dissociated enzymatically by incubation of the tissue with cell culture medium supplemented with hyaluronidase. Hyaluronidase can break down the hyaluronic acid found in tissues. In one embodiment, the final concentration of hyaluronidase in the cell culture medium is 100 units/ml. In another embodiment, the final concentration of hyaluronidase in the cell culture medium is at least 10 units/ml, at least 20 units/ml, at least 30 units/ml, at least 40 units/ml, at least 50 units/ml, at least 60 units/ml, at least 70 units/ml, at least 80 units/ml, at least 90 units/ml, at least 100 units/ml, at least 200 units/ml, at least 300 units/ml, at least 400 units/ml, at least 500 units/ml, at least 600 units/ml, at least 700 units/ml, at least 800 units/ml, at least 900 units/ml, or at least 1000 units/ml.

In one embodiment, the cell culture medium is supplemented with both collagenase and hyaluronidase. In another embodiment, a 10× concentrated solution of collagenase and hyaluronidase is diluted 10-fold in the cell culture medium.

In one embodiment, the tissue sample, for example, the prostate tissue sample, is incubated in DMEM/F-12 with 5% FBS, 300 units/ml collagenase, and 100 units/ml hyaluronidase overnight at 37° C. In one embodiment, the sample is incubated for at least 1 hours, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. In one embodiment, the sample is incubated at about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C.

In one embodiment, dissociated tissue, for example, dissociated prostate tissue, is separated from the dissociating medium by centrifugation. In one embodiment, the tissue can be further dissociated by incubation of the tissue with trypsin. Trypsin is a serine protease and can hydrolyse proteins. In one embodiment, the trypsin is added to prostate tissue at a final concentration of 6.25 mg/l. In another embodiment, the final concentration of trypsin is at least 1 mg/l, at least 2 mg/l, at least 3 mg/l, at least 4 mg/l, at least 5 mg/l, at least 6 mg/l, at least 7 mg/l, at least 8 mg/l, at least 9 mg/l, at least 10 mg/l, at least 11 mg/l, at least 12 mg/l, at least 13 mg/l, at least 14 mg/l, at least 15 mg/l, at least 16 mg/l, at least 17 mg/l, at least 18 mg/l, at least 19 mg/l, or at least 20 mg/l. In one embodiment, trypsin is added in Hanks' Balanced Salt Solution (HBSS) and EDTA. In one embodiment, the sample is incubated on ice for 1 hour. In one embodiment, the sample is incubated for at least 5 minutes, at least 10 minutes, at least 15 minutes, at least 20 minutes, at least 30 minutes, at least 45 minutes, at least 1 hour, at least 2 hours, at least 3 hours, at least 4 hours, or at least 5 hours. In one embodiment, the sample is incubated at about 0° C., about 1° C., about 2° C., about 3° C., about 4° C., about 5° C., about 6° C., about 7° C., about 8° C., about 9° C., about 10° C., about 15° C., about 20° C., or about 25° C. In one embodiment, trypsin activity is stopped by the addition of HBSS containing 2% FBS. In one embodiment, the HBSS does not contain $Ca^{2+}$. In another embodiment, the HBSS does not contain $Mg^{2+}$. In one embodiment, the HBSS contains $Ca^{2+}$. In another embodiment, the HBSS contains $Mg^{2+}$. In a further embodiment, the HBSS contains 10 mM HEPES. In one embodiment, the HBSS does not contain phenol red. In another embodiment, the HBSS does contain phenol red. In one embodiment, the HBSS contains at least 0.1% FBS, at least 0.2% FBS, at least 0.3% FBS, at least 0.4% FBS, at least 0.5% FBS, at least 0.6% FBS, at least 0.7% FBS, at least 0.8% FBS, at least 0.9% FBS, at least 1% FBS, at least 2% FBS, at least 3% FBS, at least 4% FBS, at least 5% FBS, at least 6% FBS, at least 7% FBS, at least 8% FBS, at least 9% FBS, at least 10% FBS, or at least 20% FBS.

In one embodiment, dissociated tissue, for example, dissociated prostate tissue, is separated from the trypsin solution by centrifugation. In one embodiment, the tissue can be further dissociated by incubation of tissue with dispase. Dispase is a protease and can hydrolyse proteins. In one embodiment, the dispase is dispase II. In one embodiment, the dispase is added to the tissue at a final concentration of 5 mg/ml. In another embodiment, the final concentration of dispase is at least 0.5 mg/ml, at least 1 mg/ml, at least 2 mg/ml, at least 3 mg/ml, at least 4 mg/ml, at least 5 mg/ml, at least 6 mg/ml, at least 7 mg/ml, at least 8 mg/ml, at least 9 mg/ml, at least 10 mg/ml, at least 11 mg/ml, at least 12 mg/ml, at least 13 mg/ml, at least 14 mg/ml, at least 15 mg/ml, at least 16 mg/ml, at least 17 mg/ml, at least 18 mg/ml, at least 19 mg/ml, or at least 20 mg/ml. In one embodiment, dispase is added in Hanks' Balanced Salt Solution (HBSS). In one embodiment, the dispase solution is supplemented with DNase I at a final concentration of 0.1 mg/ml. In another embodiment, the final concentration of DNase I is at least 0.01 mg/ml, at least 0.02 mg/ml, at least 0.03 mg/ml, at least 0.04 mg/ml, at least 0.05 mg/ml units/ml, at least 0.06 mg/ml, at least 0.07 mg/ml, at least 0.08 mg/ml, at least 0.09 mg/ml, at least 0.1 mg/ml, at least 0.2 mg/ml, at least 0.3 mg/ml, at least 0.4 mg/ml, at least 0.5 mg/ml, at least 0.6 mg/ml, at least 0.7 mg/ml, at least 0.8 mg/ml, at least 0.9 mg/ml, or at least 1.0 mg/ml. In one embodiment, the sample is incubated in dispase supplemented with DNase I for 1 minute with rigorous pipetting. In one embodiment, the sample is incubated for at least 30 seconds, at least 1 minute, at least 2 minutes, at least 3 minutes, at least 4 minutes, or at least 5 minutes. In one embodiment, dispase activity is stopped by the addition of HBSS containing 2% FBS. In one embodiment, the HBSS does not contain $Ca^{2+}$. In one embodiment, the HBSS does not contain $Mg^{2+}$. In one embodiment, the HBSS contains $Ca^{2+}$. In another embodiment, the HBSS contains $Mg^{2+}$. In a further embodiment, the HBSS contains 10 mM HEPES. In one embodiment, the HBSS does not contain phenol red. In another embodiment, the HBSS does contain phenol red. In one embodiment, the HBSS contains at least 0.1% FBS, at least 0.2% FBS, at least 0.3% FBS, at least 0.4% FBS, at least 0.5% FBS, at least 0.6% FBS, at least 0.7% FBS, at least 0.8% FBS, at least 0.9% FBS, at least 1% FBS, at least 2% FBS, at least 3% FBS, at least 4% FBS, at least 5% FBS, at least 6% FBS, at least 7% FBS, at least 8% FBS, at least 9% FBS, at least 10% FBS, or at least 20% FBS.

In one embodiment, the dissociated tissue cell suspension, for example, the dissociated prostate tissue cell suspension, is filtered through a 40 μm cell strainer. In one embodiment, the dissociated tissue cell suspension is filtered through a 70 μm cell strainer. In another embodiment, the dissociated tissue cell suspension is filtered through a 100 μm cell strainer.

In one embodiment, cells are dissociated from the tissue, for example, prostate tissue, and subsequently separated, enriched, isolated or purified. The methods comprise obtaining a tissue sample or mixed population of cells, contacting the population of cells with an agent that binds to epithelial cells, for example EpCAM and/or E-cadherin, and separating the subpopulation of cells that are bound by the agent from the subpopulation of cells that are not bound by the agent, wherein the subpopulation that are bound by the agent is enriched for the epithelial marker (for example, EpCAM and/or E-cadherin positive cells). The methods described herein can be performed using any epithelial marker known in the art, including but not limited to CD44R, CD66a, CD75, CD104, CD167, cytokeratin, EpCAM (CD326), CD138, or E-cadherin.

In one embodiment, epithelial cells, for example, prostate epithelial cells, are bound by an fluorescently-tagged EpCAM antibody (e.g. BioLegend, cat #324208 or #118214. In another embodiment, epithelial cells are bound by a fluorescently-tagged E-cadherin antibody (e.g. eBioscience, cat #46-3249-82). In one embodiment, cells can be incubated with ROCK inhibitor. In one embodiment, the ROCK inhibitor is Y-27632. In another embodiment, the concentration of the ROCK inhibitor is 10 μM. In one embodiment, the concentration of the ROCK inhibitor is about 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, 45 μM or 50 μM. In further embodiments, dead cells can be labeled with DAPI.

In another embodiment, the methods comprise obtaining a tissue sample or mixed population of cells, contacting the population of cells with an agent that binds to Nkx3.1, and separating the subpopulation of cells that are bound by the agent from the subpopulation of cells that are not bound by the agent, wherein the subpopulation of cells that are bound by the agent is enriched for Nkx3.1-positive stem cells (e.g., CARNs). In one embodiment, CARNs can be separated using the fluorescent signal from YFP in lineage marked cells. In one embodiment, lineage marked cells are isolated from Nkx3.1-CreER$^{T2}$; R26R-YFP mice.

The methods for separating, enriching, isolating or purifying stem cells from a mixed population of cells according to the invention may be combined with other methods for separating, enriching, isolating or purifying stem or progenitor cells, or epithelial cells, that are known in the art. For example, the methods described herein may be performed in conjunction with techniques that use other stem cell markers or other epithelial cell markers. For example, an additional selection step may be performed either before, after, or simultaneously with the epithelial cell selection step, in which a second agent, such as an antibody, that binds to a second marker is used. In other embodiments, an additional selection step may be performed either before, after, or simultaneously with the Nkx3.1 selection step, in which a second agent, such as an antibody, that binds to a second marker is used. The mixed population of cells can be any source of cells from which to obtain epithelial cells or Nkx3.1-positive cells (e.g., CARNs), including but not limited to a tissue biopsy from a subject, a dissociated cell suspension derived from a tissue biopsy, or a population of cells that have been grown in culture.

In one embodiment, the agent used can be any agent that binds to epithelial cells, for example, prostate epithelial cells, as described above. The term "agent" includes, but is not limited to, small molecule drugs, peptides, proteins, peptidomimetic molecules, and antibodies. It also includes any epithelial cell binding molecule that is labeled with a detectable moiety, such as a histological stain, an enzyme substrate, a fluorescent moiety, a magnetic moiety or a radio-labeled moiety. Such "labeled" agents are particularly useful for embodiments involving isolation or purification of prostate epithelial cells, or detection of prostate epithelials cells. In some embodiments, the agent is an antibody that binds to prostate epithelial cells.

The agent used can be any agent that binds to Nkx3.1, as described above. The term "agent" includes, but is not limited to, small molecule drugs, peptides, proteins, peptidomimetic molecules, and antibodies. It also includes any Nkx3.1 binding molecule that is labeled with a detectable moiety, such as a histological stain, an enzyme substrate, a fluorescent moiety, a magnetic moiety or a radio-labeled moiety. Such "labeled" agents are particularly useful for embodiments involving isolation or purification of Nkx3.1-positive cells, or detection of Nkx3.1-positive cells. In some embodiments, the agent is an antibody that binds to Nkx3.1.

There are many cell separation techniques known in the art (U.S. Pat. No. 4,777,145, U.S. Pat. No. 8,004,661, U.S. Pat. No. 5,367,474, U.S. Pat. No. 4,347,935), and any such technique may be used. For example magnetic cell separation techniques can be used if the agent is labeled with an iron-containing moiety. In one embodiment, cells may also be passed over a solid support that has been conjugated to an agent that binds to epithelial cells, for example, prostate epithelial cells, such that the epithelial cells will be selectively retained on the solid support. Cells may also be separated by density gradient methods, particularly if the agent selected significantly increases the density of the epithelial cells to which it binds. For example, the agent can be a fluorescently labeled antibody against prostate epithelial cells, and the prostate epithelial cells are separated from the other cells using fluorescence activated cell sorting (FACS).

In another embodiment, cells may also be passed over a solid support that has been conjugated to an agent that binds to Nkx3.1, such that the Nkx3.1-positive cells will be selectively retained on the solid support. Cells may also be separated by density gradient methods, particularly if the agent selected significantly increases the density of the Nkx3.1-positive cells to which it binds. For example, the agent can be a fluorescently labeled antibody against Nkx3.1, and the Nkx3.1-positive cells are separated from the other cells using fluorescence activated cell sorting (FACS).

The methods for separating, enriching, isolating or purifying epithelial cells from a mixed population of cells according to the invention may be combined with other methods for separating, enriching, isolating or purifying cells that are known in the art (for example, U.S. Pat. No. 4,777,145, U.S. Pat. No. 8,004,661, U.S. Pat. No. 5,367,474, U.S. Pat. No. 4,347,935) and are described in P. T. Sharpe, 1988, *Laboratory Techniques in Biochemistry and Molecular Biology Volume 18: Methods of Cell Separation*, Elsevier, Amsterdam; M. Zborowski and J. J. Chalmers, 2007, *Laboratory Techniques in Biochemistry and Molecular Biology Volume 32: Magnetic Cell Separation*, Elsevier, Amsterdam; and T. S. Hawley and R. G. Hawley, 2005, *Methods in Molecular Biology Volume 263: Flow Cytometry Protocols*, Humana Press Inc, Totowa, N.J. For example, the methods described herein may be performed in conjunction with techniques that use other markers. For example, additional selection steps maybe performed either before, after, or simultaneously with the epithelial marker selection step, in which a second agent, such as an antibody, that binds to a second marker is used, separating the subpopulation of cells that are bound by the agent from the subpopulation that are not bound by the agent, wherein the subpopulation of cells that are not bound by the agent is enriched. The second marker may be any marker known in the art that reduces the heterogeneity of the epithelial population. For example, the second marker is a marker for epithelial cells (for example, CD44R, CD66a, CD75, CD104, CD167, cytokeratin, EpCAM (CD326), CD138, or E-cadherin). In another embodiment, the second marker is a combination of any markers known in the art that reduce the heterogeneity of the epithelial population.

Isolated cells can be analyzed by any number of methods. The nucleic acids and/or polypeptides of the isolated cells can be analyzed and quantified by any of a number of general means well known to those of skill in the art. These include, for example, analytical biochemical methods such as radiography, electrophoresis, NMR, spectrophotometry, capillary electrophoresis, thin layer chromatography (TLC), high performance liquid chromatography (HPLC), and hyperdiffusion chromatography; various immunological methods, such as immuno-electrophoresis, Southern analysis, Northern analysis, dot-blot analysis, fluid or gel precipitation reactions, immunodiffusion, quadrature radioimmunoassay (RIAs), enzyme-linked immunosorbent assays (ELISAs), immuno-fluorescent assays, gel electrophoresis (e.g., SDS-PAGE), nucleic acid or target or signal amplification methods, radiolabeling, scintillation counting, and affinity chromatography.

Methods of Culturing Organoids, Metastatic Cell Lines and Culture Media

Various culturing parameters can be used with respect to the cell being cultured. Appropriate culture conditions for mammalian cells are well known in the art or can be determined by the skilled artisan (see, for example, Animal Cell Culture: A Practical Approach $2^{nd}$ Ed., Rickwood, D. and Hames, B. D., eds. (Oxford University Press: New York, 1992)), and vary according to the particular cell selected. Commercially available medium can be utilized. Non-limiting examples of medium include, for example, Dulbecco's Modified Eagle Medium (DMEM, Life Technologies), Dulbecco's Modified Eagle Medium/Nutrient Mixture F-12 (DMEM/F-12, Life Technologies), Minimal Essential Medium (MEM, Sigma, St. Louis, Mo.), and hepatocyte medium.

The media described above can be supplemented as necessary with supplementary components or ingredients, including optional components, in appropriate concentrations or amounts, as necessary or desired. Cell medium solutions provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range.

The medium also can be supplemented selectively with one or more components from any of the following categories: (1) salts, for example, magnesium, calcium, and phosphate; (2) hormones and other growth factors such as, serum, insulin, transferrin, epidermal growth factor and fibroblast growth factor; (3) protein and tissue hydrolysates, for example peptone or peptone mixtures which can be obtained from purified gelatin, plant material, or animal byproducts; (4) nucleosides and bases such as, adenosine, thymidine, and hypoxanthine; (5) buffers, such as HEPES; (6) antibiotics, such as gentamycin or ampicillin; (7) cell protective agents, for example, pluronic polyol; and (8) galactose.

The mammalian cell culture that can be used with the present invention is prepared in a medium suitable for the particular cell being cultured. In one embodiment, the culture medium can be one of the aforementioned (for example, DMEM, or basal hepatocyte medium) that is supplemented with serum from a mammalian source (for example, fetal bovine serum (FBS)). For example, DMEM supplemented with FBS can be used to sustain the growth of epithelial cells. In another embodiment, the medium can be hepatocyte medium.

Cells maintained in culture can be passaged by their transfer from a previous culture to a culture with fresh medium. In one embodiment, induced epithelial cells are stably maintained in cell culture for at least 3 passages, at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 20 passages, at least 25 passages, or at least 30 passages.

The cells suitable for culturing according to the methods of the present invention can harbor introduced expression vectors (constructs), such as plasmids and the like. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

In another aspect, the invention provides a cell culture medium comprising a basal hepatocyte medium, Matrigel, FBS and ROCK inhibitor. In one embodiment, the medium comprises 5% Matrigel. In another embodiment, the medium comprises 5% heat-inactivated charcoal-stripped FBS. In a further embodiment, the medium is used to culture prostate organoids. In one embodiment, the organoids are normal. In another embodiment, the organoids are non-cancerous. In a further embodiment, the organoids are cancerous. In a further embodiment, the medium is used to culture metastatic prostate cell lines. In a further embodiment, the medium is used to culture organoids in combination with rat urogenital mesenchyme.

In one embodiment, the culture medium does not comprise Noggin. In another embodiment, the culture medium comprises Noggin. In one embodiment, the culture medium does not comprise R-spondin. In another embodiment, the culture medium comprises R-spondin. In one embodiment, the culture medium comprises DHT. In another embodiment, the culture medium does not comprise DHT. In one embodiment, the culture medium comprises EGF. In another embodiment, the culture medium does not comprise EGF. In one embodiment, culture of the organoids is not dependent on androgens and/or androgen receptor function. In another embodiment, culture of the organoids is dependent on androgens and/or androgen receptor function. In one embodiment, the culture medium comprises serum, including, but not limited to, FBS. In another embodiment, the culture medium does not comprise serum, including, but not limited to, FBS. In one embodiment, the culture medium comprises a ROCK inhibitor. In another embodiment, the culture medium does not comprise a ROCK inhibitor. In one embodiment, the culture medium comprises Matrigel. In another embodiment, the culture medium does not comprise Matrigel.

In one embodiment, epithelial cells, for example, prostate epithelial cells, can be cultured to generate organoids using a Matrigel™ floating method. In one embodiment, metastatic prostate cell lines can generated using a Matrigel™ floating method. In one embodiment, epithelial cells are suspended in hepatocyte medium. In another embodiment, metastatic prostate cancer cells are suspended in hepatocyte medium. In one embodiment, the hepatocyte culture medium is supplemented with 10 ng/ml of EGF (e.g. BD Biosciences, cat #355056). In one embodiment, the hepatocyte culture medium is supplemented with about 1 ng/ml of EGF, 2 ng/ml of EGF, 3 ng/ml of EGF, 4 ng/ml of EGF, 5 ng/ml of EGF, 6 ng/ml of EGF, 7 ng/ml of EGF, 8 ng/ml of EGF, 9 ng/ml of EGF, 10 ng/ml of EGF, 11 ng/ml of EGF, 12 ng/ml of EGF, 13 ng/ml of EGF, 14 ng/ml of EGF, 15 ng/ml of EGF, 16 ng/ml of EGF, 17 ng/ml of EGF, 18 ng/ml of EGF, 19 ng/ml of EGF, about 20 ng/ml of EGF, about 25 ng/ml of EGF, about 30 ng/ml of EGF, about 35 ng/ml of EGF, about 40 ng/ml of EGF, about 45 ng/ml of EGF, about 50 ng/ml of EGF, or more.

In another embodiment, the hepatocyte culture medium is supplemented with at least 1 ng/ml of EGF, at least 2 ng/ml of EGF, at least 3 ng/ml of EGF, at least 4 ng/ml of EGF, at least 5 ng/ml of EGF, at least 6 ng/ml of EGF, at least 7 ng/ml of EGF, at least 8 ng/ml of EGF, at least 9 ng/ml of EGF, at least 10 ng/ml of EGF, at least 15 ng/ml of EGF, at least 20 ng/ml of EGF, at least 30 ng/ml of EGF, at least 40 ng/ml of EGF, or at least 50 ng/ml of EGF.

In one embodiment, the hepatocyte culture medium is supplemented with 2 mM of GlutaMAX™. GlutaMAX™ is the dipeptide L-alanyl-L-glutamine. In one embodiment, the hepatocyte culture medium is supplemented with at least 0.1 mM of GlutaMAX™, at least 0.5 mM of GlutaMAX™, at least 1 mM of GlutaMAX™, at least 1.5 mM of GlutaMAX™, at least 2 mM of GlutaMAX™, at least 3 mM of GlutaMAX™, at least 4 mM of GlutaMAX™, or at least 5 mM of GlutaMAX™. In another embodiment, the hepatocyte culture medium is supplemented with L-glutamine.

In one embodiment, the hepatocyte culture medium is supplemented with 5% Matrigel™. In one embodiment, the hepatocyte culture medium is supplemented with about 0.1% Matrigel™, about 0.2% Matrigel™, about 0.3% Matrigel™, about 0.4% Matrigel™, about 0.5% Matrigel™, about 0.6% Matrigel™, about 0.7% Matrigel™, about 0.8% Matrigel™, about 0.9% Matrigel™, about 1% Matrigel™, about 2% Matrigel™, about 3% Matrigel™, about 4%

Matrigel™, about 5% Matrigel™, about 6% Matrigel™, about 7% Matrigel™, about 8% Matrigel™, about 9% Matrigel™, about 10% Matrigel™, about 15% Matrigel™, or about 20% Matrigel™.

In one embodiment, the hepatocyte culture medium is supplemented with at least 0.1% Matrigel™, at least 0.2% Matrigel™, at least 0.3% Matrigel™, at least 0.4% Matrigel™, at least 0.5% Matrigel™, at least 0.6% Matrigel™, at least 0.7% Matrigel™, at least 0.8% Matrigel™, at least 0.9% Matrigel™, at least 1% Matrigel™, at least 2% Matrigel™, at least 3% Matrigel™, at least 4% Matrigel™, at least 5% Matrigel™, at least 6% Matrigel™, at least 7% Matrigel™, at least 8% Matrigel™, at least 9% Matrigel™, at least 10% Matrigel™, or at least 20% Matrigel™.

In one embodiment, the hepatocyte culture medium is supplemented with 5% FBS. In another embodiment, the FBS is heat-inactivated charcoal-stripped FBS (e.g. Gibco, cat #12676). In a further embodiment, the FBS does not contain testosterone. In another embodiment, the FBS contains testosterone. In one embodiment, the hepatocyte culture medium is supplemented with about 0.1% FBS, about 0.2% FBS, about 0.3% FBS, about 0.4% FBS, about 0.5% FBS, about 0.6% FBS, about 0.7% FBS, about 0.8% FBS, about 0.9% FBS, about 1% FBS, about 2% FBS, about 3% FBS, about 4% FBS, about 5% FBS, about 6% FBS, about 7% FBS, about 8% FBS, about 9% FBS, about 10% FBS, about 15% FBS, or about 20% FBS, or more.

In one embodiment, the hepatocyte culture medium is supplemented with at least 0.1% FBS, at least 0.2% FBS, at least 0.3% FBS, at least 0.4% FBS, at least 0.5% FBS, at least 0.6% FBS, at least 0.7% FBS, at least 0.8% FBS, at least 0.9% FBS, at least 1% FBS, at least 2% FBS, at least 3% FBS, at least 4% FBS, at least 5% FBS, at least 6% FBS, at least 7% FBS, at least 8% FBS, at least 9% FBS, at least 10% FBS, or at least 20% FBS.

In one embodiment, the hepatocyte culture medium is supplemented with a Rho-Associated Coil Kinase (ROCK) inhibitor. In one embodiment, the ROCK inhibitor is Y-27632. In one embodiment, the hepatocyte culture medium is supplemented with 10 µM of Y-27632. In another embodiment, the hepatocyte culture medium is supplemented with about 1 µM of Y-27632, about 2 µM of Y-27632, about 3 µM of Y-27632, about 4 µM of Y-27632, about 5 µM of Y-27632, about 6 µM of Y-27632, about 7 µM of Y-27632, about 8 µM of Y-27632, about 9 µM of Y-27632, about 10 µM of Y-27632, about 11 µM of Y-27632, about 12 µM of Y-27632, about 13 µM of Y-27632, about 14 µM of Y-27632, about 15 µM of Y-27632, about 20 µM of Y-27632, about 30 µM of Y-27632, about 40 µM of Y-27632, or about 50 µM of Y-27632, or more.

In another embodiment, the hepatocyte culture medium is supplemented with at least 1 µM of Y-27632, at least 2 µM of Y-27632, at least 3 µM of Y-27632, at least 4 µM of Y-27632, at least 5 µM of Y-27632, at least 6 µM of Y-27632, at least 7 µM of Y-27632, at least 8 µM of Y-27632, at least 9 µM of Y-27632, at least 10 µM of Y-27632, at least 11 µM of Y-27632, at least 12 µM of Y-27632, at least 13 µM of Y-27632, at least 14 µM of Y-27632, at least 15 µM of Y-27632, at least 20 µM of Y-27632, at least 30 µM of Y-27632, at least 40 µM of Y-27632, or at least 50 µM of Y-27632.

In another embodiment, the hepatocyte culture medium is supplemented with about 10 nM DHT, about 20 nM DHT, about 30 nM DHT, about 40 nM DHT, about 50 nM DHT, about 60 nM DHT, about 70 nM DHT, about 80 nM DHT, about 90 nM DHT, about 100 nM DHT, about 200 nM DHT, about 300 nM DHT, about 400 nM DHT, or about 500 nM DHT, or more.

In another embodiment, the hepatocyte culture medium is supplemented with at least 10 nM DHT, at least 20 nM DHT, at least 30 nM DHT, at least 40 nM DHT, at least 50 nM DHT, at least 60 nM DHT, at least 70 nM DHT, at least 80 nM DHT, at least 90 nM DHT, at least 100 nM DHT, at least 200 nM DHT, at least 300 nM DHT, at least 400 nM DHT, or at least 500 nM DHT, or more.

In one embodiment, the hepatocyte culture medium does not contain Noggin. In another embodiment, the hepatocyte culture medium contains Noggin. In another embodiment, the hepatocyte culture medium does not contain R-spondin. In a further embodiment, the hepatocyte culture medium contains R-spondin.

In one embodiment, the epithelial cells, for example, prostate epithelial cells, are plated into wells of a tissue culture plate. In another embodiment, the epithelial cells are plated into wells of a ultra low attachment 96-well plate (e.g. Corning cat. #3474). The Corning Ultra-Low Attachment cell culture plate is an example of a type of tissue culture support that minimizes or prevents attachment of the cells to the surface of the support. A variety of alternative cell culture supports that minimize or prevent attachment of cells to the surface of the support are known in the art and can be found, for example, in Corning Cell Culture Selection Guide, the contents of which is hereby incorporated by reference in its entirety. In another embodiment, the low attachment cell culture support is a polystyrene plate. In a further embodiment, the low attachment cell culture support is a surface modified polystyrene plate. For example, the surface of the support can be modified to be hydrophilic and/or neutrally charged to minimize or prevent the attachment of the cells to the surface of the support. In another embodiment, the surface of the support can be modified so the plate has a covalently bonded hydrogel surface to minimize or prevent the attachment of the cells to the surface if the plate. In one embodiment, the low attachment cell culture support is a 6 well plate, a 12 well plate, a 24 well plate, a 48 well plate, or a 96 well plate.

In one embodiment, the epithelial cells, for example, prostate epithelial cells, are plated into wells of a 96 well plate at a final density of 5,000 cells per well. In another embodiment, the cells are plated into wells of a 96 well plate at a final density of about 100 cells per well, about 200 cells per well, about 300 cells per well, about 400 cells per well, about 500 cells per well, about 600 cells per well, about 700 cells per well, about 800 cells per well, about 900 cells per well, about 1000 cells per well, about 1,500 cells per well, about 2,000 cells per well, about 2,500 cells per well, about 3,000 cells per well, about 3,500 cells per well, about 4,000 cells per well, about 4,500 cells per well, about 5,000 cells per well, about 5,500 cells per well, about 6,000 cells per well, about 6,500 cells per well, about 7,000 cells per well, about 7,500 cells per well, about 8,000 cells per well, about 8,500 cells per well, about 9,000 cells, about 9,500 cells per well, or about 10,000 cells per well, Without being bound by theory, a well of a 96 well plate has a surface area of about 0.32 cm$^2$.

In another embodiment, cells are plated into wells of a 96 well plate at a final density of at least 100 cells per well, at least 200 cells per well, at least 300 cells per well, at least 400 cells per well, at least 500 cells per well, at least 600 cells per well, at least 700 cells per well, at least 800 cells per well, at least 900 cells per well, at least 1000 cells per well, at least 1,500 cells per well, at least 2,000 cells per well, at least 2,500 cells per well, at least 3,000 cells per well, at least 3,500 cells per well, at least 4,000 cells per well, at least 4,500 cells per well, at least 5,000 cells per well, at least 5,500 cells per well, at least 6,000 cells per well, at least 6,500 cells per well, at least 7,000 cells per well, at least 7,500 cells per well, at least 8,000 cells per well, at least 8,500 cells per well, at least 9,000 cells, at least 9,500 cells per well, or at least 10,000 cells per well.

In one embodiment, the metastatic prostate cancer cells are plated into wells of a tissue culture plate. In another embodiment, the epithelial cells are plated into wells of a Primaria™ 24 well flat bottom surface modified multiwell cell culture plate. In another embodiment, the metastatic prostate cancer cells are plated in wells of a plate that enhances or maximizes attachment of the cells to the wells. In another embodiment, the plate is a polystyrene plate. In a further embodiment, the plate is a surface modified polystyrene plate. Without being bound by theory, the surface of the plate can be modified to incorporate anionic and cationic functional groups to enhance the attachment of the cells to the surface if the plate.

In one embodiment, the metastatic prostate cancer cells are plated into wells of a 24 well plate at a final density of 75,000 cells per well. In another embodiment, the cells are plated into wells of a 24 well plate at a final density of about 50,000 cells per well, about 55,000 cells per well, about 60,000 cells per well, about 65,000 cells per well, about 70,000 cells per well, about 75,000 cells per well, about 80,000 cells per well, about 85,000 cells per well, about 90,000 cells per well, about 95,000 cells per well, or about 100,000 cells per well. Without being bound by theory, a well of a 24 well plate has a surface area of about 1.9 cm$^2$.

In another embodiment, cells are plated into wells of a 24 well plate at a final density of at least 50,000 cells per well, at least 55,000 cells per well, at least 60,000 cells per well, at least 65,000 cells per well, at least 70,000 cells per well, at least 75,000 cells per well, at least 80,000 cells per well, at least 85,000 cells per well, at least 90,000 cells per well, at least 95,000 cells per well, or at least 100,000 cells per well.

In one embodiment, the epithelial cells or metastatic prostate cells are cultured with about 10 nM dihydrotestosterone (DHT), with about 20 nM DHT, with about 30 nM DHT, with about 40 nM DHT, with about 50 nM DHT, with about 60 nM DHT, with about 70 nM DHT, with about 80 nM DHT, with about 90 nM DHT, with about 100 nM DHT, with about 110 nM DHT, with about 120 nM DHT, with about 130 nM DHT, with about 140 nM DHT, with about 150 nM DHT, with about 160 nM DHT, with about 170 nM DHT, with about 180 nM DHT, with about 190 nM DHT, with about 200 nM DHT, with about 300 nM DHT, with about 400 nM DHT, or with about 500 nM DHT, or more.

In one embodiment, the epithelial cells or metastatic prostate cells are cultured with at least 10 nM dihydrotestosterone (DHT), with at least 20 nM DHT, with at least 30 nM DHT, with at least 40 nM DHT, with at least 50 nM DHT, with at least 60 nM DHT, with at least 70 nM DHT, with at least 80 nM DHT, with at least 90 nM DHT, with at least 100 nM DHT, with at least 110 nM DHT, with at least 120 nM DHT, with at least 130 nM DHT, with at least 140 nM DHT, with at least 150 nM DHT, with at least 160 nM DHT, with at least 170 nM DHT, with at least 180 nM DHT, with at least 190 nM DHT, with at least 200 nM DHT, with at least 300 nM DHT, with at least 400 nM DHT, or with at least 500 nM DHT. In one embodiment, the epithelial cells are cultured without dihydrotestosterone (DHT).

In one embodiment, a total change of media occurs every 12 days. In one embodiment, a total change of media occurs every 4 days. In another embodiment, a total change of media occurs at least every day, at least every 2 days, at least every 3 days, at least every 4 days, at least every 5 days, at least every 6 days, at least every 7 days, at least every 8 days, at least every 9 days, at least every 10 days, at least every 11 days, at least every 12 days, at least every 13 days, or at least every 14 days.

In another embodiment, epithelial cells, for example, prostate epithelial cells, can be cultured to generate organoids using a Matrigel™ embedding method. In one embodiment, epithelial cells are suspended in hepatocyte medium. In one embodiment, the hepatocyte culture medium is supplemented with 10 ng/ml of EGF (e.g. BD Biosciences, cat #355056). In one embodiment, the hepatocyte culture medium is supplemented with about 1 ng/ml of EGF, 2 ng/ml of EGF, 3 ng/ml of EGF, 4 ng/ml of EGF, 5 ng/ml of EGF, 6 ng/ml of EGF, 7 ng/ml of EGF, 8 ng/ml of EGF, 9 ng/ml of EGF, 10 ng/ml of EGF, 11 ng/ml of EGF, 12 ng/ml of EGF, 13 ng/ml of EGF, 14 ng/ml of EGF, 15 ng/ml of EGF, 16 ng/ml of EGF, 17 ng/ml of EGF, 18 ng/ml of EGF, 19 ng/ml of EGF, about 20 ng/ml of EGF, about 25 ng/ml of EGF, about 30 ng/ml of EGF, about 35 ng/ml of EGF, about 40 ng/ml of EGF, about 45 ng/ml of EGF, about 50 ng/ml of EGF, or more.

In another embodiment, the hepatocyte culture medium is supplemented with at least 1 ng/ml of EGF, at least 2 ng/ml of EGF, at least 3 ng/ml of EGF, at least 4 ng/ml of EGF, at least 5 ng/ml of EGF, at least 6 ng/ml of EGF, at least 7 ng/ml of EGF, at least 8 ng/ml of EGF, at least 9 ng/ml of EGF, at least 10 ng/ml of EGF, at least 15 ng/ml of EGF, at least 20 ng/ml of EGF, at least 30 ng/ml of EGF, at least 40 ng/ml of EGF, or at least 50 ng/ml of EGF.

In one embodiment, the hepatocyte culture medium is supplemented with 2 mM of GlutaMAX™. GlutaMAX™ is the dipeptide L-alanyl-L-glutamine. In one embodiment, the hepatocyte culture medium is supplemented with at least 0.1 mM of GlutaMAX™, at least 0.5 mM of GlutaMAX™, at least 1 mM of GlutaMAX™, at least 1.5 mM of GlutaMAX™, at least 2 mM of GlutaMAX™, at least 3 mM of GlutaMAX™, at least 4 mM of GlutaMAX™, or at least 5 mM of GlutaMAX™. In another embodiment, the hepatocyte culture medium is supplemented with L-glutamine.

In one embodiment, the hepatocyte culture medium is not supplemented with Matrigel™. In one embodiment, the hepatocyte culture medium is supplemented with Matrigel™.

In one embodiment, the hepatocyte culture medium is supplemented with 5% FBS. In another embodiment, the FBS is heat-inactivated charcoal-stripped FBS (e.g. Gibco, cat #12676). In one embodiment, the hepatocyte culture medium is supplemented with about 0.1% FBS, about 0.2% FBS, about 0.3% FBS, about 0.4% FBS, about 0.5% FBS, about 0.6% FBS, about 0.7% FBS, about 0.8% FBS, about 0.9% FBS, about 1% FBS, about 2% FBS, about 3% FBS, about 4% FBS, about 5% FBS, about 6% FBS, about 7% FBS, about 8% FBS, about 9% FBS, about 10% FBS, about 15% FBS, or about 20% FBS, or more.

In one embodiment, the hepatocyte culture medium is supplemented with at least 0.1% FBS, at least 0.2% FBS, at least 0.3% FBS, at least 0.4% FBS, at least 0.5% FBS, at least 0.6% FBS, at least 0.7% FBS, at least 0.8% FBS, at least 0.9% FBS, at least 1% FBS, at least 2% FBS, at least 3% FBS, at least 4% FBS, at least 5% FBS, at least 6% FBS, at least 7% FBS, at least 8% FBS, at least 9% FBS, at least 10% FBS, or at least 20% FBS.

In one embodiment, the hepatocyte culture medium is supplemented with a Rho-Associated Coil Kinase (ROCK) inhibitor. In one embodiment, the ROCK inhibitor is Y-27632. In one embodiment, the hepatocyte culture medium is supplemented with 10 µM of Y-27632. In another embodiment, the hepatocyte culture medium is supplemented with about 10 µM of Y-27632, about 2 µM of Y-27632, about 3 µM of Y-27632, about 4 µM of Y-27632, about 5 µM of Y-27632, about 6 µM of Y-27632, about 7 µM of Y-27632, about 8 µM of Y-27632, about 9 µM of Y-27632, about 10 µM of Y-27632, about 11 µM of Y-27632, about 12 µM of Y-27632, about 13 µM of Y-27632, about 14 µM of Y-27632, about 15 µM of Y-27632, about 20 µM of Y-27632, about 30 µM of Y-27632, about 40 µM of Y-27632, or about 50 µM of Y-27632.

In another embodiment, the hepatocyte culture medium is supplemented with at least 1 µM of Y-27632, at least 2 µM of Y-27632, at least 3 µM of Y-27632, at least 4 µM of Y-27632, at least 5 µM of Y-27632, at least 6 µM of Y-27632, at least 7 µM of Y-27632, at least 8 µM of Y-27632, at least 9 µM of Y-27632, at least 10 µM of Y-27632, at least 11 µM of Y-27632, at least 12 µM of Y-27632, at least 13 µM of Y-27632, at least 14 µM of Y-27632, at least 15 µM of Y-27632, at least 20 µM of Y-27632, at least 30 µM of Y-27632, at least 40 µM of Y-27632, or at least 50 µM of Y-27632.

In one embodiment, the hepatocyte culture medium does not contain Noggin. In another embodiment, the hepatocyte culture medium contains Noggin. In another embodiment, the hepatocyte culture medium does not contain R-spondin. In a further embodiment, the hepatocyte culture medium contains R-spondin.

In one embodiment, the epithelial cells, for example, prostate epithelial cells, are suspended in Matrigel™. In one embodiment, the epithelial cell-Matrigel™ suspension is plated around the rim of tissue culture plates. In one embodiment, the tissue culture plate is a 24 well plate. In one embodiment, after the Matrigel™ solidifies, culture media is added to the wells. In one embodiment, the cell culture support is a 6 well plate, a 12 well plate, a 24 well plate, a 48 well plate, or a 96 well plate.

In one embodiment, the cells, for example, dissociated prostate epithelial cells, dissociated metastatic prostate cancer cells, CARNs, or prostate cancer cell line cells, are contacted with a Matrigel solution that forms a matrix and an overlay layer of liquid culture medium is provided. In one embodiment, the Matrigel solution and cells are plated in a cell culture support. In one embodiment, the Matrigel solution and cells are plated into wells of a tissue culture plate. In another embodiment, the plate is a polystyrene plate. In a further embodiment, the cell culture support is a surface modified polystyrene plate. In one embodiment, the support surface is pre-coated by rinsing Matrigel solution over the support surface and incubating the cell culture support at 37° C. for at least 30 minutes. In one embodiment, the Matrigel solution comprises hepatocyte medium and Matrigel. In one embodiment, the Matrigel solution comprises serum, including, but not limited to, FBS. In another embodiment, the Matrigel solution does not comprise serum, including, but not limited to, FBS. In one embodiment, the Matrigel solution comprises 100% Matrigel. In one embodiment, the Matrigel solution comprises 3 parts Matrigel to 2 parts hepatocyte medium. In one embodiment, the Matrigel solution comprises 60% Matrigel and 40% hepatocyte medium. In one embodiment, the cells are plated into wells of a 6 well plate, a 12 well plate, a 24 well plate, a 48 well plate, or a 96 well plate.

In one embodiment, the cells, for example, dissociated prostate epithelial cells, dissociated metastatic prostate cancer cells, CARNs, or prostate cancer cell line cells, are contacted with a collagen solution that forms a matrix and an overlay layer of liquid culture medium is provided. In one embodiment the collagen solution and cells are plated in a cell culture support. In one embodiment the collagen solution and cells are plated into wells of a tissue culture plate. In another embodiment, the plate is a polystyrene plate. In a further embodiment, the cell culture support is a surface modified polystyrene plate. In one embodiment, the support surface is pre-coated by rinsing collagen solution over the support surface and incubating the cell culture support at 37° C. for at least 30 minutes. In one embodiment, the collagen solution comprises setting solution and collagen. In one embodiment, the collagen solution comprises 9 parts collagen to 1 parts setting solution. In one embodiment, setting solution comprises EBSS, sodium bicarbonate and sodium hydroxide. In one embodiment, the cells are plated into wells of a 6 well plate, a 12 well plate, a 24 well plate, a 48 well plate, or a 96 well plate. In another embodiment, the cells are combined with rat urogenital mesenchyme before contacting with the collagen solution.

In one embodiment, the epithelial cells, for example, prostate epithelial cells, are plated into wells of a 24 well plate at a final density of 5,000 cells per well. In another embodiment, the cells are plated into wells of a 96 well plate at a final density of about 100 cells per well, about 200 cells per well, about 300 cells per well, about 400 cells per well, about 500 cells per well, about 600 cells per well, about 700 cells per well, about 800 cells per well, about 900 cells per well, about 1000 cells per well, about 1,500 cells per well, about 2,000 cells per well, about 2,500 cells per well, about 3,000 cells per well, about 3,500 cells per well, about 4,000 cells per well, about 4,500 cells per well, about 5,000 cells per well, about 5,500 cells per well, about 6,000 cells per well, about 6,500 cells per well, about 7,000 cells per well, about 7,500 cells per well, about 8,000 cells per well, about 8,500 cells per well, about 9,000 cells, about 9,500 cells per well, or about 10,000 cells per well, Without being bound by theory, a well of a 24 well plate has a surface area of about 1.9 $cm^2$.

In another embodiment, cells are plated into wells of a 24 well plate at a final density of at least 100 cells per well, at least 200 cells per well, at least 300 cells per well, at least 400 cells per well, at least 500 cells per well, at least 600 cells per well, at least 700 cells per well, at least 800 cells per well, at least 900 cells per well, at least 1000 cells per well, at least 1,500 cells per well, at least 2,000 cells per well, at least 2,500 cells per well, at least 3,000 cells per well, at least 3,500 cells per well, at least 4,000 cells per well, at least 4,500 cells per well, at least 5,000 cells per well, at least 5,500 cells per well, at least 6,000 cells per well, at least 6,500 cells per well, at least 7,000 cells per well, at least 7,500 cells per well, at least 8,000 cells per well, at least 8,500 cells per well, at least 9,000 cells, at least 9,500 cells per well, or at least 10,000 cells per well.

In one embodiment, the epithelial cells are cultured with 100 nM dihydrotestosterone (DHT). In one embodiment, the epithelial cells are cultured with about 10 nM dihydrotestosterone (DHT), with about 20 nM DHT, with about 30 nM DHT, with about 40 nM DHT, with about 50 nM DHT, with about 60 nM DHT, with about 70 nM DHT, with about 80 nM DHT, with about 90 nM DHT, with about 100 nM DHT, with about 110 nM DHT, with about 120 nM DHT, with about 130 nM DHT, with about 140 nM DHT, with about 150 nM DHT, with about 160 nM DHT, with about 170 nM DHT, with about 180 nM DHT, with about 190 nM DHT, with about 200 nM DHT, with about 300 nM DHT, with about 400 nM DHT, or with about 500 nM DHT, or more.

In one embodiment, the epithelial cells are cultured with at least 10 nM dihydrotestosterone (DHT), with at least 20 nM DHT, with at least 30 nM DHT, with at least 40 nM DHT, with at least 50 nM DHT, with at least 60 nM DHT, with at least 70 nM DHT, with at least 80 nM DHT, with at least 90 nM DHT, with at least 100 nM DHT, with at least 110 nM DHT, with at least 120 nM DHT, with at least 130 nM DHT, with at least 140 nM DHT, with at least 150 nM DHT, with at least 160 nM DHT, with at least 170 nM DHT, with at least 180 nM DHT, with at least 190 nM DHT, with at least 200 nM DHT, with at least 300 nM DHT, with at least 400 nM DHT, or with at least 500 nM DHT. In one embodiment, the prostate epithelial cells are cultured without dihydrotestosterone (DHT).

In one embodiment, a change of media occurs every 4 days. In one embodiment, the change of media is a half-changed of media. In another embodiment, the change of media is a full change of media. In another embodiment, a change of media occurs at least every day, at least every 2 days, at least every 3 days, at least every 4 days, at least every 5 days, at least every 6 days, at least every 7 days, at least every 8 days, at least every 9 days, at least every 10 days, at least every 11 days, at least every 12 days, at least every 13 days, or at least every 14 days. In one embodiment, old media is removed before the addition of fresh media. In one embodiment, organoids are separated from old media by centrifugation, followed by the addition of fresh media to the organoids.

In one embodiment, a total change of media occurs every 3 days. In one embodiment, a total change of media occurs every 4 days. In another embodiment, a total change of media occurs at least every day, at least every 2 days, at least every 3 days, at least every 4 days, at least every 5 days, at least every 6 days, at least every 7 days, at least every 8 days, at least every 9 days, at least every 10 days, at least every 11 days, at least every 12 days, at least every 13 days, or at least every 14 days.

In one embodiment, when the prostate organoids become large the organoids are passaged. In one embodiment, organoids are passaged 3 to 5 weeks after plating. In another embodiment, organoids are passaged about 1 week after plating, about 2 weeks after plating, about 3 weeks after plating, about 4 weeks after plating, about 5 weeks after plating, about 6 weeks after plating, or about 7 weeks after plating.

Organoids can be passaged by their transfer from a previous culture to a culture with fresh medium. In one embodiment, induced organoids are stably maintained in cell culture for at least 3 passages, at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 20 passages, at least 25 passages, or at least 30 passages.

In one embodiment, the prostate organoids, are prepared for passaging by separation of the organoids from the media by centrifugation. In one embodiment, organoids can be washed in cold PBS.

In one embodiment, the organoids, for example, the prostate organoids, are passaged by addition of trypsin to the organoids. In one embodiment, the trypsin is added for 5 minutes at 37° C. In one embodiment, the trypsin is added for 30 minutes at 4° C. In one embodiment, the cells are incubated for at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 25 minutes, or at least 30 minutes. In one embodiment, the sample is incubated at about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. In one embodiment, the trypsin is added to the prostate organoids at a final concentration of 0.25%. In another embodiment, the final concentration of trypsin is at least 0.1%, at least 0.2%, at least 0.3%, at least 0.4%, at least 0.5%, at least 1%, at least 2%, at least 3%, at least 4%, or at least 5%. In one embodiment, trypsin is added in Hanks' Balanced Salt Solution (HBSS) and EDTA. In one embodiment the trypsin activity is stopped by the addition of HBSS containing 2% FBS. In one embodiment, the HBSS does not contain $Ca^{2+}$. In another embodiment, the HBSS does not contain $Mg^{2+}$. In one embodiment, the HBSS contains $Ca^{2+}$. In another embodiment, the HBSS contains $Mg^{2+}$. In a further embodiment, the HBSS contains 10 mM HEPES. In one embodiment, the HBSS does not contain phenol red. In another embodiment, the HBSS does contain phenol red. In one embodiment, the HBSS contains at least 0.1% FBS, at least 0.2% FBS, at least 0.3% FBS, at least 0.4% FBS, at least 0.5% FBS, at least 0.6% FBS, at least 0.7% FBS, at least 0.8% FBS, at least 0.9% FBS, at least 1% FBS, at least 2% FBS, at least 3% FBS, at least 4% FBS, at least 5% FBS, at least 6% FBS, at least 7% FBS, at least 8% FBS, at least 9% FBS, at least 10% FBS, or at least 20% FBS.

In one embodiment, trypsin treated organoids, for example, trypsin treated prostate organoids, are separated from the trypsin containing medium by centrifugation. In one embodiment, the cells are plated into a new 96-well low attachment cell culture plate. In one embodiment, the dissociated organoid cells, for example, dissociated prostate organoid cells, are plated into wells of a 96 well plate at a final density of 5,000 cells per well. In another embodiment, the cells are plated into wells of a 96 well plate at a final density of about 2,500 cells per well, about 3,000 cells per well, about 3,500 cells per well, about 4,000 cells per well, about 4,500 cells per well, about 5,000 cells per well, about 5,500 cells per well, about 6,000 cells per well, about 6,500 cells per well, about 7,000 cells per well, or about 7,500 cells per well. Without being bound by theory, a well of a 96 well plate has a surface area of about 0.32 $cm^2$.

In another embodiment, cells are plated into wells of a 96 well plate at a final density of at least 2,500 cells per well, at least 3,000 cells per well, at least 3,500 cells per well, at least 4,000 cells per well, at least 4,500 cells per well, at least 5,000 cells per well, at least 5,500 cells per well, at least 6,000 cells per well, at least 6,500 cells per well, or at least 7,000 cells per well.

In one embodiment, the organoids, for example, the prostate organoids, are prepared for passaging by releasing the organoids from the embedded Matrigel. In one embodiment, the Matrigel is dissolved by addition of Dispase to each well. In one embodiment, Dispase is added to the Matrigel matrix after removal of the overlaid liquid culture medium. In one embodiment, the Dispase is added at a final concentration of 1 mg/ml for 30 minutes at 37° C. In another embodiment, the final concentration of dispase is at least 0.2 mg/ml, at least 0.3 mg/ml, at least 0.4 mg/ml, at least 0.5 mg/ml, at least 0.6 mg/ml, at least 0.7 mg/ml, at least 0.8 mg/ml, at least 0.9 mg/ml, at least 1.0 mg/ml, at least 1.5 mg/ml, at least 2.0 mg/ml, at least 2.5 mg/ml, or at least 3 mg/ml. In one embodiment, the cells are incubated for at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 22 minutes, at least 23 minutes, at least 24 minutes, at least 25 minutes, at least 26 minutes, at least 27 minutes, at least 28 minutes, at least 29 minutes, at least 30 minutes, at least 40 minutes, at least 50 minutes, or at least 60 minutes. In one embodiment, the sample is incubated at about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. In one embodiment, the dispase solution is discarded and residual Matrigel is removed with cold PBS.

In one embodiment the Dispase activity is stopped by the addition of HBSS containing 2% FBS. In one embodiment, the HBSS does not contain $Ca^{2+}$. In another embodiment, the HBSS does not contain $Mg^{2+}$. In one embodiment, the HBSS contains $Ca^{2+}$. In another embodiment, the HBSS contains $Mg^{2+}$. In a further embodiment, the HBSS contains 10 mM HEPES. In one embodiment, the HBSS does not contain phenol red. In another embodiment, the HBSS does contain phenol red. In one embodiment, the HBSS contains at least 0.1% FBS, at least 0.2% FBS, at least 0.3% FBS, at least 0.4% FBS, at least 0.5% FBS, at least 0.6% FBS, at least 0.7% FBS, at least 0.8% FBS, at least 0.9% FBS, at least 1% FBS, at least 2% FBS, at least 3% FBS, at least 4% FBS, at least 5% FBS, at least 6% FBS, at least 7% FBS, at least 8% FBS, at least 9% FBS, at least 10% FBS, or at least 20% FBS.

The released organoids, for example, released prostate organoids, are separated from the Dispase containing medium by centrifugation. In one embodiment, the released organoids can be washed in 1× Phosphate Buffered Saline (PBS).

In one embodiment, the organoids, for example, the prostate organoids, are prepared for passaging by releasing the organoids from the embedded collagen. In one embodiment, the collagen is dissolved by addition of collagenase to each well. In one embodiment, collagenase is added to the collagen matrix after removal of the overlaid liquid culture medium. In one embodiment, the collagenase is added at a final concentration of 0.25 mg/ml for 30 minutes at 37° C. In another embodiment, the final concentration of dispase is at least 0.1 mg/ml, at least 0.3 mg/ml, at least 0.4 mg/ml, at least 0.5 mg/ml, at least 0.6 mg/ml, at least 0.7 mg/ml, at least 0.8 mg/ml, at least 0.9 mg/ml, or at least 1.0 mg/ml. In one embodiment, the cells are incubated for at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 22 minutes, at least 23 minutes, at least 24 minutes, at least 25 minutes, at least 26 minutes, at least 27 minutes, at least 28 minutes, at least 29 minutes, at least 30 minutes, at least 40 minutes, at least 50 minutes, or at least 60 minutes. In one embodiment, the sample is incubated at about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. In one embodiment, the collagenase solution is discarded and residual collagen is removed with cold PBS.

In one embodiment the collagenase activity is stopped by the addition of HBSS containing 2% FBS. In one embodiment, the HBSS does not contain $Ca^{2+}$. In another embodiment, the HBSS does not contain $Mg^{2+}$. In one embodiment, the HBSS contains $Ca^{2+}$. In another embodiment, the HBSS contains $Mg^{2+}$. In a further embodiment, the HBSS contains 10 mM HEPES. In one embodiment, the HBSS does not contain phenol red. In another embodiment, the HBSS does contain phenol red. In one embodiment, the HBSS contains at least 0.1% FBS, at least 0.2% FBS, at least 0.3% FBS, at least 0.4% FBS, at least 0.5% FBS, at least 0.6% FBS, at least 0.7% FBS, at least 0.8% FBS, at least 0.9% FBS, at least 1% FBS, at least 2% FBS, at least 3% FBS, at least 4% FBS, at least 5% FBS, at least 6% FBS, at least 7% FBS, at least 8% FBS, at least 9% FBS, at least 10% FBS, or at least 20% FBS.

The released organoids, for example, released prostate organoids, are separated from the collagenase containing medium by centrifugation. In one embodiment, the released organoids can be washed in 1× Phosphate Buffered Saline (PBS).

In one embodiment, the released prostate organoids are plated as described for the Matrigel or collagen embedding methods.

In one embodiment, the dissociated organoids are frozen by resuspending the organoids in a freezing media. In one embodiment, the freezing media comprises hepatocyte medium, FBS, and DMSO. In one embodiment, the freezing media contains about 50% FBS, about 40% hepatocyte media, and about 10% DMSO. In one embodiment, the FBS is heat-inactivated charcoal-stripped FBS. In one embodiment, cells are gradually frozen to less than or equal to −80° C.

In one embodiment, frozen cells, for example, frozen prostate organoids, can be thawed. In one embodiment, the frozen cells are thawed rapidly in at about 37° C. and immediately diluted in HBSS containing 2% FBS. In one embodiment, the thawed cells are immediately separated from the freezing media by centrifugation. In one embodiment, the cell clusters are plated as described for the Matrigel floating, Matrigel embedding, or collagen embedding method.

In one embodiment, organoids, for example, prostate organoids can be converted to two-dimensional adherent culture. In one embodiment, prostate organoids can be converted at any point after successful establishment of primary organoid cultures. In one embodiment, prostate organoids can be converted after passaging of organoids. In one embodiment, the released organoids, for example, the released prostate organoids, are dissociated into single cells and converted to two-dimensional adherent culture. For example, in one embodiment, after passaging, trypsin treated prostate organoids, are separated from the prostate containing medium by centrifugation. In another embodiment, the dissociated prostate organoid cells are plated into wells of a Primaria™ 24 well flat bottom surface modified multiwell cell culture plate. In another embodiment, the dissociated prostate organoid cells are plated in wells of a plate that enhances or maximizes attachment of the cells to the wells. In another embodiment, the plate is a polystyrene plate. In a further embodiment, the plate is a surface modified polystyrene plate. Without being bound by theory, the surface of the plate can be modified to incorporate anionic and cationic functional groups to enhance the attachment of the cells to the surface if the plate.

Prostate metastatic cell lines can be passaged by their transfer from a previous culture to a culture with fresh medium. In one embodiment, prostate metastatic cell lines are stably maintained in cell culture for at least 3 passages, at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 20 passages, at least 25 passages, or at least 30 passages.

In one embodiment, the prostate metastatic cell lines, are prepared for passaging by removal of the media by aspiration. In one embodiment, organoids can be washed in cold PBS.

In one embodiment, the prostate metastatic cell lines are passaged by addition of trypsin to each well. In one embodiment, the trypsin is added for 5 minutes at 37° C. In one embodiment, the trypsin is added for 30 minutes at 4° C. In one embodiment, the cells are incubated for at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 25 minutes, or at least 30 minutes. In one embodiment, the sample is incubated at about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. In one embodiment, the trypsin is added to the prostate metastatic cell lines at a final concentration of 0.25%. In another embodiment, the final concentration of trypsin is at least 0.1%, at least 0.2%, at least 0.3%, at least 0.4%, at least 0.5%, at least 1%, at least 2%, at least 3%, at least 4%, or at least 5%. In one embodiment, trypsin is added in Hanks' Balanced Salt Solution (HBSS) and EDTA. In one embodiment the trypsin activity is stopped by the addition of HBSS containing 2% FBS. In one embodiment, the HBSS does not contain $Ca^{2+}$. In another embodiment, the HBSS does not contain $Mg^{2+}$. In one embodiment, the HBSS contains $Ca^{2+}$. In another embodiment, the HBSS contains $Mg^{2+}$. In a further embodiment, the HBSS contains 10 mM HEPES. In one embodiment, the HBSS does not contain phenol red. In another embodiment, the HBSS does contain phenol red. In one embodiment, the HBSS contains at least 0.1% FBS, at least 0.2% FBS, at least 0.3% FBS, at least 0.4% FBS, at least 0.5% FBS, at least 0.6% FBS, at least 0.7% FBS, at least 0.8% FBS, at least 0.9% FBS, at least 1% FBS, at least 2% FBS, at least 3% FBS, at least 4% FBS, at least 5% FBS, at least 6% FBS, at least 7% FBS, at least 8% FBS, at least 9% FBS, at least 10% FBS, or at least 20% FBS.

In one embodiment, detached cells, for example, detached prostate metastatic cells, are separated from the trypsin containing medium by centrifugation. In one embodiment, the cells are plated into a new Primaria™ 24 well flat bottom surface modified multiwall cell culture plate. In one embodiment, the cells are plated into a new 96 well low attachment plate. Without being bound by theory, prostate metastatic cell lines can be converted to organoids. In one embodiment, the cells are plated as described for the Matrigel floating method. In one embodiment, the cells are plated as described for the Matrigel embedding method. In one embodiment, the cells are plated by the collagen embedding method.

In one embodiment, detached cells, for example, detached prostate metastatic cells, are separated from the trypsin containing medium by centrifugation. In one embodiment, the cells are frozen by resuspending the detached cells in a freezing media. In one embodiment, the freezing media comprises hepatocyte medium, FBS, and DMSO. In one embodiment, the freezing media contains about 50% FBS, about 40% hepatocyte media, and about 10% DMSO. In one embodiment, the FBS is heat-inactivated charcoal-stripped FBS. In one embodiment, cells are gradually frozen to less than or equal to −80° C.

In one embodiment, frozen cells, for example, frozen prostate metastatic cell lines, can be thawed. In one embodiment, the frozen cells are thawed rapidly in at about 37° C. and immediately diluted in HBSS containing 2% FBS. In one embodiment, the thawed cells are immediately separated from the freezing media by centrifugation. In one embodiment, the cells are plated into a new Primaria™ 24 well flat bottom surface modified multiwell cell culture plate. In one embodiment, the cells are plated into a new 96 well low attachment plate. Without being bound by theory, prostate metastatic cell lines can be converted to organoids. In one embodiment, the cells are plated as described for the Matrigel floating method. In one embodiment, the cells are plated as described for the Matrigel embedding method. In one embodiment, the cells are plated by the collagen embedding method.

Organoids

In another aspect, the invention provides a prostate organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate organoids in culture. In one embodiment, the organoid displays the luminal differentiation of non-cancerous prostate. In another embodiment, the organoid displays the basal differentiation of non-cancerous prostate. In one embodiment, the organoid expresses CK8 and/or CK18. In another embodiment, the organoid expresses CK5 and/or p63. In one embodiment, the organoid expresses Nkx3.1. In another embodiment, the organoid expresses androgen receptor and/or Foxa1.

In another aspect, the invention provides a prostate organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the organoid displays the luminal differentiation of non-cancerous prostate. In another embodiment, the organoid displays the basal differentiation of non-cancerous prostate. In one embodiment, the organoid expresses CK8 and/or CK18. In another embodiment, the organoid expresses CK5 and/or p63. In one embodiment, the organoid expresses Nkx3.1. In another embodiment, the organoid expresses androgen receptor and/or Foxa1.

In another aspect, the invention provides a prostate organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the organoid displays the luminal differentiation of non-cancerous prostate. In another embodiment, the organoid displays the basal differentiation of non-cancerous prostate. In one embodiment, the organoid expresses CK8 and/or CK18. In another embodiment, the organoid expresses CK5 and/or p63. In one embodiment, the organoid expresses Nkx3.1. In another embodiment, the organoid expresses androgen receptor and/or Foxa1.

In another aspect, the invention provides a prostate organoid, wherein the organoid is obtained by a method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate organoids in culture. In one embodiment, the organoid displays the luminal differentiation of non-cancerous prostate. In another embodiment, the organoid displays the basal differentiation of non-cancerous prostate. In one embodiment, the organoid expresses CK8 and/or CK18. In another embodiment, the organoid expresses CK5 and/or p63. In one embodiment, the organoid expresses Nkx3.1. In another embodiment, the organoid expresses androgen receptor and/or Foxa1.

In another aspect, the invention provides a prostate organoid, wherein the organoid is obtained by a method comprising: (a) obtaining a sample of prostate tissue from a subject; (b) isolating CARNs from the sample of prostate tissue; (c) contacting the CARNs with a Matrigel solution and plating in a cell culture support, wherein the Matrigel solution forms a matrix; (d) providing an overlay layer of liquid culture medium comprising basal hepatocyte medium, FBS and ROCK inhibitor; and (e) incubating the culture of (d) wherein the CARNs form prostate organoids in culture. In one embodiment, the organoid displays the luminal differentiation of non-cancerous prostate. In another embodiment, the organoid displays the basal differentiation of non-cancerous prostate. In one embodiment, the organoid expresses CK8 and/or CK18. In another embodiment, the organoid expresses CK5 and/or p63. In one embodiment, the organoid expresses Nkx3.1. In another embodiment, the organoid expresses androgen receptor and/or Foxa1.

In another aspect, the invention provides a prostate organoid, wherein the organoid is obtained by a method comprising: (a) obtaining a sample of prostate tissue from a subject; (b) isolating CARNs from the sample of prostate tissue; (c) contacting the CARNs with a collagen solution and plating in a cell culture support, wherein the collagen solution forms a matrix; (d) providing an overlay layer of liquid culture medium comprising basal hepatocyte medium, FBS and ROCK inhibitor; and (e) incubating the culture of (d) wherein the CARNs form prostate organoids in culture. In one embodiment, the CARNs are non-cancerous cells. In another embodiment, the CARNs are transformed cells. In yet another embodiment, the CARNs are cancerous cells. In one embodiment, the organoid displays the luminal differentiation of non-cancerous prostate. In another embodiment, the organoid displays the basal differentiation of non-cancerous prostate. In one embodiment, the organoid expresses CK8 and/or CK18. In another embodiment, the organoid expresses CK5 and/or p63. In one embodiment, the organoid expresses Nkx3.1. In another embodiment, the organoid expresses androgen receptor and/or Foxa1.

In another aspect, the invention provides a prostate tumor organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate tumor organoids in culture. In one embodiment, the organoid displays the luminal phenotype of prostate tumors. In another embodiment, the organoid expresses pAkt. In one embodiment, the organoid expresses Nkx3.1. In another embodiment, the organoid expresses androgen receptor and/or Foxa1.

In another aspect, the invention provides a prostate tumor organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the organoid displays the luminal phenotype of prostate tumors. In another embodiment, the organoid expresses pAkt. In one embodiment, the organoid expresses Nkx3.1. In another embodiment, the organoid expresses androgen receptor and/or Foxa1.

In another aspect, the invention provides a prostate tumor organoid, wherein the organoid is obtained by a method comprising: (a) obtaining a sample of prostate tissue from a subject; (b) dissociating the sample of prostate tissue; (c) isolating dissociated prostate epithelial cells from the sample of prostate tissue; (d) contacting the dissociated prostate epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate organoids in culture. In one embodiment, the organoid displays the luminal phenotype of prostate tumors. In another embodiment, the organoid expresses pAkt. In one embodiment, the organoid expresses Nkx3.1. In another embodiment, the organoid expresses androgen receptor and/or Foxa1.

In another aspect, the invention provides a prostate tumor organoid, wherein the organoid is obtained by a method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate tumor organoids in culture. In one embodiment, the organoid displays the luminal phenotype of prostate tumors. In another embodiment, the organoid expresses pAkt. In one embodiment, the organoid expresses Nkx3.1. In another embodiment, the organoid expresses androgen receptor and/or Foxa1.

In another aspect, the invention provides a prostate tumor organoid, wherein the organoid is obtained by a method comprising: (a) obtaining a sample of prostate tissue from a subject; (b) isolating CARNs from the sample of prostate tissue; (c) contacting the CARNs with a Matrigel solution and plating in a cell culture support, wherein the Matrigel solution forms a matrix; (d) providing an overlay layer of liquid culture medium comprising basal hepatocyte medium, FBS and ROCK inhibitor; and (e) incubating the culture of (d) wherein the CARNs form prostate tumor organoids in culture. In one embodiment, the organoid displays the luminal phenotype of prostate tumors. In another embodiment, the organoid expresses pAkt. In one embodiment, the organoid expresses Nkx3.1. In another embodiment, the organoid expresses androgen receptor and/or Foxa1.

In another aspect, the invention provides a prostate tumor organoid, wherein the organoid is obtained by a method comprising: (a) obtaining a sample of prostate tissue from a subject; (b) isolating CARNs from the sample of prostate tissue; (c) contacting the CARNs with a collagen solution and plating in a cell culture support, wherein the collagen solution forms a matrix; (d) providing an overlay layer of liquid culture medium comprising basal hepatocyte medium, FBS and ROCK inhibitor; and (e) incubating the culture of (d) wherein the CARNs form prostate tumor organoids in culture. In one embodiment, the organoid displays the luminal phenotype of prostate tumors. In another embodiment, the organoid expresses pAkt. In one embodiment, the organoid expresses Nkx3.1. In another embodiment, the organoid expresses androgen receptor and/or Foxa1. In one embodiment, the prostate organoids display the luminal differentiation of the non-cancerous prostate tissue. In another embodiment, the prostate organoids display the basal differentiation of the non-cancerous prostate tissue. In another embodiment, the prostate organoids display the luminal phenotype of the cancerous prostate tissue. In another embodiment, the prostate organoids maintain the transformed phenotype of the cancerous prostate tissue. In another embodiment, the prostate organoids maintain the luminal differentiation of the CARNs. In a further embodiment, the prostate organoids maintain the transformed phenotype of the transformed CARNs. In one embodiment, the organoids are not dependent on androgens. In another embodiment, the organoids are dependent on androgens. In one embodiment, the organoids are not dependent on androgen receptor function. In another embodiment, the organoids are dependent on androgen receptor function.

In one embodiment, the subject is a mouse. In another embodiment, the organoid displays the luminal phenotype of prostate tumors. In one embodiment, the subject is a human. In another embodiment, the organoid maintains the luminal phenotype of prostate tumors. In one embodiment, the organoid is preserved in a tissue bank. In one embodiment, the organoid can be preserved in a tissue bank.

In some embodiments, all cells comprised in the organoid display the luminal phenotype of prostate tumors. In other embodiments, a subset of the cells comprised in the organoid display the luminal phenotype of prostate tumors. In some embodiments, all cells comprised in the organoid maintain the luminal phenotype of prostate tumors. In other embodiments, a subset of the cells comprised in the organoid maintain the luminal phenotype of prostate tumors.

In one embodiment, the organoid is a prostate organoid. In another embodiment, the organoid is a prostate tumor organoid. In one embodiment, the organoid displays the luminal differentiation of non-cancerous prostate. In another embodiment, the organoid displays the luminal phenotype of prostate tumors. In one embodiment, the organoid displays basal differentiation of non-cancerous prostate. In one embodiment, the organoid displays both basal and luminal differentiation. In one embodiment, the organoid comprises an outer basal layer and inner luminal cells. In one embodiment, the organoid displays the phenotype of the sample from which is was derived. In a further embodiment, the organoid is a luminal derived organoid. In one embodiment, the organoid comprises basal cells. In another embodiment, the organoid comprises luminal cells. In one embodiment, the organoid comprises basal cells derived from luminal cells. In one embodiment, the organoid comprises epithelial cells. In another embodiment, the organoid does not comprise stromal cells. In another embodiment, the organoid comprises stromal cells. In one embodiment, the organoid contains only epithelial cells.

In another embodiment, the organoid expresses basal markers. In one embodiment, the organoid expresses cytokeratin 5 (CK5). In one embodiment, the organoid expresses p63. In another embodiment, the organoid expresses luminal markers. In another embodiment, the organoid expresses cytokeratin 8 (CK8). In another embodiment, the organoid expresses cytokeratin 18 (CK18). In another embodiment, the organoid expresses androgen receptor (AR) and/or Foxa1. In yet another embodiment, the organoid expresses Ki67. In one embodiment, the organoid expresses PIN4. In a further embodiment, the organoid expresses Nkx3.1. In one embodiment, the organoid is composed of epithelial cells. In another embodiment, the organoid has stromal components. In another embodiment, the organoid does not have stromal components. In one embodiment, the organoid contains only epithelial cells. In one embodiment, the organoid comprises an outer basal layer that expresses CK5, p63, or a combination thereof. In one embodiment, the organoid comprises inner luminal cells that expresses CK8, CK18, or a combination thereof. In one embodiment, the organoid comprises an outer basal layer that expresses CK5, p63, or a combination thereof and an inner luminal cells that expresses CK8, CK18, or a combination thereof.

In one embodiment, the organoid is an organoid obtained by a method comprising: (a) obtaining a sample of organ tissue from a subject; (b) dissociating the sample of organ tissue; (c) isolating dissociated epithelial cells from the sample of organ tissue; and (d) culturing the dissociated epithelial cells in a culture medium comprising basal hepatocyte medium, Matrigel, FBS and ROCK inhibitor; wherein the dissociated epithelial cells form organoids in culture. In another embodiment, the organoid is a tumor organoid obtained by a method comprising: (a) obtaining a sample of tumor tissue from a subject; (b) dissociating the sample of tumor tissue; (c) isolating dissociated epithelial cells from the sample of tumor tissue; and (d) culturing the dissociated epithelial cells in a culture medium comprising basal hepatocyte medium, Matrigel, FBS and ROCK inhibitor; wherein the dissociated epithelial cells form tumor organoids in culture.

In one embodiment, the organoid is an organoid obtained by a method comprising: (a) obtaining a sample of organ tissue from a subject; (b) dissociating the sample of organ tissue; (c) isolating dissociated cells from the sample of organ tissue; (d) contacting the dissociated organ tissue with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated cells form organoids in culture. In another embodiment, the organoid is a tumor organoid obtained by a method comprising: (a) obtaining a sample of tumor tissue from a subject; (b) dissociating the sample of tumor tissue; (c) isolating dissociated epithelial cells from the sample of tumor tissue; (a) obtaining a sample of organ tissue from a subject; (b) dissociating the sample of organ tissue; (c) isolating dissociated cells from the sample of organ tissue; (d) contacting the dissociated organ tissue with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated cells form tumor organoids in culture.

In one embodiment, the organoid is an organoid obtained by a method comprising: (a) obtaining a sample of organ tissue from a subject; (b) dissociating the sample of organ tissue; (c) isolating dissociated cells from the sample of organ tissue; (d) contacting the dissociated organ tissue with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated cells form organoids in culture. In another embodiment, the organoid is a tumor organoid obtained by a method comprising: (a) obtaining a sample of tumor tissue from a subject; (b) dissociating the sample of tumor tissue; (c) isolating dissociated epithelial cells from the sample of tumor tissue; (a) obtaining a sample of organ tissue from a subject; (b) dissociating the sample of organ tissue; (c) isolating dissociated cells from the sample of organ tissue; (d) contacting the dissociated organ tissue with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated cells form tumor organoids in culture.

In one embodiment, the organ is a bladder. In another embodiment, the organ is liver. In yet another embodiment, the organ is kidney. In a further embodiment, the organ is breast. In another embodiment, the organ is lung. In one embodiment, the organ is heart. In another embodiment, the organ is skin. In one embodiment, the organ is stomach. In another embodiment, the organ is brain. In one embodiment, the organ is pancreas. In one embodiment, the organ is colon. In another embodiment, the organ is intestine. In yet other embodiments, any human organ can be used in the methods of the invention.

In one embodiment, the organoid is a prostate organoid. In another embodiment, the organoid is a bladder organoid. In another embodiment, the organoid is a liver organoid. In yet another embodiment, the organoid is a kidney organoid. In a further embodiment, the organoid is a breast organoid. In another embodiment, the organoid is a lung organoid. In one embodiment, the organoid is a heart organoid. In another embodiment, the organoid is a skin organoid. In one embodiment, the organoid is a stomach organoid. In another embodiment, the organoid is a brain organoid. In one embodiment, the organoid is a pancreas organoid. In another embodiment, the organoid is a colon organoid. In yet another embodiment, the organoid is an intestine organoid. In yet other embodiments, any organoid can be used in the methods of the invention.

In one embodiment, the organoid comprises epithelial cells. In another embodiment, the organoid does not comprise stromal cells. In another embodiment, the organoid comprises stromal cells. In one embodiment, the organoid contains only epithelial cells.

In one embodiment, epithelial cells, for example, prostate epithelial cells, can be cultured to generate organoids using a Matrigel™ floating method. In another embodiment, prostate epithelials cells can be cultured to generate organoids using a Matrigel™ embedding method. In another embodiment, prostate epithelials cells can be cultured to generate organoids using a collagen embedding method. In one embodiment, prostate organoids can be grown for at least 3 weeks. In further embodiments, prostate organoids can be growth for at least 1 week, at least 2 weeks, at least 3 weeks, at least 4 weeks, at least 5 weeks, at least 6 weeks, at least 7 weeks, at least 8 weeks, at least 3 months, at least 4 months, at least 5 months, at least 6 months, at least 7 months, or at least 8 months.

In one embodiment, the method can comprise analyzing the phenotype of organoids by detecting the presence of a marker gene (such as, but not limited to, CK5, CK8, CK18, AR, Ki67, p63 and Nkx3.1) polypeptide expression. Polypeptide expression includes the presence of a marker gene polypeptide sequence, or the presence of an elevated quantity of marker gene polypeptide as compared to non-epithelial cells. These can be detected by various techniques known in the art, including by sequencing and/or binding to specific ligands (such as antibodies). For example, polypeptide expression maybe evaluated by methods including, but not limited to, immunostaining, FACS analysis, or Western blot. These methods are well known in the art (for example, U.S. Pat. No. 8,004,661, U.S. Pat. No. 5,367,474, U.S. Pat. No. 4,347,935) and are described in T. S. Hawley & R. G. Hawley, 2005, *Methods in Molecular Biology Volume* 263: *Flow Cytometry Protocols*, Humana Press Inc; I. B. Buchwalow & W. BoEcker, 2010, *Immunohistochemistry: Basics & Methods*, Springer, Medford, Mass.; O. J. Bjerrum & N. H. H. Heegaard, 2009, *Western Blotting: Immunoblotting*, John Wiley & Sons, Chichester, UK.

In another embodiment, the method can comprise detecting the presence of marker gene (such as, but not limited to, CK5, CK8, CK18, AR, Ki67, p63, Foxa1 and Nkx3.1) RNA expression, in organoids, for example in prostate organoids. RNA expression includes the presence of an RNA sequence, the presence of an RNA splicing or processing, or the presence of a quantity of RNA. These can be detected by various techniques known in the art, including by sequencing all or part of the marker gene RNA, or by selective hybridization or selective amplification of all or part of the RNA.

In one embodiment, organoids are derived from a single cell. In another embodiment, organoids are derived from more than one cell. In another embodiment organoids are derived from a single epithelial cell, for example, a single prostate epithelial cell. In a further embodiment, organoids can be derived from CARNs. In yet another embodiment, organoids can be derived from a single CARN cell.

The present invention provides methods involving prostate cancer cells. These methods are based on the discovery that Nkx3.1 is a marker of cancer stem cells, such as those giving rise to prostate cancer. For example, CARNs, a population of luminal prostate stem cells, expresses Nkx3.1, are cells of origin for prostate cancer. In one embodiment, organoids can be derived from luminal prostate stem cells expressing Nkx3.1. The drug targeting methods described herein, can be used with organoids derived from Nkx3.1-positive cancer cells. Such methods can be used to test chemotherapeutic drugs, radionuclide drugs, or other toxic agents to Nkx3.1-positive cancer cells.

Metastatic Cell Lines

In one aspect, the invention provides a metastatic prostate cell line, wherein the cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) plating the isolated dissociated metastatic prostate cancer cells of (c) on an adherent cell culture support; and (e) culturing the dissociated metastatic prostate cancer cells in a culture medium comprising basal hepatocyte medium, Matrigel, FBS and ROCK inhibitor; wherein the dissociated metastatic prostate cancer cells form metastatic prostate cell lines in culture. In one embodiment, the metastatic prostate cell line displays the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland. In another embodiment, the cell line is preserved in a tissue bank. In some embodiments the metastatic prostate cell line has a neuroendocrine phenotype.

In one aspect, the invention provides a metastatic prostate cell line, wherein the cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form metastatic prostate cell lines in culture. In one embodiment, the metastatic prostate cell lines display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland. In another embodiment, the cell line is preserved in a tissue bank. In some embodiments the metastatic prostate cell line has a neuroendocrine phenotype.

In one aspect, the invention provides a metastatic prostate cell line, wherein the cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form metastatic prostate cell lines in culture. In one embodiment, the organoids display the metastatic phenotype of the metastatic prostate cancer tissue from the subject. In another embodiment, the sample of metastatic prostate cancer tissue is obtained from a subject with a prior medical history of prostate cancer. In another embodiment, the sample of metastatic prostate cancer tissue is obtained from the brain. In another embodiment, the sample of metastatic prostate cancer tissue is obtained from the liver. In another embodiment, the sample of metastatic prostate cancer tissue is obtained from the adrenal gland. In another embodiment, the cell line is preserved in a tissue bank. In some embodiments the metastatic prostate cell line has a neuroendocrine phenotype.

In one embodiment, a metastatic prostate cell line can be grown for at least 3 weeks. In further embodiments, metastatic prostate cell lines can be growth for at least 1 week, at least 2 weeks, at least 3 weeks, at least 4 weeks, at least 5 weeks, at least 6 weeks, at least 7 weeks, at least 8 weeks, at least 3 months, at least 4 months, at least 5 months, at least 6 months, at least 7 months, or at least 8 months.

In one embodiment, the method can comprise analyzing the phenotype of a metastatic prostate cell line by detecting the presence of a marker gene (such as, but not limited to, CK5, androgen receptor, Foxa1, Nkx3.1, Chromogranin A, Amacr, or synaptophysin) polypeptide expression. Polypeptide expression includes the presence of a marker gene polypeptide sequence, or the presence of an elevated quantity of marker gene polypeptide as compared to metastatic cells. These can be detected by various techniques known in the art, including by sequencing and/or binding to specific ligands (such as antibodies). For example, polypeptide expression maybe evaluated by methods including, but not limited to, immunostaining, FACS analysis, or Western blot. These methods are well known in the art (for example, U.S. Pat. No. 8,004,661, U.S. Pat. No. 5,367,474, U.S. Pat. No. 4,347,935) and are described in T. S. Hawley & R. G. Hawley, 2005, *Methods in Molecular Biology Volume 263: Flow Cytometry Protocols*, Humana Press Inc; I. B. Buchwalow & W. BoEcker, 2010, *Immunohistochemistry: Basics & Methods*, Springer, Medford, Mass.; O. J. Bjerrum & N. H. H. Heegaard, 2009, *Western Blotting: Immunoblotting*, John Wiley & Sons, Chichester, UK.

In another embodiment, the method can comprise detecting the presence of marker gene (such as, but not limited to CK5, androgen receptor, Foxa1, Nkx3.1, Chromogranin A, Amacr, or synaptophysin) RNA expression, in cell lines, for example in a metastatic prostate cell line. RNA expression includes the presence of an RNA sequence, the presence of an RNA splicing or processing, or the presence of a quantity of RNA. These can be detected by various techniques known in the art, including by sequencing all or part of the marker gene RNA, or by selective hybridization or selective amplification of all or part of the RNA.

In some embodiments, the metastatic prostate cell line expresses CK5. In some embodiments, the metastatic prostate cell line expresses androgen receptor. In some embodiments, the metastatic prostate cell line expresses Foxa1. In some embodiments, the metastatic prostate cell line expresses Nkx3.1. In some embodiments, the metastatic prostate cell line expresses Chromogranin A. In some embodiments, the metastatic prostate cell line expresses Amacr. In some embodiments, the metastatic prostate cell line expresses synaptophysin. In some embodiments, the metastatic prostate cell line is chemotherapy resistant. In some embodiments, the metastatic prostate cell line can be used to screen for a compound that inhibits cancer.

Recombination of Organoids with Urogenital Mesenchyme

In some aspects the invention provides methods for culturing prostate organoids with rat urogenital mesenchyme ("rUGM"). In some embodiments, culturing of prostate oraganoids with rUGM generates organoids comprising epithelial and stromal cells.

Prostate organoids can be generated as described herein by the Matrigel floating method, the Matrigel embedding method, or the collagen embedding method. Prostate organoids combined with rUGM can be prostate organoids generated from prostate epithelial cells, metastatic prostate cancer cells, CARNs, or prostate cancer cell line cells, as described herein. In one embodiment, the prostate organoids are then combined with rUGM and cultured in a culture medium comprising basal hepatocyte medium, Matrigel, FBS and ROCK inhibitor. In another embodiment, the prostate organoids are combined with rUGM and then cultured by the Matrigel embedding method. In a further embodiment, prostate organoids are combined with rUGM and then cultured by the collagen embedding method.

In one aspect, the invention provides a method for culturing a prostate organoid with rat urogenital mesenchyme, the method comprising: (a) culturing a prostate organoid; (b) contacting the prostate organoid with rat urogenital mesenchyme; (c) contacting the prostate organoid and rat urogenital mesenchyme with a Matrigel solution and plating in a cell culture support, wherein the Matrigel solution forms a matrix; (d) providing an overlay layer of liquid culture medium comprising hepatocyte medium and FBS; and (e) incubating the culture of (d), wherein prostate organoids are formed. In one embodiment, the prostate organoids formed comprise epithelial and stromal cells.

In one aspect, the invention provides a method for culturing a prostate organoid with rat urogenital mesenchyme, the method comprising: (a) culturing a prostate organoid; (b) contacting the prostate organoid with rat urogenital mesenchyme; (c) contacting the prostate organoid and rat urogenital mesenchyme with a collagen solution and plating in a cell culture support, wherein the collagen solution forms a matrix; (d) providing an overlay layer of liquid culture medium comprising hepatocyte medium and FBS; and (e) incubating the culture of (d), wherein prostate organoids are formed. In one embodiment, the prostate organoids formed comprise epithelial and stromal cells.

In one embodiment, the culture medium further comprises Glutamax. In another embodiment, the culture medium further comprises EGF. In a further embodiment, the culture medium further comprises antibiotic-antimycotic. In another embodiment, the culture medium comprises 10 ng/ml of EGF. In another embodiment, the culture medium comprises 5% heat-inactivated charcoal stripped FBS. In another embodiment, the culture medium contains a ROCK inhibitor. In another embodiment, the ROCK inhibitor is Y-27632. In another embodiment, the culture medium comprises 10 µM of Y-27632.

In one embodiment, the prostate organoid of (a) is grown by the method comprising: (i) obtaining a sample of organ tissue from a subject; (ii) dissociating the sample of organ tissue; (iii) isolating dissociated cells from the sample of organ tissue; and (iv) culturing the dissociated cells in a culture medium comprising basal hepatocyte medium, Matrigel, FBS and ROCK inhibitor; wherein the dissociated cells form organoids in culture.

In one embodiment, the prostate organoid of (a) is grown by the method comprising: (i) obtaining a sample of organ tissue from a subject; (ii) dissociating the sample of organ tissue; (iii) isolating dissociated cells from the sample of organ tissue; (iv) contacting the dissociated organ tissue with a Matrigel solution and plating in a cell culture support, wherein the Matrigel solution forms a matrix; (v) providing an overlay layer of liquid culture medium comprising basal hepatocyte medium, FBS and ROCK inhibitor; and (vi) incubating the culture of (v) wherein the dissociated cells form organoids in culture.

In one embodiment, the prostate organoid of (a) is grown by the method comprising: (i) obtaining a sample of organ tissue from a subject; (ii) dissociating the sample of organ tissue; (iii) isolating dissociated cells from the sample of organ tissue; (iv) contacting the dissociated organ tissue with a collagen solution and plating in a cell culture support, wherein the collagen solution forms a matrix; (v) providing an overlay layer of liquid culture medium comprising basal hepatocyte medium, FBS and ROCK inhibitor; and (vi) incubating the culture of (v) wherein the dissociated cells form organoids in culture.

In one embodiment, before plating the combined organoid and rUGM and Matrigel solution in the cell culture support, the cell culture support is surface modified. In one embodiment, the support surface is pre-coated by rinsing Matrigel solution over the support surface and incubating the cell culture support at 37° C. for at least 30 minutes. In one embodiment, the Matrigel solution comprises hepatocyte medium and Matrigel. In one embodiment, the Matrigel solution comprises serum, including, but not limited to, FBS. In another embodiment, the Matrigel solution does not comprise serum, including, but not limited to, FBS. In one embodiment, the Matrigel solution comprises 3 parts Matrigel to 2 parts hepatocyte medium. In one embodiment, the Matrigel solution comprises 60% Matrigel and 40% hepatocyte medium.

In one embodiment, the Matrigel solution comprises hepatocyte medium and Matrigel. In one embodiment, the Matrigel solution comprises serum, including, but not limited to, FBS. In another embodiment, the Matrigel solution does not comprise serum, including, but not limited to, FBS. In one embodiment, the Matrigel solution comprises 100% Matrigel. In one embodiment, the Matrigel solution comprises 3 parts Matrigel to 2 parts hepatocyte medium. In one embodiment, the Matrigel solution comprises 60% Matrigel and 40% hepatocyte medium. In one embodiment, the cells are plated into wells of a 6 well plate, a 12 well plate, a 24 well plate, a 48 well plate, or a 96 well plate.

In one embodiment, before plating the organoids and rUGM and collagen solution in the cell culture support, the cell culture support is surface modified. In one embodiment, the support surface is pre-coated by rinsing collagen solution over the support surface and incubating the cell culture support at 37° C. for at least 30 minutes. In one embodiment, the collagen solution comprises setting solution and collagen. In one embodiment, the collagen solution comprises 9 parts collagen to 1 parts setting solution. In one embodiment, setting solution comprises EBSS, sodium bicarbonate and sodium hydroxide.

The prostate organoids generated by culturing prostate organoids with rat urogenital mesenchyme can be analyzed, passaged, grown, modified and frozen as described herein for prostate organoids.

Methods of Modifying Organoids

A eukaryotic expression vector can be introduced into organoids in order to produce proteins encoded by nucleotide sequences of the vector. Organoids (such as prostate organoids can harbor an expression vector via introducing the expression vector into the cells of the organoid via methods known in the art.

An exogenous nucleic acid can be introduced into a cell via a variety of techniques known in the art. For example, a retrovirus can be used to introduce a nucleotide sequence into cells of an organoid. In one embodiment, the retrovirus is a lentivirus. Other viral vectors known in the art can be used to introduce a nucleotide sequence, including, but not limited to an adenovirus, an adeno-associated virus, or a Rebna retrovirus.

In one embodiment, a retrovirus can be used to introduce a nucleotide sequence into an organoid, in order to produce proteins encoded by said nucleotide sequences. For example, the lentivirus is used to introduce DNA into cells of an organoid to confer high-level stable expression of a protein of interest. The nucleic acid of interest can encode only a single protein, or can encode for more than one proteins of interest. In one embodiment, doxycycline-inducible expression vectors can be used.

A eukaryotic expression vector can be used to transfect cells in order to produce proteins encoded by nucleotide sequences of the vector. Mammalian cells of an organoid can harbor an expression vector via introducing the expression vector into an appropriate host cell via methods known in the art.

An exogenous nucleic acid can be introduced into a cell of an organoid via a variety of techniques known in the art, such as lipofection, microinjection, calcium phosphate or calcium chloride precipitation, DEAE-dextrin-mediated transfection, or electroporation. Other methods used to transfect cells of an organoid can also include calcium phosphate precipitation, modified calcium phosphate precipitation, polybrene precipitation, microinjection liposome fusion, and receptor-mediated gene delivery.

Methods of Screening Compounds

In one aspect, the invention provides a method for identifying a compound that inhibits cancer, the method comprising: (a) contacting an organoid with a test compound; (b) determining whether growth of the organoid is inhibited in the presence of the test compound, as compared to growth of the organoid in the absence of the test compound; wherein inhibition of growth of the organoid indicates the identification of a compound that inhibits cancer.

In one embodiment, the organoid is an organoid obtained by a method comprising: (a) obtaining a sample of organ tissue from a subject; (b) dissociating the sample of organ tissue; (c) isolating dissociated epithelial cells from the sample of organ tissue; and (d) culturing the dissociated epithelial cells in a culture medium comprising basal hepatocyte medium, Matrigel, FBS and ROCK inhibitor; wherein the dissociated epithelial cells form organoids in culture. In another embodiment, the organoid is a tumor organoid obtained by the method comprising: (a) obtaining a sample of tumor tissue from a subject; (b) dissociating the sample of tumor tissue; (c) isolating dissociated epithelial cells from the sample of tumor tissue; and (d) culturing the dissociated epithelial cells in a culture medium comprising basal hepatocyte medium, Matrigel, FBS and ROCK inhibitor; wherein the dissociated epithelial cells form tumor organoids in culture.

In one embodiment, the organoid is an organoid obtained by a method comprising: (a) obtaining a sample of organ tissue from a subject; (b) dissociating the sample of organ tissue; (c) isolating dissociated epithelial cells from the sample of organ tissue; (d) contacting the isolated dissociated epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated epithelial cells form organoids in culture. In another embodiment, the organoid is a tumor organoid obtained by the method comprising: (a) obtaining a sample of tumor tissue from a subject; (b) dissociating the sample of tumor tissue; (c) isolating dissociated epithelial cells from the sample of tumor tissue; (d) contacting the dissociated epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated epithelial cells form organoids in culture.

In one embodiment, the organoid is an organoid obtained by a method comprising: (a) obtaining a sample of organ tissue from a subject; (b) dissociating the sample of organ tissue; (c) isolating dissociated epithelial cells from the sample of organ tissue; (d) contacting the isolated dissociated epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated epithelial cells form organoids in culture. In another embodiment, the organoid is a tumor organoid obtained by the method comprising: (a) obtaining a sample of tumor tissue from a subject; (b) dissociating the sample of tumor tissue; (c) isolating dissociated epithelial cells from the sample of tumor tissue; (d) contacting the dissociated epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated epithelial cells form organoids in culture.

In one embodiment, the organoid is an organoid obtained by a method comprising: (a) culturing a prostate organoid; (b) contacting the prostate organoid with rat urogenital mesenchyme; (c) contacting the prostate organoid and rat urogenital mesenchyme with a Matrigel solution and plating in a cell culture support, wherein the Matrigel solution forms a matrix; (d) providing an overlay layer of liquid culture medium comprising hepatocyte medium and FBS; and (e) incubating the culture of (d), wherein prostate organoids are formed.

In one embodiment, the organoid is an organoid obtained by a method comprising: (a) culturing a prostate organoid; (b) contacting the prostate organoid with rat urogenital mesenchyme; (c) contacting the prostate organoid and rat urogenital mesenchyme with a collagen solution and plating in a cell culture support, wherein the collagen solution forms a matrix; (d) providing an overlay layer of liquid culture medium comprising hepatocyte medium and FBS; and (e) incubating the culture of (d), wherein prostate organoids are formed.

In one embodiment, the organoid is a prostate organoid. In another embodiment, the organoid is a bladder organoid. In another embodiment, the organoid is a liver organoid. In yet another embodiment, the organoid is a kidney organoid. In a further embodiment, the organoid is a breast organoid. In another embodiment, the organoid is a lung organoid. In one embodiment, the organoid is a heart organoid. In another embodiment, the organoid is a skin organoid. In one embodiment, the organoid is a stomach organoid. In another embodiment, the organoid is a brain organoid. In one embodiment, the organoid is a pancreas organoid. In another embodiment, the organoid is a colon organoid. In another embodiment, the organoid is an intestine organoid. In yet other embodiments, any organoid can be used in the methods of the invention.

In one embodiment, the organoid is a prostate organoid obtained by a method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate organoids in culture. In another embodiment, the organoid is a prostate organoid obtained by a method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate organoids in culture. In a further embodiment, the organoid is a prostate tumor organoid obtained by the method comprising: (a) obtaining a sample of prostate tissue from a subject; (b) dissociating the sample of prostate tissue; (c) isolating dissociated prostate epithelial cells from the sample of prostate tissue; and (d) culturing the dissociated prostate epithelial cells in a culture medium comprising basal hepatocyte medium, Matrigel, FBS and ROCK inhibitor; wherein the dissociated prostate epithelial cells form prostate tumor organoids in culture. In another embodiment, the organoid is a prostate tumor organoid obtained by the method comprising: (a) obtaining a sample of prostate tissue from a subject; (b) isolating CARNs from the sample of prostate tissue; (c) culturing the CARNs in a culture medium comprising basal hepatocyte medium, Matrigel, FBS and ROCK inhibitor; wherein the CARNs form prostate tumor organoids in culture. In one embodiment, the test compound is a small molecule. In another embodiment, the test compound is a peptide. In one embodiment, the test compound is a protein. In another embodiment, the test compound is a peptidomimetic molecule. In yet another embodiment, the test compound is an antibody.

In one embodiment, the organoid is a prostate organoid obtained by a method comprising: (a) obtaining a sample of prostate tissue from a subject; (b) dissociating the sample of prostate tissue; (c) isolating dissociated prostate epithelial cells from the sample of prostate tissue; (d) contacting the isolated dissociated prostate epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated prostate epithelial cells form organoids in culture. In another embodiment, the organoid is a prostate organoid obtained by a method comprising: (a) obtaining a sample of prostate tissue from a subject; (b) isolating CARNs from the sample of prostate tissue; (c) contacting the CARNs with a Matrigel solution and plating in a cell culture support, wherein the Matrigel solution forms a matrix; (d) providing an overlay layer of liquid culture medium comprising basal hepatocyte medium, FBS and ROCK inhibitor; and (e) incubating the culture of (d) wherein the CARNs form organoids in culture. In a further embodiment, the organoid is a prostate tumor organoid obtained by the method comprising: (a) obtaining a sample of prostate tissue from a subject; (b) dissociating the sample of prostate tissue; (c) isolating dissociated prostate epithelial cells from the sample of prostate tissue; (d) contacting the isolated dissociated prostate epithelial cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate tumor organoids in culture. In another embodiment, the organoid is a prostate tumor organoid obtained by the method comprising: (a) obtaining a sample of prostate tissue from a subject; (b) isolating CARNs from the sample of prostate tissue; (c) contacting the CARNs with a Matrigel solution and plating in a cell culture support, wherein the Matrigel solution forms a matrix; (d) providing an overlay layer of liquid culture medium comprising basal hepatocyte medium, FBS and ROCK inhibitor; and (e) incubating the culture of (d) wherein the CARNs form prostate tumor organoids in culture. In one embodiment, the test compound is a small molecule. In another embodiment, the test compound is a peptide. In one embodiment, the test compound is a protein. In another embodiment, the test compound is a peptidomimetic molecule. In yet another embodiment, the test compound is an antibody.

In one embodiment, the organoid is a prostate organoid obtained by a method comprising: (a) obtaining a sample of prostate tissue from a subject; (b) dissociating the sample of prostate tissue; (c) isolating dissociated prostate epithelial cells from the sample of prostate tissue; (d) contacting the isolated dissociated prostate epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated prostate epithelial cells form organoids in culture. In another embodiment, the organoid is a prostate organoid obtained by a method comprising: (a) obtaining a sample of prostate tissue from a subject; (b) isolating CARNs from the sample of prostate tissue; (c) contacting the CARNs with a collagen solution and plating in a cell culture support, wherein the collagen solution forms a matrix; (d) providing an overlay layer of liquid culture medium comprising basal hepatocyte medium, FBS and ROCK inhibitor; and (e) incubating the culture of (d) wherein the CARNs form organoids in culture. In a further embodiment, the organoid is a prostate tumor organoid obtained by the method comprising: (a) obtaining a sample of prostate tissue from a subject; (b) dissociating the sample of prostate tissue; (c) isolating dissociated prostate epithelial cells from the sample of prostate tissue; (d) contacting the isolated dissociated prostate epithelial cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated prostate epithelial cells form prostate tumor organoids in culture. In another embodiment, the organoid is a prostate tumor organoid obtained by the method comprising: (a) obtaining a sample of prostate tissue from a subject; (b) isolating CARNs from the sample of prostate tissue; (c) contacting the CARNs with a collagen solution and plating in a cell culture support, wherein the collagen solution forms a matrix; (d) providing an overlay layer of liquid culture medium comprising basal hepatocyte medium, FBS and ROCK inhibitor; and (e) incubating the culture of (d) wherein the CARNs form prostate tumor organoids in culture. In one embodiment, the test compound is a small molecule. In another embodiment, the test compound is a peptide. In one embodiment, the test compound is a protein. In another embodiment, the test compound is a peptidomimetic molecule. In yet another embodiment, the test compound is an antibody.

In one aspect, the invention provides a method for identifying a compound that inhibits cancer, the method comprising: (a) contacting metastatic prostate cell line with a test compound; (b) determining whether growth of the metastatic prostate cell line is inhibited in the presence of the test compound, as compared to growth of the metastatic prostate cell line in the absence of the test compound; wherein inhibition of growth of the metastatic prostate cell line indicates the identification of a compound that inhibits cancer.

In one embodiment, the metastatic prostate cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; and (d) culturing the dissociated metastatic prostate cancer cells in a culture medium comprising basal hepatocyte medium, Matrigel, FBS and ROCK inhibitor; wherein the dissociated metastatic prostate cancer cells form metastatic prostate cell lines in culture. In one embodiment, the test compound is a small molecule. In another embodiment, the test compound is a peptide. In one embodiment, the test compound is a protein. In another embodiment, the test compound is a peptidomimetic molecule. In yet another embodiment, the test compound is an antibody.

In one embodiment, the metastatic prostate cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a Matrigel solution and plating in a cell culture support, wherein the Matrigel solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form metastatic prostate cell lines in culture. In one embodiment, the test compound is a small molecule. In another embodiment, the test compound is a peptide. In one embodiment, the test compound is a protein. In another embodiment, the test compound is a peptidomimetic molecule. In yet another embodiment, the test compound is an antibody.

In one embodiment, the metastatic prostate cell line is obtained by the method comprising: (a) obtaining a sample of metastatic prostate cancer tissue from a subject; (b) dissociating the sample of metastatic prostate cancer tissue; (c) isolating the dissociated metastatic prostate cancer cells from the sample of tissue; (d) contacting the dissociated metastatic prostate cancer cells with a collagen solution and plating in a cell culture support, wherein the collagen solution forms a matrix; (e) providing an overlay layer of liquid culture medium comprising basal hepatocyte medium, FBS and ROCK inhibitor; and (f) incubating the culture of (e) wherein the dissociated metastatic prostate cancer cells form metastatic prostate cell lines in culture. In one embodiment, the test compound is a small molecule. In another embodiment, the test compound is a peptide. In one embodiment, the test compound is a protein. In another embodiment, the test compound is a peptidomimetic molecule. In yet another embodiment, the test compound is an antibody.

The invention provides for methods used to identify compounds that inhibit cancer. The method can further comprise determining whether the growth of cancer organoids is inhibited in the presence of a test compound as compared to growth of the organoids in the absence of the test compound. The cancer comprises, but is not limited to, prostate cancer, breast cancer, liver cancer, lung cancer, bladder cancer, renal cancer, skin cancer, stomach cancer, brain cancer, pancreatic cancer, colon cancer, or intestinal cancer.

Test compounds that modulate the function of Nkx3.1 can be useful. In one embodiment, the present invention is directed to agents that modulate the function of Nkx3.1 and to methods of identifying such compounds. These test compounds can be useful as anti-tumor drugs, or as agents for maintaining organoids in culture.

Test compounds can be screened from large libraries of synthetic or natural compounds (see Wang et al., (2007) *Curr Med Chem,* 14(2):133-55; Mannhold (2006) *Curr Top Med Chem,* 6 (10):1031-47; and Hensen (2006) *Curr Med Chem* 13(4):361-76). Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) *Tib Tech* 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries, neurotransmitter libraries, and chemical libraries. The libraries can also comprise cyclic carbon or heterocyclic structure and/or aromatic or polyaromatic structures substituted with one or more of the functional groups.

Small molecule combinatorial libraries can also be generated and screened. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

Examples of chemically synthesized libraries are described in Fodor et al., (1991) *Science* 251:767-773; Houghten et al., (1991) *Nature* 354:84-86; Lam et al., (1991) *Nature* 354:82-84; Medynski, (1994) *BioTechnology* 12:709-710; Gallop et al., (1994) *J. Medicinal Chemistry* 37(9):1233-1251; Ohlmeyer et al., (1993) *Proc. Natl. Acad. Sci. USA* 90:10922-10926; Erb et al., (1994) *Proc. Natl. Acad. Sci. USA* 91:11422-11426; Houghten et al., (1992) *Biotechniques* 13:412; Jayawickreme et al., (1994) *Proc. Natl. Acad. Sci. USA* 91:1614-1618; Salmon et al., (1993) *Proc. Natl. Acad. Sci. USA* 90:11708-11712; PCT Publication No. WO 93/20242, dated Oct. 14, 1993; and Brenner et al., (1992) *Proc. Natl. Acad. Sci. USA* 89:5381-5383.

Screening the libraries can be accomplished by any variety of commonly known methods. See, for example, the following references, which disclose screening of peptide libraries: Parmley and Smith, (1989) *Adv. Exp. Med. Biol.* 251:215-218; Scott and Smith, (1990) *Science* 249:386-390; Fowlkes et al., (1992) *BioTechniques* 13:422-427; Oldenburg et al., (1992) *Proc. Natl. Acad. Sci. USA* 89:5393-5397; Yu et al., (1994) *Cell* 76:933-945; Staudt et al., (1988) *Science* 241:577-580; Bock et al., (1992) *Nature* 355:564-566; Tuerk et al., (1992) *Proc. Natl. Acad. Sci. USA* 89:6988-6992; Ellington et al., (1992) *Nature* 355:850-852; U.S. Pat. Nos. 5,096,815; 5,223,409; and 5,198,346, all to Ladner et al.; Rebar et al., (1993) *Science* 263:671-673; and PCT Pub. WO 94/18318.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—Materials and Methods for Prostate Cell Culture

Preparation of Single Cell Suspension

Normal and cancerous prostate specimens were obtained directly from the operation room at the Department of Urology, Columbia University Medical Center. Dissociation of prostate specimen was performed according to an adapted protocol from Stem Cell Technology with modifications. Briefly, 1 gram of prostate specimen was cut into small chunks, and was then incubated in 25 ml of DMEM/F12 (Gibco, cat. #10565) supplemented with 5% FBS and collagenase/hyaluronidase (Stem Cell Technologies, cat. #07912) (1:10) overnight at 37° C. In the following day, dissociated prostate tissues were spun down at 350 g for 5 minutes, and dissociating medium was then removed. Subsequently, dissociated prostate tissue was resuspended with 25 ml of ice-cold 0.25% trypsin-EDTA (Stem Cell Technologies, cat. #07901), and the suspension was incubated on ice for an hour. At the end of the procedures, trypsin activity was stopped by adding 50 ml of Hanks' Balanced Salt Solution Modified (HBSS) (Stem Cell Technologies, cat. #37150) medium supplemented with 2% FBS into the suspension. Dissociated prostate tissue was spun down and supernatant was removed. Cell pellet was then resuspended with 10 ml of pre-warmed 5 mg/ml dispase (Stem Cell Technologies, cat. #07913) supplemented with 1 mg/ml DNase I (Stem Cell Technologies, cat. #07900) (1:10). The sample was pipetted up and down rigorously for 1 minute. Subsequently, 60 ml of HBSS/2% FBS was added to neutralize dispase activity, and the cell suspension was gone through a 40 μm cell strainer (BD Biosciences, cat. 352340). Dissociated cells were spun down again and the supernatant was discarded. Lastly, cells were resuspended in medium suitable for subsequent staining and flow sorting.

For dissociation of normal mouse prostate and mouse prostate tumor tissues, 1.5 ml of dissociating medium (DMEM/F12/5% FBS/collagenase/hyaluronidase) was used for each prostate. The tissues were chopped with scissors to avoid big chunks, and then incubated in dissociating medium for 3 hours at 37° C. Subsequently, dissociation procedures were continued with steps as abovementioned with scaled down volume of solution.

Isolation of Prostate Epithelial Population

Isolation of prostate epithelial cells was done with flow sorting. Prior to cell sorting, single cell suspension was stained with fluorescent-tagged EpCAM (BioLegend, cat. #324208 and #118214 for human and mouse cells respectively) and E-cadherin (eBioscience, cat. #46-3249-82, against both human and mouse cells) antibodies. Staining was carried out on ice for 25 minutes. At the end of the staining procedure, cell suspension was spun down, and the cell pellet was washed with HBSS/2% FBS for once to remove all unbound antibodies. Subsequently, cell pellet was resuspended with HBSS/2% FBS supplemented with rock inhibitor, Y-27632 at 10 μM. DAPI was added into cell suspension to exclude dead cells during cell sorting (0.5 mg/ml, 1:10000). To perform cell sorting through flow cytometry, unstained cells as well as cells stained with fluorescent-tagged EpCAM or E-cadherin were used for compensation. Side scatter pulse width (SSC-W) and area (SSC-A) were used to isolate single dissociated cells. Cells express either EpCAM and/or E-cadherin were sorted out for cell culture. Lineage-marked CARNs and transformed CARNs was sorted accordingly based on their YFP positivity.

Prostate Epithelial Cell Culture

Isolated prostate epithelial cells were cultured using either Matrigel floating and embedding methods. For floating method, prostate epithelial cells was first resuspended in hepatocyte medium supplemented with 10 ng/ml of EGF (BD Biosciences, cat. #355056), glutamax (Gibco, cat. #35050) 5% Matrigel (BD Biosciences, cat. #354234), 5% heat-inactivated charcoal-stripped FBS (Gibco, cat. #12676) (55° C. for 1 hour) and 10 µM Y-27632 (Stem Cell Technologies, cat. #07171). 500-3000 cells were then replated into wells of ultra low attachment 96-well plate (Corning, cat. #3474) with and without addition of 100 nM DHT (Sigma, A-8380). 100 µl of medium was added into the wells every four days and total change of new medium would be done every 12 days.

Medium used for the embedding method was same as the floating method with the exception of Matrigel inclusion. Briefly, 40 µl of cell suspension with 500-3000 cells was mixed with 60 µl of Matrigel. The mixture was pipetted around the rim of wells in a 24 well plate. The mixture was allowed to solidify for 30 minutes at 37° C. prior to addition of 400 µl medium into each well, with and without addition of 100 nM DHT. A half media change was performed every 4 days, and the prostate organoids were grown for 3-4 weeks prior to further assessment.

Example 2—Growth of Prostate Organoids

Figures 3A, 3B:
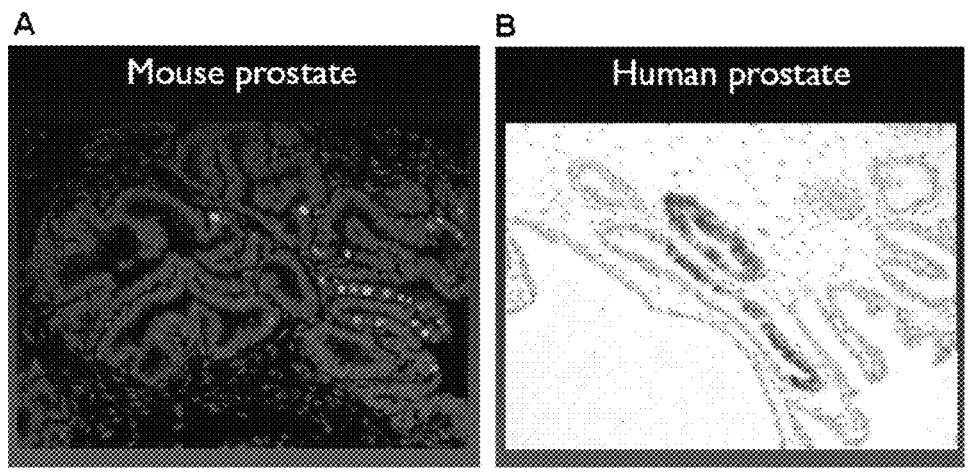
FIGS. 3A-B. Comparison of CARNs in mouse prostate (FIG. 3A) and human prostate (FIG. 3B).
Figure 5A:
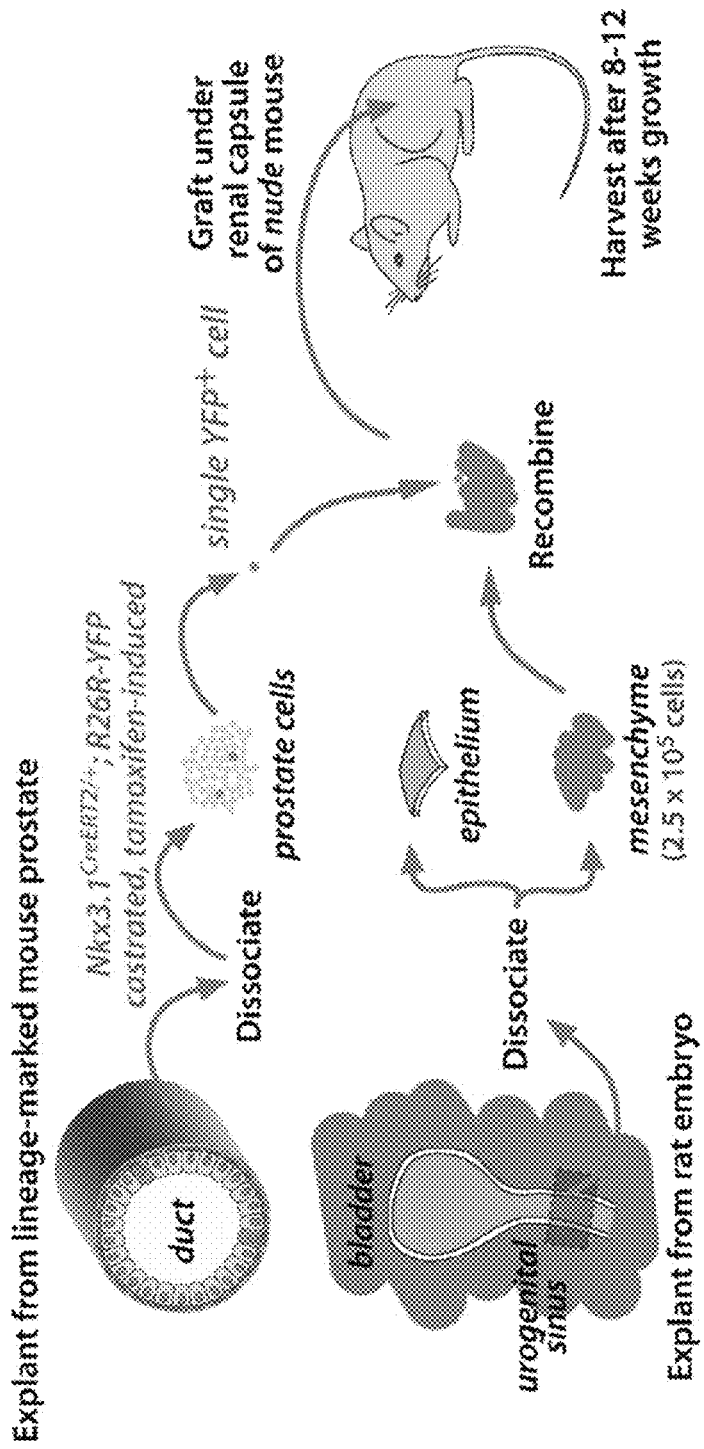
FIGS. 5A-D. Generation of prostate ducts in renal grafts by single lineage-marked CARNs.
Figures 5B, 5C, 5D:
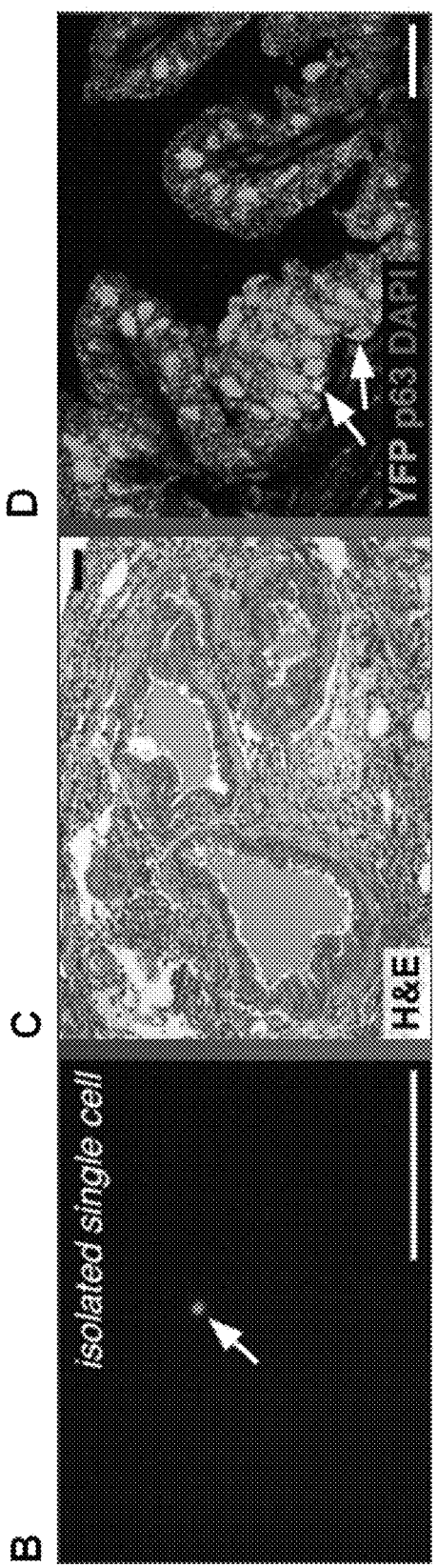
Figures 6A, 6B, 6C, 6D:
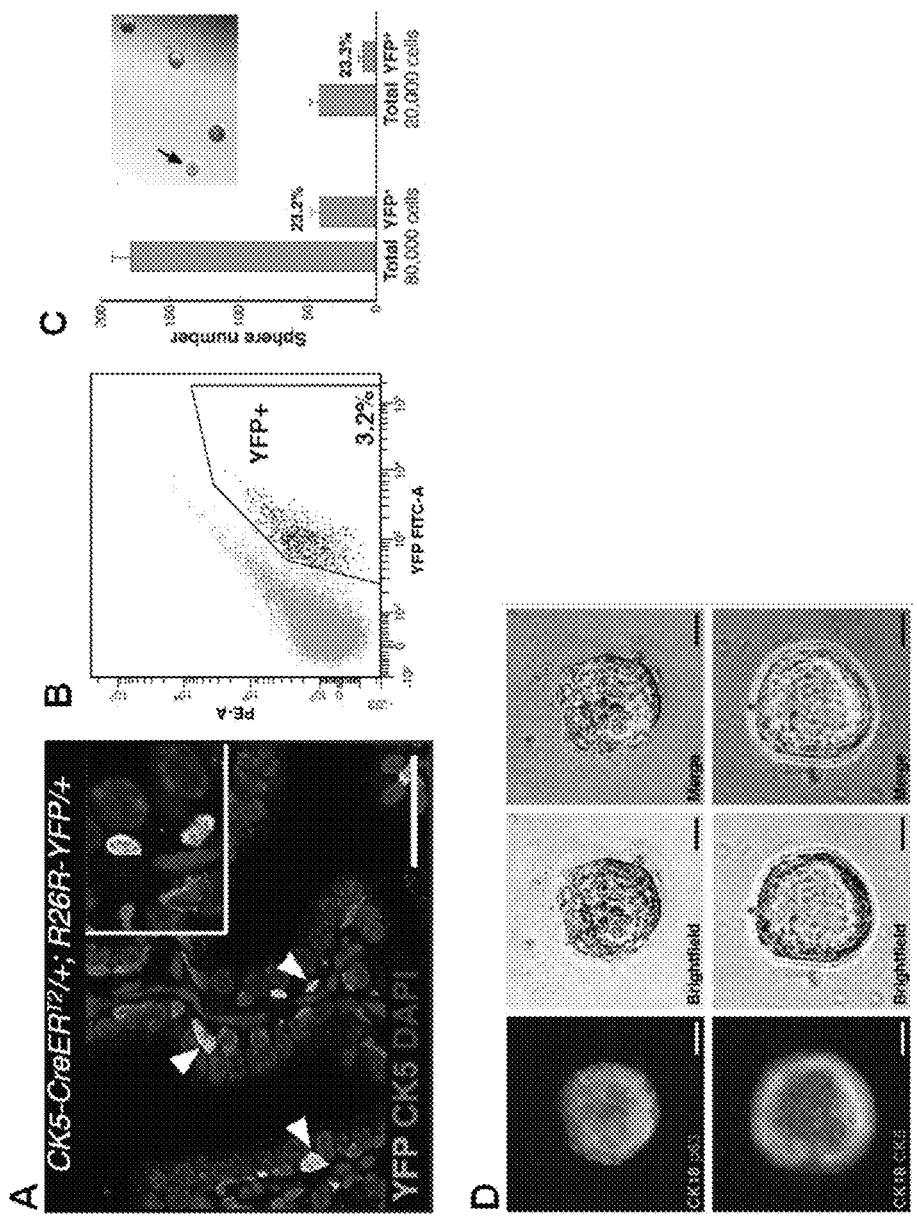
FIGS. 6A-D. "Prostaspheres" originate from basal cells and display poor luminal differentiation.

Nkx3.1 is the earliest specific prostate epithelial marker (FIG. 1A-F). Castration-resistant Nkx3.1-expressing cells (CARNs) can be detected in the intact, regressed and regenerated prostate (FIGS. 2A-D) (see Wang et al. (2009) Nature 461: 495-500). Nkx3.1 is expressed in all luminal cells of intact prostate (FIG. 2B). Nkx3.1 expression is mostly absent in regressed prostate, except for rare castration-resistant Nkx3.1-expressing cells (CARNs) (FIG. 2C) (see Wang et al. (2009) Nature 461: 495-500). The CARNs population contains bipotential progenitors and can self renew in vivo (FIG. 4A-D) (see Wang et al. (2009) Nature 461: 495-500). Single lineage-marked CARNs can generate prostate ducts in renal grafts (FIGS. 5A-D) (see Wang et al. (2009) Nature 461: 495-500). CARNs are present in mouse and human prostate (FIG. 3A-B). "Prostaspheres" originate from basal cells and display poor luminal differentiation (FIG. 6A-D).

Various culture conditions for prostate luminal epithelial cells have been established (see, e.g., Cano, P. et al., Stromal-Epithelial Cell Interactions and Androgen Receptor-Coregulator Recruitment Is Altered in the Tissue Microenvironment of Prostate Cancer. (2007) Cancer Res. 67: 511-519; Guo, W. et al., Slug and Sox9 Cooperatively Determine the Mammary Stem Cell State (2012) Cell 148: 1015-1028; and Liu, X., et al., ROCK Inhibitor and Feeder Cells Induce the Conditional Reprogramming of Epithelial Cells (2012) Am. J. Pathol. 180: 599-607).

Figure 7:
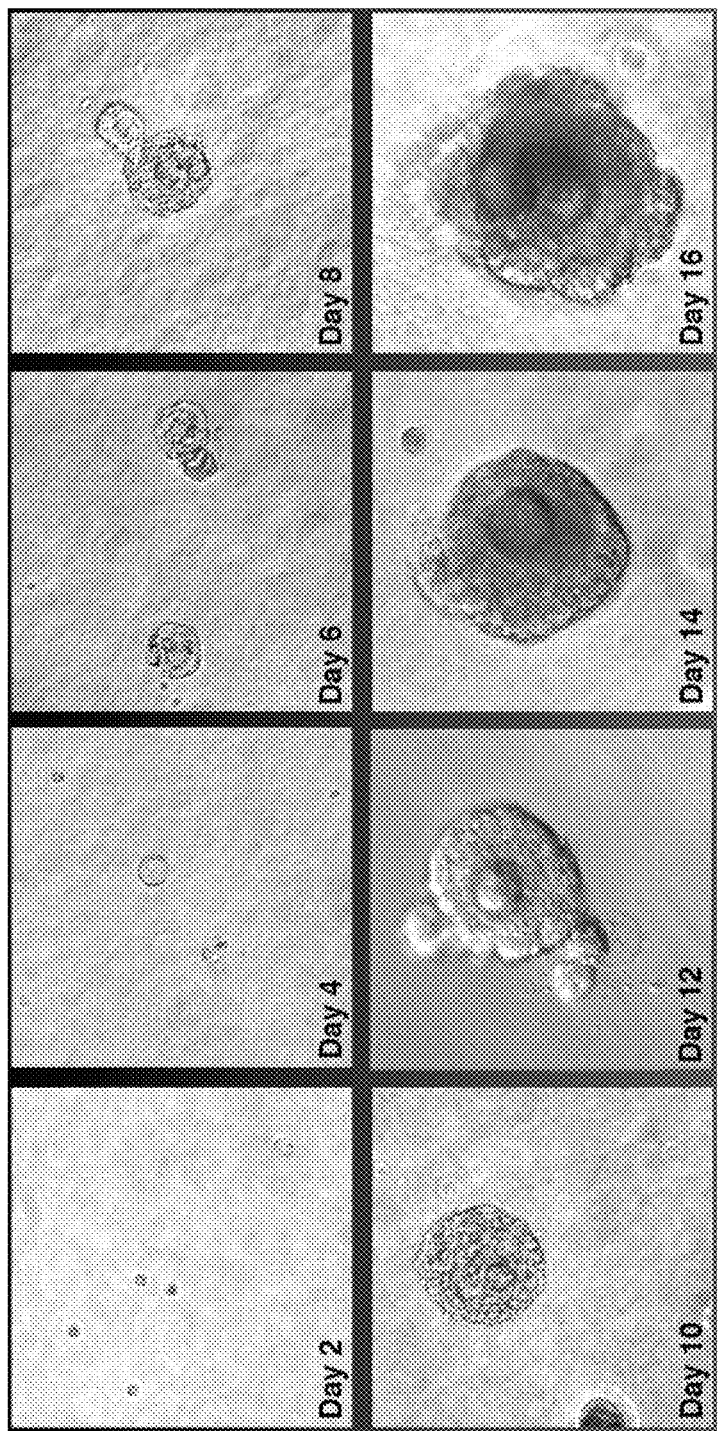
FIG. 7. Microscopic images showing human prostate organoids grown from cystectomy.
Figure 8:
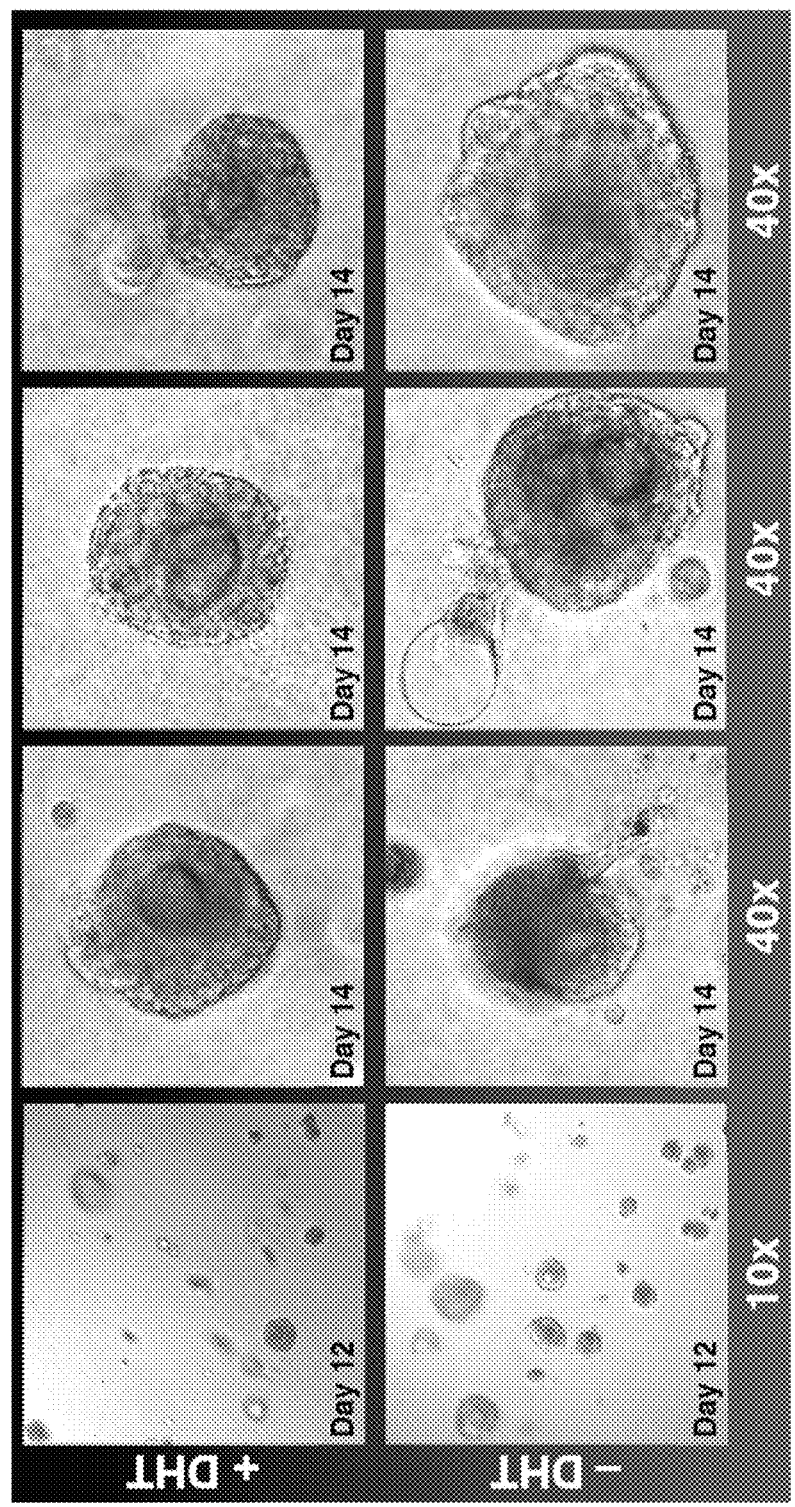
FIG. 8. Microscopic images showing human prostate organoid growth in the presence and absence of DHT.

Described herein is the growth of organoids from human prostate tissue derived from cystectomy, radical prostatectomy or LuCAP xenografts. Human prostate tissue can be grown from cystectomy (FIG. 7). Similar growth is observed in the presence and absence of DHT (FIG. 8). Some key questions about this organoid assay were investigated, including, but not limited to, whether the assay was simply an improved prostasphere assay, the cell type(s) that originate the organoid formation, and whether organoids from tumors display a transformed luminal phenotype.

Figure 9A:
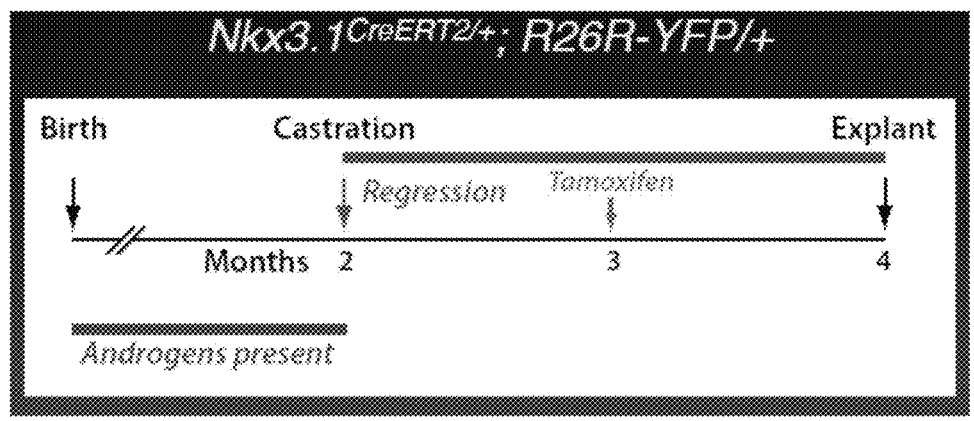
FIG. 9A. Timeline showing the isolation of lineage-marked CARNs.
Figure 9B:
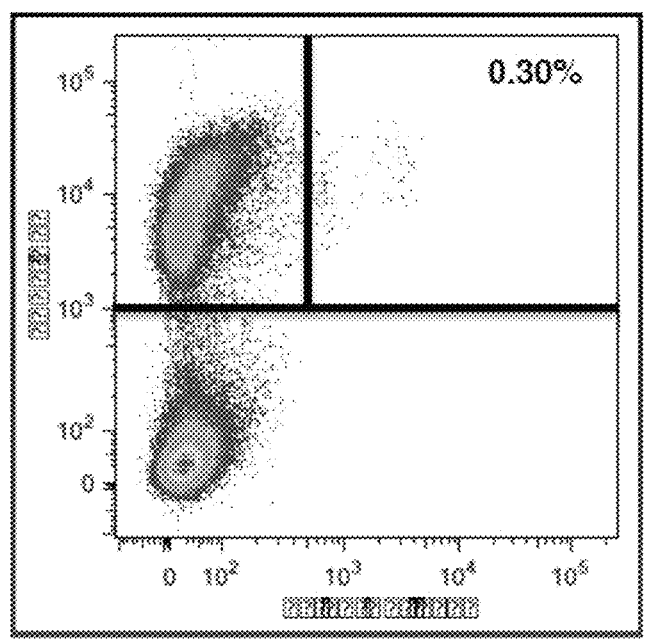
FIG. 9B. FACS analysis of purified CARNs as a starting population for organoid formation.
Figure 10:
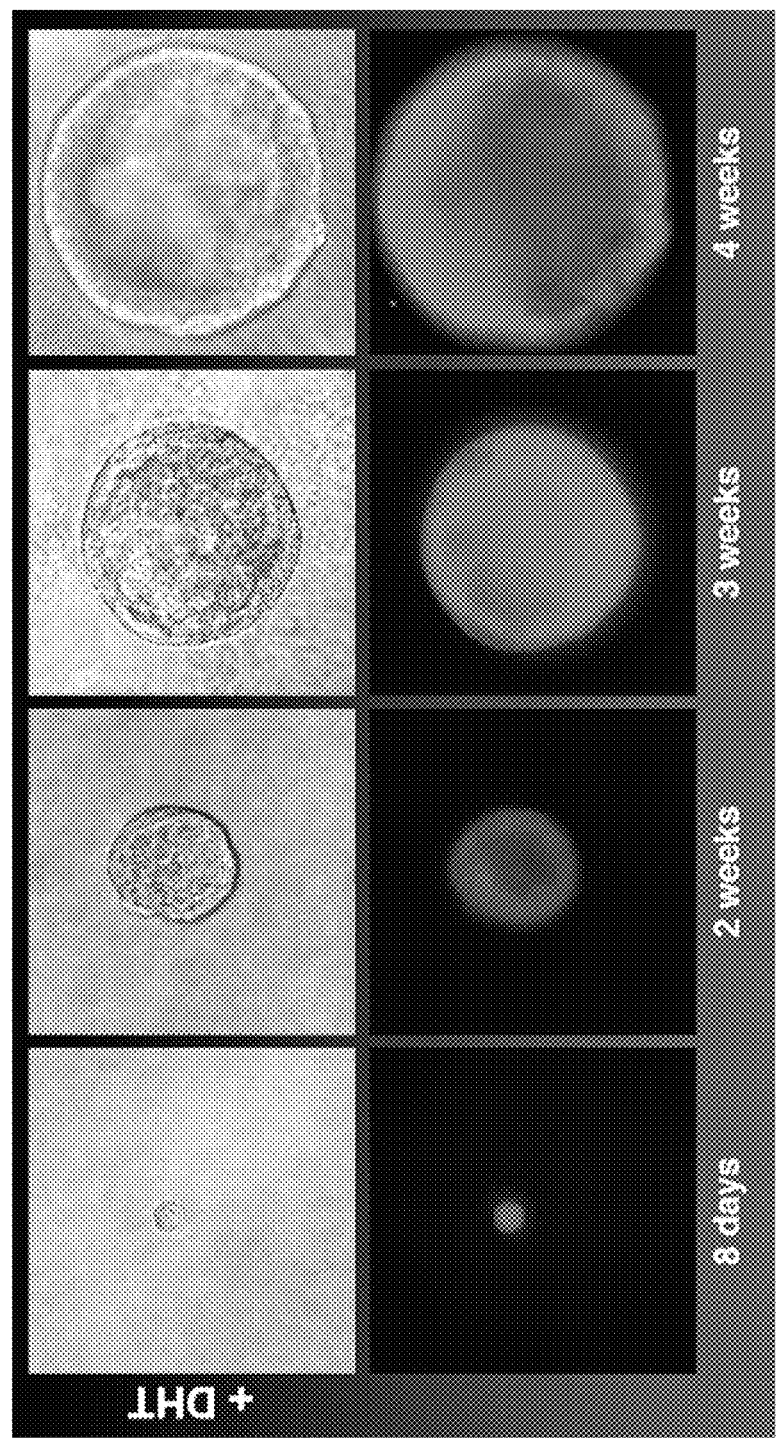
FIG. 10. Microscopic images of organoids grown from lineage-marked CARNs in the presence of DHT.
Figure 11:
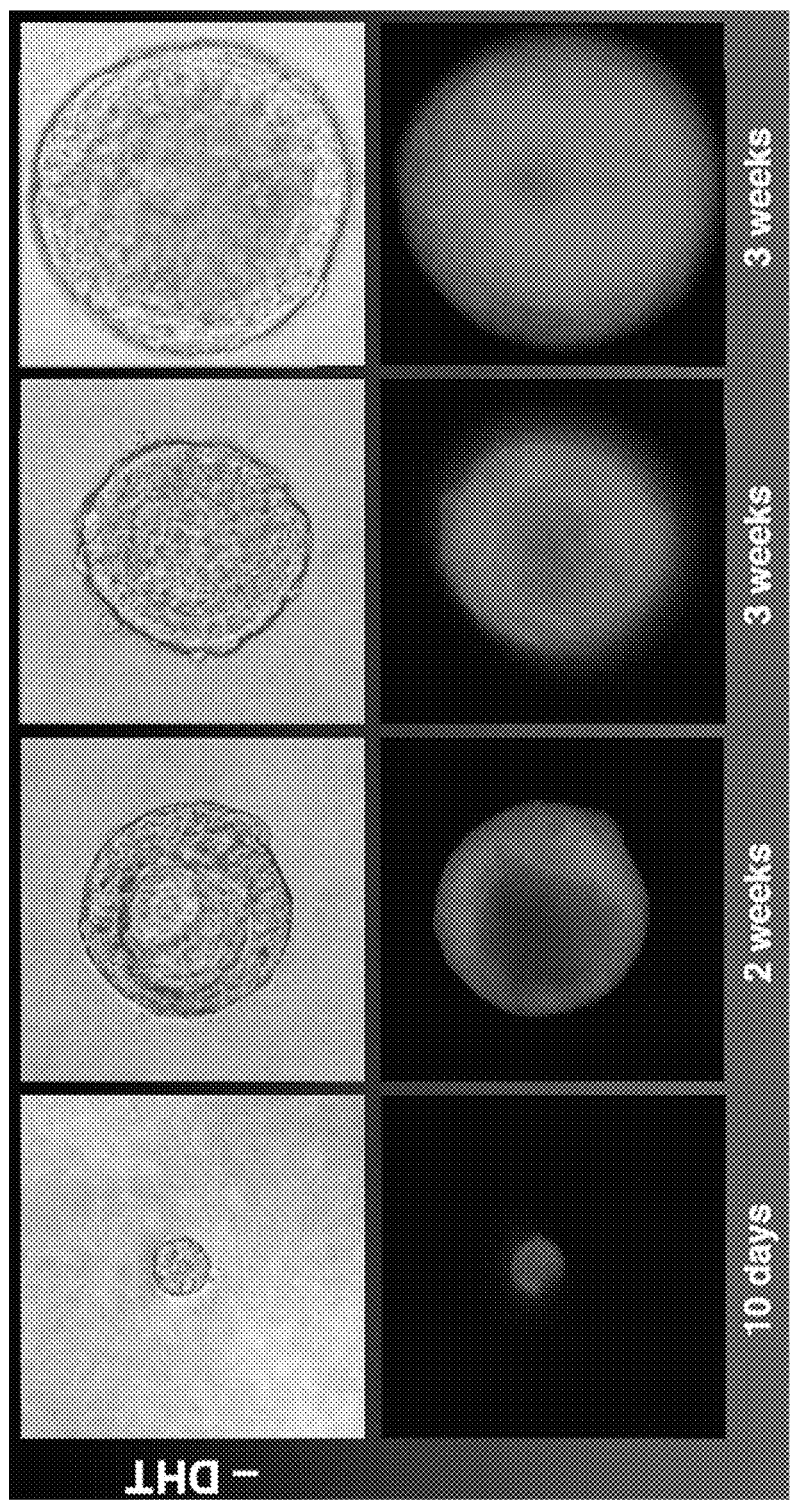
FIG. 11. Microscopic images of organoids grown from lineage-marked CARNs in the absence of DHT.
Figure 12:
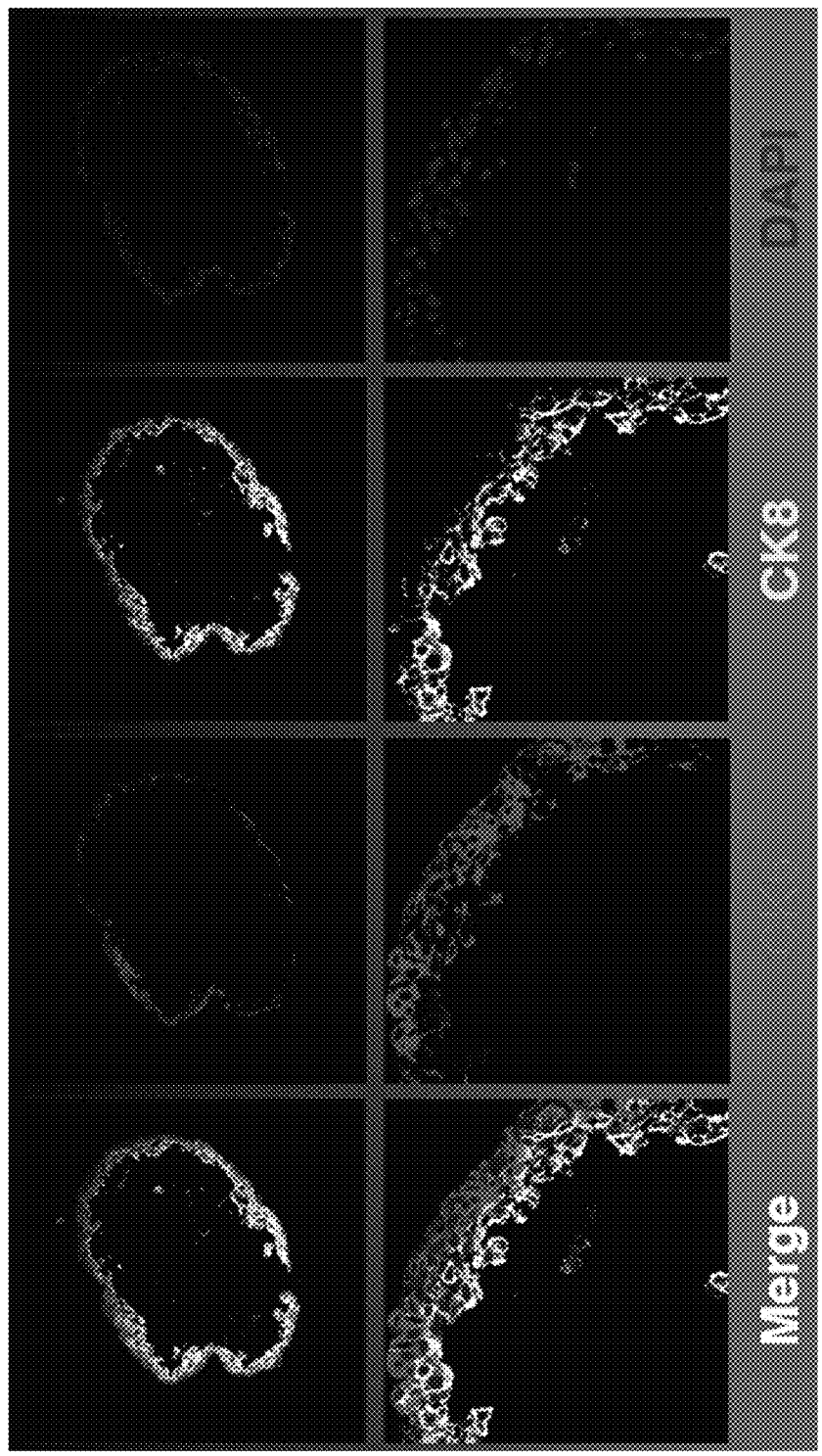
FIG. 12. Immunostaining for CK5 and CK8 showing luminal and basal epithelial differentiation in organoids.
Figure 13:
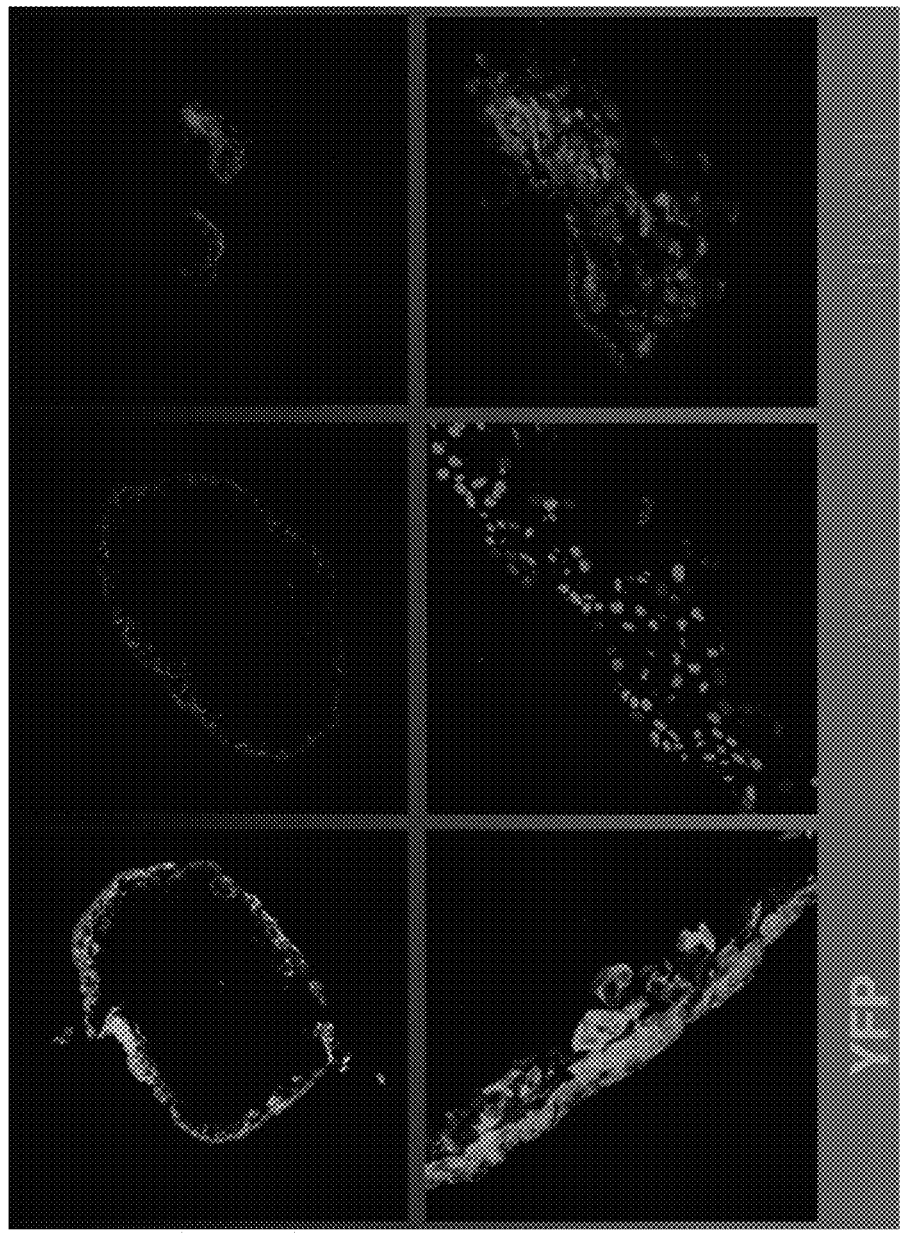
FIG. 13. Immunostaining showing expression of androgen receptor (AR) and Nkx3.1 in organoids.

Lineage-marked CARNs were isolated from Nkx3.1$^{CreERT/+}$; R26R-YFP/+ mice according to the timeline shown in FIG. 9A. Purified CARNs were used as a starting population for organoid formation (FIG. 9B). Organoids were grown from lineage-marked CARNs in the presence (FIG. 10) and absence (FIG. 11) of DHT. Similar growth was observed in both conditions. Immunostaining for CK5 and CK8 revealed that luminal and basal epithelial differentiation was observed in the organoids (FIG. 12). Immunostaining also showed expression of androgen receptor (AR) and Nkx3.1 in the organoids (FIG. 13).

Figure 14:
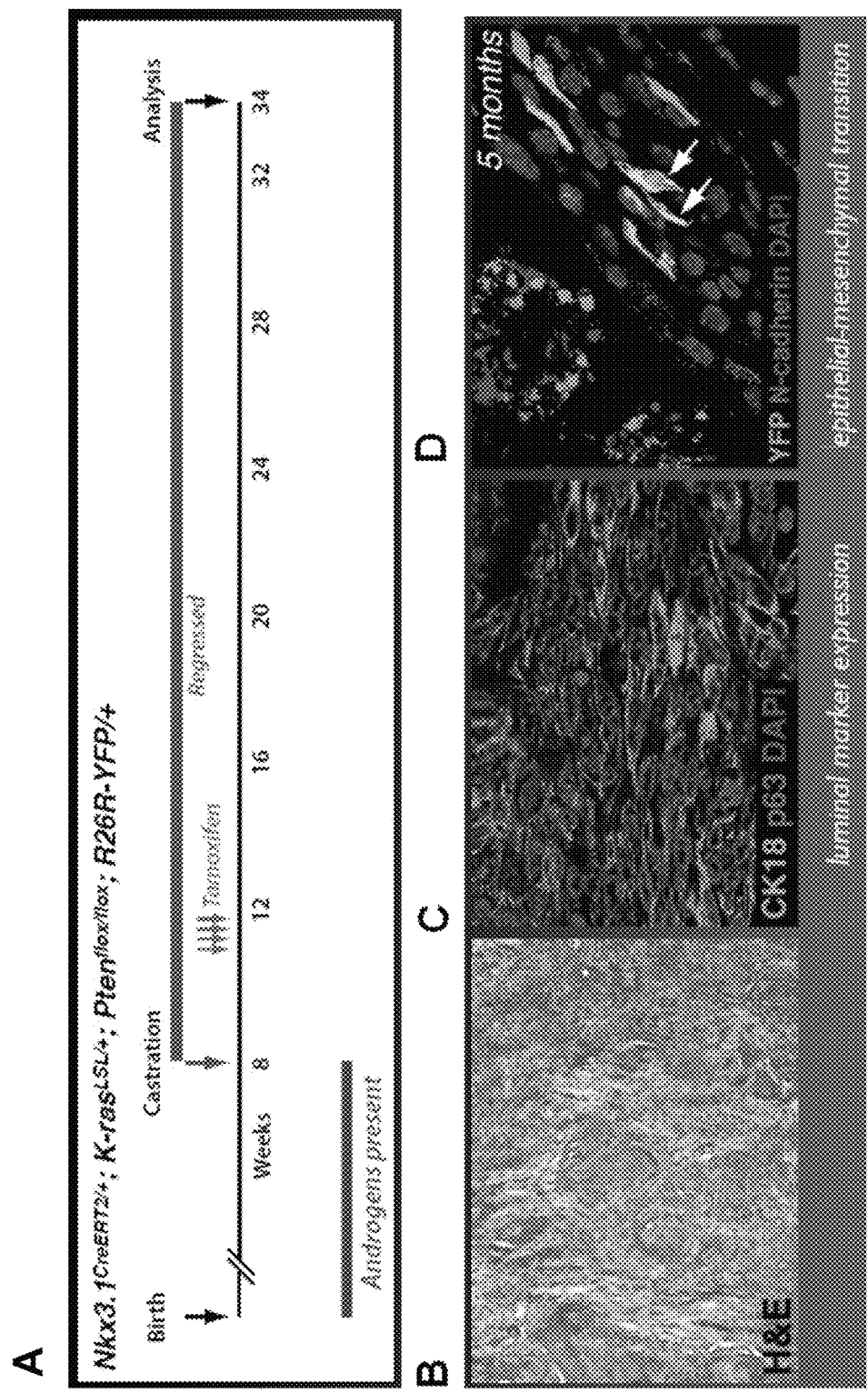
FIGS. 14A-D. Castration-resistant prostate cancer originating from CARNs FIG. 14A. Diagram showing the strategy for lineage-marking experiments in Nkx3.1$^{CreERT2/+}$; K-ras$^{LSL/+}$; Pten$^{flox/flox}$; R26R-YFP/+.
Figure 15:
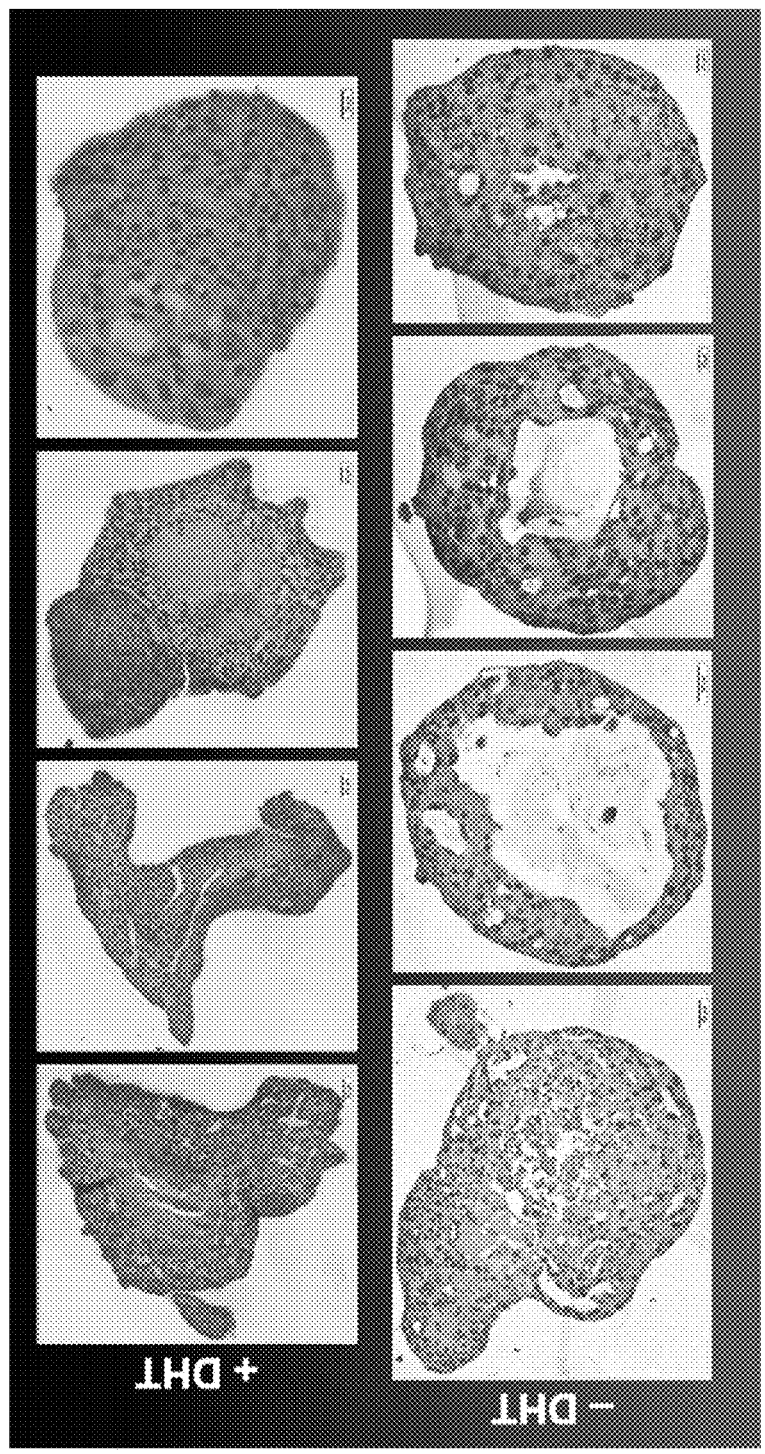
FIG. 15. Histology of tumor organoids grown in the presence of DHT and the absence of DHT.
Figure 16:
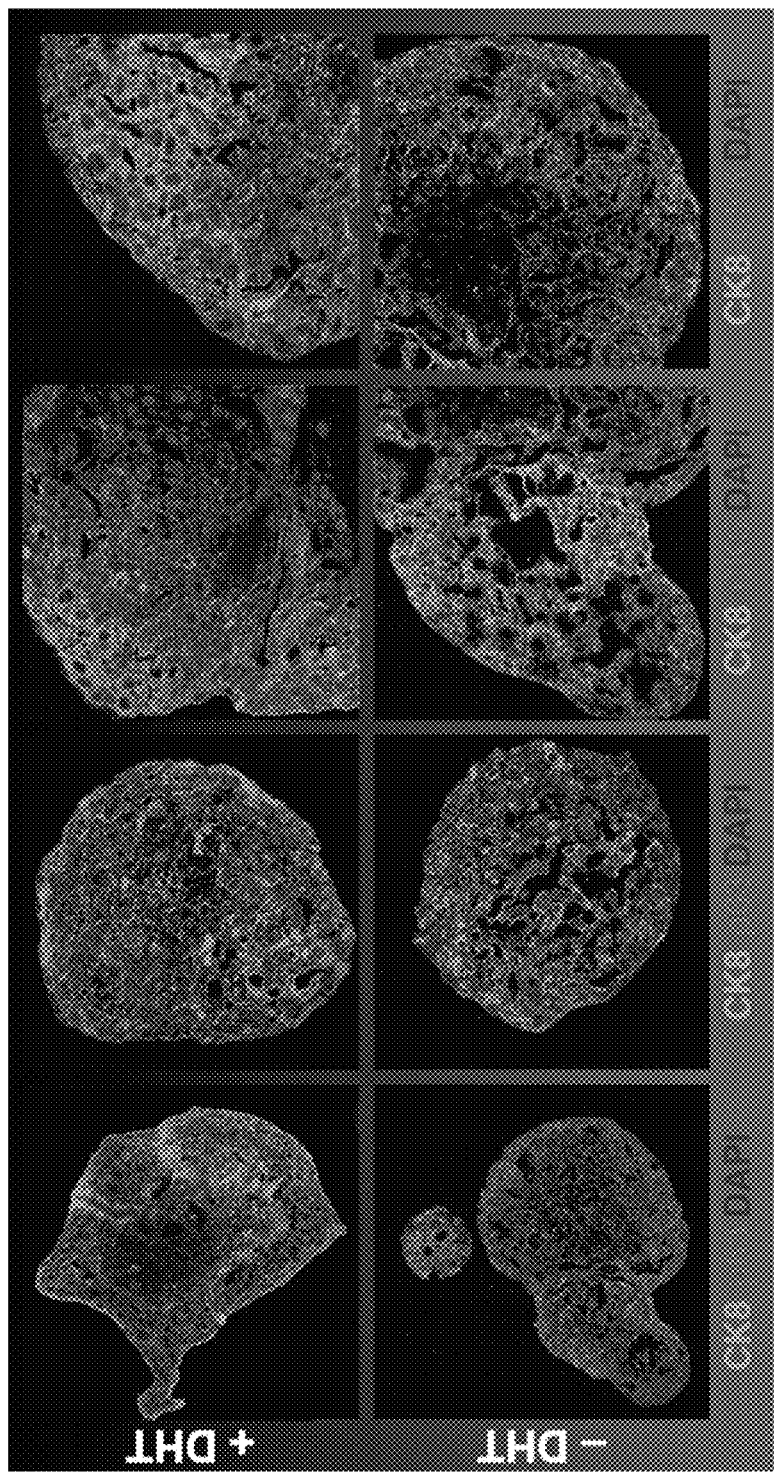
FIG. 16. Immunostaining showing the luminal phenotype of tumor organoids grown in the presence of DHT (top) and the absence of DHT (bottom). CK8 is shown in green and p63 or CK5 is shown in red, as indicated.
Figure 17:
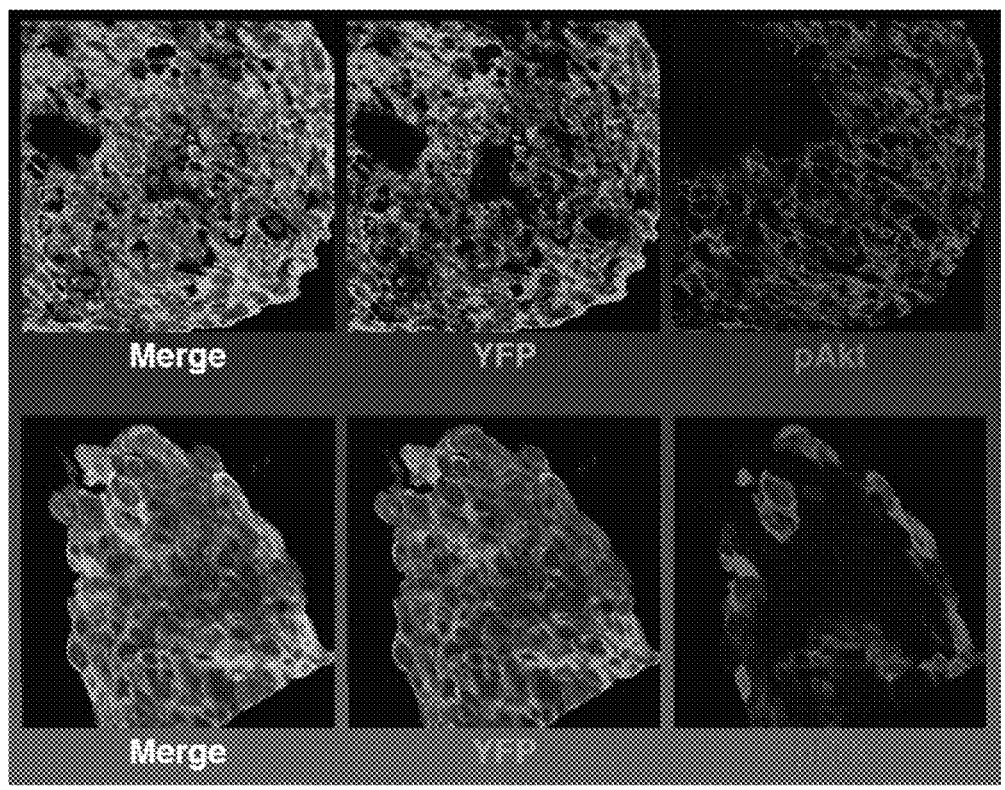
FIG. 17. Immunostaining showing the transformed phenotype of tumor organoids. Top row: YFP (green) and pAkt (red); Bottom row: YFP (green) and pErk (red).
Figure 18:
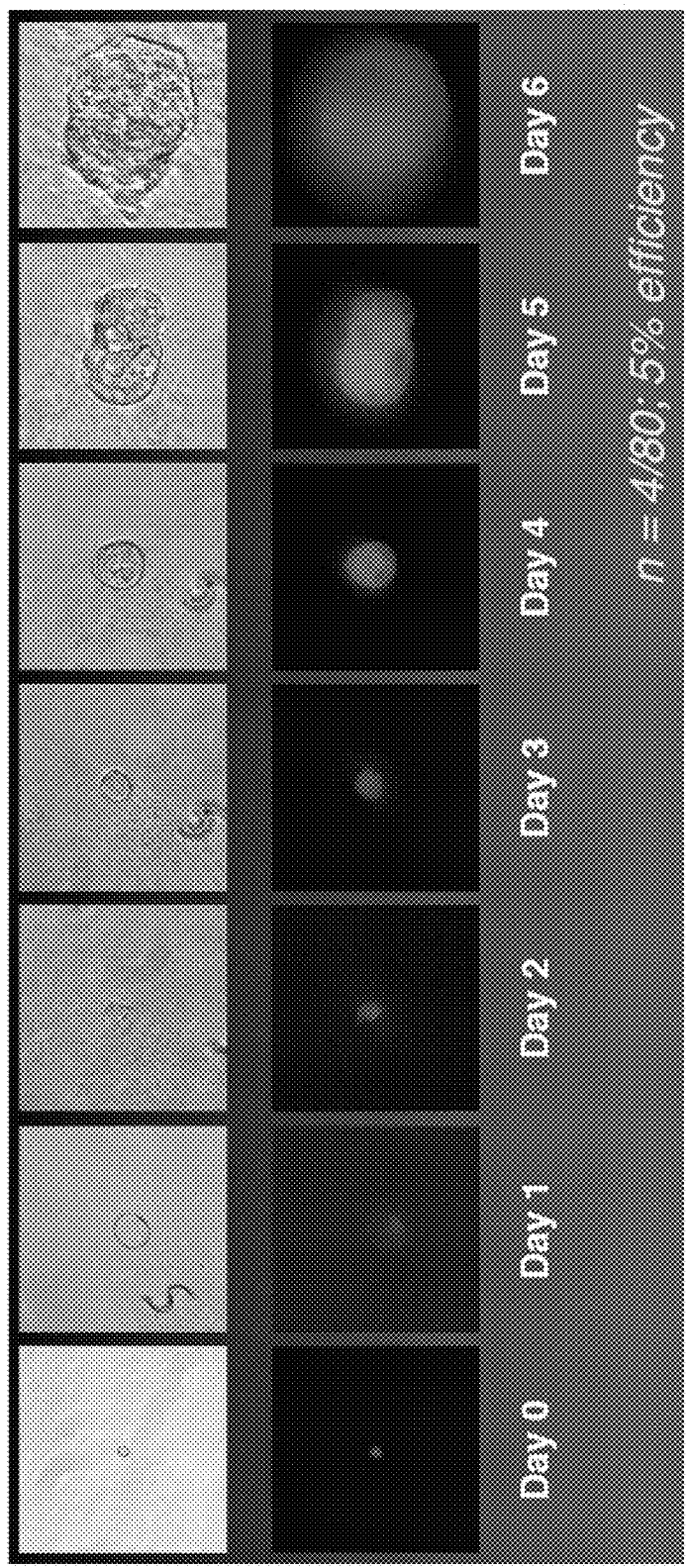
FIG. 18. Microscopic images showing growth of tumor organoids from single cells. n=4/80; 5% efficiency.
Figures 19A, 19B, 19C, 19D:
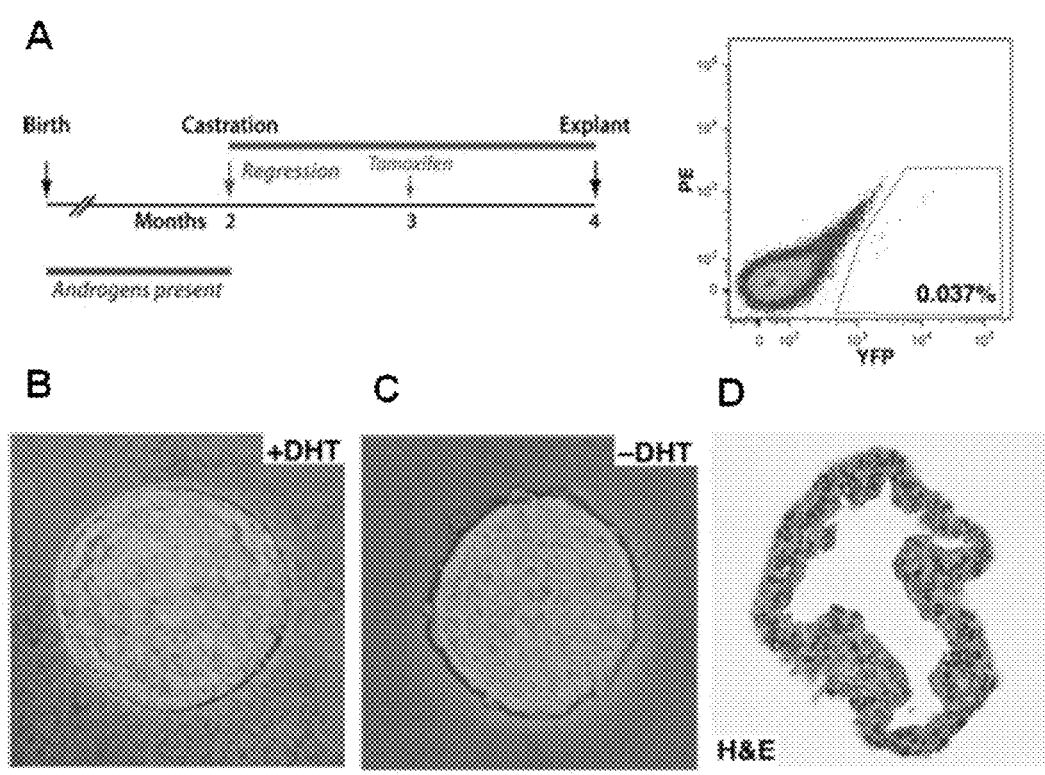
FIGS. 19A-H. Growth of prostate organoids from mouse CARNs. Mouse CARNs are isolated by flow-cytometry (FIG. 19A) and organoids are grown in 3-dimensional culture using hepatocyte media, charcoal-stripped serum (to remove testosterone), Matrigel, and ROCK inhibitor, either in the presence (FIG. 19 B) or absence (FIG. 19C) of dihydrotestosterone (DHT). In these conditions, the organoids form an outer basal layer (marked by CK5 and p63 expression) and inner luminal cells (marked by CK8 and CK18 expression). Organoids are stained with H&E (FIG. 19D). Immunostaining for the expression of outer basal layer marker CK5 (red) (FIG. 19F) and inner luminal cell marker CK8 (white) (FIG. 19G).
Figure 19E:
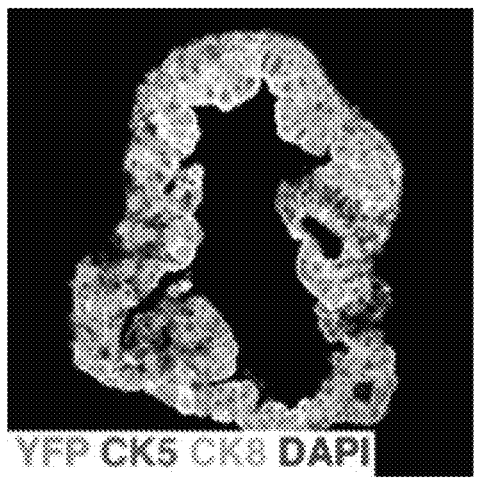
Figure 19F:
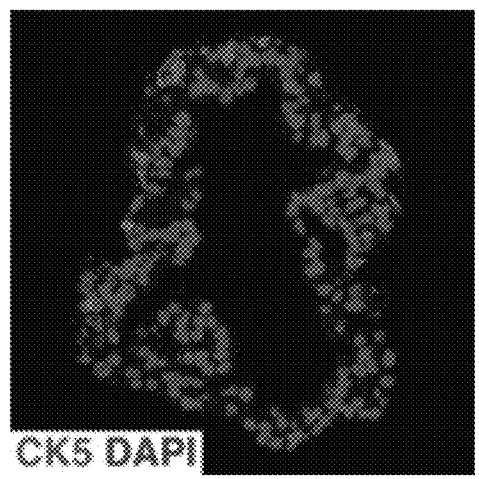
Figure 19G:
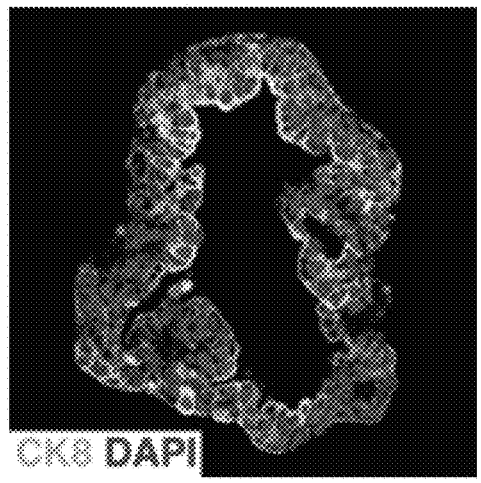
Figure 19H:
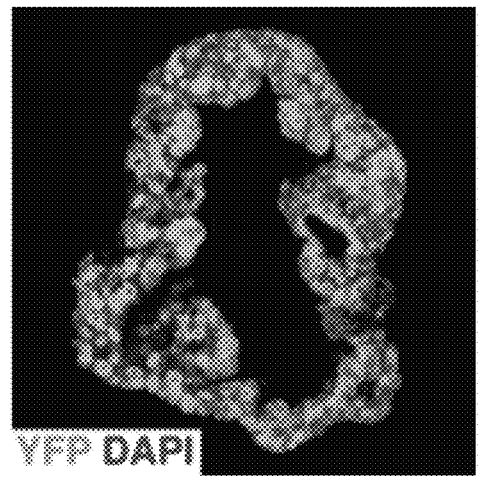

Castration resistant prostate cancer can originate from CARNs (FIG. 14). Tumor organoids can be grown in the presence and absence of DHT (FIG. 15) and display luminal phenotypes (FIG. 16) and transformed phenotype (FIG. 17). Tumor organoids can also be grown from single cells (FIG. 18).

Without being bound by theory, additional embodiments include the cell type of origin for organoid formation. The organoid phenotype can also be dependent on androgen and androgen receptor (AR) function. In other embodiments organoids can be used for small molecule screens for the identification of candidate therapeutics.

Example 3—Prostate Organoid Culture

The objectives of the studies herein include the following:
Development of a culture-based system for rapid investigation of prostate biology
Accurate modeling of human prostate cancer using patient-derived tissues
Patient-specific analyses of drug response for personalized medicine.

Single CARNs (castration-resistant Nkx3.1 cells) from androgen-deprived mouse prostate can be cultured by the methods described herein and give rise to the organoids of the present invention. Previous studies showed that CARNs have stem cell properties, for example as shown by their ability to generate prostate ducts in single-cell transplantation assays (FIGS. 5A-D).

Figure 20:
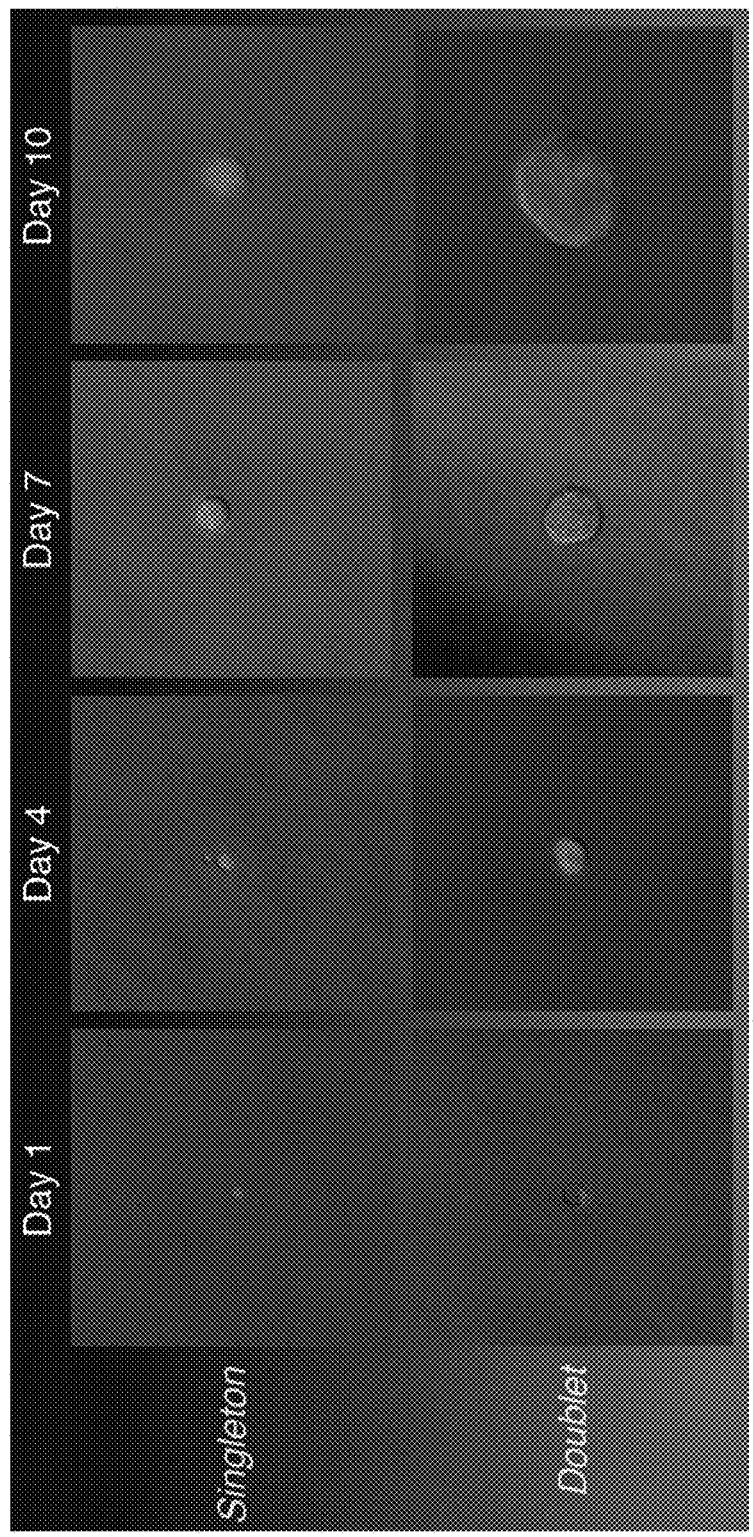
FIG. 20. Generation of organoids from single CARNs. Microscopic images showing culture of organoids from single mouse CARNs, at a frequency of approximately 2%.
Figures 21A, 21B, 21C, 21D, 21E, 21F:
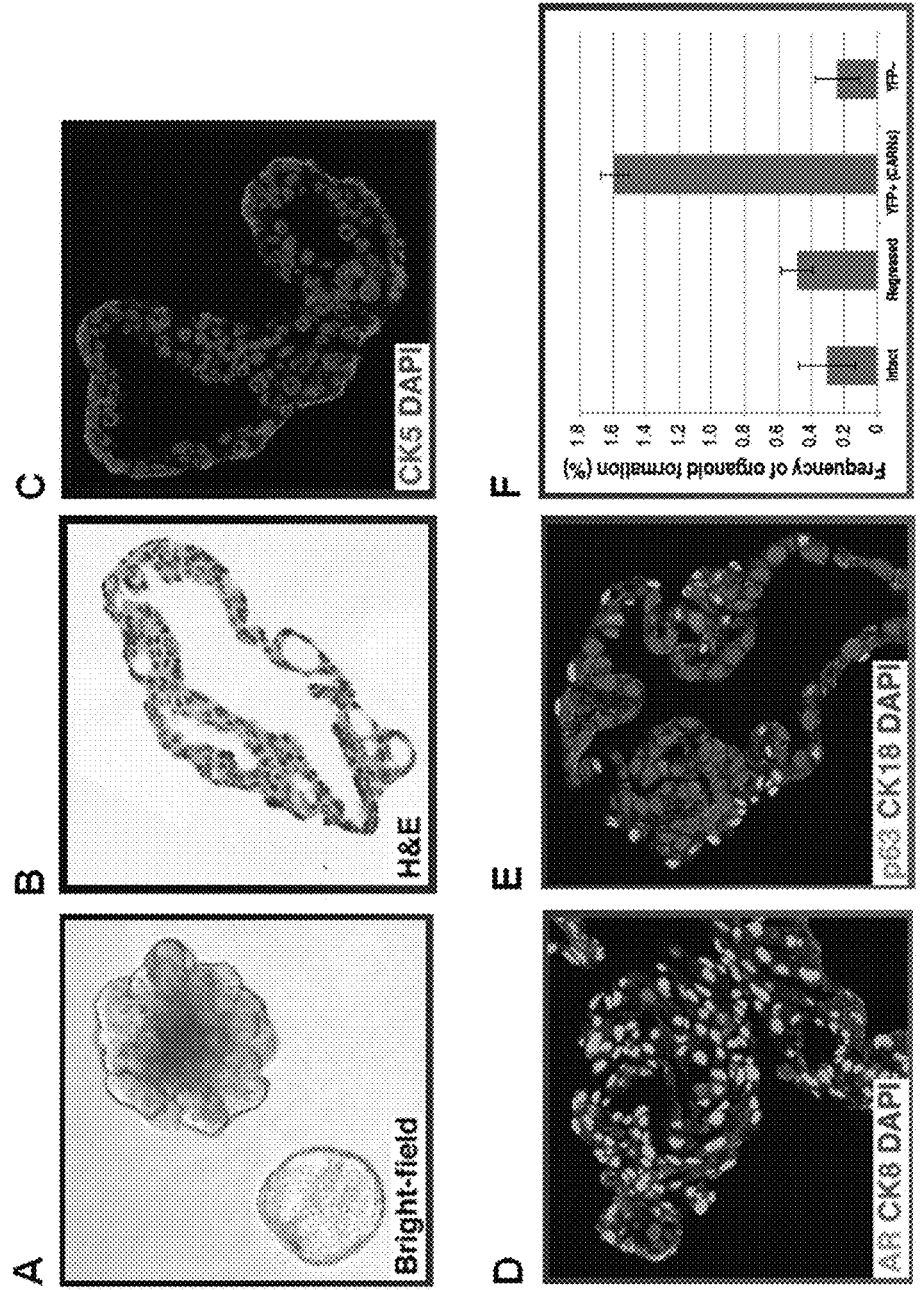
FIGS. 21A-F. Growth of organoids from normal mouse prostate epithelium. Microscopic images showing growth of organoids viewed with brightfield microscopy (FIG. 21A) and stained with H&E (FIG. 21B). Immunostaining for CK5 (red) (FIG. 21C), CK8 (red) and androgen receptor (AR) (green) (FIG. 21D), or p63 (green) and CK18 (red) (FIG. 21E). Graph showing the frequency of organoid formation (FIG. 21F).
Figures 22A, 22B, 22C, 22D:
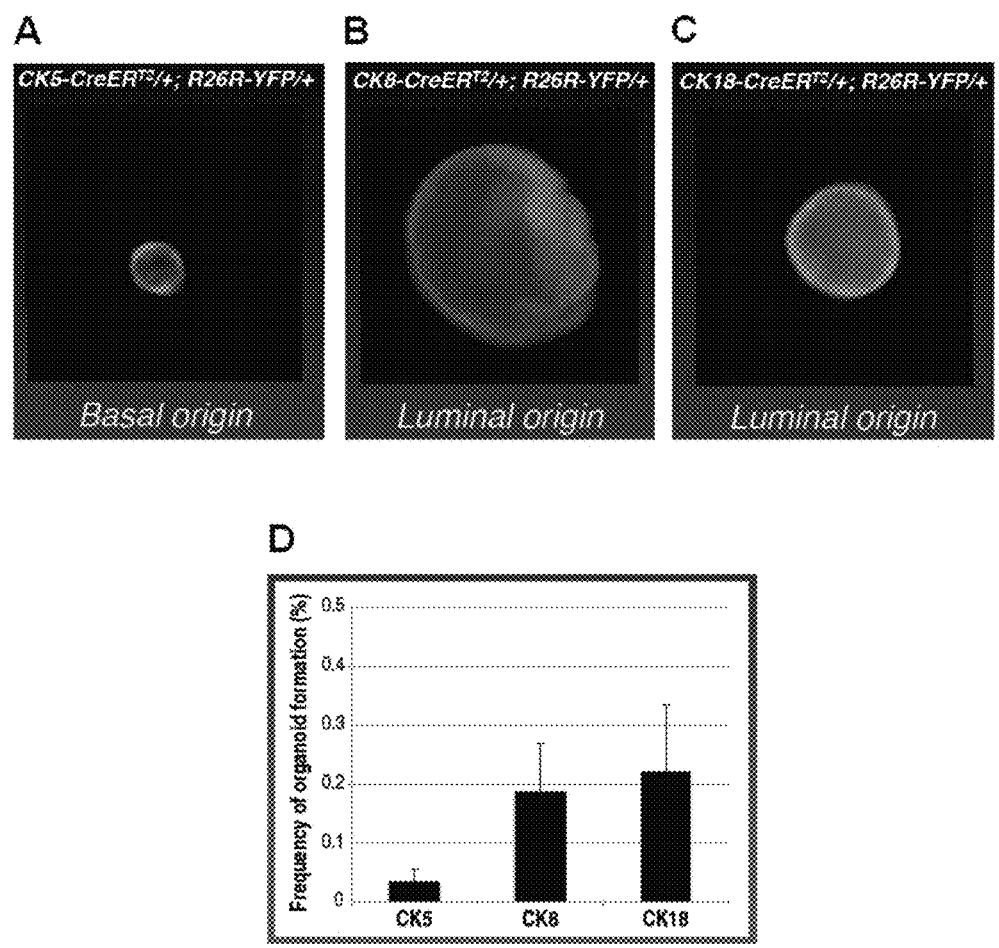
FIGS. 22A-D. Cell types of origin for mouse prostate organoid formation. Mouse prostate organoids grow from flow-sorted basal cells (lineage-traced from CK5-CreER$^{T2}$/+; R26R-YFP/+ mice) (FIG. 22A) or luminal cells (lineage-traced from CK8-CreER$^{T2}$/+; R26R-YFP/+ or CK18-CreER$^{T2}$/+; R26R-YFP/+ mice) (FIGS. 22B-C) Graph showing the frequency of organoid formation for different cells of origin (FIG. 22 D).
Figures 23A, 23B, 23C, 23D, 23E, 23F, 23G, 23H:
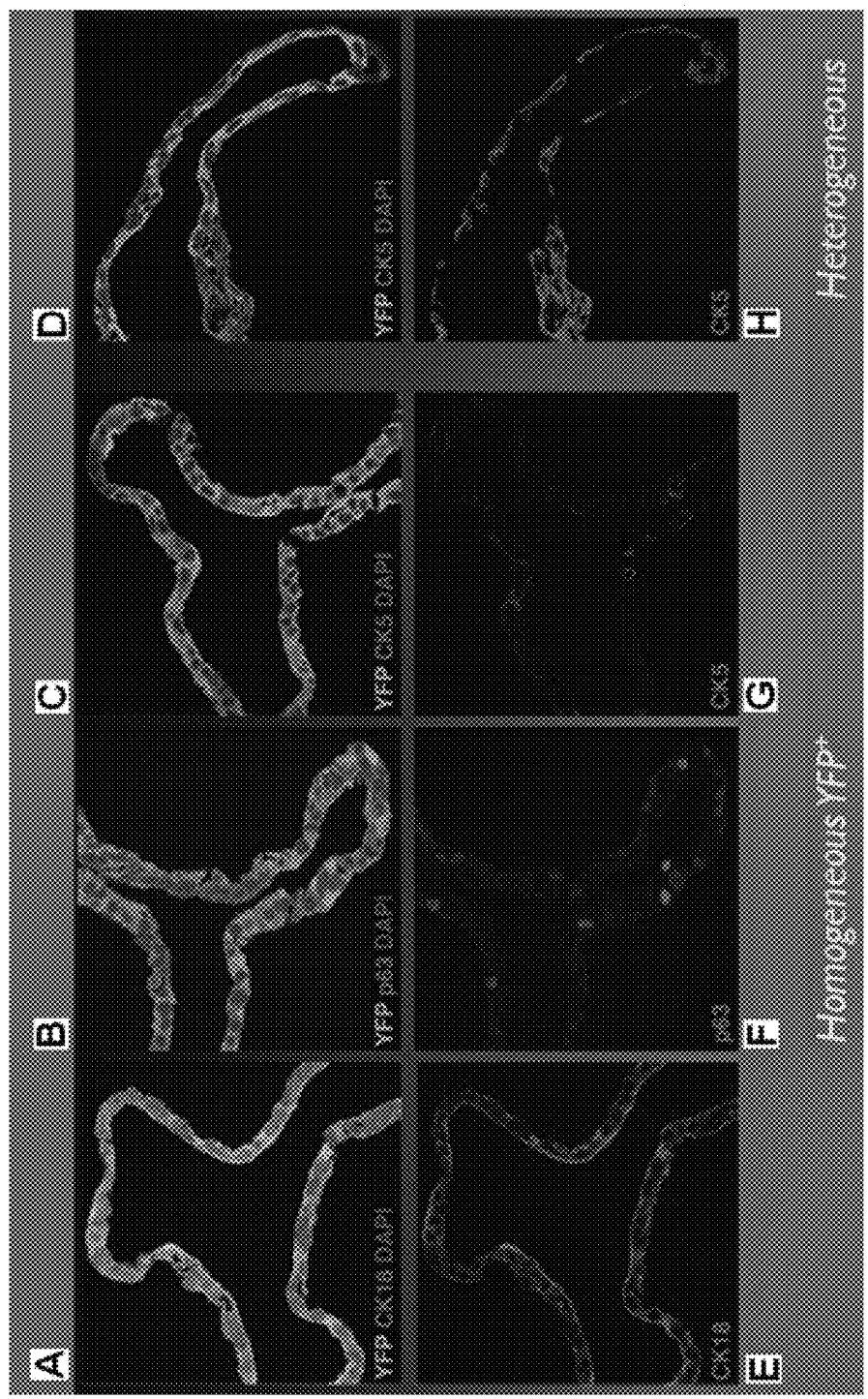
FIGS. 23A-H. Shows luminal derived organoids contain basal-like cells. Immunostaining for CK18 (red) (FIG. 23E) and overlay with YFP (green) and DAPI (blue) (FIG. 23A) in homogenous YFP+ organoids. Immunostaining for p63 (red) (FIG. 23F), and overlay with YFP (green) and DAPI (blue) (FIG. 23B) in homogenous YFP+ organoids. Immunostaining for CK5 (red) (FIG. 23G) and overlay with YFP (green) and DAPI (blue) (FIG. 23C) in homogenous YFP+ organoids. Immunostaining for CK5 (red) (FIG. 23H) and overlay with YFP (green) and DAPI (blue) (FIG. 23D) in heterogenous organoids.
Figures 24A, 24B, 24C, 24D, 24E:
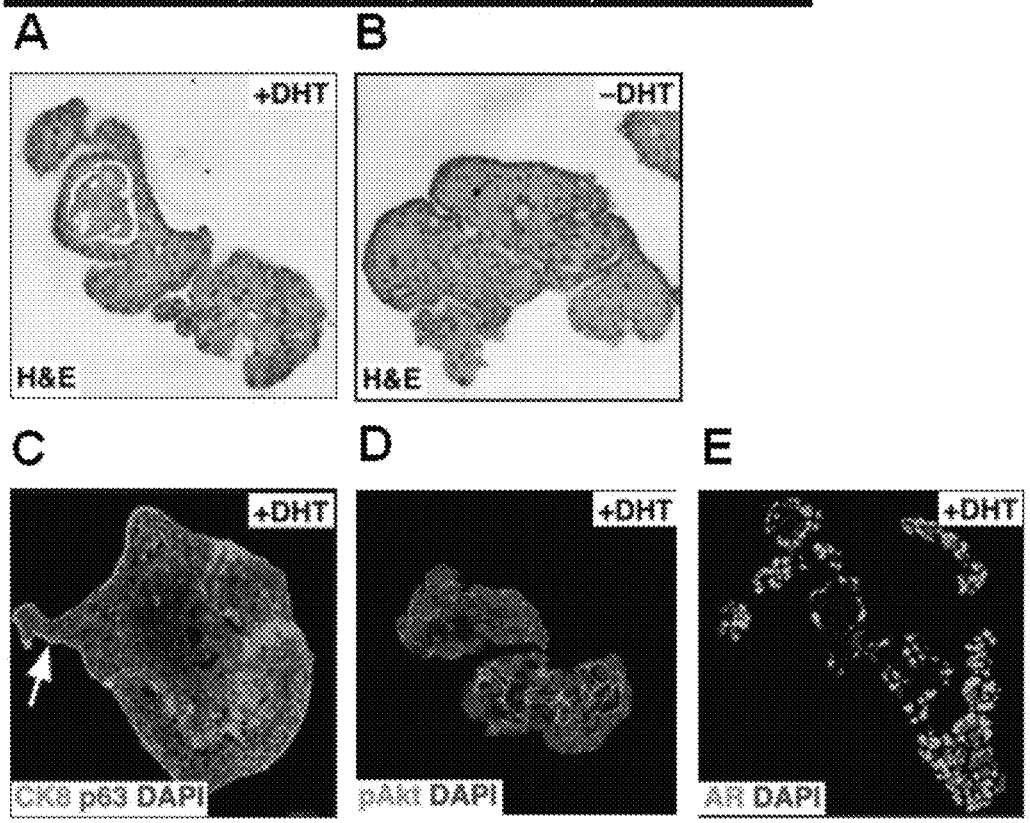
Figure 24F:
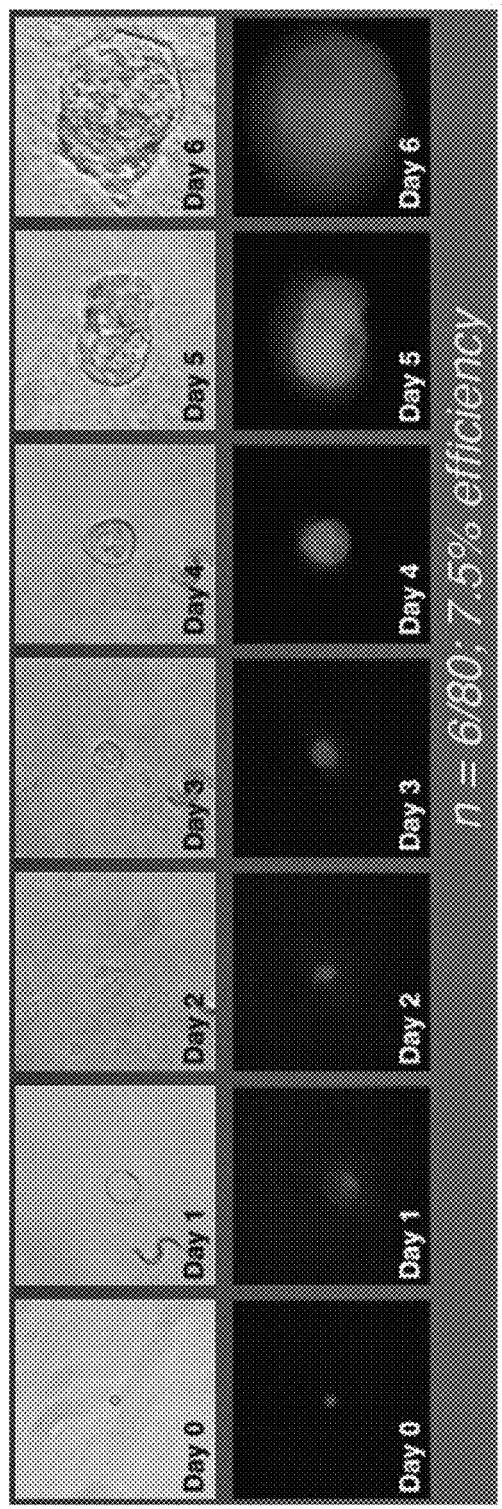
Figure 26A:
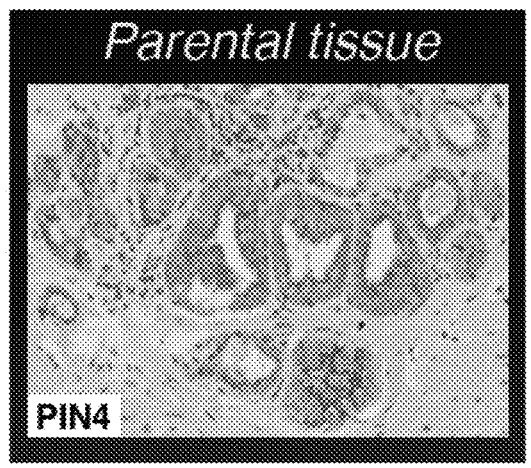
FIGS. 26A-J. Prostate organoids can be grown from human prostatectomy specimens. PIN4 staining of primary specimens (FIG. 26A) and growth of organoids (FIG. 26B). Organoids grown from the primary specimens in the presence of DHT stained with H&E (FIGS. 26A, D) or imaged with brightfield microscopy (FIG. 26C). Immunostaining of an organoid grown without DHT for pAKT (green) (FIG. 26E). AMACR staining of an organoid grown in the presence of DHT (FIG. 26F). Immunostaining of an organoid grown in the presence of DHT for p63 (green) and CK8 (red) (FIG. 26G). Immunostaining of an organoid grown in the presense of DHT for Ki67 (red) (FIG. 26H). Immunostaining for AR (green) of an organoid grown in the presence of DHT (FIG. 26I) or the absence of DHT (FIG. 26J).
Figure 26B:
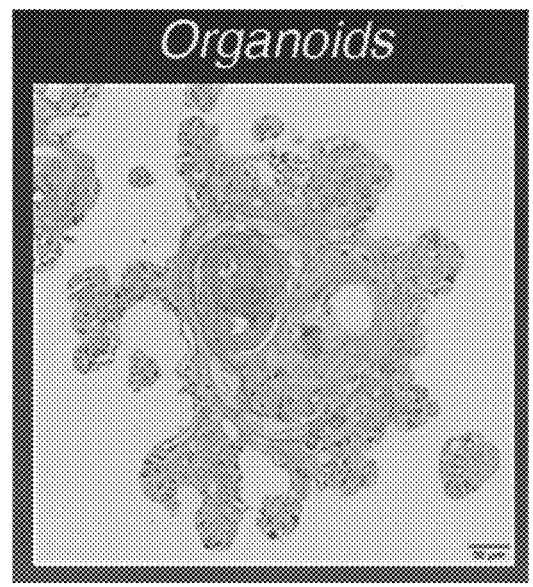
Figures 26C, 26D, 26E, 26F, 26G, 26H, 26I, 26J:
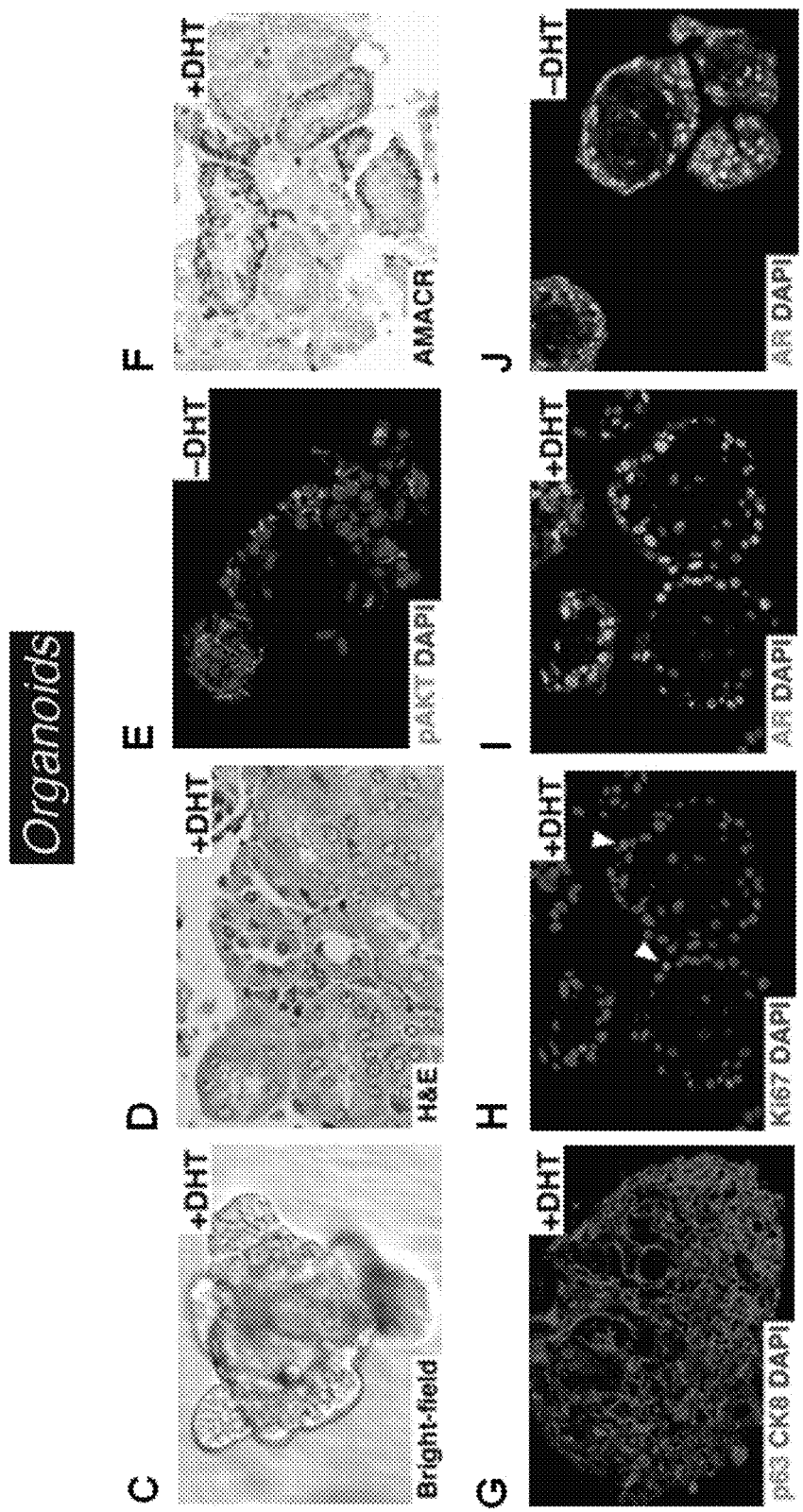

Prostate organoids can be grown from mouse CARNs (FIGS. 19A-H). Mouse CARNs were isolated by flow cytometry and organoids were grown in 3-dimensional culture using hepatocyte media, charcoal-stripped serum (to remove testosterone), Matrigel, and ROCK inhibitor, either in the presence or absence of dihydrotestosterone (DHT). In these conditions, the organoids form an outer basal layer (marked by CK5 and p63 expression) and inner luminal cells (marked by CK8 and CK18 expression). Organoids can also be cultured from single mouse CARNs, at a frequency of approximately 2% (FIG. 20).

Organoids can also be cultured from hormonally-intact ("normal") mouse prostate epithelium (FIGS. 21A-F). These organoids have stratified basal and luminal layers, and express nuclear androgen receptor (AR). The plating efficiency from hormonally-intact and androgen-deprived prostate epithelium is about 0.3-0.4%, which is approximately 5-fold lower than the efficiency using purified CARNs.

Lineage-tracing using flow-sorted basal or luminal mouse epithelial cells shows that basal cells are a poor origin for organoids, while luminal cells are preferred origins (FIGS. 22A-D).

Organoids generated from luminal cells contain basal cells that are derived from luminal cells (FIGS. 23A-H). However, these basal cells do not display completely normal morphologies, unlike in organoids in which basal cells may not be derived from luminal cells.

Mouse CARNs that are deleted for Pten and have oncogenic K-ras can generate tumor organoids (FIGS. 24A-G). These tumor organoids have a luminal phenotype (mostly CK8-positive with few p63-positive cells), express membrane-localized phosphorylated Akt (pAkt), and have nuclear androgen receptor. Single transformed CARNs can generate tumor organoids with 7.5% plating efficiency.

Isolation of normal human basal and luminal prostate epithelial populations by flow cytometry shows that human basal cells are more efficient at organoid formation than luminal cells (FIGS. 25A-C). However, normal human luminal cells can serve as origins for organoid formation.

Prostate organoids can be cultured from human prostatectomy specimens containing localized tumors (as shown by PIN4 staining of primary specimens) (FIGS. 26A-J). These prostate organoids contain mixtures of normal or benign, as well as cancer cells. In many of these organoids, the presence of cancer cells is indicated by histology, by positive pAkt staining, by AMACR staining, and/or by a predominantly luminal phenotype.

Figures 27A, 27B, 27C:
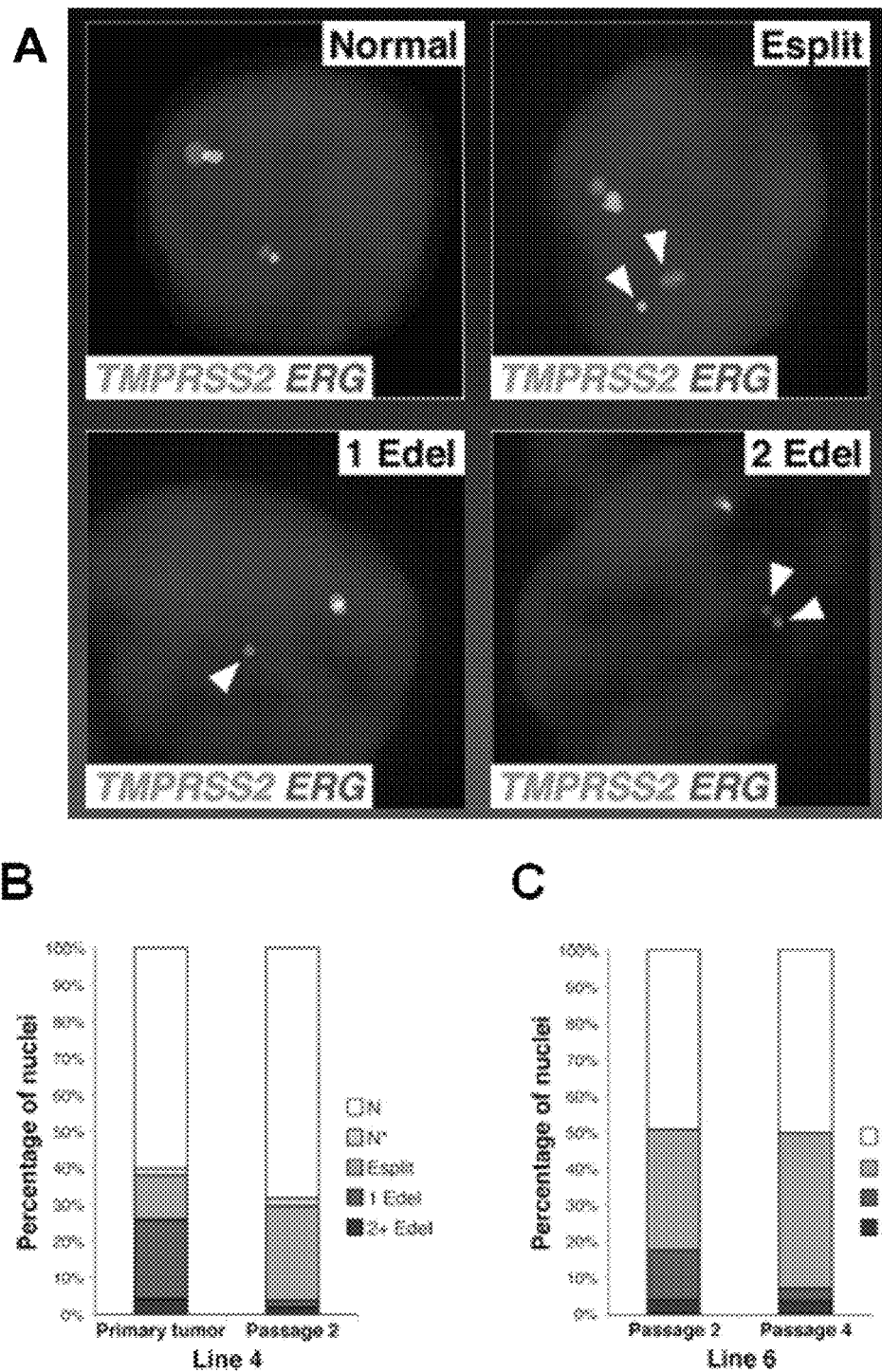
FIGS. 27A-C. Fluorescence in situ hybridization (FISH) of human prostate organoid lines for detection of TMPRSS2-ERG rearrangements (FIG. 27A). Graph showing the percentage of nuclei with TMPRSS2-ERG rearrangements for human prostate organoid line 4 (FIG. 27B) and line 6 (FIG. 27C).

Several of the human prostate organoid lines contain cells with TMPRSS2-ERG rearrangements (which are present in approximately 50% of prostate tumors), as detected by fluorescence in situ hybridization (FISH) (FIGS. 27A-C).

Figure 28:
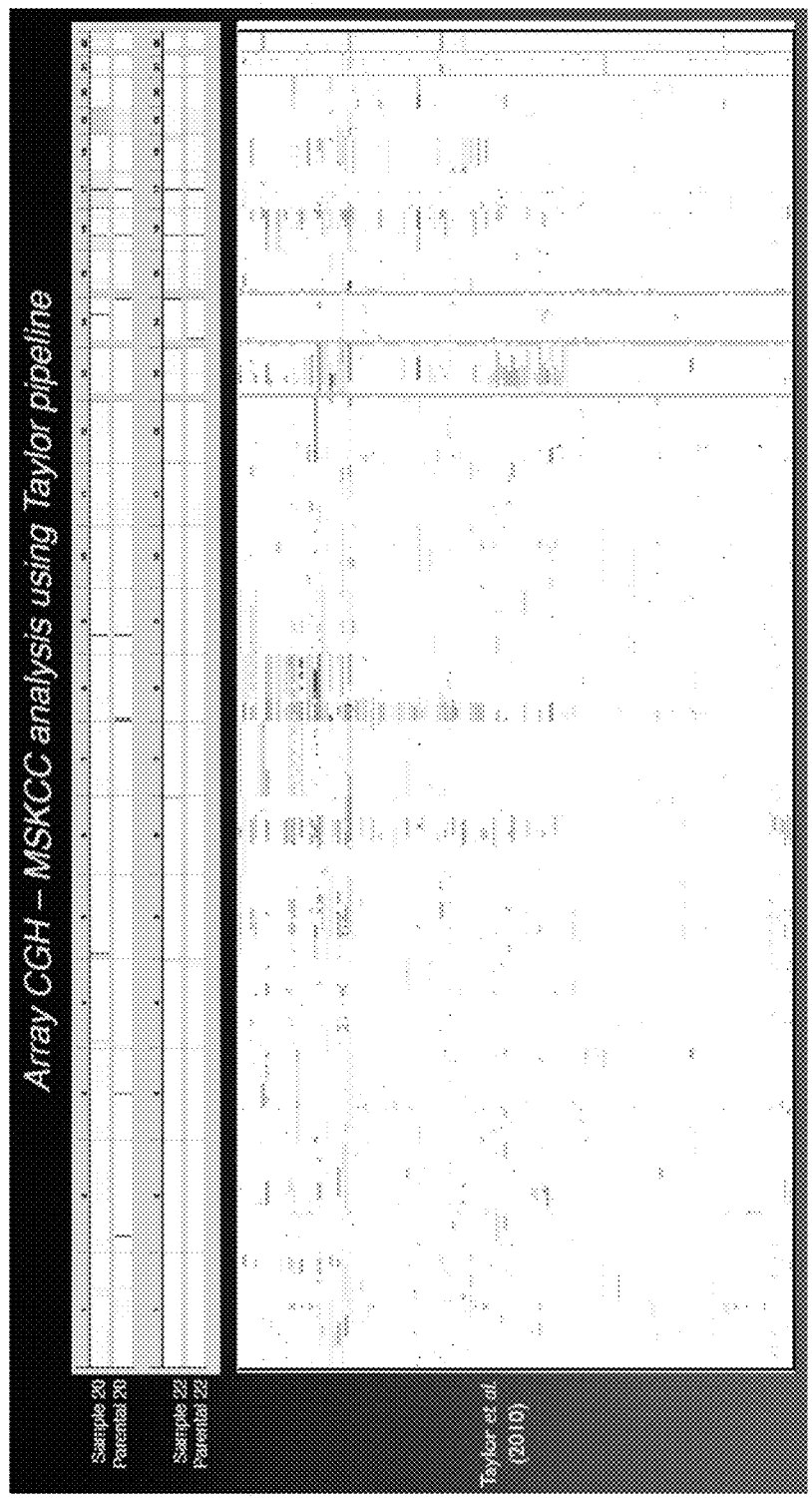
FIG. 28. Copy number analysis of two prostate organoid lines by array comparative genomic hybridization (aCGH).
Figures 29A, 29B, 29C:
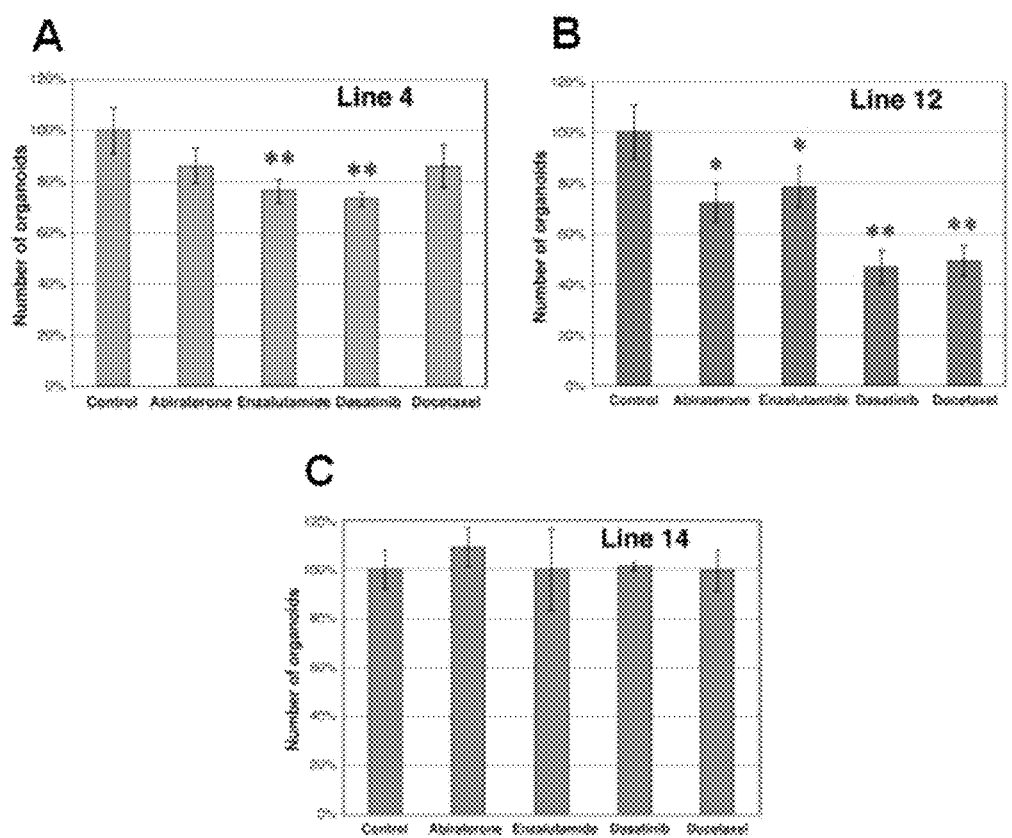
FIGS. 29A-G. Drug treatment response of human prostate organoids. Graphs showing the number of organoids grown for different organoid lines in the presence of a panel of drugs used to treat prostate cancer (FIGS. 29A-C). Immunostaining of organoids for Ki67 (red) without any drugs (FIG. 29D) and with Abiratrone (FIG. 29E), Dasatinib (FIG. 29F), or Docetaxel (FIG. 29G).
Figures 29D, 29E, 29F, 29G:
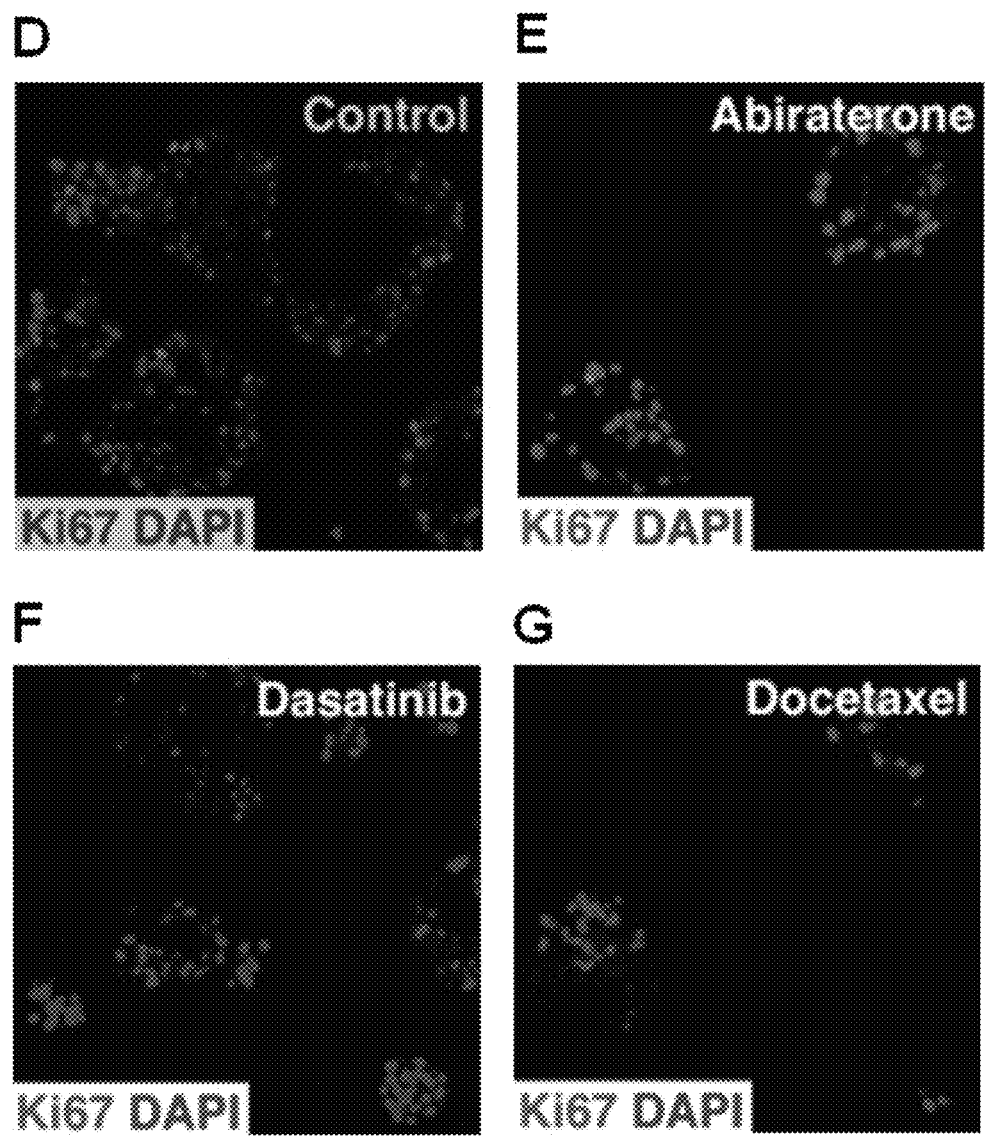

Copy number analysis of two lines by array comparative genomic hybridization (aCGH) shows that these lines contain genomic gains (red) and losses (blue) that are similar between the organoid line and the parental prostatectomy sample (FIG. 28). The pattern of these gains and losses has several features in common with the range of alterations previously described for localized prostate tumors (see Taylor et al. (2010)).

Different human organoid lines display distinct responses to a panel of drugs used to treat prostate cancer (FIGS. 29A-G).

The organoids (both mouse and human) are composed strictly of epithelial cells, and lack stromal components.

One is able to culture both mouse and human prostate epithelial cells as organoids in three-dimensional culture, and derive from these cell cultures that grow as attached cells in more conventional two-dimensional culture, using the same culture media as for organoids. Thus, these conditions can be permissive for the derivation of new prostate cancer cell lines.

Example 4—Single Luminal Epithelial Progenitors can Generate Prostate Organoids in Culture Generation of prostate organoids in culture is described in Chua C. W. et al., "Single luminal epithelial progenitors can generate prostate organoids in culture," Nature Cell Biology, 16 (10) pp 951-61 (2014), the contents of which is hereby incorporated by reference in its entirety.

The intrinsic ability to display self-organizing morphogenetic properties in ex vivo culture may represent a general property of tissue stem cells. Described herein are single luminal stem/progenitor cells that can generate prostate organoids in a three-dimensional culture system in the absence of stroma. Organoids generated from CARNs (castration-resistant Nkx3.1-expressing cells) or normal prostate epithelium exhibit tissue architecture containing luminal and basal cells, undergo long-term expansion in culture, and display functional androgen receptor signaling. Lineage-tracing demonstrates that luminal cells are favored for organoid formation, and generate basal cells in culture. Furthermore, tumor organoids can initiate from CARNs after oncogenic transformation, and from mouse models of prostate cancer, and can facilitate analyses of drug response. Also described herein is evidence supporting the feasibility of organoid studies of human prostate tissue. These studies underscore the progenitor properties of luminal cells, and identify in vitro approaches for studying prostate biology.

Despite the apparent simplicity of cell types in the prostate epithelium, there has long been a dearth of suitable cell culture-based systems for investigating prostate biology [1]. In the normal prostate, there are three epithelial cell types, corresponding to: 1) luminal cells, which are columnar cells expressing cytokeratin (CK) 8, CK18, and high levels of androgen receptor (AR); 2) basal cells, which express CK5 and p63; and 3) rare neuroendocrine cells [2]. During prostate tumorigenesis, basal cells undergo progressive loss in pre-neoplastic lesions known as prostatic intraepithelial neoplasia (PIN), and are essentially absent in prostate adenocarcinoma, which typically has a luminal phenotype [3, 4].

Historically, prostate luminal cells have been difficult to grow in culture, which has hindered the establishment of cell lines from normal or transformed prostate epithelium. One approach to circumvent this limitation has been culture of three-dimensional "prostaspheres" containing epithelial cells explanted from primary mouse or human prostate tissue [5-8]. Such prostaspheres can be serially passaged and used in assays for prostate epithelial stem cells and tumor-initiating cells [9, 10]. However, prostaspheres typically originate from basal epithelial cells and fail to display complete luminal differentiation in the presence of androgens [9, 11-13]. Notably, prostaspheres fail to demonstrate strong nuclear AR expression in the presence of androgens or a functional response to androgen-deprivation [6, 9].

Recent work has described alternative explant approaches for three-dimensional culture of epithelial cells in the absence of stroma. Such "organoid" culture systems contain similar extracellular matrix components as often used in sphere assays, but also utilize conditions that enhance the survival, proliferation, and/or differentiation of stem/progenitor populations [14]. In particular, cultured stem cells of the mouse small intestine and colon [15, 16] can form organoids that display normal epithelial architecture and serve as the basis for tissue repair [17], while tumor organoids can be established from transformed colon as a model of colon adenocarcinoma [18, 19]. Additional studies of organoids from intestine [20], stomach [21], liver [22], and pancreas [23, 24] have demonstrated the general feasibility of this approach.

Previous work identified a luminal epithelial stem/progenitor population known as CARNs (castration-resistant Nkx3.1-expressing cells), which are also cells of origin for prostate cancer [25]. It was shown that single CARNs can reconstitute prostate ducts in a renal grafting assay [25]. Described herein is an ex vivo culture system that can support the growth and serial passaging of epithelial organoids derived from CARNs or more generally from normal prostate epithelium. It is shown that these prostate organoids are primarily derived from luminal epithelial cells, and display functional AR activity in culture. It is demonstrated that mouse tumor organoids can model tumor phenotypes and drug response, and it is shown that organoids can be established from benign human prostate tissue and a luminal prostate cancer cell line. Consequently, organoid culture represents an excellent system for investigating prostate biology and cancer.

Results

Establishment of Prostate Epithelial Organoids from CARNs

Previously, a rare luminal epithelial population in the regressed prostate epithelium was identified that has stem cell properties in vivo and in tissue reconstitution assays [25]. To pursue further analyses of these CARNs, conditions for their isolation and successful propagation in culture were established. For this purpose, adult male Nkx3.1$^{CreERT2/+}$; R26R-YFP/+ mice were surgically castrated to induce androgen-deprivation, followed by tamoxifen induction to lineage-mark CARNs (FIG. 30A). Following dissociation of prostate tissue into a single-cell suspension, flow-sorting was used to isolate CARNs based on their yellow fluorescent protein (YFP) expression (FIG. 30B).

To culture CARNs, a protocol was developed based in part on the importance of Matrigel in three-dimensional culture of prostate and mammary epithelium [26, 27], hepatocyte medium for prostate epithelial cell culture [28], and ROCK inhibitor to improve the survival of dissociated epithelial cells [29-31]. The resulting protocol involves low-percentage Matrigel floating culture in the presence of epidermal growth factor, heat-inactivated charcoal-stripped fetal bovine serum (FBS), which lacks androgens, and supplementation with dihydrotestosterone (DHT) (see Methods). Under these conditions, isolated CARNs formed epithelial "organoids" that could grow for at least 3-4 weeks in culture (FIG. 30C), displaying a range of morphologies, and varying in size from 15 microns in diameter to greater than 0.5 mm in diameter. Importantly, most organoids were homogeneously composed of YFP-expressing cells, indicating their derivation from lineage-marked CARNs (FIG. 30d), and lacked stroma (FIG. 30E, F). Consistent with their growth in culture, many cells within organoids were positive for Ki67 (FIG. 30G). CARN-derived organoids typically displayed an outer rim of cells positive for the basal marker cytokeratin 5 (CK5), and internal cells positive for the luminal marker cytokeratin 8 (CK8) (FIG. 30H); few "intermediate" cells that co-express basal and luminal markers were observed. Notably, the organoids expressed nuclear AR (FIG. 30I), as well as nuclear Foxa1, a transcription factor that is essential for prostate organogenesis [32] (FIG. 30J). Thus, lineage-marked CARNs are able to generate basal cells in organoid culture, similar to their ability in vivo and in tissue reconstitution assays.

To confirm that these organoids retained properties of prostate epithelium, tissue reconstitution assays were performed [13]. CARN-derived organoids were recombined with urogenital mesenchyme from rat embryos, followed by implantation under the kidney capsule of immunodeficient mice. The resulting grafts displayed prostate ductal structures (FIG. 30K) and expressed both basal (p63) and luminal (CK8) markers (FIG. 30L). Furthermore, the epithelial cells were completely YFP-positive and expressed nuclear AR (FIG. 30M), indicating that the CARN-derived organoids could successfully reconstitute prostate tissue.

Establishment of Prostate Organoids from Single CARNs

To determine the efficiency of organoid formation, the number of organoids formed after 7 days of culture were assessed. It was found that the average efficiency of organoid formation by lineage-marked CARNs was 1.42% (FIG. 30N; Table 1). For comparison, non-YFP expressing epithelial cells from the same mice used to isolate the lineage-marked CARNs were also assayed. These non-YFP expressing cells could also form organoids in culture, but at a nearly 6-fold lower average frequency of 0.24% (FIG. 30N; Table 1; Methods), suggesting that non-CARNs can also form organoids, but at a reduced efficiency.

Figure 30O:
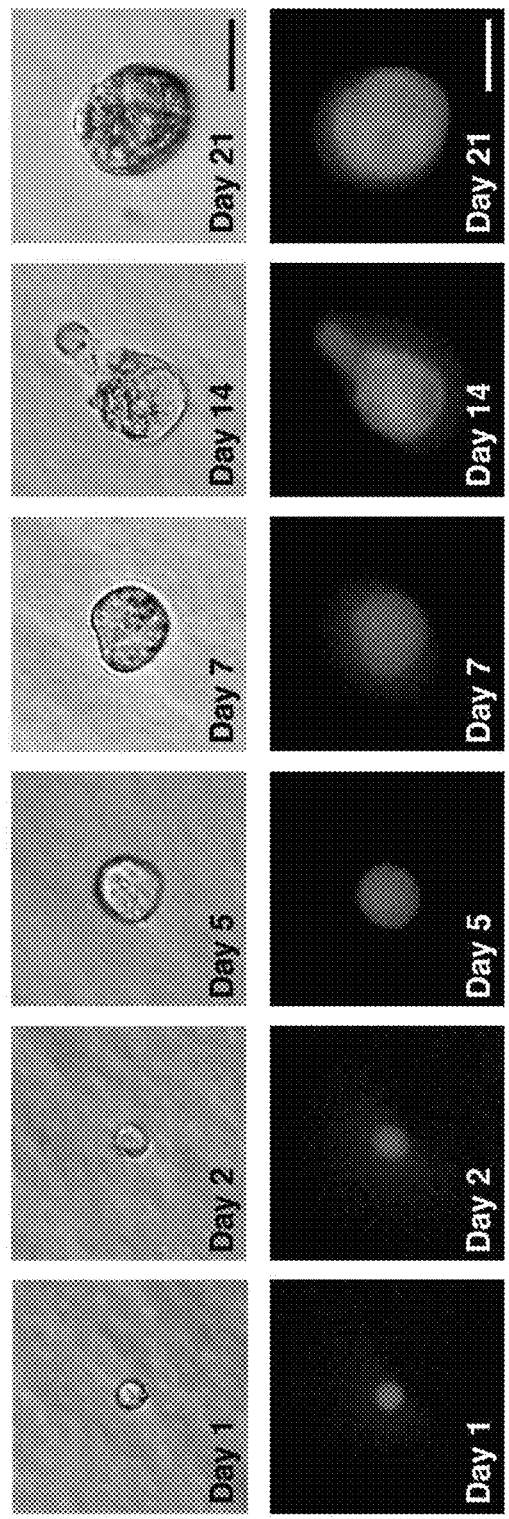

Given their stem cell properties, its was examined whether individual lineage-marked CARNs could form an organoid. To isolate single cells, flow cytometry was used to purify lineage-marked CARNs, and then mouth-pipetted single fluorescent cells into individual wells of a 96-well plate. Each well was imaged to confirm plating of single cells, and followed their potential growth every other day (FIG. 30O). It was found that organoids formed from 5 out of 300 individual lineage-marked CARNs, with an overall frequency (1.67%) similar to that after plating of CARNs as a population (1.42%).

Organoid Formation by Prostate Epithelial Cells from Hormonally-Intact Mice

Since both CARNs and non-CARNs could form organoids, it was investigated whether normal prostate epithelial cells could initiate organoid formation. For this purpose, flow-sorting of dissociated prostate cells was performed to remove non-epithelial EpCAM⁻E-cadherin⁻ cells (FIG. 31A). The resulting organoids displayed variable morphology and growth rates, suggesting heterogeneity in the starting population (FIG. 3B, C). Many organoids had a ductal structure resembling that of normal prostates, with a bi-layered epithelium surrounding a lumen (FIG. 31D), while other organoids contained multi-layered masses of cells (FIG. 31E). The organoids contained proliferating cells (FIG. 31F), and showed stratification into an outer basal layer and an internal luminal layer (FIG. 31G-I), with intermediate cells co-expressing luminal and basal markers rarely observed; neuroendocrine cells have not been detected to date. Furthermore, the organoids displayed nuclear expression of AR and Foxa1 (FIG. 31I, J), and could reconstitute prostate tissue in grafts (FIG. 31K). Importantly, organoids derived from normal prostate epithelium could be grown for at least 13 passages, with no apparent alterations in growth rate or phenotype (FIG. 36A-C), and could be frozen and thawed with no loss of viability. After passaging, organoids continued to express luminal and basal markers, as well as nuclear AR, and were indistinguishable from low-passage number organoids (FIG. 36D, E).

TABLE 1

Efficiency of organoid formation. Shown are source data for FIG. 30N, FIG. 31G and FIG. 35A accompanied by mean and standard deviation.

| Mouse ID | Sorting | Cells/Well | Frequency | Total organoids counted |
|---|---|---|---|---|
| FIG. 30N Hormonally-intact wild-type | | | | |
| BL6-a | EpCAM/E-cadherin | 3000 | 0.12% | 11 |
| 3339 | EpCAM/E-cadherin | 5000 | 0.46% | 69 |
| 3339 | EpCAM/E-cadherin | 10000 | 0.33% | 167 |
| Average | | | 0.30% | |
| Standard Deviation | | | 0.17% | |
| Androgen-deprived (castrated) wild-type | | | | |
| BL6-b, BL6-c | EpCAM/E-cadherin | 1000 | 0.57% | 17 |
| BL6-b, BL6-c | EpCAM/E-cadherin | 5000 | 0.41% | 102 |

TABLE 1-continued

Efficiency of organoid formation. Shown are source data for FIG. 30N, FIG. 31G and FIG. 35A accompanied by mean and standard deviation.

| | | | | |
|---|---|---|---|---|
| BL6-d, BL6-e | EpCAM/ E-cadherin | 1000 | 0.40% | 16 |
| BL6-d, BL6-e | EpCAM/ E-cadherin | 5000 | 0.56% | 84 |
| Average | | | 0.49% | |
| Standard Deviation | | | 0.09% | |

YFP-positive CARNs (Nkx3.1$^{CreERT2/+}$; R26R-YFP/+)

| | | | | |
|---|---|---|---|---|
| 4250, 4251, 3156, 4003 | YFP | 100 | 1.50% | 6 |
| 4348-51, 4356-47, 4359-60 | YFP | 100 | 1.67% | 5 |
| 4348-51, 4356-47, 4359-60 | YFP | 250 | 1.60% | 16 |
| 4242, 4244 | YFP | 250 | 0.90% | 9 |
| Average | | | 1.42% | |
| Standard Deviation | | | 0.35% | |

YFP-negative (Nkx3.1$^{CreERT2/+}$; R26R-YFP/+)

| | | | | |
|---|---|---|---|---|
| 4250, 4251, 3156, 4003 | EpCAM/ E-cadherin, no YFP | 5000 | 0.14% | 28 |
| 4348-51, 4356-47, 4359-60 | EpCAM/ E-cadherin, no YFP | 1000 | 0.40% | 12 |
| 4348-51, 4356-47, 4359-60 | EpCAM/ E-cadherin, no YFP | 5000 | 0.19% | 48 |
| Average | | | 0.24% | |
| Standard Deviation | | | 0.14% | |

FIG. 31A
Basal lineage-tracing (CK5-CreER$^{T2}$; R26R-YFP)

| | | | | |
|---|---|---|---|---|
| 3745, 4125 | YFP | 5000 | 0.03% | 5 |
| 2393 | YFP | 5000 | 0.02% | 6 |
| 2394 | YFP | 3000 | 0.06% | 7 |
| 5654 | YFP | 3000 | 0.06% | 10 |
| Average | | | 0.04% | |
| Standard Deviation | | | 0.02% | |

Luminal lineage-tracing (CK8-CreER$^{T2}$; R26R-YFP)

| | | | | |
|---|---|---|---|---|
| 4541 | YFP | 1000 | 0.25% | 5 |
| 4367 | YFP | 3000 | 0.17% | 10 |
| 4368 | YFP | 1000 | 0.25% | 5 |
| Average | | | 0.22% | |
| Standard Deviation | | | 0.05% | |

Luminal lineage-tracing (CK18-CreER$^{T2}$; R26R-YFP)

| | | | | |
|---|---|---|---|---|
| 4330 | YFP | 1000 | 0.30% | 3 |
| 5993 | YFP | 1000 | 0.30% | 3 |
| Average | | | 0.30% | |

Luminal lineage-tracing (castrated CK8/18-CreER$^{T2}$; R26R-Tomato)

| | | | | |
|---|---|---|---|---|
| 6308 (CK8-trace) | Tomato | 5000 | 0.28% | 56 |
| 6310 (CK8-trace) | Tomato | 5000 | 0.11% | 17 |
| 6102, 6104 (CK18-trace) | Tomato | 250 | 0.40% | 4 |
| 6102, 6104 (CK18-trace) | Tomato | 5000 | 0.56% | 111 |
| Average | | | 0.34% | |
| Standard Deviation | | | 0.19% | |

FIG. 35A

TABLE 1-continued

Efficiency of organoid formation. Shown are source data for FIG. 30N, FIG. 31G and FIG. 35A accompanied by mean and standard deviation.

| Well ID | Cells/well | Frequency | Total organoids counted |
|---|---|---|---|
| DHT | | | |
| 1 | 1000 | 16.6% | 166 |
| 2 | 1000 | 19.4% | 194 |
| 3 | 1000 | 16.2% | 162 |
| Average | | 17.4% | |
| Std. Dev. | | 1.7% | |
| no additions | | | |
| 1 | 1000 | 17.8% | 178 |
| 2 | 1000 | 17.1% | 171 |
| 3 | 1000 | 18.9% | 189 |
| Average | | 17.9% | |
| Std. Dev. | | 0.9% | |
| DMSO | | | |
| 1 | 1000 | 16.8% | 168 |
| 2 | 1000 | 17.8% | 178 |
| 3 | 1000 | 19.8% | 198 |
| Average | | 18.1% | |
| Std. Dev. | | 1.5% | |
| Enzalutamide | | | |
| 1 | 1000 | 13.4% | 134 |
| 2 | 1000 | 16.3% | 163 |
| 3 | 1000 | 15.0% | 150 |
| Average | | 14.9% | |
| Std. Dev. | | 1.5% | |
| MK-8669 | | | |
| 1 | 1000 | 17.9% | 179 |
| 2 | 1000 | 15.4% | 154 |
| 3 | 1000 | 14.5% | 145 |
| Average | | 15.9% | |
| Std. Dev. | | 1.8% | |
| Enzalutamide + MK-8669 | | | |
| 1 | 1000 | 4.4% | 44 |
| 2 | 1000 | 5.7% | 57 |
| 3 | 1000 | 4.1% | 41 |
| Average | | 4.7% | |
| Std. Dev. | | 0.9% | |

Interestingly, the efficiency of organoid formation from normal hormonally-intact prostate epithelium was 0.30%, significantly lower than from lineage-marked CARNs (Table 1), which are isolated from the androgen-deprived regressed prostate. It was also found that the efficiency of organoid formation from wild-type regressed prostate epithelium was 0.49%, which is not significantly different than that of hormonally-intact epithelium. (Table 1). These efficiencies are also similar to that of YFP-negative cells in the CARNs lineage-marking experiment (FIG. 30N), suggesting that cells distinct from CARNs can form organoids, but at a lower efficiency.

To examine the effects of androgen-deprivation, organoids established from normal prostate epithelium were cultured and passaged in the presence or absence of DHT. It was found that organoids could still form in the absence of DHT, but were reduced in size (FIG. 31L, M). Notably, AR immunostaining was nuclear in the presence of DHT, but was weaker and mostly cytoplasmic in the absence of DHT (FIG. 31N, O). To assess the molecular response to androgen-deprivation, quantitative RT-PCR (qPCR) analysis of the expression of several known AR-regulated genes was performed at passage 1. It was found that Fkbp5, Mme, and Psca were down-regulated in organoids after DHT withdrawal, whereas expression of Igfbp3 was up-regulated, as expected for decreased AR activity (FIG. 31P). These findings indicate that organoids are highly responsive to androgen-deprivation.

Lineage-Tracing Demonstrates the Preferential Origin of Organoids from Luminal Cells Next lineage-tracing was used to investigate which epithelial cell type(s) can give rise to organoids (FIG. 32A). To mark basal cells, the tamoxifen-inducible CK5-CreER$^{T2}$ transgene [13] was used in combination with the R26R-YFP reporter allele [33]. For marking of luminal cells, the CK8-CreER$^{T2}$ or CK18-CreER$^{T2}$ transgenes were used [34, 35], either in combination with the R26R-YFP reporter or R26R-Tomato reporter [36]. Notably, these inducible Cre drivers were highly specific in marking basal or luminal epithelial cells in vivo at efficiencies similar to those previously observed [13, 35] (FIG. 37; Table 2).

Using tamoxifen-induced CK5-CreER$^{T2}$; R26R-YFP mice (which is termed CK5-trace), YFP-positive cells were isolated by flow cytometry for organoid culture (FIG. 32B). It was found that the isolated CK5-trace cells were extremely inefficient at organoid formation (0.04% efficiency) (Table 1). Moreover, when organoids did form, they were often heterogeneous, containing regions derived from non-YFP expressing cells; for example, such organoids could arise from doublets containing a YFP-expressing and a non-expressing cell after flow sorting. The few homogeneously YFP-expressing CK5-trace organoids were small and contained both CK5-expressing and non-expressing cells (FIG. 32C,D).

In contrast, YFP-positive cells from tamoxifen-induced CK8-CreER$^{T2}$; R26R-YFP mice (CK8-trace) or CK18-CreER$^{T2}$; R26R-YFP mice (CK18-trace) gave rise to hollow organoids with large lumens (FIG. 32E, F), most of which were homogeneously YFP-positive. Interestingly, the efficiency of organoid formation by luminal CK8-trace cells (0.22%) and CK18-trace cells (0.30%) was significantly higher than that of basal CK5-trace cells (FIG. 32G; Table 1). In addition, the efficiency of organoid formation by CK8-trace or CK18-trace cells from castrated mice was similar (0.34%), consistent with the enhanced efficiency of CARNs relative to other luminal cells in the regressed prostate (Table 1). Thus, both basal and luminal cells can give rise to organoids, potentially explaining the heterogeneity of organoids from normal prostate epithelium (FIG. 31B, C), but luminal cells are favored for organoid formation.

Notably, luminal cells could generate basal cells in organoid culture, as CK8-trace organoids with homogeneous YFP expression contained cells expressing basal markers (CK5, p63) (FIG. 32H-M). These basal cells were typically found on the outer layer of the organoids, as for normal organoids, but displayed an irregular morphology that might suggest incomplete basal differentiation. To assess whether luminal cells would give rise to basal cells in the presence of normal basal cells, green CK5-trace cells from CK5-CreER$^{T2}$ were mixed with R26R-YFP mice with red CK8-trace cells isolated from CK18-CreER$^{T2}$; R26R-Tomato mice. In the resulting cultures, organoids were found with an outer layer of green cells and inner red cells (FIG. 32N), suggesting that both basal and luminal cells are preferentially lineage-restricted, consistent with lineage-tracing analyses in vivo [13, 37, 38].

The properties of luminal-derived organoids generated from lineage-marked CK18-CreER$^{T2}$; R26R-Tomato mice (CK18-trace) were further investigated. These organoids could be serially passaged at least 9 times without apparent loss of viability (FIG. 32O, P), suggesting that the normal luminal compartment contains a stem/progenitor population that can propagate organoids in culture. Moreover, following androgen-deprivation after passaging, these luminal-derived organoids were decreased in size and lacked nuclear AR expression (FIG. 32Q-S). Thus, lineage-marked luminal cells generate organoids that recapitulate key properties of organoids cultured from the bulk prostate epithelium.

TABLE 2

Lineage-marking efficiencies in vivo.

| Mouse ID | YFP$^+$ CK5$^-$ | YFP$^+$ CK5$^+$ | Total cells examined |
|---|---|---|---|
| Basal lineage-tracing (CK5-CreER$^{T2}$; R26R-YFP/+) | | | |
| 4613 | 0.0% | 38.20% | 119 |
| 5643 | 0.0% | 46.20% | 100 |
| 2394 | 0.0% | 21.30% | 135 |
| Average | 0.0% | 35.20% | Total n = 354 |
| Luminal lineage-tracing (CK8-CreER$^{T2}$; R26R-YFP/+) | | | |
| 4638 | 4.2% | 0% | 334 |
| 4637 | 4.7% | 0% | 362 |
| Average | 4.5% | 0% | Total n = 696 |
| Luminal lineage-tracing (CK18-CreER$^{T2}$; R26R-YFP/+) | | | |
| 4329 | 1.3% | 0% | 290 |
| 4330 | 2.2% | 0% | 241 |
| Average | 1.8% | 0% | Total n = 531 |

| Mouse ID | Tomato$^+$ CK5$^-$ | Tomato$^+$ CK5$^+$ | Total cells examined |
|---|---|---|---|
| Luminal lineage-tracing (CK8-CreER$^{T2}$; R26R-Tomato/+) | | | |
| 5369 | 29.9% | 0% | 350 |
| 5639 | 35.6% | 0% | 229 |
| Average | 32.8% | 0% | Total n = 579 |
| Luminal lineage-tracing (CK18-CreER$^{T2}$; R26R-Tomato/+) | | | |
| 5633 | 44.6% | 0% | 216 |
| 5641 | 36.4% | 0% | 57 |
| 5642 | 68.9% | 0% | 60 |
| Average | 50.0% | 0% | Total n = 333 | n = total number of cells examined from 2 or 3 independent mice, with mean values as indicated.

Establishment of Tumor Organoids from Single Transformed CARNs

Since CARNs are a cell of origin for prostate cancer in vivo [25], organoid formation from CARNs that had undergone oncogenic transformation in the context of a model of aggressive lethal prostate cancer [39] were investigated. In particular, Nkx3.1$^{CreERT2/+}$; Pten$^{flox/flox}$; Kras$^{LSL-G12D/+}$; R26R-YFP/+ mice (termed NPK) were castrated and induced with tamoxifen, so that combined Pten deletion, Kras$^{G12D}$ activation, and YFP expression occurred specifically in CARNs (FIG. 33A). Transformed lineage-marked CARNs were isolated by flow cytometry on the basis of their YFP expression, and used for organoid culture. The resulting NPK-CARN tumor organoids grew rapidly and displayed extensive budding and branching (FIG. 33B). Notably, these NPK-CARN organoids displayed histological phenotypes resembling PIN (FIG. 33C), and contained many proliferating cells (FIG. 33D). Immunostaining of NPK-CARN organoids showed membrane-localized phospho-Akt (pAkt)

(FIG. 33E), as well as patchy expression of phospho-Erk (pErk) (FIG. 33F). Consistent with a tumor phenotype, the organoids displayed strong luminal features, with relatively few cells expressing the basal markers p63 and CK5 (FIG. 33G, H); in addition, the NPK-CARN organoids showed nuclear Foxa1 expression (FIG. 33I). Importantly, the organoids displayed nuclear AR in the presence of DHT, but mostly cytoplasmic AR in the absence of DHT (FIG. 33J, K). Furthermore, these tumor organoids could be frozen and thawed, and passaged at least 10 times without apparent loss of viability. Finally, these tumor organoids could be used to generate renal grafts that displayed a high-grade PIN phenotype (FIG. 33L), and contained proliferating cells (FIG. 33M). These grafts displayed membrane-localized phospho-Akt, patchy pErk expression, and nuclear AR, and were uniformly YFP-positive (FIG. 33N-P) indicating their phenotypic similarity to donor tumors in vivo [39].

Figure 33Q:
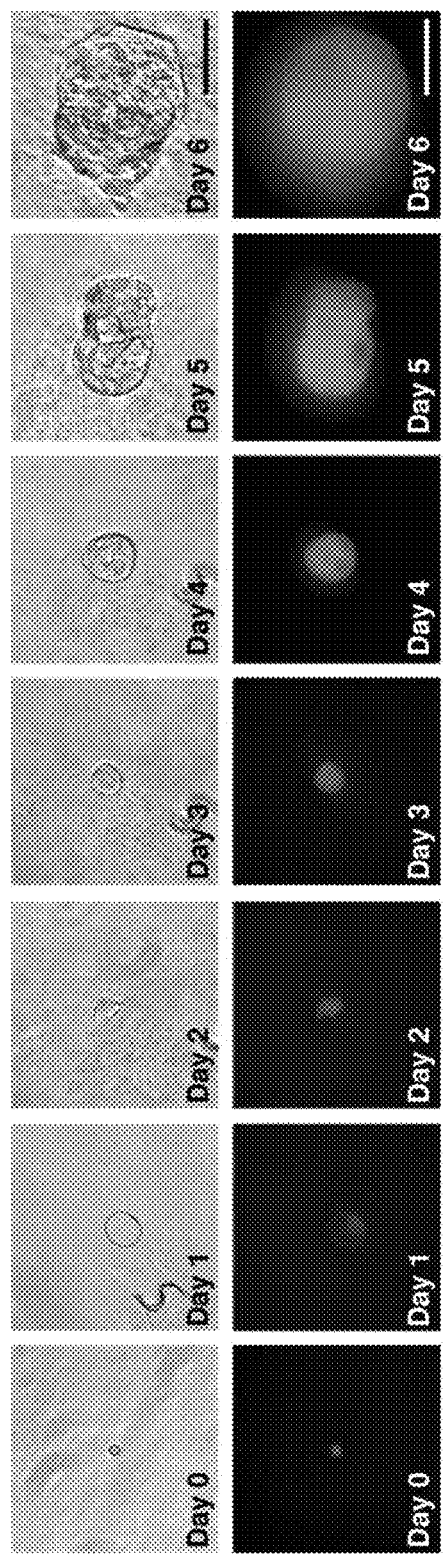

Given the tumor phenotype of NPK-CARN organoids, it was investigated whether organoids could be derived from single transformed CARNs. Flow-sorting was used to isolate transformed YFP-positive cells from $Nkx3.1^{CreERT2/+}$; $Pten^{flox/flox}$; $Kras^{LSL-G12D/+}$; R26R-YFP/+ mice that were castrated and induced with tamoxifen, and mouth-pipetted individual cells into a 96-well plate. It was found that 6/80 (7.5%) of single transformed CARNs could form organoids after ten days of culture (FIG. 33Q). Thus, single NPK-CARNs can initiate organoid formation at a frequency significantly higher than that of untransformed CARNs.

Tumor Organoids can Model Prostate Cancer Phenotypes in Culture

These findings suggest that organoid culture might represent a suitable system for modeling of tumor phenotypes and drug treatment responses. To test this idea, it was first investigated whether tumor organoids could be generated from a range of well-studied mouse models of prostate cancer, namely: 1) $Nkx3.1^{-/-}$ null mutants [40, 41]; 2) $Nkx3.1^{+/-}$; $Pten^{+/-}$ double mutants [42]; 3) TRAMPtransgenic mice [43, 44]; 4) Hi-Myc transgenic mice [45]; and 5) tamoxifen-induced $Nkx3.1^{CreERT2/+}$; $Pten^{flox/flox}$; $p53^{flox/flox}$ (NPP53) mice [46] (FIG. 34A-J). Interestingly, many of these organoids displayed filled morphologies consistent with oncogenic transformation; in contrast, the $Nkx3.1^{-/-}$ organoids displayed a more normal morphology, consistent with the low-grade PIN phenotype of Nkx3.1 mutant mice [41, 47]. Moreover, all of these mouse models displayed significantly enhanced efficiencies of organoid formation (FIG. 34K).

It was also examined whether organoid culture could be used for the rapid induction of tumor phenotypes, using tamoxifen-inducible organoids from $CK8-CreER^{T2}$; $Pten^{flox/flox}$; $Kras^{LSL-G12D/+}$; R26R-CAG-YFP mice (FIG. 34L). Although these organoids had normal phenotypes, they displayed YFP expression and membrane-localized phospho-Akt after induction in culture with 4-hydroxytamoxifen (4-OHT) (FIG. 34M, N). Following serial passaging in the absence of 4-OHT, the control organoids retained a hollow morphology without any detectable YFP expression. In contrast, in the presence of 4-OHT, the organoids were mostly YFP and pAkt-positive, and displayed PIN-like phenotypes (FIG. 34O-R).

Next it was determined whether tumor organoids could be utilized to assess drug response, using organoids from $Nkx3.1^{CreERT2/+}$; $Pten^{flox/flox}$; R26R-YFP/+ (NP) mice, which were previously used to analyze therapeutic response in vivo [48]. Although NP mice initially form castration-sensitive prostate tumors, they eventually develop castration-resistant disease that is sensitive to combined treatment with the Akt inhibitor MK-2206 and the mTOR inhibitor MK-8669 (ridaforolimus) [48]. To assess therapeutic response, YFP-positive prostate cells were isolated from tamoxifen-induced NP mice for organoid culture, and subsequently dissociated organoids at the third passage to single cell suspensions, followed by plating at 1,000 cells/well embedded within Matrigel/culture medium. Control cultures were established in the presence of DHT, while treatment cultures were established without DHT. Treatment with the DMSO solvent control had no effect, as expected, while either the AR antagonist enzalutamide or MK-8669 had minimal effects on organoid formation (FIG. 35A-F, H). In contrast, combined treatment with enzalutamide and MK-8669 inhibited organoid formation (FIG. 35A, G, I), consistent with the known synergistic activities of AR and PI3K signaling in human prostate cancer [49]. Interestingly, these effects were not simply due to inhibition of AR and PI3K pathway activities, as combined treatment with enzalutamide and MK-8669 could greatly reduce nuclear AR expression (FIG. 35J, K), but had no effect on phospho-Akt (FIG. 35L, M).

Culture of Human Prostate Organoids

It was examined whether organoids could be established from human prostate tissue and cell lines. Therefore, tissue samples were obtained from three radical prostatectomies, confirmed that they contained benign glands, and epithelial cells isolated by flow-sorting for EpCAM and E-cadherin. All three patient-derived samples could establish organoids over the course of three weeks and could be passaged successfully, with organoids displaying cystic morphologies and containing proliferative cells (FIG. 38A-C). These organoids displayed outer $p63^+CK8^+$ double-positive intermediate cells, and inner $CK8^+$ luminal cells (FIG. 38D), with nearly all of the cells expressing AR and CK18 (FIG. 38E). Thus, benign human organoids resemble normal mouse organoids, except that outer cells mostly co-express basal and luminal markers.

It was also examined whether organoid culture could be used to propagate the VCaP human prostate cancer cell line, which has a luminal phenotype [50]. VCaP organoids displayed a relatively solid morphology, contained proliferating cells, and were successfully passaged (FIG. 38F-H) Notably, VCaP organoids expressed luminal markers including AR, but not the basal marker p63 (FIG. 38I, J). Consequently, the organoid culture conditions described herein could readily maintain the VCaP luminal phenotype, and may therefore be suitable for studies of human prostate cancer.

Discussion

The establishment of self-organizing organoids in ex vivo culture has become an emerging paradigm for the study of tissue stem cells [51]. Described herein are results showing that organoids derived from normal mouse prostate can self-renew, generate differentiated basal and luminal cells, and display long-term expansion of prostate epithelial progenitors for at least 13 passages. In addition, luminal cells are favored for organoid formation, and at least some luminal cells display bipotentiality in culture. Moreover, organoids can reconstitute either normal or transformed prostate tissue in renal grafts, depending upon the starting material. These findings indicate that prostate organoids represent an excellent system for investigating prostate biology.

AR signaling represents a central theme in studies of prostate development and cancer. Although there have been many efforts to develop culture systems for prostate epithelium, functional AR activity has not been unambiguously demonstrated in previous studies [27, 29, 52-54]. For instance, prostaspheres exhibit low or absent AR expression in the presence of DHT [6, 9], while other spheroid culture methods show nuclear AR but not alterations of growth or AR-regulated gene expression after androgen withdrawal [27, 54]. In prostate organoids, however, AR protein is localized to the nucleus in the presence of DHT, while DHT withdrawal affects organoid growth, AR subcellular localization, and expression of AR-regulated genes. These responses to androgen withdrawal suggest that molecular mechanisms of castration-resistance in prostate tumors can be effectively investigated in organoid culture.

Interestingly, despite the importance of epithelial-mesenchymal interactions in prostate organogenesis and regeneration [55, 56], much of the stromal requirement for prostate epithelial self-renewal and differentiation can apparently be replaced by soluble factors in the presence of extracellular matrix components found in Matrigel, such as collagen IV and laminin. Furthermore, prostate organoids generated from normal tissue appear to have unlimited potential for expansion of epithelial progenitors, similar to organoids established from other tissue types. Since prostate epithelium in vivo is generally quiescent [13], the organoid culture conditions described herein may contain potent proliferative signals and/or lack anti-proliferative signals derived from the adult stroma in vivo. In this regard, it is noted that the culture conditions described herein are distinct from conditions employed in other organoid studies [16, 22, 23, 57] that utilize defined media containing EGF, the BMP inhibitor Noggin, and the canonical Wnt pathway activator R-spondin, in contrast with the serum-containing media described herein. Future analyses may yield insights into improved culture protocols, and optimization through approaches such as epithelial-stromal co-culture.

The studies described herein provide important insights into luminal progenitors in the prostate epithelium. Although lineage-tracing studies have reported that luminal cells in the hormonally-intact prostate epithelium do not display bipotentiality in vivo [37, 38, 58], luminal cells can generate basal cells in organoid culture. This bipotentiality resembles that of CARNs in the regressed (androgen-deprived) epithelium during prostate regeneration. Notably, CARNs have a six-fold higher efficiency of organoid formation than that of non-CARNs. However, since CARNs represent less than 1% of epithelial cells in the regressed prostate [25], a substantial proportion of organoid-forming ability within the regressed epithelium appears to arise from cells that are not CARNs. One likely interpretation is that luminal progenitors distinct from CARNs exist within the regressed prostate epithelium, and perhaps in the hormonally-intact epithelium as well. Another, non-mutually exclusive possibility is that some prostate luminal progenitors are lineage-restricted in vivo, but can display plasticity in culture, similar to prostate basal cells [13].

Since luminal cells are favored for organoid formation, the culture conditions described herein can be suitable for analyses of prostate tumor initiation and progression, as prostate adenocarcinoma has a luminal phenotype. Indeed, prostate tumor organoids can be established from genetically-engineered mouse models ranging from relatively indolent (Nkx3.1 null) to highly aggressive (Hi-Myc, NPP53). Moreover, tumor phenotypes can be experimentally induced in phenotypically normal organoids in culture, indicating that stromal cells are not required for oncogenic transformation. The ability to passage organoids as single cells suggests that manipulations such as lentiviral infection and CRISPR/Cas9 targeting can be feasible for genetic-engineering of tumor phenotypes in vitro, as shown for intestinal organoids [59, 60]. Furthermore, the ability to recapitulate treatment responses observed in human prostate cancer [49] suggests that organoid culture can be used for drug screens and mechanistic studies of therapeutic response and resistance [61, 62].

Finally, it has been shown that organoids can be established from benign human prostate tissue as well as a luminal human prostate cancer cell line. Given the presence of intermediate cells in the benign human organoids, further optimization of the culture conditions described herein may be advantageous. Nonetheless, a logical next step is to establish organoid cultures from human prostate tumor samples. Organoid culture may provide an alternative to tissue slice cultures [63], which are short-lived and display varying androgen responsiveness, and to patient-derived xenografts [64, 65], which are laborious and require large numbers of immunodeficient mice. In particular, patient-derived organoids established from primary tumors or metastases can be suitable for generation of a cryopreserved tumor organoid bank, and could potentially be used for prospective drug screening. Therefore, the continuing development of organoid culture systems may ultimately lead to advances in personalized medicine.

Methods

Mouse Strains and Genotyping

The Nkx3.1$^{CreERT2}$ allele (Nkx3-1$^{tm4(cre/ERT2)Mms}$) has been previously described [25]. The CK8-CreER$^{T2}$ (Tg (Krt8-cre/ERT2)17Blpn/J, #017947) [34], CK18-CreER$^{T2}$ (Tg(KRT18-cre/ERT2)23Blpn/J, #017948) [66], R26R-YFP (B6.129X1-Gt(ROSA)26Sor$^{tm1(EYFP)Cos}$/J, #006148) [33], R26R-CAG-YFP (B6.Cg-Gt(ROSA)26Sor$^{tm3(CAG-EYFP)Hze}$/J, #007903) [36], R26R-Tomato (B6; 129S6-Gt(ROSA) 26Sor$^{tm14(CAG-tdTomato)Hze}$/J, #007908) [36], and conditional Pten$^{flox}$ (B6.129S4-Pten$^{tm1Hwu}$/J, #006440) [67] strains were obtained from the Jackson Laboratory Induced Mutant Resource. The inducible Kras$^{LSL-G12D}$ (B6.129-Kras$^{tm4Tyj}$/Nci) [68] allele was obtained from the National Cancer Institute Mouse Models of Human Cancer Consortium Repository. CK5-CreER$^{T2}$ (Krt5$^{tm1.1(cre/ERT2)Blh}$) mice were generously provided by Brigid Hogan [69]. Animals were maintained on a congenic C57BL/6N background. Genotyping was performed using the primers listed in Table 3.

For lineage-marking of CARNs, Nkx3.1$^{CreERT2/+}$; R26R-YFP/+ males were castrated after 8 weeks of age and allowed to regress for 4 weeks, then treated with tamoxifen (Sigma) (9 mg/40 g body weight in corn oil) by daily oral gavage for 4 consecutive days, followed by a chase period as previously described [25]. For lineage-marking with the CK5-CreER$^{T2}$, CK8-CreER$^{T2}$, and CK18-CreER$^{T2}$ drivers, 8 week old hormonally-intact males were treated with tamoxifen as previously described [13]. To generate androgen-deprived males with lineage-marked cells using CK8-CreER$^{T2}$ and CK18-CreER$^{T2}$ drivers, tamoxifen-treated animals were castrated and allowed to regress for 2-3 weeks. Lineage marking efficiencies were calculated using sections from anterior prostate lobes. No statistical methods were used to pre-determine sample size, and experiments were not randomized; investigators were not blinded to allocation during experiments and outcome assessment. All animal experiments received approval from the Institutional Animal Care and Use Committee at Columbia University Medical Center.

Sample Acquisition for Human Organoids

Benign human organoids were derived from radical prostatectomy samples obtained from patients undergoing surgery at Columbia University Medical Center. All patients gave informed consent under the auspices of an Institutional Review Board approved protocol. Candidate benign regions were dissected and transported to the laboratory in DMEM/F12 (Gibco #10565) supplemented with 5% FBS for tissue dissociation. Benign pathology was initially confirmed by H&E analyses of adjacent rapid frozen sections, and was further confirmed by immunostaining of paraffin sections from the primary sample used for organoid establishment for p63, high-molecular weight cytokeratins, and α-methyl acyl coenzyme-A racemase (AMACR) using the PIN-4 cocktail [70] (Biocare Medical #PPM 225 DSAA). The VCaP cell line was purchased from the American Type Culture Collection (CRL-2876).

Tissue Dissociation and Isolation of Prostate Epithelial Cells

For tissue dissociation, dissected mouse prostate tissue (all lobes combined) from male mice at two to six months of age (five to fourteen months for tumor models) were dissected away from other urogenital tissues in cold phosphate buffered saline (PBS) and minced with scissors. Human tissue was prepared by mincing with scalpels and washing three times in PBS with 4 mg/ml Gentamycin (Gibco #15750-060). Prostate tissues were then incubated in 1.5 ml of DMEM/F12 (Gibco #10565), supplemented with 5% FBS and 1:10 dilution of collagenase/hyaluronidase (STEMCELL Technologies #07912) at 37° C. for 3 hrs. Dissociated tissues were then spun down at 350 g for 5 min, and resuspended in 1.5 ml of ice-cold 0.25% trypsin-EDTA (STEMCELL Technologies #07901), followed by incubation at 4° C. for 1 hr. Trypsinization was then stopped by addition of 3 ml Modified Hank's Balanced Salt Solution (HBSS) (STEMCELL Technologies #37150) medium supplemented with 2% FBS, followed by centrifugation at 350 g. The cell pellet was resuspended with 1 ml prewarmed 5 mg/ml dispase (STEMCELL Technologies #07913) supplemented with 1:10 dilution of 1 mg/ml DNase I (STEMCELL Technologies #07900). The sample was triturated vigorously for 1 min, followed by addition of 5 ml HBSS/2% FBS to neutralize dispase activity, and passed through a 40 µm cell strainer (Corning #352340). Dissociated cells were spun down again and resuspended in HBSS/2% FBS. Dissociation of human tissue was performed using the same protocol with 10-fold reagent volume and overnight digestion in collagenase/hyaluronidase solution.

Flow Cytometry

For isolation of normal and transformed prostate epithelial cells, single-cell suspensions were stained using fluorescent-tagged EpCAM (BioLegend #118214 for mouse and #324208 for human) and E-cadherin (eBioscience #46-3249-82) antibodies on ice for 25 min. The stained cells were spun down, and the cell pellet washed with HBSS/2% FBS, followed by resuspension in HBSS/2% FBS with 10 µM Y-27632 (ROCK inhibitor; STEMCELL Technologies #07171) and a 1:1,000 dilution of 0.5 mg/ml DAPI to exclude dead cells during sorting. For flow cytometry, unstained cells as well as cells stained with fluorescent-tagged EpCAM or E-cadherin were used for compensation. Both side-scatter pulse width (SSC-W) vs. area (SSC-A) and forward side-scatter pulse area (FSC-A) vs. heights (FSC-H) were used to isolate single dissociated cells. For normal prostate epithelium, cells expressing either EpCAM and/or E-cadherin were isolated. For isolation of lineage-marked CARNs and transformed CARNs, as well as lineage-marked basal or luminal populations, cells were sorted based on their YFP or Tomato expression; non-YFP expressing cells were obtained by sorting EpCAM and/or E-cadherin positive but YFP-negative cells. Sorted cells were plated in low-attachment 96-well plates at densities ranging from 100 (for CARNs) to 10000 cells/well. For single cell experiments, sorted YFP-positive cells were picked by mouth-pipetting using an inverted microscope, followed by re-plating in wells of 96-well low attachment plates.

Organoid Culture

Two methods were used for three-dimensional culture of prostate organoids from isolated prostate epithelial cells, corresponding to flotation on top of Matrigel or embedding within Matrigel; the embedding method was used for drug treatment experiments and is described below. For the floating method, prostate epithelial cells were resuspended in prostate organoid culture medium, consisting of: hepatocyte medium supplemented with 10 ng/ml epidermal growth factor (EGF) (Corning #355056), 10 µM Y-27632 (STEMCELL Technologies #07171), 1× glutamax (Gibco #35050), 5% Matrigel (Corning #354234), and 5% charcoal-stripped FBS (Gibco #12676), which had been heat-inactivated at 55° C. for 1 hr. After resuspension in prostate organoid medium, 100-10,000 dissociated cells were plated into wells of ultra low-attachment 96 well plates (Corning #3474) in the presence of 100 nM DHT for mouse or 10 nM DHT for human (Sigma A-8380). 100 µl of fresh organoid medium was added to the wells every four days, and the medium changed every 12 days for up to one month.

For serial passaging experiments, organoids were passaged at a 1:4 dilution every 1-2 weeks with 0.25% trypsin for 5 minutes at 37° C., followed by mechanical dissociation to nearly single-cell suspensions. Organoids were frozen in complete media with 50% FBS and 10% DMSO. The efficiency of organoid formation was calculated by averaging the number of organoids visible in each well after 7 days of growth using a 10× objective. For statistical analyses, efficiency percentages were arcsin converted to perform unpaired two-tailed Student's t-tests.

For analyses of androgen withdrawal, organoids were passaged and then cultured for 7-10 days in culture medium in the presence or absence of DHT. For induction of Cre recombinase activity in culture, epithelial cells from un-induced CK8-CreER$^{T2}$; Pten$^{flox/flox}$; Kras$^{LSL-G12D/+}$; R26R-CAG-YFP mice were sorted based on EpCAM and E-cadherin expression, and cultured until organoid formation was evident. The resulting organoids were passaged, followed by addition of 1 µM 4-OHT on the day after passaging to induce Cre recombination.

A detailed protocol for organoid establishment and culture is described in Example 5.

Drug Treatments

The embedding method was used to culture organoids for drug treatment experiments. Organoids were dissociated by digestion with 0.25% trypsin-EDTA (STEMCELL Technologies #07901) and passed through a 40 µm cell strainer. 40 µl of the resulting cell suspension containing 500-3,000 dissociated cells were mixed with 60 µl of Matrigel, and the mixture pipetted around the rim of wells in a 24 well plate. The mixture was allowed to solidify for 30 minutes at 37° C., prior to addition of 400 µl organoid culture medium to each well, with or without supplementation with 100 nm DHT in the presence or absence of drugs. The culture medium was changed every other day, and organoids were counted after 8 days. Drugs were dissolved in DMSO to generate a final concentration of 0.1% in all drug-treated groups. Drug concentrations were as follows: 100 nM DHT, no additions, 0.1% DMSO, 10 µM enzalutamide (provided by Charles Sawyers, Memorial Sloan-Kettering Cancer Center), 1 nM MK-8669 (provided by Cory Abate-Shen, Columbia University Medical Center).

Tissue Recombination and Renal Grafting

For tissue recombination, organoids from one well of a 96-well plate were mixed with 250,000 dissociated rat urogenital mesenchyme cells from embryonic day 18.5 rat embryos and resuspended in 12 μl of 9:1 collagen:setting buffer solution (10× Earle's Balanced Salt Solution (Life Technologies), 0.2 M NaHCO$_3$ and 50 mM NaOH). The recombinants were cultured overnight in DMEM with 10% FBS and 100 nM DHT, followed by grafting under the kidney capsules of male NOD.Cg-Prkdc$^{scid}$ Il2rg$^{tm1Sug}$/JicTac (NOG) mice (Taconic). Renal grafts were harvested for analysis at 8 weeks after grafting.

Histology and Immunostaining

Tissues were processed for cryosections or paraffin sectioning using standard protocols. For cryosections, organoids and tissues were fixed in 4% paraformaldehyde in PBS at 4° C. for 1 hr, placed in 30% sucrose in PBS, and embedded in OCT (Tissue-Tek). For paraffin sectioning, organoids were fixed in 10% formalin for 1 hr and placed in Histogel (Thermo Scientific) prior to tissue processing and embedding.

For immunostaining, sections underwent antigen-retrieval by boiling in citrate acid-based antigen unmasking solution (Vector Labs) for 10 min. Primary antibodies were applied to sections and incubated at 4° C. overnight in a humidified chamber. Alexa Fluors (Life Technologies) were used for secondary antibodies. Tyramide amplification (Life Technologies) or ABC Elite (Vector Labs) kits were used for signal detection. For lineage-tracing experiments, analysis of marked basal or luminal cells was performed by manual counting of cells from confocal images taken with a 40× objective. Details on antibodies used are provided in Table 4.

Quantitative Real-Time PCR Analysis

For RNA extraction, 4-6 wells of organoids were pooled, pelleted, and dissolved in Trizol reagent prior to processing by the MagMAX 96 Total RNA Isolation Kit (Ambion, Life Technologies). 300-500 ng of RNA was used for cDNA synthesis using the Superscript First Strand Synthesis System (Invitrogen). Quantitative real-time PCR was carried out using SYBR green master mix reagent (QIAGEN) in the Realplex2 instrument (Eppendorf). cDNA samples were diluted 1:5 to 1:10 for all analyses, which were performed in triplicate. Expression values were obtained using the ΔΔCT method and normalized to GAPDH expression; average values are shown as the mean±standard deviation (SD). Primer sequences are provided in Table 3.

Repeatability of Experiments

For histological and immunofluorescence analyses of organoids and tissue recombination experiments, representative staining patterns were confirmed in at least 3 samples from at least 2 independent experiments. All DHT withdrawal experiments were repeated at least twice. Data shown for quantitative real-time PCR analysis are from a single experiment that was representative of 2 independent experiments. The drug treatment experiment was repeated at a different passage and gave similar results and statistical significance.

TABLE 3

Primers used in this study

Primers used for qRT-PCR analyses

| Gene | Primer Bank ID | Amplicon size | Sequence | SEQ ID NO |
|---|---|---|---|---|
| Fkbp5 | 6753884a1 | 172 bp | F 5'-TGA GGC CAC CAG TAA CAA TGG-3' | 1 |
|  |  |  | R 5'-CAA CAT CCC TTT GTA GTG GAC AT-3' | 2 |
| Phlpp1 | 26006185a1 | 102 bp | F 5'-AGG GTC CCG GAG ACG ATA AG-3' | 3 |
|  |  |  | R 5'-AGG GCG GAG ATG TCT TTT GC-3' | 4 |
| Mme | 31543255a1 | 198 bp | F 5'-CTC TCT GTG CTT GTC TTG CTC-3' | 5 |
|  |  |  | R 5'-GAC GTT GCG TTT CAA CCA GC-3' | 6 |
| Psca | 12312316a1 | 103 bp | F 5'-GGA CCA GCA CAG TTG CTT TAC-3' | 7 |
|  |  |  | R 5'-GTA GTT CTC CGA GTC ATC CTC A-3' | 8 |
| Igfbp3 | 6680385a1 | 101 bp | F 5'-CCA GGA AAC ATC AGT GAG TCC-3' | 9 |
|  |  |  | R 5'-GGA TGG AAC TTG GAA TCG GTC A-3' | 10 |

Primer sequences above are from PrimerBank-MGH-PGA.
(www.pga.mgh.harvard.edu/primerbank/)

Primers used for mouse genotyping

| Allele | Amplicon size | Sequence | SEQ ID NO |
|---|---|---|---|
| Nkx3.1 CreErt2 | 500 bp | F 5'-CAG ATG GCG CGG CAA CAC C-3' | 11 |
|  |  | R 5'-GCG CGG TCT GGC AGT AAA AAC-3' | 12 |
| Nkx3.1 wild-type | 500 bp | F 5'-CTC CGC TAC CCT AAG CAT CC-3' | 13 |
|  |  | R 5'-GAC ACT GTC ATA TTA CTT GGA CC-3' | 14 |

TABLE 3-continued

Primers used in this study

| Name | Size | Primer | SEQ ID |
|---|---|---|---|
| Nkx3.1 null | 232 bp | F 5'-TTC CAC ATA CAC TTC ATT CTC AGT-3' | 15 |
| | | R 5'-GCC AAC CTG CCT CAA TCA CTA AGG-3' | 16 |
| Nkx3.1 wild-type | 707 bp | F 5'-GTC TTG GAG AAG AAC TCA CCA TTG-3' | 17 |
| | | R | |
| CrERT2 | 500 bp | F 5'-CAG ATG GCG CGG CAA CAC C-3' | 18 |
| | | R 5'-GCG CGG TCT GGC AGT AAA AAC-3' | 19 |
| R26R YFP | 320 bp | F 5'-AAA GTC GCT CTG AGT TGT TAT-3' | 20 |
| | | R 5'-AAG ACC GCG AAG AGT TTG TC-3' | 21 |
| R26R wild-type | 600 bp | F | 22 |
| | | R 5'-GGA GCG GGA GAA ATG GAT ATG-3' | 23 |
| R26R-Tomato | 196 bp | F 5'-CTG TTC CTG TAC GGC ATG G-3' | 24 |
| | | R 5'-GGC ATT AAA GCA GCG TAT CC-3' | 25 |
| R26R-CAG-YFP | 212 bp | F 5'-ACA TGG TCC TGC TGG AGT TC-3' | 26 |
| | | R 5'-GGC ATT AAA GCA GCG TAT CC-3' | 27 |
| R26R wild-type | 297 bp | F 5'-AAG GGA GCT GCA GTG GAG TA-3' | 28 |
| | | R 5'-CCG AAA ATC TGT GGG AAG TC-3' | 29 |
| Ptenflox | 328 bp | F 5'-CAA GCA CTC TGC GAA CTG AG-3' | 30 |
| | | R 5'-AAG TTT TTG AAG GCA AGA TGC-3' | 31 |
| Pten wild-type | 156 bp | F | |
| | | R | |
| Pten null | 320 bp | F 5'-TTG CAC AGT ATC CTT TTG AAG-3' | 32 |
| | | R 5'-ACG AGA CTA GTG AGA CGT GC-3' | 33 |
| Pten wild-type | 240 bp | F | 34 |
| | | R 5'-GTC TCT GGT CCT TAC TTC C-3' | 35 |
| KrasLSL-G12D | 550 bp | F 5'-AGC TAG CCA CCA TGG CTT GAG TAA GTC TGC A-3' | 36 |
| | | R 5'-CCT TTA CAA GCG CAC GCA GAC TGT AGA-3' | 37 |
| Kras wild-type | 500 bp | F 5'-GTC GAC AAG CTC ATG CGG GTG-3' | 38 |
| | | R | |
| TRAMP | 650 bp | F 5'-GCG CTG CTG ACT TTC TAA ACA TAA G-3' | 39 |
| | | R 5'-GAG CTC ACG TTA AGT TTT GAT GTG T-3' | 40 |
| p53flox | 370 bp | F 5'-CAC AAA AAC AGG TTA AAC CCA G-3' | 41 |
| | | R 5'-AGC ACA TAG GAG GCA GAG AC-3' | 42 |
| p53 wild-type | 288 bp | F | |
| | | R | |
| Hi-myc | 177 bp | F 5'-AAA CAT GAT GAC TAC CAA GCT TGG C-3' | 43 |
| | | R 5'-ATG ATA GCA TCT TGT TCT TAG TCT TTT TCT TAA TAG GG-3' | 44 |

TABLE 4

Antibodies used in this study.

For immunofluorescence and immunohistochemistry

| Antigen | Supplier | Ig type | Dilution |
|---|---|---|---|
| AR | Santa Cruz sc-816 | rabbit IgG | 1:500 |
| CK5 | Covance PRB-160P | rabbit IgG | 1:500 |
| CK5 | Covance SIG-3475 | chicken IgY | 1:500 |
| CK8 | Abcam ab14053 | chicken IgY | 1:500 |
| CK8 | Abcam ab53280 | rabbit IgG | 1:200 |
| CK8 | Developmental Studies Hybridoma Bank, clone TROMA-1 | rat IgG2a | 1:100 |
| CK18 | Abcam ab668, clone C-04 | mouse IgG1 | 1:100 |
| CK18 | Sigma SAB3300015, clone 10 | mouse IgG1 | 1:500 |
| FoxA1 | Abcam ab55178 | mouse IgG2a | 1:100 |
| GFP | Abcam ab13970 | chicken IgY | 1:1000 |
| Ki67 | eBiosciences 14-5698, clone SolA15 | rat IgG2a | 1:1000 |
| p63 | Santa Cruz sc-8431 | mouse IgG2a | 1:200-1:600 |
| p63 | Santa Cruz sc-8343 | rabbit IgG | 1:50 |
| phospho-Akt | Cell Signaling 3787 | rabbit IgG | 1:50 |
| phospho-Erk | Cell Signaling 4370 | rabbit IgG | 1:200 |

For flow cytometry

| Antibody | Supplier | Dilution |
|---|---|---|
| CD324 (E-cadherin)-PerCP-eFluor710 | eBiosciences 46-3249-82 | 1:100 (mouse) 1:200 (human) |
| mouse CD326 (EPCAM)-APC | BioLegend 118214 | 1:100 |
| human CD326 (EPCAM)-APC | BioLegend 324208 | 1:50 |

REFERENCES FOR EXAMPLE 4

1. Peehl D M. Primary cell cultures as models of prostate cancer development. Endocr Relat Cancer. 2005; 12:19-47.
2. Shen M M, Abate-Shen C. Molecular genetics of prostate cancer: new prospects for old challenges. Genes Dev. 2010; 24:1967-2000.
3. Grisanzio C, Signoretti S. p63 in prostate biology and pathology. J Cell Biochem. 2008; 103:1354-1368.
4. Humphrey P A. Diagnosis of adenocarcinoma in prostate needle biopsy tissue. J Clin Pathol. 2007; 60:35-42.
5. Lawson D A, Xin L, Lukacs R U, Cheng D, Witte O N. Isolation and functional characterization of murine prostate stem cells. Proc Natl Acad Sci USA. 2007; 104:181-186.
6. Xin L, Lukacs R U, Lawson D A, Cheng D, Witte O N. Self-renewal and multilineage differentiation in vitro from murine prostate stem cells. Stem Cells. 2007; 25:2760-2769.
7. Shi X, Gipp J, Bushman W. Anchorage-independent culture maintains prostate stem cells. Dev Biol. 2007; 312:396-406.
8. Garraway I P, et al. Human prostate sphere-forming cells represent a subset of basal epithelial cells capable of glandular regeneration in vivo. Prostate. 2010; 70:491-501.
9. Lukacs R U, Goldstein A S, Lawson D A, Cheng D, Witte O N. Isolation, cultivation and characterization of adult murine prostate stem cells. Nat Protoc. 2010; 5:702-713.
10. Guo C, Zhang B, Garraway I P. Isolation and characterization of human prostate stem/progenitor cells. Methods Mol Biol. 2012; 879:315-326.
11. Goldstein A S, et al. Trop2 identifies a subpopulation of murine and human prostate basal cells with stem cell characteristics. Proc Natl Acad Sci USA. 2008; 105:20882-20887.
12. Lawson D A, et al. Basal epithelial stem cells are efficient targets for prostate cancer initiation. Proc Natl Acad Sci USA. 2010; 107:2610-2615.
13. Wang Z A, et al. Lineage analysis of basal epithelial cells reveals their unexpected plasticity and supports a cell-of-origin model for prostate cancer heterogeneity. Nature Cell Biology. 2013; 15:274-283.
14. Lancaster M A, Knoblich J A. Organogenesis in a dish: modeling development and disease using organoid technologies. Science. 2014; 345:1247125.
15. Sato T, et al. Paneth cells constitute the niche for Lgr5 stem cells in intestinal crypts. Nature. 2011; 469:415-418.
16. Sato T, et al. Single Lgr5 stem cells build crypt-villus structures in vitro without a mesenchymal niche. Nature. 2009; 459:262-265.
17. Yui S, et al. Functional engraftment of colon epithelium expanded in vitro from a single adult Lgr5(+) stem cell. Nat Med. 2012; 18:618-623.
18. Sato T, et al. Long-term expansion of epithelial organoids from human colon, adenoma, adenocarcinoma, and Barrett's epithelium. Gastroenterology. 2011; 141:1762-1772.
19. Kondo J, et al. Retaining cell-cell contact enables preparation and culture of spheroids composed of pure primary cancer cells from colorectal cancer. Proc Natl Acad Sci USA. 2011; 108:6235-6240.
20. Ootani A, et al. Sustained in vitro intestinal epithelial culture within a Wnt-dependent stem cell niche. Nat Med. 2009; 15:701-706.
21. Barker N, et al. Lgr5(+ve) stem cells drive self-renewal in the stomach and build long-lived gastric units in vitro. Cell Stem Cell. 2010; 6:25-36.
22. Huch M, et al. In vitro expansion of single Lgr5+ liver stem cells induced by Wnt-driven regeneration. Nature. 2013; 494:247-250.
23. Huch M, et al. Unlimited in vitro expansion of adult bi-potent pancreas progenitors through the Lgr5/R-spondin axis. EMBO J. 2013; 32:2708-2721.
24. Greggio C, et al. Artificial three-dimensional niches deconstruct pancreas development in vitro. Development. 2013; 140:4452-4462.
25. Wang X, et al. A luminal epithelial stem cell that is a cell of origin for prostate cancer. Nature. 2009; 461:495-500.
26. Guo W, et al. Slug and Sox9 cooperatively determine the mammary stem cell state. Cell. 2012; 148:1015-1028.
27. Lang S H, et al. Experimental prostate epithelial morphogenesis in response to stroma and three-dimensional matrigel culture. Cell Growth Differ. 2001; 12:631-640.
28. Cano P, Godoy A, Escamilla R, Dhir R, Onate S A. Stromal-epithelial cell interactions and androgen receptor-coregulator recruitment is altered in the tissue microenvironment of prostate cancer. Cancer Res. 2007; 67:511-519.
29. Liu X, et al. ROCK inhibitor and feeder cells induce the conditional reprogramming of epithelial cells. Am J Pathol. 2012; 180:599-607.
30. Zhang L, et al. ROCK inhibitor Y-27632 suppresses dissociation-induced apoptosis of murine prostate stem/progenitor cells and increases their cloning efficiency. PLoS One. 2011; 6:e18271.

31. Xu Y, et al. Revealing a core signaling regulatory mechanism for pluripotent stem cell survival and self-renewal by small molecules. Proc Natl Acad Sci USA. 2010; 107:8129-8134.
32. Gao N, et al. Forkhead box A1 regulates prostate ductal morphogenesis and promotes epithelial cell maturation. Development. 2005; 132:3431-3443.
33. Srinivas S, et al. Cre reporter strains produced by targeted insertion of EYFP and ECFP into the ROSA26 locus. BMC Dev Biol. 2001; 1:4.
34. Van Keymeulen A, et al. Distinct stem cells contribute to mammary gland development and maintenance. Nature. 2011; 479:189-193.
35. Ousset M, et al. Multipotent and unipotent progenitors contribute to prostate postnatal development. Nat Cell Biol. 2012; 14:1131-1138.
36. Madisen L, et al. A robust and high-throughput Cre reporting and characterization system for the whole mouse brain. Nature neuroscience. 2010; 13:133-140.
37. Choi N, Zhang B, Zhang L, Ittmann M, Xin L. Adult murine prostate basal and luminal cells are self-sustained lineages that can both serve as targets for prostate cancer initiation. Cancer Cell. 2012; 21:253-265.
38. Lu T L, et al. Conditionally ablated Pten in prostate basal cells promotes basal-to-luminal differentiation and causes invasive prostate cancer in mice. Am J Pathol. 2013; 182:975-991.
39. Aytes A, et al. ETV4 promotes metastasis in response to activation of PI3-kinase and Ras signaling in a mouse model of advanced prostate cancer. Proc Natl Acad Sci USA. 2013; 110:E3506-3515.
40. Bhatia-Gaur R, et al. Roles for Nkx3.1 in prostate development and cancer. Genes Dev. 1999; 13:966-977.
41. Kim M J, et al. Nkx3.1 mutant mice recapitulate early stages of prostate carcinogenesis. Cancer Res. 2002; 62:2999-3004.
42. Kim M J, et al. Cooperativity of Nkx3.1 and Pten loss of function in a mouse model of prostate carcinogenesis. Proc Natl Acad Sci USA. 2002; 99:2884-2889.
43. Greenberg N M, et al. Prostate cancer in a transgenic mouse. Proc Natl Acad Sci USA. 1995; 92:3439-3443.
44. Masumori N, et al. A probasin-large T antigen transgenic mouse line develops prostate adenocarcinoma and neuroendocrine carcinoma with metastatic potential. Cancer Res. 2001; 61:2239-2249.
45. Ellwood-Yen K, et al. Myc-driven murine prostate cancer shares molecular features with human prostate tumors. Cancer Cell. 2003; 4:223-238.
46. Aytes A, et al. Cross-species analysis of genome-wide regulatory networks identifies a synergistic interaction between FOXM1 and CENPF that drives prostate cancer malignancy. Cancer Cell. 2014; 25:638-651.
47. Irshad S, et al. A molecular signature predictive of indolent prostate cancer. Sci Transl Med. 2013; 5:202ra122.
48. Floc'h N, et al. Dual targeting of the Akt/mTOR signaling pathway inhibits castration-resistant prostate cancer in a genetically engineered mouse model. Cancer Res. 2012; 72:4483-4493.
49. Carver B S, et al. Reciprocal feedback regulation of PI3K and androgen receptor signaling in PTEN-deficient prostate cancer. Cancer Cell. 2011; 19:575-586.
50. Korenchuk S, et al. VCaP, a cell-based model system of human prostate cancer. In Vivo. 2001; 15:163-168.
51. Sasai Y. Next-generation regenerative medicine: organogenesis from stem cells in 3D culture. Cell Stem Cell. 2013; 12:520-530.
52. McKeehan W L, Adams P S, Rosser M P. Direct mitogenic effects of insulin, epidermal growth factor, glucocorticoid, cholera toxin, unknown pituitary factors and possibly prolactin, but not androgen, on normal rat prostate epithelial cells in serum-free, primary cell culture. Cancer Res. 1984; 44:1998-2010.
53. Lang S H, et al. Differentiation of prostate epithelial cell cultures by matrigel/stromal cell glandular reconstruction. In vitro cellular & developmental biology. Animal. 2006; 42:273-280.
54. Lamb L E, Knudsen B S, Miranti C K. E-cadherin-mediated survival of androgen-receptor-expressing secretory prostate epithelial cells derived from a stratified in vitro differentiation model. J Cell Sci. 2010; 123:266-276.
55. Marker P C, Donjacour A A, Dahiya R, Cunha G R. Hormonal, cellular, and molecular control of prostatic development. Dev Biol. 2003; 253:165-174.
56. Cunha G R. Mesenchymal-epithelial interactions: past, present, and future. Differentiation. 2008; 76:578-586.
57. Stange D E, et al. Differentiated Troy+ chief cells act as reserve stem cells to generate all lineages of the stomach epithelium. Cell. 2013; 155:357-368.
58. Liu J, et al. Regenerated luminal epithelial cells are derived from preexisting luminal epithelial cells in adult mouse prostate. Mol Endocrinol. 2011; 25:1849-1857.
59. Koo B K, et al. Controlled gene expression in primary Lgr5 organoid cultures. Nature methods. 2012; 9:81-83.
60. Schwank G, et al. Functional repair of CFTR by CRISPR/Cas9 in intestinal stem cell organoids of cystic fibrosis patients. Cell Stem Cell. 2013; 13:653-658.
61. Sachs N, Clevers H. Organoid cultures for the analysis of cancer phenotypes. Curr Opin Genet Dev. 2014; 24C: 68-73.
62. Ranga A, Gjorevski N, Lutolf M P. Drug discovery through stem cell-based organoid models. Advanced drug delivery reviews. 2014; 69-70C:19-28.
63. Centenera M M, Raj G V, Knudsen K E, Tilley W D, Butler L M. Ex vivo culture of human prostate tissue and drug development. Nat Rev Urol. 2013; 10:483-487.
64. Toivanen R, et al. A preclinical xenograft model identifies castration-tolerant cancer-repopulating cells in localized prostate tumors. Sci Transl Med. 2013; 5:187ra171.
65. Lin D, et al. High fidelity patient-derived xenografts for accelerating prostate cancer discovery and drug development. Cancer Res. 2014; 74:1272-1283.
66. Van Keymeulen A, et al. Epidermal progenitors give rise to Merkel cells during embryonic development and adult homeostasis. J Cell Biol. 2009; 187:91-100.
67. Lesche R, et al. Cre/loxP-mediated inactivation of the murine Pten tumor suppressor gene. Genesis. 2002; 32:148-149.
68. Jackson E L, et al. Analysis of lung tumor initiation and progression using conditional expression of oncogenic K-ras. Genes Dev. 2001; 15:3243-3248.
69. Rock J R, et al. Basal cells as stem cells of the mouse trachea and human airway epithelium. Proc Natl Acad Sci USA. 2009; 106:12771-12775.
70. Giannico G A, Ross H M, Lotan T, Epstein M. Aberrant expression of p63 in adenocarcinoma of the prostate: a radical prostatectomy study. Am J Surg Pathol. 2013; 37:1401-1406.

Example 5—Culture of Mouse Prostate Organoids

This protocol describes a novel three-dimensional "organoid" culture for prostate epithelial cells. Described is the digestion and dissociation of prostate tissue into single-cell suspensions containing both prostatic epithelial and stromal cells, the isolation of epithelial cells from the parental population via fluorescence activated cell sorting, and the plating conditions and medium for prostate organoid culture. Also described is the serial passaging and freezing of cultures, which can resume growth after thawing. The dissection and dissociation of prostate tissue and the preparation of cells for plating takes 8-9 hours. Organoids that can be quantified and analyzed are obtained after 7-10 days. The culture system described herein supports the growth and serial passaging of both normal and transformed organoids, and is useful for studies of normal prostate as well as prostate cancer.

Three-dimensional "organoid" culture techniques have been used for culture of stem/progenitor cells from tissues including the small intestine, stomach, liver and pancreas [1-4]. A novel method has been developed for the culture of prostate epithelial organoids that display tissue architecture resembling that of the normal prostate [5]. The culture system described herein supports the growth and serial passaging of prostate luminal cells, which have historically been difficult to grow, and differs from previous "prostasphere" conditions, which favor the growth of prostate basal cells and fail to display a response to androgen deprivation[6]. In particular, the organoid culture conditions described herein allow for the growth of prostate organoids from single luminal stem/progenitor cells, as well as mouse tumor organoids, and thus are be widely applicable for studies of prostate biology. Notably, the culture methods described herein are distinct from recently published conditions for prostate organoid culture using defined media conditions [7,8].

In the following protocol, described is the digestion and dissociation of prostate tissue into single-cell suspensions containing both prostatic epithelial and stromal cells, the isolation of epithelial cells from the parental population via fluorescence activated cell sorting (FACS) using antibodies against epithelial cell adhesion molecule (EpCAM, also CD326) and epithelial cadherin (E-cadherin, also CD324), and the plating conditions and medium for prostate organoid culture using supplemented hepatocyte medium with 5% Matrigel. Also described is the serial passaging and freezing of cultures, which can resume growth after thawing.

Reagents 1.1. Prostate Dissection and Collagenase Digestion
1. 1 or 2 male C57BL/6 mice (or mice of interest)
2. PBS (for dissection)
3. 10× collagenase/hyaluronidase solution (STEMCELL Technologies #07912)
4. Dulbecco's Modified Eagle Medium: Nutrient Mixture F-12 (DMEM/F-12, Gibco #10565) supplemented with 5% fetal bovine serum (FBS)

1.2. Enzymatic Dissociation to Single Cell Suspension
1. 0.25% Trypsin/EDTA (STEMCELL Technologies #07901)
2. Hanks' Balanced Salt Solution Modified (HBSS, STEMCELL Technologies #37150), supplemented with 2% FBS
3. Dispase 5 mg/mL (STEMCELL Technologies #07913)
4. DNaseI 1 mg/mL (STEMCELL Technologies #07900)
5. Trypan blue solution 0.4% (Gibco #15250-061)
6. HBSS+2% FBS+10 µM ROCK inhibitor Y-27632 (STEMCELL Technologies #07171) (Important: ROCK inhibitor from STEMCELLTechnologies is recommended for consistent results.)

1.3. Fluorescence Activated Cell Sorting (FACS) Preparation
1. Anti-mouse EpCAM APC antibody (BioLegend 118214)
2. Anti-mouse E-Cadherin PerCP-Efluor710 antibody (eBiosciences 46-3249-82)
3. 0.5 mg/mL DAPI
4. HBSS+2% FBS+10 µM ROCK inhibitor Y-27632

1.4. Medium Preparation and Cell Plating
1. 96-well low-attachment plate (Corning #3474)
2. 24-well flat bottom plate (BD #353047) (for embedding culture)
3. Hepatocyte medium (Corning #355056) (Tip: This reagent has regularly been on back order. Check in advance for availability.)
4. 10 ng/mL epidermal growth factor (EGF; comes with Corning #3555056)
5. Heat-inactivated, charcoal stripped FBS (Gibco #12676) (Important: Charcoal-stripped FBS must be heat-inactivated prior to use by heating in 55° C. water bath for 60 min. Heat-inactivated charcoal-stripped FBS can be aliquoted and stored at −20° C.)
6. 100× Glutamax (Gibco #35050)
7. Thawed matrigel (Corning #354234) (Important: After removal of Matrigel from storage at −20° C., it must remain on ice at all times until use to prevent polymerization. It is recommend to place Matrigel on ice in a 4° C. refrigerator overnight to thaw and keeping it on ice until it is added to media. Unused Matrigel can be refrozen, but avoid multiple freeze-thaw cycles.)
8. 5 mM ROCK inhibitor Y-27632
9. $10^{-5}$ M dihydrotestosterone (DHT) in ethanol (Sigma #A-8380)
10. 100× antibiotic-antimycotic (Caution: It is recommend to culture without antibiotics, but antibiotics can be added during the initial culture period or if there is concern for contamination from other sources.)

1.5. Passaging and Freezing Organoids
1. Cold phosphate buffered saline (PBS)
2. 0.25% Trypsin/EDTA
3. HBSS+2% FBS
4. Prepared organoid media (see 2.4)
5. Heat-inactivated, charcoal stripped FBS
6. Dimethyl sulfoxide (DMSO, Sigma #D2650)

Equipment
CO2 euthanasia chamber
Dissecting microscope
Micro-dissecting instruments
Water baths set at 37° C. and 55° C.
Sterile petri dishes
Eppendorf tubes (1.5 mL)
Incubator, humidified at 37° C., with 5% CO2
Laminar flow hood or biological safety cabinet
Centrifuges (for Eppendorf and Falcon tubes)
Falcon tubes (15 and 50 mL)
Orbital shaker
Cell strainer 40 uM (Corning #352340)
Hemocytometer
BD FACSAria cell sorter (or similar)

Procedure
Important:
The volumes detailed below are for dissociation of an intact prostate from an 8-12 week wild type mouse. For larger prostate samples such as those from aggressive tumor models, all reagents should be increased proportionally from the volumes suggested below. For example, if a prostate tumor is approximately twice the size of a wild type prostate, 2× the volume of suggested reagents should be used.

2.1. Prostate Dissection and Collagenase Digestion

1. In tissue culture hood, combine 200 µL 10× collagenase/hyaluronidase mixture with 1.8 mL DMEM/F12+5% FBS. Place in 37° C. water bath until ready to use.

2. Resect mouse prostates and transfer to sterile petri dish containing cold PBS for dissection. Using a dissecting microscope, fine forceps, and sharp scissors, remove residual fat from prostate tissue.

3. Fill 1.5 mL Eppendorf tube with 1 mL of diluted pre-warmed collagenase/hyaluronidase solution and transfer prostate tissue into the tube.

4. Using small, sharp sterile scissors, macerate the prostate tissue by rapidly opening and closing the scissors inside the tube to cut the tissue into small pieces. Fill the tube with an additional 400-500 µL dilute collagenase/hyaluronidase solution until almost full.

5. Incubate in 37° C. incubator for 3 hours. (Tip: The Eppendorf tube may be placed on its side in a sterile petri dish to maximize the surface area of prostate tissue exposed to collagenase/hyaluronidase solution. Periodic shaking of the tube to redistribute prostate tissue is helpful.)

2.2. Enzymatic Dissociation to Single Cell Suspension

1. Centrifuge digested tissue at 350 rcf for 5 minutes and discard supernatant.

2. Resuspend pellet in 1.5 mL cold 0.25% trypsin-EDTA and transfer to 50 mL conical tube. Incubate in 4° C. refrigerator for 1 hour. (Caution: To minimize cell death, keep trypsin ≤4° C. prior to and during use. Trypsin can be gently thawed overnight with Matrigel and kept on ice. An orbital shaker can be used during the trypsinization step for optimal digestion.)

3. During trypsinization, place 900 µL dispase in 37° C. water bath at least 10 minutes prior to use. Immediately before use, add 100 µL DNaseI to dispase solution.

4. After trypsinization is complete (1 hour), add cold HBSS+2% FBS (equal to 2× volume of trypsin) to quench reaction. Centrifuge at 350 rcf for 5 minutes and discard supernatant.

5. Add 1 mL of pre-warmed dispase/DNaseI solution. Pipette the sample vigorously for 1-2 minutes using P1000 pipette until solution is homogenously translucent with no visible tissue fragments. (Do not allow digestion to continue for more than 2 minutes.) (Important: To maximize cell dissociation, this pipetting step should be done continuously.)

6. Add cold HBSS+2% FBS (equal to 5× volume of dispase) to quench reaction.

7. Filter cell suspension through a 40 µm cell strainer into a new 50 mL conical tube.

8. Centrifuge filtered suspension at 350 rcf for 5 minutes and discard supernatant.

9. Resuspend pellet in 1 mL HBSS+2% FBS and transfer to 1.5 mL Eppendorf tube.

10. Count viable cells using a hemacytometer and trypan blue.

11. Centrifuge and resuspend cells in HBSS+2% FBS at 100 µL/1×10$^6$ cells. (If fewer than 1×10$^6$ cells are obtained, resuspend in 100 µL)

2.3. Fluorescence Activated Cell Sorting (FACS)

Keep cell suspension and reagents on ice until sorting is finished.

1. Divide cell suspension into four 1.5 mL Eppendorf tubes as follows: a. Tube 1 (unstained control): 100 µL (1×10$^6$ cells); b. Tube 2 (PerCP control): 100 µL (1×10$^6$ cells); c. Tube 3 (APC control): 100 µL (1×10$^6$ cells); d. Tube 4 (sample for collection): remaining sample (up to 1 mL);

2. Add FACS antibodies as follows: a. Tube 1: no antibody; b. Tube 2: 1 µL (1:100) anti-mouse E-cadherin PerCP-Efluor710 antibody; c. Tube 3: 1 µL (1:100) anti-mouse APC-EpCAM antibody; d. Tube 4: both antibodies at 1:100 dilution (1 µL antibody per 100 µL cell suspension). (Important: If fewer than 4×10$^6$ cells are obtained after enzymatic dissociation, use 10 µL of cell suspension for control tubes 1-3 and dilute with 90 µL HBSS+2% FBS for a total of 100 µL. Use the same antibody concentrations. Resuspend tubes 1-3 in 50 µL cold HBSS+2% FBS instead of 500 µL in step 6 of cell sorting and use 1 µL of dilute DAPI instead of 10 µL.)

3. Cover with foil and incubate on ice for 25 minutes.

4. Spin tubes at 350 rcf at 4° C. for 5 minutes and discard supernatant.

5. Add 500 µL cold HBSS+2% FBS to all tubes. Spin at 350 rcf at 4° C. for 5 minutes and discard supernatant.

6. Resuspend all tubes in 500 µL cold HBSS+2% FBS+10 µM ROCK inhibitor Y-27632.

7. Prepare a 1:100 dilution of 0.5 mg/mL DAPI by adding 5 µL DAPI to 495 µL HBSS+2% FBS. Add 10 µL of dilute DAPI to each tube.

8. Transfer each suspension into a labeled round-bottom clear rubber-top plastic test tube for loading into sorter.

9. Prior to sorting, prepare multiple 1.5 mL Eppendorf tubes pre-filled with 500 µL cold HBSS+2% FBS+10 µM ROCK inhibitor Y-27632 for collecting cells.

10. Perform sorting via sterile FACS facility (tubes 1-3 will be used to set appropriate gates; tube 4 will be used to collect cells for plating). Collecting cells at 60,000 cells per tube will facilitate easier plating. Keep collected cells on ice until ready to plate.

2.4. Medium Preparation and Cell Plating

1. Prepare desired amount of culture medium by combining the following components to the indicated final concentrations (a-d can be combined and stored as a 50 mL aliquot at 4° C. for up to 4 weeks; e-h should be added on the day of use based on the amount of media needed): a. Hepatocyte medium (47 mL per 50 mL media); b. 10 ng/mL EGF (100 µL of 5 µg/mL stock per 50 mL media); c. 5% heat-inactivated, charcoal-stripped FBS (2.5 mL per 50 mL media); d. 1× Glutamax (500 µL per 50 mL media); e. 5% Matrigel (50 µL per 1 mL media); f. 10 µM ROCK inhibitor Y-27632 (2 µL of 5 mM stock per 1 mL media); g. 100 nM DHT (10 µL of 10$^{-5}$ M stock per 1 mL media); h. 1× antibiotic-antimycotic (10 µL per 1 mL media; optional)

2. Keep prepared culture media at room temperature until use (rapid warming in 37° C. water bath may cause Matrigel to solidify at top of tube).

3. Centrifuge sorted cells at 350 rcf for 5 minutes and resuspend in prepared media at 5,000 cells per 100 µL media. (If cells were collected at 60,000 cells per Eppendorf tube, resuspend in 1.2 mL media. If there is concern for cell death, count viable cells prior to centrifuging and resuspend accordingly.)

4. Add resuspended cells to 96-well low attachment plate at 100 µL per well for a final plating density of 5,000 cells per well.

5. Change media every 4 days by adding 100 µL fresh media to each well on days 4 and 8 after plating. On day 12, when wells are full (300 µL), transfer each well to a 1.5 ml Eppendorf tube and centrifuge at 250 rcf for 5 minutes. Remove 200 µL of supernatant and add 100 µL fresh media (total volume will be 200 µL). Transfer onto a new 96-well plate using P1000 pipet tip (smaller tips may damage organoids). Alternate every 4 days between either adding 100 μL media or spinning down to remove 200 μL and add 100 μL until ready for passage. (Multiple wells can be pooled prior to centrifuging and redistributed evenly if there are many wells.)

2.5. Cell Plating Using Embedding Conditions

1. Medium preparation is the same as in 2.4.1 except that component e (5% Matrigel) is not added. Media can be pre-warmed in a 37° C. water bath. This pre-warmed media will be used to cover the solidified Matrigel ring in 2.5.7.

2. Prepare cold media as in 2.4.1 except that component e (5% Matrigel) is not added and f (ROCK inhibitor Y-27632) is at a final concentration of 25 μM (5 μL of 5 mM stock per 1 mL media). Keep this media on ice and it will be used to resuspend cells.

3. Pellet cells as in 2.4.3 and resuspend in prepared cold media at 5,000 cells per 40 μL media. (If cells were collected at 60,000 cells per Eppendorf tube, resuspend in 480 μL media.) (Tip: For the embedding condition, the number of cells plated can be much lower.)

4. Mix the 40 μL media containing cells thoroughly with 60 μL Matrigel (If 60,000 cells are resuspended in 480 μL media, mix with 720 μL Matrigel). Avoid bubbles. This step should be done on ice to prevent Matrigel solidification.

5. Plate the 100 μL media Matrigel mixture around the ring of a well in a 24-well plate.

6. Incubate the 24-well plate in 37° C. incubator for 30 minutes to allow the Matrigel ring to solidify.

7. Add 400 μL pre-warmed media as prepared in 2.5.1 to each well. (Important: Make sure that the media is warm enough prior to addition to the well to avoid dissolving the Matrigel ring.)

8. Change media every 4 days by aspirating the media off the Matrigel ring and adding fresh media. (Tip: Aspiration should be performed from the middle of the well to avoid disturbing the Matrigel ring.)

2.6. Passaging and Freezing Organoids

1. When organoids are large (usually 3-5 weeks after plating), prepare organoids for passage by transferring into 1.5 mL Eppendorf tubes and spinning at 250 rcf for 5 minutes. (Multiple wells can be pooled.) Discard supernatant.

2. Wash cells in cold PBS and spin again at 250 rcf for 5 minutes. (Important: Without this PBS washing step, the trypsin reaction will not be optimal due to residual FBS in the medium, resulting in incomplete dissociation into single cells.)

3. Add 1 mL warm 0.25% trypsin/EDTA and incubate in a 37° C. water bath for 5 minutes. (Tip: In the context of very large organoids or organoids that are difficult to dissociate, step 3 can be replaced by incubation in cold 0.25% trypsin/EDTA at 4° C. for 30 minutes.)

4. Pipette up and down with P200 pipet tip for 30 seconds to dissociate cells.

5. Transfer suspension into a 15 mL conical tube prefilled with 2 mL cold HBSS+2% FBS.

6. Centrifuge at 350 rcf for 5 minutes and discard supernatant.

7. Resuspend cell pellet in fresh media and plate into a new low-attachment 96-well plate. Cells can be plated by either replating 4× the number of wells passaged in 100 μL per well or by counting viable cells and replating at 5,000 cells/100 μL media per well.

8. Organoids can be frozen at any point during a passage cycle by centrifuging at 250 rcf for 5 minutes and resuspending in 1 mL freezing media in 1.8 mL cryo tubes (50% FBS, 40% hepatocyte media, 10% DMSO). Gradual freezing to ≤−80° using an insulated cryofreezing container is recommended. Organoids should be thawed rapidly in a 37° C. water bath and immediately diluted in 10 mL HBSS+2% FBS per 1 mL freezing media. Centrifuge thawed organoids at 250 rcf for 5 minutes and resuspend in organoid culture media for plating.

2.7. Passaging and Freezing of Embedded Organoids

1. Dissolve the Matrigel ring by adding about 125 μL dispase at 5 mg/mL to each well of the 24-well plate to make the final concentration of dispase 1 mg/ml.

2. Incubate in 37° C. incubator for 10 minutes.

3. If the Matrigel ring dissolves, proceed as in 2.6.1. If not, incubate at 37° C. for another 5 minutes.

Timing

It should take approximately 8-9 hours (depending on experience) from dissection of mouse tissue to plating of sorted epithelial cells.

Troubleshooting 3.1. Incomplete Cell Dissociation after Dispase Step

1. Check that all reagents are within the use by date

2. Make sure to thoroughly mince tissues prior to collagenase/hyaluronidase digestion.

3. During the dispase step, make sure the solution is pre-warmed at 37° C. for at least 10 minutes and perform vigorous pipetting of sample for up to 2 minutes.

3.2. Organoids Fail to Form from Plated Cells

1. Ensure the DAPI aliquot being used results in optimal exclusion of dead cells during sorting. Replace if necessary.

2. Decrease the speed and pressure used during sorting.

3.3. Plated Cells Form Adherent Cultures Instead of Organoids

1. Ensure you are using a low-attachment surface plate.

2. Some low-attachment brands will still result in adherent cultures. Costar plates from Corning are optimal for minimizing cell adherence.

Anticipated Results

Organoid formation from plated cells is a rapid process, and small organoids should be identifiable after about 3 days for organoids from wild-type mice, or within 24 hours for organoids derived from mouse models of prostate cancer. Organoid forming efficiency should be quantitated approximately 7-10 days after plating of sorted cells. Wild-type cells should generate large cystic structures, while tumor cells will form more solid organoids. If the EpCAM E-Cadherin sorting strategy is utilized, there should not be any evidence of fibroblast cells in organoid cultures.

Results

Figure 58:
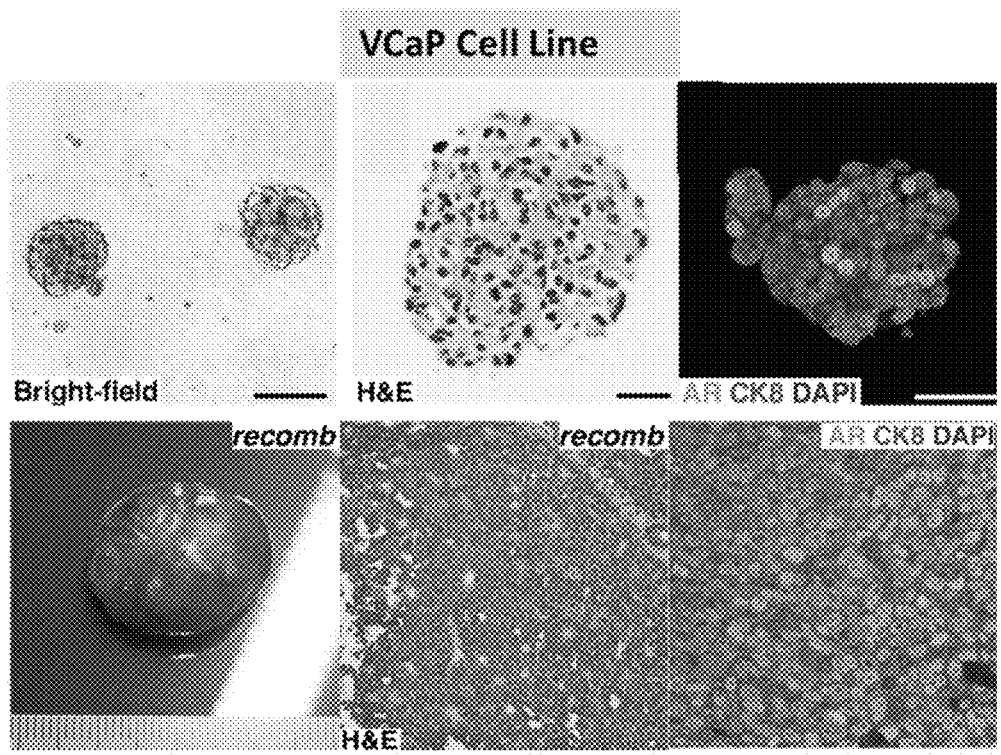
FIG. 58 shows tumor organoids derived from human VCaP prostate cancer cell line.
Figure 59:
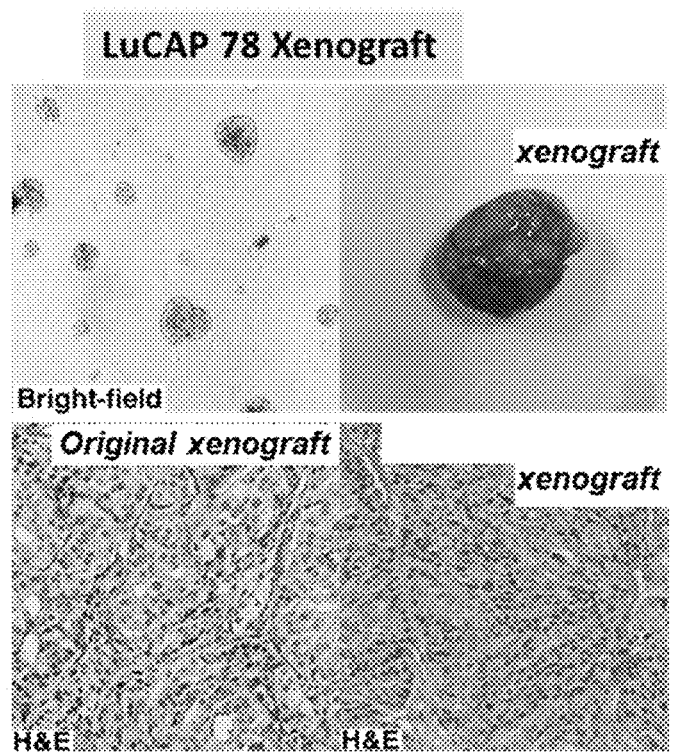
FIG. 59 shows tumor organoids derived from human LuCaP xenografts.

Organoids were cultured from human prostate cancer cell lines or xenograft lines, that are difficult or impossible to culture using standard culture protocols (FIGS. 58-59).

Figure 60:
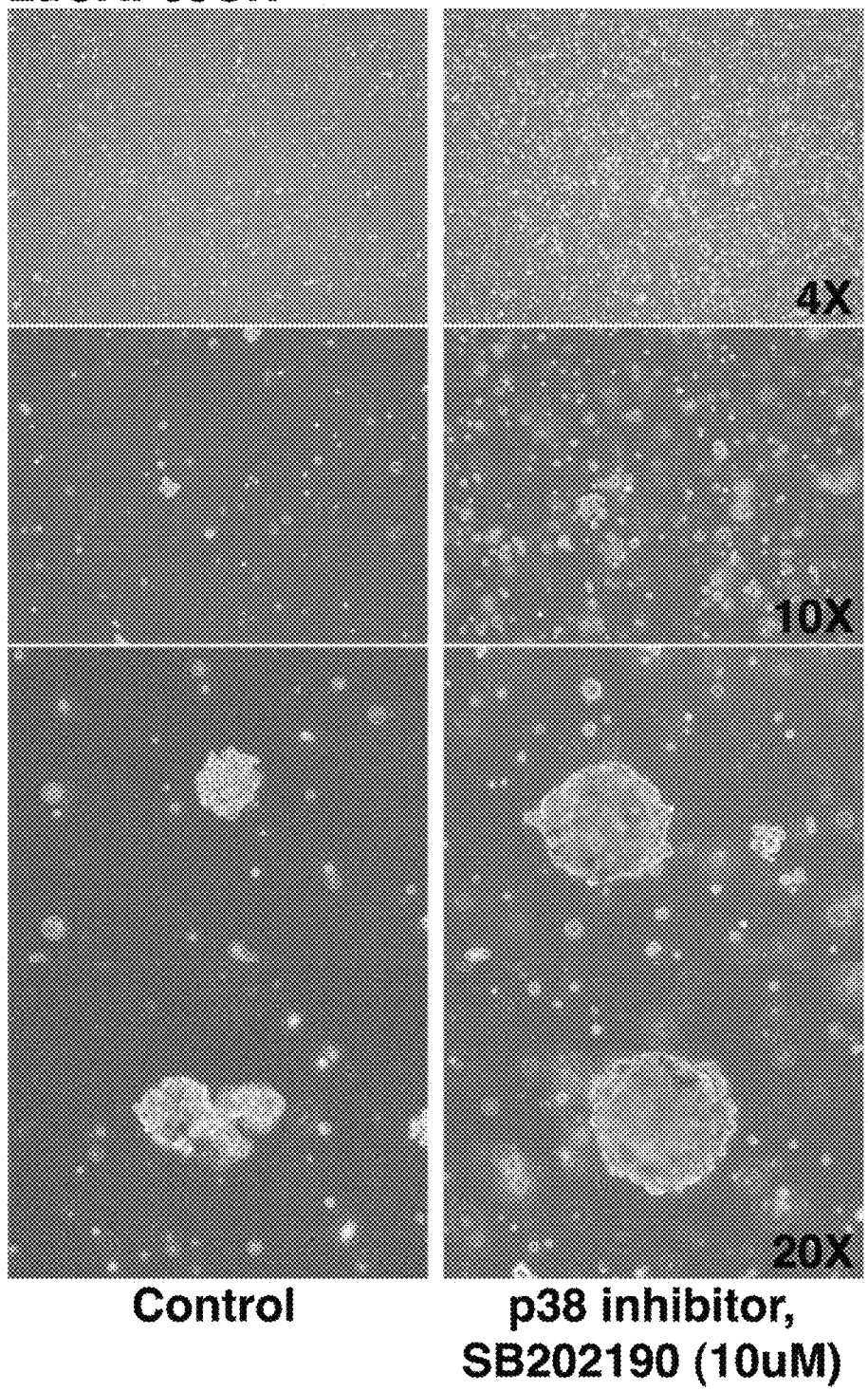
FIG. 60 shows LuCAP35CR lines with and without p38 inhibitor.
Figure 61:
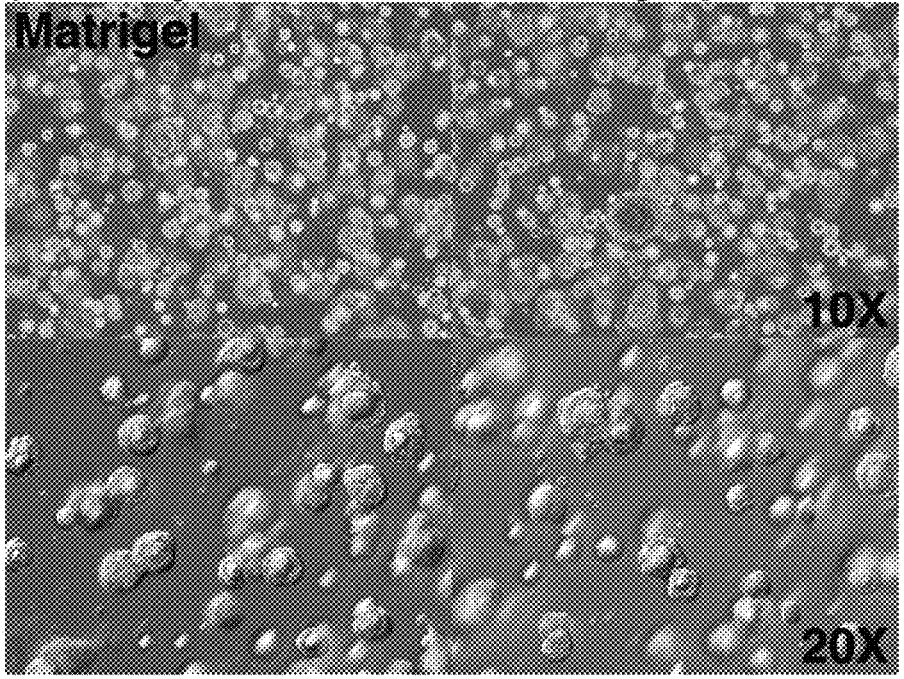
FIG. 61 shows human prostate organoids grown in Matrigel vs collagen.
Figure 62:
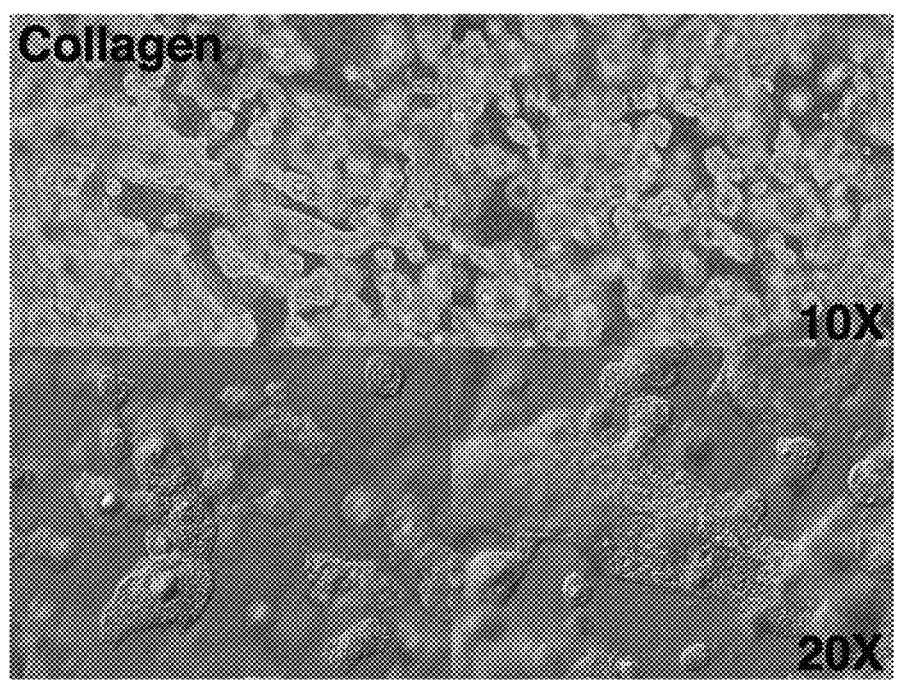
FIG. 62 shows human prostate organoids grown in Matrigel vs collagen.

Human prostate organoids were cultured from biopsy specimens (as opposed to prostatectomy specimens) in either Matrigel or collagen matrix (see below) (FIGS. 60-62).

REFERENCES FOR EXAMPLE 5

1. Sato, T. et al. Single Lgr5 stem cells build crypt-villus structures in vitro without a mesenchymal niche. Nature 459, 262-265 (2009).

2. Stange, Daniel E. et al. Differentiated Troy+ Chief Cells Act as Reserve Stem Cells to Generate All Lineages of the Stomach Epithelium. Cell 155, 357-368 (2013).

3. Huch, M. et al. In vitro expansion of single Lgr5+ liver stem cells induced by Wnt-driven regeneration. Nature 494, 247-250 (2013).

4. Huch, M. et al. Unlimited in vitro expansion of adult bi-potent pancreas progenitors through the Lgr5/R-spondin axis. EMBO J 32, 2708-2721 (2013).
5. Chua, C. W. et al. Single luminal epithelial progenitors can generate prostate organoids in culture. Nat Cell Biol (2014) DOI: 10.1038/ncb3047.
6. Lukacs, R. U., Goldstein, A. S., Lawson, D. A., Cheng, D. & Witte, O. N. Isolation, cultivation and characterization of adult murine prostate stem cells. Nat Protoc 5, 702-713 (2010).
7. Gao, D. et al. Organoid Cultures Derived from Patients with Advanced Prostate Cancer. Cell (2014) DOI: 10.1016/j.cell.2014.08.016.
8. Karthaus, W. R. et al. Identification of Multipotent Luminal Progenitor Cells in Human Prostate Organoid Cultures. Cell (2014) DOI: 10.1016/j.cell.2014.08.017.

Example 6—Culture of Metastatic Prostate Cell Lines from Metastases Samples

Method

Metastases are dissociated using a protocol that is identical to prostate tissue dissociation protocol described in Example 5. The dissociated cells from metastases are cultured using attached conditions. The medium used is hepatocyte medium supplemented with 10 ng/ml of EGF (BD Biosciences, cat. #355056), glutamax (Gibco, cat. #35050) 5% Matrigel (BD Biosciences, cat. #354234), 5% heat-inactivated charcoal-stripped FBS (Gibco, cat. #12676) (55° C. for 1 hour) and 10 mM Y-27632 (Stem Cell Technologies, cat. #07171) with and without addition of 100 nM DHT (Sigma, A-8380). 24- or 6-well Primaria plates instead of low attaching plates are used to allow the cells to attach to the bottom of the wells. Medium changes are performed by removing all the medium and adding new medium into the wells every four days (0.75 ml for wells of 24-well plate; 1.5 ml for wells of 6-well plate). Some of the metastatic cells require long expansion times (up to 2-3 months), while other cells do not grow.

Liver Metastasis.

One clone was derived from a liver metastasis and was very slow growing. The colony was found after 3.5 months of culture and named Clone B2. Clone B2 was cultured without DHT and was adherent on a Primaria plate (See FIGS. 39A-E).

Brain Metastasis

Multiple clones were derived from brain metastasis. Frozen stock of four different clones was generated. Pellets of three clones were collected for DNA isolation. One clone was collected at two different passages.

Clone C5 was cultured without DHT (See FIGS. 40A-D). Clone C5 expresses androgen receptor, CK5, Foxa1, Chromogranin A (FIGS. 42A-F; FIGS. 44A-D; FIGS. 47A-D; FIG. 48D).

Clone B4 was cultured with DHT (See FIGS. 41A-E). Clone B4 expresses androgen receptor, CK5, Foxa1, Chromogranin A (FIGS. 43A-F; FIGS. 45A-F; FIGS. 46A-D; FIGS. 48A-C).

Clone B1 was cultured without DHT and expressed Amacr (FIGS. 49A-B)

Clone B5 was cultured without DHT and expressed synaptophysin (FIGS. 50A-C).

Clones derived from brain metastasis expressed Nkx3.1, synaptophysin, Amacr, and Chromogranin A (FIGS. 51A-D).

Adrenal Metastasis

Clones can be derived from adrenal metastasis.

TABLE 5

Brain Metastasis Samples

| clone | DHT | P2 | termination |
|---|---|---|---|
| C2 | No | Jan. 13, 2014 | No signs of potential for expanding, discard on Jul. 21, 2014 |
| C3 | + | Jan. 3, 2014 | No signs of potential for expanding, discard on Jul. 21, 2014 |
| C6 | + | Feb. 24, 2014 | No signs of potential for expanding, discard on Jul. 21, 2014 |

TABLE 6

Metastasis clones culture conditions and passage number

| clone | DHT | P2 | P3 | P4 | P5 | P6 | P7 | P8 | P9 |
|---|---|---|---|---|---|---|---|---|---|
| B1 | No | Jan. 3, 2014 | Jan. 13, 2014 | Mar. 10, 2014* 4 wells for → DNA | Jun. 2, 2014 Freeze 4 vials 4 wells for → DNA | Aug. 26, 2014 | | | |
| C5 | No | Jan. 3, 2014 | Jan. 24, 2014 | Feb. 5, 2014 | Feb. 24, 2014 Freeze 3 vials | Mar. 10, 2014* Freeze 4 vials | May 6, 2014 Save 2 wells for RNA | | |
| B4 | No | Jan. 13, 2014 | Mar. 21, 2014 | | | | | | |
| B5 | No | Feb. 24, 2014 | Mar. 21, 2014 | Apr. 1, 2014 | May 2, 2014 Freeze 4 vials | Jun. 2, 2014 4 wells for → DNA Jul. 11, 2014 Freeze 3 vials | Aug. 26, 2014 Freeze 4 vials | | |
| B2 ENR →Hepa | No | Mar. 21, 2014 | May 6, 2014 | | | | | | |
| B4 | + | Jan. 3, 2014 | Jan. 13, 2014 | Jan. 24, 2014 | Feb. 5, 2014 | Feb. 24, 2014 Freeze 3 vials | Mar. 10, 2014 Freeze 4 vials | May 6, 2014 Save 2 wells for RNA | Jun. 25, 2014 Save 4 wells for DNA |
| B3 | + | Jan. 13, 2014 | Mar. 21, 2014 | | | | | | |

TABLE 7

DNA Samples

| clone | DHT | Passage | DNA |
|---|---|---|---|
| B1 | No | P5 (P4) | 4 wells (6-well plate) |
|  |  | P6 (P5) | 4 wells (6-well plate) |
| B5 | No | P6 (P5) | 4 wells (6-well plate) |
| B4 | + | P9 (P8) | 4 wells (6-well plate) |

TABLE 8

Frozen Stocks

| clone | DHT | Passage | vials |
|---|---|---|---|
| B1 | No | P6 (P5) | 4 |
| C5 | No | P5 (P4) | 3 |
|  |  | P6 (P3) | 4 |
| B5 | No | P5 (P4) | 4 |
|  |  | P6 (P5) | 3 |
|  |  | P7 (P6) | 4 |
| B5 | + | P6 (P5) | 3 |
|  |  | P7 (P6) | 4 |

Example 7—Infection of Organoids with Lentivirus

Lentiviral infection of organoids was performed showing the ability for genetic modification of organoids (FIGS. 52A-D).

Example 8—Growth of Prostate Organoids in a Collagen Matrix

Figure 53:
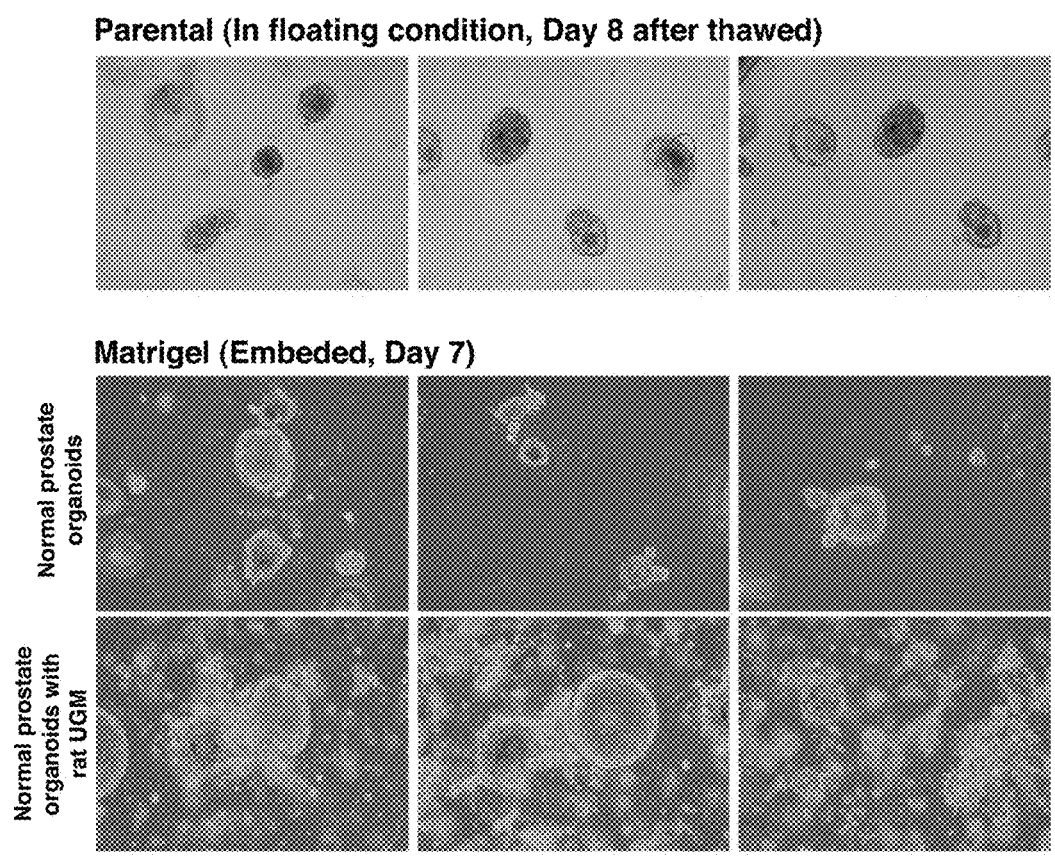
FIG. 53 shows parental organoids grown by the Matrigel floating method at Day 8 after thawing (top panel). Normal prostate organoids at day 7 grown by the Matrigel embedding method with and without rat urogenital mesenchyme are shown (bottom panel).
Figure 54:
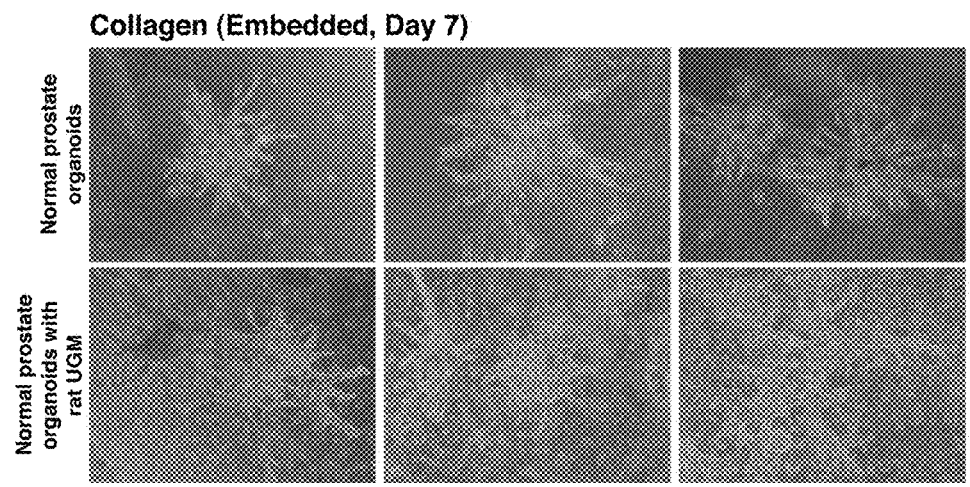
FIG. 54 shows normal prostate organoids at day 7 grown by the Collagen method with and without rat urogenital mesenchyme are shown (bottom panel).
Figure 55:
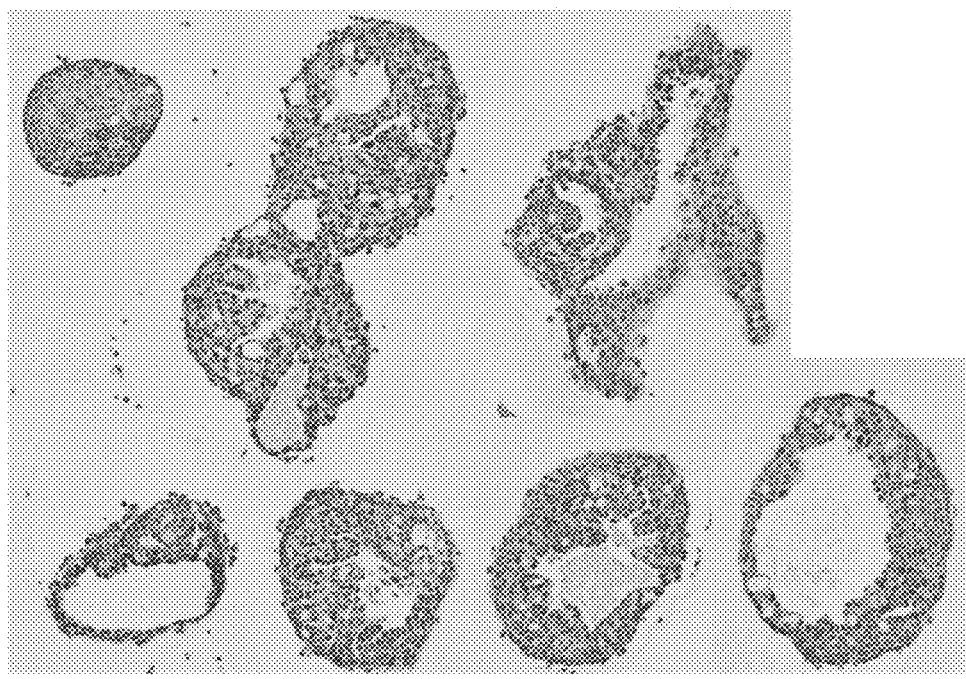
FIG. 55 shows rat urogenital mesenchyme with prostate organoids grown by the Matrigel embedding method.
Figure 56:
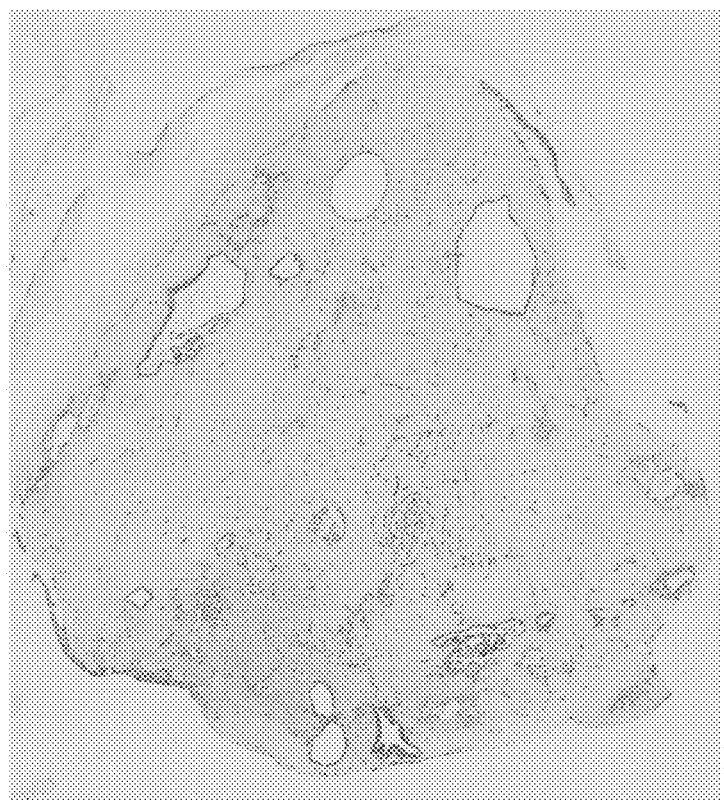
FIG. 56 shows rat urogenital mesenchyme with prostate organoids grown by the Collagen method.
Figure 57:
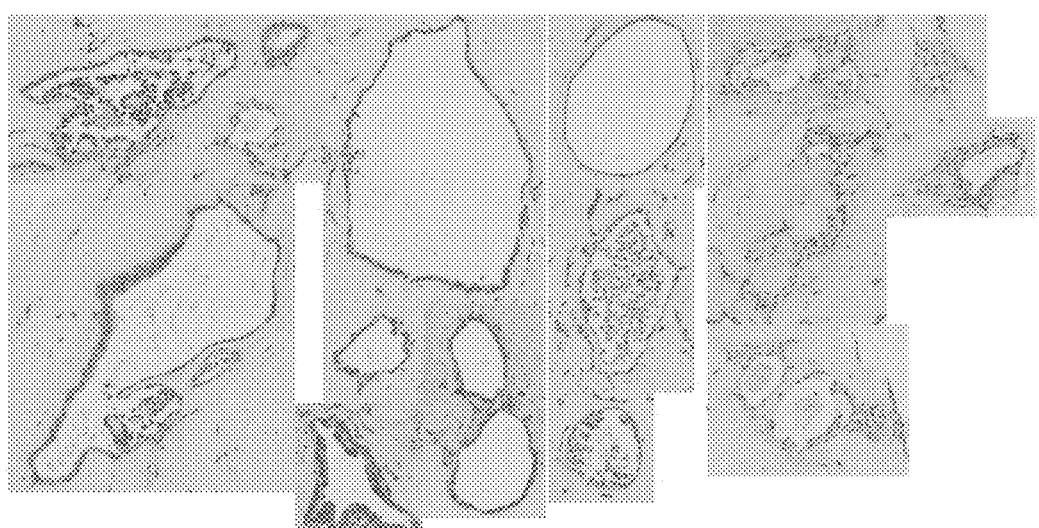
FIG. 57 shows rat urogenital mesenchyme with prostate organoids grown by the Collagen method.

Mouse and human prostate organoids were grown in a collagen matrix (as an alternative to the Matrigel floating and embedding methods). Culture in collagen resulted in different organoid morphology (FIGS. 53-54).

Collagen Embedding Method

Cells are prepared as described in Example 5 for the Matrigel embedding method (up to step 2.5.3). The media containing the cells is then mixed with 0.5 ml of a collagen mixture solution—9 Part of Collagen I, High Concentration, Rat tail, Cat. #354249 and 1 Part of setting solution formulated as follows: 10×EBSS—100 ml; Sodium bicarbonate—2.45 g; 1M NaOH—7.5 ml; Sterile milliQ water—42.5 ml (10× Earle's Balanced Salt Solution (Life Technologies), 0.2 M NaHCO$_3$ and 50 mM NaOH). It is important that the plate is pre-coated with 200 ul of collagen mixture solution and followed by the incubation of the precoated plate at 37° C. for at least 30 minutes prior to use. In addition, collagen mixture will only be prepared prior to used.

The embedded cells in the collagen mixture solution can be allowed to solidify in 37° C. incubator for 30 minutes. Warmed complete hepatocyte medium (supplemented with EGF/Glutamax/5% Heat-inactivated FBS) can then be carefully applied to the solidified collagen from the edge of the well.

In order to passage the cell clusters embedded in collagen, medium can be replaced with collagenase solution (Sigma, C9697—Stock at 25 mg/ml prepared in HBSS supplemented with 2% FBS) at 0.25 mg/ml in hepatocyte medium for 30 minutes at 37° C. Collagen can be digested and the organoids can be released from the collagen.

Example 9—Growth of Mouse Prostate Organoids in Presence of Stroma

Recombination of Organoids with Rat Embryonic Urogenital Mesenchyme (rUGM)

Mouse prostate organoids were grown in the presence of stroma (derived from rat embryonic urogenital mesenchyme (UGM)) and in a collagen matrix (FIGS. 53-57). The co-culture of mouse prostate organoids together with rat embryonic urogenital mesenchyme reconstituted prostatic tissue containing both epithelial and stromal components.

Protocol

1. Prostate organoids are generated from dissociated prostate cells by the Matrigel floating, Matrigel embedding or collagen embedding method as described herein.

2. The organoids are released from the embedded Matrigel or collagen, or separated from the Matrigel media as described above.

3. 30 min before embedding, a well of a 6-well tissue culture support is coated with a thin layer of Matrigel (Matrigel:Hepatocyte Medium at a ratio of 6 parts Matrigel to 4 parts Hepatocyte Medium) and the Matrigel is allowed to solidify at 37° C. Pre-coated wells minimize detachment of the Matrigel pad.

4. The organoids are combined with rat UGM and then mixed with 500 ul of Matrigel:Hepatocyte Medium mixture (6 parts Matrigel to 4 parts Hepatocyte Medium), and the complete mixture is plated in the middle of the pre-coated wells of a 6-well plate and allowed to spread out evenly to form a thin Matrigel pad.

5. The Matrigel pad is allowed to solidify for at least 30 min prior to applying medium onto it. Medium should be added from the side of the well to avoid breaking the Matrigel pad.

6. When collagen is used, the protocol is identical, except that collagen is used for coating and embedding. Note that collagen has to be neutralized to solidify using 9:1 collagen: setting buffer solution (10× Earle's Balanced Salt Solution (Life Technologies), 0.2 M NaHCO$_3$ and 50 mM NaOH).

Human prostate organoids were cultured from biopsy specimens (as opposed to prostatectomy specimens) in either Matrigel or collagen matrix (FIGS. 60-62).

What is claimed:

1. A method for culturing prostate organoids, the method comprising:
    a) obtaining a sample of prostate tissue from a subject;
    b) dissociating the sample of prostate tissue;
    c) isolating dissociated prostate epithelial cells from the sample of prostate tissue; and
    d) culturing the dissociated prostate epithelial cells in a culture medium comprising basal hepatocyte medium, Matrigel, FBS and ROCK inhibitor;
        wherein if the sample of prostate tissue in step (a) is non-cancerous the dissociated prostate epithelial cells form prostate organoids comprising luminal cells and basal cells, or
        wherein if the sample of prostate tissue in step (a) is cancerous the dissociated prostate epithelial cells form prostate organoids with the same differentiated state as the cancerous prostate tissue sample.

2. A method for culturing prostate organoids, the method comprising:
    a) obtaining a sample of prostate tissue from a subject;
    b) isolating Castration-Resistant NKx3.1-expressing cells (CARNs) from the sample of prostate tissue;
    c) culturing the CARNs in a culture medium comprising basal hepatocyte medium, Matrigel, FBS and ROCK inhibitor;
        wherein if the sample of prostate tissue in step (a) is non-cancerous the CARNs form prostate organoids comprising luminal cells and basal cells, or
        wherein if the sample of prostate tissue in step (a) is cancerous the CARNs form prostate organoids with the same differentiated state as the cancerous prostate tissue sample.

3. A method for culturing prostate organoids, the method comprising:
    a) obtaining a sample of prostate tissue from a subject;
    b) dissociating the sample of prostate tissue;
    c) isolating dissociated prostate epithelial cells from the sample of prostate tissue;
    d) contacting the dissociated prostate epithelial cells with a Matrigel solution and plating the dissociated prostate epithelial cells and Matrigel solution in a cell culture support, wherein the Matrigel solution forms a matrix;
    e) providing an overlay layer of liquid culture medium to the matrix formed in (d), wherein the liquid culture medium comprises basal hepatocyte medium, FBS and ROCK inhibitor; and
    f) incubating the culture of (e);
        wherein if the sample of prostate tissue in step (a) is non-cancerous the dissociated prostate epithelial cells form prostate organoids comprising luminal cells and basal cells, or
        wherein if the sample of prostate tissue in step (a) is cancerous the dissociated prostate epithelial cells form prostate organoids with the same differentiated state as the cancerous prostate tissue sample.

4. A method for culturing prostate organoids, the method comprising:
    a) obtaining a sample of prostate tissue from a subject;
    b) isolating CARNs from the sample of prostate tissue;
    c) contacting the CARNs with a Matrigel solution and plating the CARNs and Matrigel solution in a cell culture support, wherein the Matrigel solution forms a matrix;
    d) providing an overlay layer of liquid culture medium to the matrix formed in (d), wherein the liquid culture medium comprises basal hepatocyte medium, FBS and ROCK inhibitor; and
    e) incubating the culture of (d);
        wherein if the sample of prostate tissue in step (a) is non-cancerous the CARNs form prostate organoids comprising luminal cells and basal cells, or
        wherein if the sample of prostate tissue in step (a) is cancerous the CARNs form prostate organoids with the same differentiated state as the cancerous prostate tissue sample.

5. The method claim 1, 2, 3, or 4, wherein the medium further comprises EGF.

6. The method of claim 5, wherein the medium comprises 10 ng/ml of EGF.

7. The method of claim 1, 2, 3, or 4, wherein the medium further comprises DHT.

8. The method of claim 1 or 2, wherein the medium comprises 5% Matrigel.

9. The method of claim 1, 2, 3, or wherein the medium comprises 5% heat-inactivated charcoal-stripped FBS.

10. The method of claim 1, 2, 3, or wherein the ROCK inhibitor is Y-27632.

11. The method of claim 1, 2, 3, or 4, wherein the prostate tissue sample is non-cancerous.

12. The method of claim 1, 2, 3, or 4, wherein the prostate tissue sample is cancerous.

13. The method of claim 12, wherein the organoid maintains the transformed phenotype of the cancerous prostate tissue sample.

14. The method of claim 1, 2, 3, or 4, wherein adherent two-dimensional prostate cell cultures are obtained from the organoids.

* * * * *